(12) United States Patent
Grunwald

(10) Patent No.: US 10,912,488 B2
(45) Date of Patent: Feb. 9, 2021

(54) APPARATUS AND METHOD FOR CATHETER NAVIGATION AND TIP LOCATION

(71) Applicant: Bard Access Systems, Inc., Salt Lake City, UT (US)

(72) Inventor: Sorin Grunwald, Paris (FR)

(73) Assignee: Bard Access Systems, Inc., Salt Lake City, UT (US)

( * ) Notice: Subject to any disclaimer, the term of this patent is extended or adjusted under 35 U.S.C. 154(b) by 93 days.

(21) Appl. No.: 15/816,932

(22) Filed: Nov. 17, 2017

(65) Prior Publication Data
US 2018/0070856 A1 Mar. 15, 2018

Related U.S. Application Data

(60) Division of application No. 14/846,496, filed on Sep. 4, 2015, now Pat. No. 10,231,643, which is a division (Continued)

(51) Int. Cl.
*A61B 5/06* (2006.01)
*A61B 5/04* (2006.01)
(Continued)

(52) U.S. Cl.
CPC .............. *A61B 5/068* (2013.01); *A61B 5/042* (2013.01); *A61B 5/044* (2013.01);
(Continued)

(58) Field of Classification Search
CPC ......... A61B 5/0452; A61B 5/06; A61B 5/061; A61B 2019/5246; A61B 5/068;
(Continued)

(56) References Cited

U.S. PATENT DOCUMENTS 3,133,244 A 5/1964 Inojtulewicz
3,297,020 A 1/1967 Mathiesen
(Continued)

FOREIGN PATENT DOCUMENTS

AU 642647 B2 10/1993
AU 1860597 B2 6/1999
(Continued)

OTHER PUBLICATIONS

EP 12177438.4 filed Jul. 23, 2012 Examination Report dated Dec. 5, 2014.
(Continued)

*Primary Examiner* — Tammie K Marlen
(74) *Attorney, Agent, or Firm* — Rutan & Tucker LLP

(57) ABSTRACT

Devices and methods obtain and use endovascular electrograms in a number of clinical applications and settings. In one embodiment, methods for triggering analysis of an endovascular ECG waveform are based on the detection of a peak in a skin-based ECG waveform in order to determine a location of an indwelling medical device, such as a catheter. In another embodiment, the position of a catheter or other medical device within the vasculature can be determined by analysis of the energy profile of a detected P-wave. In yet other embodiments, magnetic connecting devices are used for establishing an operable connection through a sterile field.

14 Claims, 34 Drawing Sheets

Related U.S. Application Data of application No. 13/019,939, filed on Feb. 2, 2011, now Pat. No. 9,125,578, which is a continuation-in-part of application No. 12/854,083, filed on Aug. 10, 2010, now Pat. No. 9,445,734, which is a continuation-in-part of application No. 12/815,331, filed on Jun. 14, 2010, now Pat. No. 8,339,206.

(60) Provisional application No. 61/213,474, filed on Jun. 12, 2009, provisional application No. 61/272,025, filed on Aug. 10, 2009, provisional application No. 61/282,397, filed on Feb. 2, 2010.

(51) Int. Cl.

| | | |
|---|---|---|
| *A61B 5/042* | (2006.01) | |
| *A61B 5/0456* | (2006.01) | |
| *A61B 5/0452* | (2006.01) | |
| *A61B 5/044* | (2006.01) | |
| *H01R 13/62* | (2006.01) | |
| *A61B 5/00* | (2006.01) | |
| *A61M 25/00* | (2006.01) | |
| *A61M 25/01* | (2006.01) | |
| *A61M 25/09* | (2006.01) | |
| *A61B 34/20* | (2016.01) | |

(52) U.S. Cl.
CPC ........ *A61B 5/04017* (2013.01); *A61B 5/0452* (2013.01); *A61B 5/0456* (2013.01); *A61B 5/06* (2013.01); *A61B 5/061* (2013.01); *A61B 5/063* (2013.01); *H01R 13/6205* (2013.01); *A61B 5/7203* (2013.01); *A61B 5/726* (2013.01); *A61B 2034/2046* (2016.02); *A61B 2562/227* (2013.01); *A61M 25/0026* (2013.01); *A61M 25/0102* (2013.01); *A61M 25/0147* (2013.01); *A61M 25/0194* (2013.01); *A61M 2025/09116* (2013.01)

(58) Field of Classification Search
CPC ..... A61B 5/04017; A61B 5/042; A61B 5/044; A61B 5/063; A61B 5/7203; A61B 5/726; A61B 2034/2046; A61B 2562/227; H01R 13/6205; A61M 25/0026; A61M 25/0102; A61M 25/0147; A61M 25/0194; A61M 2025/09116

See application file for complete search history.

(56) References Cited

U.S. PATENT DOCUMENTS

| | | |
|---|---|---|
| 3,625,200 A | 12/1971 | Muller |
| 3,674,014 A | 7/1972 | Tillander |
| 3,795,855 A | 3/1974 | Browning |
| 3,817,241 A | 6/1974 | Grausz |
| 3,847,157 A | 11/1974 | Caillouette et al. |
| 3,868,565 A | 2/1975 | Kuipers |
| 3,896,373 A | 7/1975 | Zelby |
| 3,902,501 A | 9/1975 | Citron et al. |
| 3,986,373 A | 10/1976 | Goodlaxson |
| 3,995,623 A | 12/1976 | Blake et al. |
| 4,003,369 A | 1/1977 | Heilman et al. |
| 4,063,561 A | 12/1977 | McKenna |
| 4,072,146 A | 2/1978 | Howes |
| 4,114,601 A | 9/1978 | Abels |
| 4,149,535 A | 4/1979 | Volder |
| 4,173,228 A | 11/1979 | Van Steenwyk et al. |
| 4,175,566 A | 11/1979 | Millar |
| 4,181,120 A | 1/1980 | Kunii et al. |
| 4,224,949 A | 9/1980 | Scott |
| 4,244,362 A | 1/1981 | Anderson |
| 4,289,139 A | 9/1981 | Enjoji et al. |
| 4,317,078 A | 2/1982 | Weed et al. |
| 4,327,722 A | 5/1982 | Groshong et al. |
| 4,327,723 A | 5/1982 | Frankhouser |
| 4,362,166 A | 12/1982 | Furler et al. |
| 4,365,639 A | 12/1982 | Goldreyer |
| 4,380,237 A | 4/1983 | Newbower |
| 4,407,294 A | 10/1983 | Vilkomerson |
| 4,417,886 A | 11/1983 | Frankhouser et al. |
| 4,429,693 A | 2/1984 | Blake et al. |
| 4,431,005 A | 2/1984 | McCormick |
| 4,431,214 A | 2/1984 | Buffington |
| 4,445,501 A | 5/1984 | Bresler |
| 4,459,854 A | 7/1984 | Richardson et al. |
| 4,469,106 A | 9/1984 | Harui |
| 4,483,343 A | 11/1984 | Beyer et al. |
| 4,491,137 A | 1/1985 | Jingu |
| 4,565,201 A | 1/1986 | Lass |
| 4,572,198 A | 2/1986 | Codrington |
| 4,577,634 A | 3/1986 | Gessman |
| 4,582,067 A | 4/1986 | Silverstein et al. |
| 4,587,975 A | 5/1986 | Salo et al. |
| 4,588,394 A | 5/1986 | Schulte et al. |
| 4,593,687 A | 6/1986 | Gray |
| 4,595,012 A | 6/1986 | Webler et al. |
| 4,601,706 A | 7/1986 | Aillon |
| 4,608,989 A | 9/1986 | Drue |
| 4,608,992 A | 9/1986 | Hakim et al. |
| 4,619,247 A | 10/1986 | Inoue et al. |
| 4,622,644 A | 11/1986 | Hansen |
| 4,644,960 A | 2/1987 | Johans |
| 4,652,820 A | 3/1987 | Maresca |
| 4,660,571 A | 4/1987 | Hess et al. |
| 4,665,925 A | 5/1987 | Millar |
| 4,667,230 A | 5/1987 | Arakawa et al. |
| 4,674,518 A | 6/1987 | Salo |
| 4,676,249 A | 6/1987 | Arenas et al. |
| 4,681,106 A | 7/1987 | Kensey et al. |
| 4,681,117 A | 7/1987 | Brodman et al. |
| 4,688,578 A | 8/1987 | Takano et al. |
| 4,692,148 A | 9/1987 | Kantrowitz et al. |
| 4,697,595 A | 10/1987 | Breyer et al. |
| 4,700,997 A | 10/1987 | Strand |
| 4,706,681 A | 11/1987 | Breyer et al. |
| 4,710,708 A | 12/1987 | Rorden et al. |
| 4,733,669 A | 3/1988 | Segal |
| 4,737,794 A | 4/1988 | Jones |
| 4,741,356 A | 5/1988 | Letzo et al. |
| 4,742,356 A | 5/1988 | Kuipers |
| 4,753,247 A | 6/1988 | Kirsner |
| 4,770,185 A | 9/1988 | Silverstein et al. |
| 4,771,788 A | 9/1988 | Millar |
| 4,781,685 A | 11/1988 | Lehmann et al. |
| 4,784,646 A | 11/1988 | Feingold |
| 4,787,070 A | 11/1988 | Suzuki et al. |
| 4,787,396 A | 11/1988 | Pidorenko |
| 4,790,809 A | 12/1988 | Kuntz |
| 4,793,361 A | 12/1988 | DuFault |
| 4,794,930 A | 1/1989 | Machida et al. |
| 4,796,632 A | 1/1989 | Boyd et al. |
| 4,798,588 A | 1/1989 | Aillon |
| 4,798,598 A | 1/1989 | Bonello et al. |
| 4,809,681 A | 3/1989 | Kantrowitz et al. |
| 4,809,713 A | 3/1989 | Grayzel |
| 4,813,729 A | 3/1989 | Speckhart |
| 4,821,731 A | 4/1989 | Martinelli et al. |
| 4,834,709 A | 5/1989 | Banning et al. |
| 4,836,214 A | 6/1989 | Sramek |
| 4,840,182 A | 6/1989 | Carlson |
| 4,840,622 A | 6/1989 | Hardy |
| 4,841,977 A | 6/1989 | Griffith et al. |
| 4,849,692 A | 7/1989 | Blood |
| 4,850,358 A | 7/1989 | Millar |
| 4,852,580 A | 8/1989 | Wood |
| 4,856,317 A | 8/1989 | Pidorenko et al. |
| 4,856,529 A | 8/1989 | Segal |
| 4,860,757 A | 8/1989 | Lynch et al. |
| 4,867,169 A | 9/1989 | Machida et al. |
| 4,869,263 A | 9/1989 | Segal et al. |
| 4,869,718 A | 9/1989 | Brader |
| 4,873,987 A | 10/1989 | Djordjevich et al. |

(56) References Cited

U.S. PATENT DOCUMENTS

| | | |
|---|---|---|
| 4,887,606 A | 12/1989 | Yock et al. |
| 4,887,615 A | 12/1989 | Taylor |
| 4,889,128 A | 12/1989 | Millar |
| 4,899,756 A | 2/1990 | Sonek |
| 4,901,725 A | 2/1990 | Nappholz et al. |
| 4,905,698 A | 3/1990 | Strohl, Jr. et al. |
| 4,911,173 A | 3/1990 | Terwilliger |
| 4,911,174 A | 3/1990 | Pederson et al. |
| 4,917,669 A | 4/1990 | Bonaldo |
| 4,924,870 A | 5/1990 | Wlodarczyk et al. |
| 4,943,770 A | 7/1990 | Ashley-Rollman et al. |
| 4,945,305 A | 7/1990 | Blood |
| 4,947,852 A | 8/1990 | Nassi et al. |
| 4,957,110 A | 9/1990 | Vogel et al. |
| 4,957,111 A | 9/1990 | Millar |
| 4,961,433 A | 10/1990 | Christian |
| 4,966,148 A | 10/1990 | Millar |
| 4,967,753 A | 11/1990 | Haase et al. |
| 4,977,886 A | 12/1990 | Takehana et al. |
| 4,989,608 A | 2/1991 | Ratner |
| 4,989,610 A | 2/1991 | Patton et al. |
| 4,995,396 A | 2/1991 | Inaba et al. |
| 4,998,916 A | 3/1991 | Hammerslag et al. |
| 5,004,456 A | 4/1991 | Botterbusch et al. |
| 5,005,592 A | 4/1991 | Cartmell |
| 5,016,173 A | 5/1991 | Kenet et al. |
| 5,025,799 A | 6/1991 | Wilson |
| 5,029,585 A | 7/1991 | Lieber et al. |
| 5,040,548 A | 8/1991 | Yock |
| 5,042,486 A | 8/1991 | Pfeiler et al. |
| 5,045,071 A | 9/1991 | McCormick et al. |
| 5,046,497 A | 9/1991 | Millar |
| 5,050,607 A | 9/1991 | Bradley et al. |
| 5,057,095 A | 10/1991 | Fabian |
| 5,058,583 A | 10/1991 | Geddes et al. |
| 5,058,595 A | 10/1991 | Kern |
| 5,067,489 A | 11/1991 | Lind |
| 5,076,278 A | 12/1991 | Vilkomerson et al. |
| 5,078,140 A | 1/1992 | Kwoh |
| 5,078,148 A | 1/1992 | Nassi et al. |
| 5,078,149 A | 1/1992 | Katsumata et al. |
| 5,078,678 A | 1/1992 | Katims |
| 5,078,714 A | 1/1992 | Katims |
| 5,084,022 A | 1/1992 | Claude |
| 5,092,341 A | 3/1992 | Kelen |
| 5,099,845 A | 3/1992 | Besz et al. |
| 5,099,850 A | 3/1992 | Matsui et al. |
| 5,100,387 A | 3/1992 | Ng |
| 5,105,829 A | 4/1992 | Fabian et al. |
| 5,109,862 A | 5/1992 | Kelen et al. |
| 5,114,401 A | 5/1992 | Stuart et al. |
| 5,121,750 A | 6/1992 | Katims |
| 5,125,410 A | 6/1992 | Misono et al. |
| 5,134,370 A | 7/1992 | Jefferts et al. |
| 5,144,955 A | 9/1992 | O'Hara |
| 5,146,151 A | 9/1992 | Korn |
| 5,156,151 A | 10/1992 | Imran |
| 5,158,086 A | 10/1992 | Brown et al. |
| 5,160,342 A | 11/1992 | Reger et al. |
| 5,161,536 A | 11/1992 | Vilkomerson et al. |
| 5,174,295 A | 12/1992 | Christian et al. |
| 5,174,299 A | 12/1992 | Nelson |
| 5,184,601 A | 2/1993 | Putman |
| 5,184,627 A | 2/1993 | de Toledo |
| 5,190,045 A | 3/1993 | Frazin |
| 5,202,985 A | 4/1993 | Goyal |
| 5,205,830 A | 4/1993 | Dassa et al. |
| 5,211,165 A | 5/1993 | Dumoulin et al. |
| 5,211,636 A | 5/1993 | Mische |
| 5,212,988 A | 5/1993 | White et al. |
| 5,214,615 A | 5/1993 | Bauer |
| 5,217,026 A | 6/1993 | Stoy et al. |
| 5,220,924 A | 6/1993 | Frazin |
| 5,233,994 A | 8/1993 | Shmulewitz |
| 5,235,987 A | 8/1993 | Wolfe |
| 5,239,464 A | 8/1993 | Blair et al. |
| 5,240,004 A | 8/1993 | Walinsky et al. |
| 5,243,995 A | 9/1993 | Maier |
| 5,246,007 A | 9/1993 | Frisbie et al. |
| 5,246,426 A | 9/1993 | Lewis et al. |
| 5,247,171 A | 9/1993 | Wlodarczyk et al. |
| 5,251,635 A | 10/1993 | Dumoulin et al. |
| 5,255,680 A | 10/1993 | Darrow et al. |
| 5,257,636 A | 11/1993 | White |
| 5,257,979 A | 11/1993 | Jagpal |
| 5,261,409 A | 11/1993 | Dardel |
| 5,265,610 A | 11/1993 | Darrow et al. |
| 5,265,614 A | 11/1993 | Hayakawa et al. |
| 5,267,569 A | 12/1993 | Lienhard |
| 5,269,306 A | 12/1993 | Warnking et al. |
| 5,270,810 A | 12/1993 | Nishimura |
| 5,271,404 A | 12/1993 | Corl et al. |
| 5,273,025 A | 12/1993 | Sakiyama et al. |
| 5,273,042 A | 12/1993 | Lynch et al. |
| 5,274,551 A | 12/1993 | Corby, Jr. |
| 5,275,053 A | 1/1994 | Wlodarczyk et al. |
| 5,279,129 A | 1/1994 | Ito |
| 5,279,607 A | 1/1994 | Schentag et al. |
| 5,280,786 A | 1/1994 | Wlodarczyk et al. |
| 5,287,331 A | 2/1994 | Schindel et al. |
| 5,289,373 A | 2/1994 | Zarge et al. |
| 5,292,342 A | 3/1994 | Nelson et al. |
| 5,307,072 A | 4/1994 | Jones, Jr. |
| 5,311,871 A | 5/1994 | Yock |
| 5,313,949 A | 5/1994 | Yock |
| 5,318,025 A | 6/1994 | Dumoulin et al. |
| 5,325,860 A | 7/1994 | Seward et al. |
| 5,325,873 A | 7/1994 | Hirschi et al. |
| 5,330,496 A | 7/1994 | Alferness |
| 5,331,966 A | 7/1994 | Bennett et al. |
| 5,333,614 A | 8/1994 | Feiring |
| 5,337,678 A | 8/1994 | Grout |
| 5,341,807 A | 8/1994 | Nardella |
| 5,343,865 A | 9/1994 | Gardineer et al. |
| 5,345,940 A | 9/1994 | Seward et al. |
| 5,348,020 A | 9/1994 | Hutson |
| 5,350,352 A | 9/1994 | Buchholtz et al. |
| 5,357,961 A | 10/1994 | Fields et al. |
| 5,365,935 A | 11/1994 | Righter et al. |
| 5,366,443 A | 11/1994 | Eggers et al. |
| 5,368,048 A | 11/1994 | Stoy et al. |
| 5,375,596 A | 12/1994 | Twiss et al. |
| 5,376,083 A | 12/1994 | Mische |
| 5,377,678 A | 1/1995 | Dumoulin et al. |
| 5,385,053 A | 1/1995 | Wlodarczyk et al. |
| 5,385,146 A | 1/1995 | Goldreyer |
| 5,391,199 A | 2/1995 | Ben-Haim |
| 5,394,876 A | 3/1995 | Ma |
| 5,394,877 A | 3/1995 | Orr et al. |
| 5,395,366 A | 3/1995 | D'Andrea et al. |
| 5,398,683 A | 3/1995 | Edwards et al. |
| 5,398,691 A | 3/1995 | Martin et al. |
| 5,411,485 A | 5/1995 | Tennican et al. |
| 5,413,107 A | 5/1995 | Oakley et al. |
| 5,417,208 A | 5/1995 | Winkler |
| 5,417,701 A | 5/1995 | Holmes |
| 5,422,478 A | 6/1995 | Wlodarczyk et al. |
| 5,423,334 A | 6/1995 | Jordan |
| 5,423,877 A | 6/1995 | Mackey |
| 5,425,367 A | 6/1995 | Shapiro et al. |
| 5,425,370 A | 6/1995 | Vilkomerson |
| 5,425,382 A | 6/1995 | Golden et al. |
| 5,427,114 A | 6/1995 | Colliver et al. |
| 5,429,132 A | 7/1995 | Guy et al. |
| 5,429,617 A | 7/1995 | Hammersmark et al. |
| 5,431,641 A | 7/1995 | Grozinger et al. |
| 5,433,729 A | 7/1995 | Adams et al. |
| 5,437,276 A | 8/1995 | Takada |
| 5,437,277 A | 8/1995 | Dumoulin et al. |
| 5,438,873 A | 8/1995 | Wlodarczyk et al. |
| 5,443,066 A | 8/1995 | Dumoulin et al. |
| 5,443,489 A | 8/1995 | Ben-Haim |
| 5,445,150 A | 8/1995 | Dumoulin et al. |
| 5,445,166 A | 8/1995 | Taylor |

(56) References Cited

U.S. PATENT DOCUMENTS

| | | |
|---|---|---|
| 5,450,846 A | 9/1995 | Goldreyer |
| 5,453,575 A | 9/1995 | O'Donnell et al. |
| 5,453,576 A | 9/1995 | Krivitski |
| 5,456,256 A | 10/1995 | Schneider et al. |
| 5,456,718 A | 10/1995 | Szymaitis |
| 5,464,016 A | 11/1995 | Nicholas et al. |
| 5,474,065 A | 12/1995 | Meathrel et al. |
| 5,476,090 A | 12/1995 | Kishi |
| 5,480,422 A | 1/1996 | Ben-Haim |
| 5,487,729 A | 1/1996 | Avellanet et al. |
| 5,490,522 A | 2/1996 | Dardel |
| 5,492,538 A | 2/1996 | Johlin, Jr. |
| 5,494,038 A | 2/1996 | Wang et al. |
| 5,500,011 A | 3/1996 | Desai |
| 5,500,012 A | 3/1996 | Brucker et al. |
| 5,505,205 A | 4/1996 | Solomon et al. |
| 5,509,822 A | 4/1996 | Negus et al. |
| 5,513,637 A | 5/1996 | Twiss et al. |
| 5,515,160 A | 5/1996 | Schulz et al. |
| 5,515,853 A | 5/1996 | Smith et al. |
| 5,517,989 A | 5/1996 | Frisbie et al. |
| 5,522,878 A | 6/1996 | Montecalvo et al. |
| 5,522,880 A | 6/1996 | Barone et al. |
| 5,526,812 A | 6/1996 | Dumoulin et al. |
| 5,531,664 A | 7/1996 | Adachi et al. |
| 5,536,248 A | 7/1996 | Weaver et al. |
| 5,540,230 A | 7/1996 | Vilkomerson |
| 5,540,681 A | 7/1996 | Strul et al. |
| 5,542,938 A | 8/1996 | Avellanet et al. |
| 5,546,949 A | 8/1996 | Frazin et al. |
| 5,546,951 A | 8/1996 | Ben-Haim |
| 5,555,618 A | 9/1996 | Winkler |
| 5,558,091 A | 9/1996 | Acker et al. |
| 5,568,809 A | 10/1996 | Ben-haim |
| D375,450 S | 11/1996 | Bidwell et al. |
| 5,570,671 A | 11/1996 | Hickey |
| 5,575,291 A | 11/1996 | Flayakawa et al. |
| 5,588,442 A | 12/1996 | Scovil et al. |
| 5,592,939 A | 1/1997 | Martinelli |
| 5,598,846 A | 2/1997 | Peszynski |
| 5,599,299 A | 2/1997 | Weaver et al. |
| 5,600,330 A | 2/1997 | Blood |
| 5,603,333 A | 2/1997 | Konings |
| 5,606,981 A | 3/1997 | Tartacower et al. |
| 5,610,967 A | 3/1997 | Moorman et al. |
| 5,617,866 A | 4/1997 | Marian, Jr. |
| 5,622,169 A | 4/1997 | Golden et al. |
| 5,622,170 A | 4/1997 | Schulz |
| 5,622,184 A | 4/1997 | Ashby et al. |
| 5,623,931 A | 4/1997 | Wung et al. |
| 5,624,430 A | 4/1997 | Eton et al. |
| 5,626,554 A | 5/1997 | Ryaby et al. |
| 5,626,870 A | 5/1997 | Monshipouri et al. |
| 5,630,419 A | 5/1997 | Ranalletta |
| 5,638,819 A | 6/1997 | Manwaring et al. |
| 5,640,967 A | 6/1997 | Fine et al. |
| 5,644,612 A | 7/1997 | Moorman et al. |
| 5,645,065 A | 7/1997 | Shapiro et al. |
| 5,651,047 A | 7/1997 | Moorman et al. |
| 5,654,864 A | 8/1997 | Ritter et al. |
| D383,968 S | 9/1997 | Bidwell et al. |
| 5,662,115 A | 9/1997 | Torp et al. |
| 5,665,103 A | 9/1997 | Lafontaine et al. |
| 5,665,477 A | 9/1997 | Meathrel et al. |
| 5,666,473 A | 9/1997 | Wallace |
| 5,666,958 A | 9/1997 | Rothenberg et al. |
| 5,669,383 A | 9/1997 | Johnson |
| 5,669,388 A | 9/1997 | Vilkomerson |
| 5,676,159 A | 10/1997 | Navis |
| 5,676,673 A | 10/1997 | Ferre et al. |
| 5,682,890 A | 11/1997 | Kormos et al. |
| 5,691,898 A | 11/1997 | Rosenberg et al. |
| 5,694,945 A | 12/1997 | Ben-Haim |
| 5,695,479 A | 12/1997 | Jagpal |
| 5,697,377 A | 12/1997 | Wittkampf |
| 5,699,801 A | 12/1997 | Atalar et al. |
| 5,700,889 A | 12/1997 | Blair |
| 5,701,898 A | 12/1997 | Adam et al. |
| 5,702,433 A | 12/1997 | Taylor et al. |
| 5,711,299 A | 1/1998 | Manwaring et al. |
| 5,713,362 A | 2/1998 | Vilkomerson |
| 5,713,363 A | 2/1998 | Seward et al. |
| 5,713,858 A | 2/1998 | Heruth et al. |
| 5,713,946 A | 2/1998 | Ben-Haim |
| 5,715,817 A | 2/1998 | Stevens-Wright et al. |
| 5,716,389 A | 2/1998 | Walinsky et al. |
| 5,718,241 A | 2/1998 | Ben-Haim et al. |
| D391,838 S | 3/1998 | Bidwell et al. |
| 5,722,412 A | 3/1998 | Pflugrath et al. |
| 5,727,550 A | 3/1998 | Montecalvo |
| 5,727,552 A | 3/1998 | Ryan |
| 5,727,553 A | 3/1998 | Saad |
| 5,729,055 A | 3/1998 | Manning |
| 5,729,129 A | 3/1998 | Acker |
| 5,729,584 A | 3/1998 | Moorman et al. |
| 5,730,129 A | 3/1998 | Darrow et al. |
| 5,731,996 A | 3/1998 | Gilbert |
| 5,733,323 A | 3/1998 | Buck et al. |
| 5,738,096 A | 4/1998 | Ben-Haim |
| 5,740,808 A | 4/1998 | Panescu et al. |
| 5,742,394 A | 4/1998 | Hansen |
| 5,744,953 A | 4/1998 | Hansen |
| 5,748,767 A | 5/1998 | Raab |
| 5,749,835 A | 5/1998 | Glantz |
| 5,749,938 A | 5/1998 | Coombs |
| 5,751,785 A | 5/1998 | Moorman et al. |
| 5,752,513 A | 5/1998 | Acker et al. |
| 5,758,650 A | 6/1998 | Miller et al. |
| 5,762,064 A | 6/1998 | Polvani |
| 5,767,669 A | 6/1998 | Hansen et al. |
| 5,767,960 A | 6/1998 | Orman |
| 5,769,786 A | 6/1998 | Wiegel |
| 5,769,843 A | 6/1998 | Abela et al. |
| 5,769,881 A | 6/1998 | Schroeppel et al. |
| 5,771,896 A | 6/1998 | Sliwa, Jr. et al. |
| 5,775,322 A | 7/1998 | Silverstein et al. |
| 5,775,332 A | 7/1998 | Goldman |
| 5,776,064 A | 7/1998 | Kalfas et al. |
| 5,776,080 A | 7/1998 | Thome et al. |
| 5,779,638 A | 7/1998 | Vesely et al. |
| 5,782,767 A | 7/1998 | Pretlow, III |
| 5,782,773 A | 7/1998 | Kuo et al. |
| 5,785,657 A | 7/1998 | Breyer |
| 5,792,055 A | 8/1998 | McKinnon |
| 5,795,297 A | 8/1998 | Daigle |
| 5,795,298 A | 8/1998 | Vesely et al. |
| 5,795,632 A | 8/1998 | Buchalter |
| 5,797,849 A | 8/1998 | Vesely et al. |
| 5,800,352 A | 9/1998 | Ferre et al. |
| 5,800,410 A | 9/1998 | Gawreluk |
| 5,800,497 A | 9/1998 | Bakels et al. |
| 5,803,089 A | 9/1998 | Ferre et al. |
| 5,810,733 A | 9/1998 | Van Creveld et al. |
| RE35,924 E | 10/1998 | Winkler |
| 5,817,022 A | 10/1998 | Vesely |
| 5,817,024 A | 10/1998 | Ogle et al. |
| 5,820,549 A | 10/1998 | Marian, Jr. |
| 5,820,560 A | 10/1998 | Sinderby et al. |
| 5,824,031 A | 10/1998 | Cookston et al. |
| 5,827,192 A | 10/1998 | Gopakumaran et al. |
| 5,829,444 A | 11/1998 | Ferre et al. |
| 5,830,145 A | 11/1998 | Tenhoff |
| 5,831,260 A | 11/1998 | Hansen |
| 5,833,608 A | 11/1998 | Acker |
| 5,833,622 A | 11/1998 | Meathrel et al. |
| 5,835,561 A | 11/1998 | Moorman et al. |
| 5,836,882 A | 11/1998 | Frazin |
| 5,836,990 A | 11/1998 | Li |
| 5,840,024 A | 11/1998 | Taniguchi et al. |
| 5,840,025 A | 11/1998 | Ben-Haim |
| 5,840,030 A | 11/1998 | Ferek-Petric et al. |
| 5,840,031 A | 11/1998 | Crowley |
| 5,842,986 A | 12/1998 | Avrin |
| 5,842,998 A | 12/1998 | Gopakumaran et al. |

(56) References Cited

U.S. PATENT DOCUMENTS

| | | |
|---|---|---|
| 5,843,076 A | 12/1998 | Webster, Jr. et al. |
| 5,843,153 A | 12/1998 | Johnston et al. |
| 5,844,140 A | 12/1998 | Seale |
| 5,846,198 A | 12/1998 | Killmann |
| 5,855,553 A | 1/1999 | Tajima et al. |
| 5,859,893 A | 1/1999 | Moorman et al. |
| 5,865,748 A | 2/1999 | Co et al. |
| 5,868,673 A | 2/1999 | Vesely |
| 5,873,822 A | 2/1999 | Ferre et al. |
| 5,876,328 A | 3/1999 | Fox et al. |
| 5,879,297 A | 3/1999 | Haynor et al. |
| 5,893,363 A | 4/1999 | Little et al. |
| 5,897,495 A | 4/1999 | Aida et al. |
| 5,899,860 A | 5/1999 | Pfeiffer et al. |
| 5,902,238 A | 5/1999 | Golden et al. |
| 5,907,487 A | 5/1999 | Rosenberg et al. |
| 5,908,385 A | 6/1999 | Chechelski et al. |
| 5,910,113 A | 6/1999 | Pruter |
| 5,910,120 A | 6/1999 | Kim et al. |
| 5,913,820 A | 6/1999 | Bladen et al. |
| 5,913,830 A | 6/1999 | Miles |
| 5,919,141 A | 7/1999 | Money et al. |
| 5,919,170 A | 7/1999 | Woessner |
| 5,928,145 A | 7/1999 | Ocali et al. |
| 5,929,607 A | 7/1999 | Rosenberg et al. |
| 5,931,788 A | 8/1999 | Keen et al. |
| 5,931,818 A | 8/1999 | Werp et al. |
| 5,931,863 A | 8/1999 | Griffin, III et al. |
| 5,935,160 A | 8/1999 | Auricchio et al. |
| 5,941,858 A | 8/1999 | Johnson |
| 5,941,889 A | 8/1999 | Cermak |
| 5,941,904 A | 8/1999 | Johnston et al. |
| 5,944,022 A | 8/1999 | Nardella et al. |
| 5,944,023 A | 8/1999 | Johnson et al. |
| 5,951,472 A | 9/1999 | Van Vaals et al. |
| 5,951,598 A | 9/1999 | Bishay et al. |
| 5,953,683 A | 9/1999 | Hansen et al. |
| 5,957,857 A | 9/1999 | Hartley |
| 5,961,923 A | 10/1999 | Nova et al. |
| 5,967,978 A | 10/1999 | Littmann et al. |
| 5,967,980 A | 10/1999 | Ferre et al. |
| 5,967,991 A | 10/1999 | Gardineer et al. |
| 5,969,722 A | 10/1999 | Palm |
| 5,971,933 A | 10/1999 | Gopakumaran et al. |
| 5,971,983 A | 10/1999 | Lesh |
| 5,978,705 A | 11/1999 | KenKnight et al. |
| 5,983,126 A | 11/1999 | Wittkampf |
| 5,984,908 A | 11/1999 | Davis et al. |
| 5,991,693 A | 11/1999 | Zalewski |
| 5,997,473 A | 12/1999 | Taniguchi et al. |
| 5,997,481 A | 12/1999 | Adams et al. |
| 6,006,123 A | 12/1999 | Nguyen et al. |
| 6,011,988 A | 1/2000 | Lynch et al. |
| 6,014,473 A | 1/2000 | Hossack et al. |
| 6,014,580 A | 1/2000 | Blume et al. |
| 6,015,414 A | 1/2000 | Werp et al. |
| 6,017,496 A | 1/2000 | Nova et al. |
| 6,019,724 A | 2/2000 | Gronningsaeter et al. |
| 6,019,725 A | 2/2000 | Vesely et al. |
| 6,022,342 A | 2/2000 | Mukherjee |
| 6,023,638 A | 2/2000 | Swanson |
| 6,026,312 A | 2/2000 | Shemwell et al. |
| 6,031,765 A | 2/2000 | Lee et al. |
| 6,032,070 A | 2/2000 | Flock et al. |
| 6,039,694 A | 3/2000 | Larson et al. |
| 6,050,718 A | 4/2000 | Schena et al. |
| 6,052,610 A | 4/2000 | Koch |
| 6,052,618 A | 4/2000 | Dahlke et al. |
| D424,693 S | 5/2000 | Pruter |
| 6,058,323 A | 5/2000 | Lemelson |
| 6,059,718 A | 5/2000 | Taniguchi et al. |
| 6,063,032 A | 5/2000 | Grunwald |
| 6,064,905 A | 5/2000 | Webster, Jr. et al. |
| 6,066,094 A | 5/2000 | Ben-Haim |
| 6,068,599 A | 5/2000 | Saito et al. |
| 6,073,043 A | 6/2000 | Schneider |
| 6,074,367 A | 6/2000 | Hubbell |
| 6,075,442 A | 6/2000 | Welch |
| 6,076,007 A | 6/2000 | England et al. |
| 6,081,737 A | 6/2000 | Shah |
| 6,082,366 A | 7/2000 | Andra et al. |
| 6,083,170 A | 7/2000 | Ben-Haim |
| 6,099,524 A | 8/2000 | Lipson et al. |
| 6,100,026 A | 8/2000 | Nova et al. |
| 6,102,044 A | 8/2000 | Naidyhorski |
| 6,102,862 A | 8/2000 | Grunwald et al. |
| 6,107,699 A | 8/2000 | Swanson |
| 6,112,111 A | 8/2000 | Glantz |
| 6,112,115 A | 8/2000 | Feldman et al. |
| 6,113,504 A | 9/2000 | Kuesters |
| 6,115,624 A | 9/2000 | Lewis et al. |
| 6,120,445 A | 9/2000 | Grunwald |
| 6,122,538 A | 9/2000 | Sliwa, Jr. et al. |
| 6,128,174 A | 10/2000 | Ritter et al. |
| 6,129,668 A | 10/2000 | Haynor et al. |
| 6,129,724 A | 10/2000 | Fleischman et al. |
| 6,132,378 A | 10/2000 | Marino |
| 6,132,379 A | 10/2000 | Patacsil et al. |
| 6,135,961 A | 10/2000 | Pflugrath et al. |
| 6,136,274 A | 10/2000 | Nova et al. |
| 6,138,681 A | 10/2000 | Chen et al. |
| 6,139,496 A | 10/2000 | Chen et al. |
| 6,139,502 A | 10/2000 | Fredriksen |
| 6,139,540 A | 10/2000 | Rost et al. |
| 6,144,300 A | 11/2000 | Dames |
| 6,148,823 A | 11/2000 | Hastings |
| 6,152,933 A | 11/2000 | Werp et al. |
| 6,157,853 A | 12/2000 | Blume et al. |
| 6,165,144 A | 12/2000 | Talish et al. |
| 6,165,977 A | 12/2000 | Mochly-Rosen |
| 6,166,496 A | 12/2000 | Lys et al. |
| 6,166,806 A | 12/2000 | Tjin |
| 6,167,765 B1 | 1/2001 | Weitzel |
| 6,172,499 B1 | 1/2001 | Ashe |
| 6,173,199 B1 | 1/2001 | Gabriel |
| 6,173,715 B1 | 1/2001 | Sinanan et al. |
| 6,175,756 B1 | 1/2001 | Ferre et al. |
| 6,176,829 B1 | 1/2001 | Vilkomerson |
| 6,187,744 B1 | 2/2001 | Rooney |
| 6,190,370 B1 | 2/2001 | Tsui |
| 6,191,136 B1 | 2/2001 | Marban |
| 6,193,743 B1 | 2/2001 | Brayton et al. |
| 6,197,001 B1 | 3/2001 | Wilson et al. |
| 6,200,305 B1 | 3/2001 | Berthiaume et al. |
| 6,203,499 B1 | 3/2001 | Imling et al. |
| 6,208,884 B1 | 3/2001 | Kumar |
| 6,211,626 B1 | 4/2001 | Lys et al. |
| 6,211,666 B1 | 4/2001 | Acker |
| 6,212,426 B1 | 4/2001 | Swanson |
| 6,212,430 B1 | 4/2001 | Kung |
| 6,216,027 B1 | 4/2001 | Willis et al. |
| 6,216,028 B1 | 4/2001 | Raynor et al. |
| 6,216,029 B1 | 4/2001 | Paltieli |
| 6,217,517 B1 | 4/2001 | Grunwald |
| 6,223,087 B1 | 4/2001 | Williams |
| 6,226,547 B1 | 5/2001 | Lockhart et al. |
| 6,230,042 B1 | 5/2001 | Slettenmark |
| 6,230,046 B1 | 5/2001 | Crane et al. |
| 6,231,518 B1 | 5/2001 | Grabek et al. |
| 6,233,476 B1 | 5/2001 | Strommer et al. |
| 6,233,994 B1 | 5/2001 | Roy et al. |
| 6,236,883 B1 | 5/2001 | Ciaccio et al. |
| 6,238,344 B1 | 5/2001 | Gamelsky et al. |
| 6,241,673 B1 | 6/2001 | Williams |
| 6,246,231 B1 | 6/2001 | Ashe |
| 6,246,898 B1 | 6/2001 | Vesely et al. |
| 6,248,072 B1 | 6/2001 | Murkin |
| 6,248,074 B1 | 6/2001 | Ohno et al. |
| 6,248,075 B1 | 6/2001 | McGee et al. |
| 6,249,234 B1 | 6/2001 | Ely et al. |
| 6,253,770 B1 | 7/2001 | Acker et al. |
| 6,254,543 B1 | 7/2001 | Grunwald et al. |
| 6,258,035 B1 | 7/2001 | Hoeksel et al. |
| 6,259,938 B1 | 7/2001 | Zarychta et al. |

(56) References Cited

U.S. PATENT DOCUMENTS

| | | |
|---|---|---|
| 6,259,941 B1 | 7/2001 | Chia et al. |
| 6,261,231 B1 | 7/2001 | Damphousse et al. |
| 6,263,230 B1 | 7/2001 | Haynor et al. |
| 6,266,550 B1 | 7/2001 | Selmon et al. |
| 6,266,551 B1 | 7/2001 | Osadchy et al. |
| 6,266,552 B1 | 7/2001 | Slettenmark |
| 6,266,563 B1 | 7/2001 | KenKnight et al. |
| 6,270,493 B1 | 8/2001 | Lalonde et al. |
| 6,271,833 B1 | 8/2001 | Rosenberg et al. |
| 6,272,371 B1 | 8/2001 | Shlomo |
| 6,272,374 B1 | 8/2001 | Flock et al. |
| 6,275,258 B1 | 8/2001 | Chim |
| 6,275,724 B1 | 8/2001 | Dickinson et al. |
| 6,277,077 B1 | 8/2001 | Brisken et al. |
| 6,284,459 B1 | 9/2001 | Nova et al. |
| 6,285,898 B1 | 9/2001 | Ben-Haim |
| 6,287,259 B1 | 9/2001 | Grunwald |
| 6,287,260 B1 | 9/2001 | Hascoet et al. |
| 6,288,704 B1 | 9/2001 | Flack et al. |
| 6,292,678 B1 | 9/2001 | Hall et al. |
| 6,292,680 B1 | 9/2001 | Somogyi et al. |
| 6,292,901 B1 | 9/2001 | Lys et al. |
| 6,293,955 B1 | 9/2001 | Houser et al. |
| 6,296,604 B1 | 10/2001 | Garibaldi et al. |
| 6,298,261 B1 | 10/2001 | Rex |
| 6,304,768 B1 | 10/2001 | Blume et al. |
| 6,306,097 B1 | 10/2001 | Park et al. |
| 6,306,105 B1 | 10/2001 | Rooney et al. |
| 6,311,082 B1 | 10/2001 | Creighton, IV et al. |
| 6,315,709 B1 | 11/2001 | Garibaldi et al. |
| 6,315,727 B1 | 11/2001 | Coleman et al. |
| 6,319,668 B1 | 11/2001 | Nova et al. |
| 6,323,769 B1 | 11/2001 | Dames |
| 6,323,770 B1 | 11/2001 | Dames |
| 6,324,416 B1 | 11/2001 | Seibert |
| 6,325,540 B1 | 12/2001 | Lounsberry et al. |
| 6,325,762 B1 | 12/2001 | Tjin |
| 6,329,139 B1 | 12/2001 | Nova et al. |
| 6,329,916 B1 | 12/2001 | Dames |
| 6,330,467 B1 | 12/2001 | Creighton, IV et al. |
| 6,332,089 B1 | 12/2001 | Acker et al. |
| 6,332,874 B1 | 12/2001 | Eliasen et al. |
| 6,340,588 B1 | 1/2002 | Nova et al. |
| 6,340,868 B1 | 1/2002 | Lys et al. |
| 6,341,231 B1 | 1/2002 | Ferre et al. |
| 6,346,081 B1 | 2/2002 | Vilkomerson |
| 6,348,911 B1 | 2/2002 | Rosenberg et al. |
| 6,350,160 B1 | 2/2002 | Feuersanger et al. |
| 6,352,363 B1 | 3/2002 | Munger et al. |
| 6,354,999 B1 | 3/2002 | Dgany et al. |
| 6,355,026 B1 | 3/2002 | Mick |
| 6,356,791 B1 | 3/2002 | Westlund et al. |
| 6,360,123 B1 | 3/2002 | Kimchi et al. |
| 6,361,499 B1 | 3/2002 | Bates et al. |
| 6,364,823 B1 | 4/2002 | Garibaldi et al. |
| 6,364,839 B1 | 4/2002 | Little et al. |
| 6,366,804 B1 | 4/2002 | Mejia |
| 6,368,285 B1 | 4/2002 | Osadchy et al. |
| 6,370,411 B1 | 4/2002 | Osadchy et al. |
| 6,373,240 B1 | 4/2002 | Govari |
| 6,373,388 B1 | 4/2002 | Dames |
| 6,374,134 B1 | 4/2002 | Bladen et al. |
| 6,374,670 B1 | 4/2002 | Spelman et al. |
| 6,375,606 B1 | 4/2002 | Garibaldi et al. |
| 6,375,639 B1 | 4/2002 | Duplessie et al. |
| 6,377,857 B1 | 4/2002 | Brayton et al. |
| 6,379,302 B1 | 4/2002 | Kessman et al. |
| 6,379,303 B1 | 4/2002 | Seitz et al. |
| 6,379,307 B1 | 4/2002 | Filly et al. |
| 6,381,485 B1 | 4/2002 | Hunter et al. |
| 6,385,472 B1 | 5/2002 | Hall et al. |
| 6,385,476 B1 | 5/2002 | Osadchy et al. |
| 6,398,736 B1 | 6/2002 | Seward |
| 6,398,738 B1 | 6/2002 | Millar |
| 6,401,723 B1 | 6/2002 | Garibaldi et al. |
| 6,406,422 B1 | 6/2002 | Landesberg |
| 6,406,442 B1 | 6/2002 | McFann et al. |
| 6,412,978 B1 | 7/2002 | Watanabe et al. |
| 6,412,980 B1 | 7/2002 | Lounsberry et al. |
| 6,417,839 B1 | 7/2002 | Odell |
| 6,418,332 B1 | 7/2002 | Mastrototaro et al. |
| 6,418,335 B2 | 7/2002 | Avrin |
| 6,423,002 B1 | 7/2002 | Hossack |
| 6,423,050 B1 | 7/2002 | Twardowski |
| 6,427,079 B1 | 7/2002 | Schneider et al. |
| 6,428,551 B1 | 8/2002 | Hall et al. |
| 6,430,315 B1 | 8/2002 | Makram-Ebeid |
| 6,432,069 B1 | 8/2002 | Godo et al. |
| 6,438,411 B1 | 8/2002 | Guttman et al. |
| 6,442,416 B1 | 8/2002 | Schultz |
| 6,445,943 B1 | 9/2002 | Ferre et al. |
| 6,456,874 B1 | 9/2002 | Hafer et al. |
| 6,459,919 B1 | 10/2002 | Lys et al. |
| 6,463,121 B1 | 10/2002 | Milnes |
| 6,466,815 B1 | 10/2002 | Saito et al. |
| 6,471,656 B1 | 10/2002 | Shalman et al. |
| 6,471,658 B1 | 10/2002 | Daniels et al. |
| 6,471,700 B1 | 10/2002 | Burbank et al. |
| 6,473,167 B1 | 10/2002 | Odell |
| 6,474,341 B1 | 11/2002 | Hunter et al. |
| 6,475,152 B1 | 11/2002 | Kelly, Jr. et al. |
| 6,475,223 B1 | 11/2002 | Werp et al. |
| 6,477,402 B1 | 11/2002 | Lynch et al. |
| 6,484,118 B1 | 11/2002 | Govari |
| 6,487,916 B1 | 12/2002 | Gomm et al. |
| 6,491,671 B1 | 12/2002 | Larson, III et al. |
| 6,493,573 B1 | 12/2002 | Martinelli et al. |
| 6,494,832 B1 | 12/2002 | Feldman et al. |
| 6,496,715 B1 | 12/2002 | Lee et al. |
| 6,498,944 B1 | 12/2002 | Ben-Haim et al. |
| 6,500,141 B1 | 12/2002 | Irion et al. |
| 6,505,062 B1 | 1/2003 | Ritter et al. |
| 6,506,159 B2 | 1/2003 | Hascoet et al. |
| 6,507,751 B2 | 1/2003 | Blume et al. |
| 6,508,802 B1 | 1/2003 | Rosengart et al. |
| 6,511,413 B2 | 1/2003 | Landesberg |
| 6,512,958 B1 | 1/2003 | Swoyer et al. |
| 6,514,202 B2 | 2/2003 | Grunwald |
| 6,514,226 B1 | 2/2003 | Levin et al. |
| 6,514,249 B1 | 2/2003 | Maguire et al. |
| 6,515,657 B1 | 2/2003 | Lanelli |
| 6,516,212 B1 | 2/2003 | Bladen et al. |
| 6,516,231 B1 | 2/2003 | Flammang |
| 6,516,807 B1 | 2/2003 | Panescu et al. |
| 6,517,520 B2 | 2/2003 | Chang et al. |
| 6,522,906 B1 | 2/2003 | Salisbury, Jr. et al. |
| 6,522,907 B1 | 2/2003 | Bladen et al. |
| 6,522,909 B1 | 2/2003 | Garibaldi et al. |
| 6,524,303 B1 | 2/2003 | Garibaldi |
| 6,528,954 B1 | 3/2003 | Lys et al. |
| 6,528,991 B2 | 3/2003 | Ashe |
| 6,529,761 B2 | 3/2003 | Creighton, IV et al. |
| 6,529,766 B1 | 3/2003 | Guendel |
| 6,534,982 B1 | 3/2003 | Jakab |
| 6,535,625 B1 | 3/2003 | Chang |
| 6,537,192 B1 | 3/2003 | Elliott et al. |
| 6,537,196 B1 | 3/2003 | Creighton, IV et al. |
| 6,538,634 B1 | 3/2003 | Chui et al. |
| 6,540,699 B1 | 4/2003 | Smith |
| 6,542,766 B2 | 4/2003 | Hall et al. |
| 6,544,251 B1 | 4/2003 | Crawford |
| 6,545,678 B1 | 4/2003 | Ohazama |
| 6,546,270 B1 | 4/2003 | Goldin et al. |
| 6,546,279 B1 | 4/2003 | Bova et al. |
| 6,546,787 B1 | 4/2003 | Schiller et al. |
| 6,552,841 B1 | 4/2003 | Lasser et al. |
| 6,556,858 B1 | 4/2003 | Zeman |
| 6,562,019 B1 | 5/2003 | Sell |
| 6,564,087 B1 | 5/2003 | Pitris et al. |
| 6,569,101 B2 | 5/2003 | Quistgaard et al. |
| 6,569,103 B2 | 5/2003 | Hoeksel et al. |
| 6,569,160 B1 | 5/2003 | Goldin et al. |
| 6,569,862 B1 | 5/2003 | Marban |
| 6,571,004 B1 | 5/2003 | Florent et al. |

(56) References Cited

U.S. PATENT DOCUMENTS

| | | |
|---|---|---|
| 6,574,518 B1 | 6/2003 | Lounsberry et al. |
| 6,575,908 B2 | 6/2003 | Barnes et al. |
| 6,577,080 B2 | 6/2003 | Lys et al. |
| 6,577,896 B2 | 6/2003 | Werner et al. |
| 6,584,343 B1 | 6/2003 | Ransbury et al. |
| 6,589,181 B2 | 7/2003 | Grunwald et al. |
| 6,593,754 B1 | 7/2003 | Steber et al. |
| 6,593,884 B1 | 7/2003 | Gilboa et al. |
| 6,597,943 B2 | 7/2003 | Taha et al. |
| 6,599,249 B1 | 7/2003 | Nordgren et al. |
| 6,607,488 B1 | 8/2003 | Jackson et al. |
| 6,610,058 B2 | 8/2003 | Flores |
| 6,611,141 B1 | 8/2003 | Schulz et al. |
| 6,615,071 B1 | 9/2003 | Casscells, III et al. |
| 6,615,155 B2 | 9/2003 | Gilboa |
| 6,616,610 B2 | 9/2003 | Steininger et al. |
| 6,618,612 B1 | 9/2003 | Acker et al. |
| 6,626,832 B1 | 9/2003 | Paltieli et al. |
| 6,626,834 B2 | 9/2003 | Dunne et al. |
| 6,626,902 B1 | 9/2003 | Kucharczyk et al. |
| 6,630,879 B1 | 10/2003 | Creighton, IV et al. |
| 6,635,027 B1 | 10/2003 | Cragg et al. |
| 6,645,148 B2 | 11/2003 | Nguyen-Dinh et al. |
| 6,648,875 B2 | 11/2003 | Simpson et al. |
| 6,649,914 B1 | 11/2003 | Moorman et al. |
| 6,652,505 B1 | 11/2003 | Tsugita |
| 6,652,506 B2 | 11/2003 | Bowe et al. |
| 6,660,024 B1 | 12/2003 | Flaherty et al. |
| 6,662,034 B2 | 12/2003 | Segner et al. |
| 6,663,661 B2 | 12/2003 | Boneau |
| 6,666,828 B2 | 12/2003 | Greco et al. |
| 6,672,308 B1 | 1/2004 | Gaspari |
| 6,677,752 B1 | 1/2004 | Creighton, IV et al. |
| 6,679,857 B1 | 1/2004 | Bastia et al. |
| 6,684,176 B2 | 1/2004 | Willins et al. |
| 6,685,644 B2 | 2/2004 | Seo et al. |
| 6,687,531 B1 | 2/2004 | Ferre et al. |
| 6,689,119 B1 | 2/2004 | Di Caprio et al. |
| 6,690,963 B2 | 2/2004 | Ben-Haim et al. |
| 6,690,964 B2 | 2/2004 | Bieger et al. |
| 6,690,968 B2 | 2/2004 | Mejia |
| 6,694,167 B1 | 2/2004 | Ferre et al. |
| 6,695,786 B2 | 2/2004 | Wang et al. |
| 6,701,179 B1 | 3/2004 | Martinelli et al. |
| 6,701,918 B2 | 3/2004 | Fariss et al. |
| 6,702,804 B1 | 3/2004 | Ritter et al. |
| 6,704,590 B2 | 3/2004 | Haldeman |
| 6,709,390 B1 | 3/2004 | Marie Pop |
| 6,711,429 B1 | 3/2004 | Gilboa et al. |
| 6,711,431 B2 | 3/2004 | Sarin et al. |
| 6,719,699 B2 | 4/2004 | Smith |
| 6,719,724 B1 | 4/2004 | Walker et al. |
| 6,719,756 B1 | 4/2004 | Muntermann |
| 6,720,745 B2 | 4/2004 | Lys et al. |
| 6,733,458 B1 | 5/2004 | Steins et al. |
| 6,733,473 B1 | 5/2004 | Reifart et al. |
| 6,733,511 B2 | 5/2004 | Hall et al. |
| 6,736,782 B2 | 5/2004 | Pfeiffer et al. |
| 6,738,656 B1 | 5/2004 | Ferre et al. |
| 6,740,103 B2 | 5/2004 | Hall et al. |
| 6,743,177 B2 | 6/2004 | Ito |
| 6,754,596 B2 | 6/2004 | Ashe |
| 6,755,789 B2 | 6/2004 | Stringer et al. |
| 6,755,816 B2 | 6/2004 | Ritter et al. |
| 6,755,822 B2 | 6/2004 | Reu et al. |
| 6,757,557 B1 | 6/2004 | Bladen et al. |
| 6,763,261 B2 | 7/2004 | Casscells, III et al. |
| 6,764,449 B2 | 7/2004 | Lee et al. |
| 6,768,496 B2 | 7/2004 | Bieger et al. |
| 6,772,001 B2 | 8/2004 | Maschke |
| 6,774,624 B2 | 8/2004 | Anderson et al. |
| 6,783,536 B2 | 8/2004 | Vilsmeier et al. |
| 6,784,660 B2 | 8/2004 | Ashe |
| 6,785,571 B2 | 8/2004 | Glossop |
| 6,786,219 B2 | 9/2004 | Garibaldi et al. |
| 6,786,870 B2 | 9/2004 | Miyaki et al. |
| 6,788,967 B2 | 9/2004 | Ben-Haim et al. |
| 6,794,667 B2 | 9/2004 | Noshi |
| 6,799,066 B2 | 9/2004 | Steines et al. |
| 6,815,651 B2 | 11/2004 | Odell |
| 6,816,266 B2 | 11/2004 | Varshneya et al. |
| 6,817,364 B2 | 11/2004 | Garibaldi et al. |
| 6,834,201 B2 | 12/2004 | Gillies et al. |
| 6,844,713 B2 | 1/2005 | Steber et al. |
| 6,845,142 B2 | 1/2005 | Ohishi |
| 6,856,823 B2 | 2/2005 | Ashe |
| 6,860,422 B2 | 3/2005 | Hull et al. |
| 6,862,467 B2 | 3/2005 | Moore et al. |
| 6,869,390 B2 | 3/2005 | Elliott et al. |
| 6,875,179 B2 | 4/2005 | Ferguson et al. |
| 6,879,160 B2 | 4/2005 | Jakab |
| 6,887,206 B2 | 5/2005 | Hoeksel et al. |
| 6,889,091 B2 | 5/2005 | Hine et al. |
| 6,895,268 B1 | 5/2005 | Rahn et al. |
| 6,902,528 B1 | 6/2005 | Garibaldi et al. |
| 6,905,469 B2 | 6/2005 | Hascoet et al. |
| 6,908,433 B1 | 6/2005 | Pruter |
| 6,911,026 B1 | 6/2005 | Hall et al. |
| 6,923,782 B2 | 8/2005 | O'Mahony et al. |
| 6,926,673 B2 | 8/2005 | Roberts et al. |
| 6,926,674 B2 | 8/2005 | Tenerz et al. |
| 6,934,575 B2 | 8/2005 | Ferre et al. |
| 6,936,010 B2 | 8/2005 | Fang et al. |
| 6,939,313 B2 | 9/2005 | Saadat et al. |
| 6,940,379 B2 | 9/2005 | Creighton |
| 6,941,166 B2 | 9/2005 | MacAdam et al. |
| 6,945,938 B2 | 9/2005 | Grunwald |
| 6,947,788 B2 | 9/2005 | Gilboa et al. |
| 6,950,689 B1 | 9/2005 | Willis et al. |
| 6,953,754 B2 | 10/2005 | Machida et al. |
| 6,958,677 B1 | 10/2005 | Carter |
| 6,959,214 B2 | 10/2005 | Pape et al. |
| 6,962,566 B2 | 11/2005 | Quistgaard et al. |
| 6,968,846 B2 | 11/2005 | Viswanathan |
| 6,975,197 B2 | 12/2005 | Creighton, IV |
| 6,976,962 B2 | 12/2005 | Bullis |
| 6,976,987 B2 | 12/2005 | Flores |
| 6,980,843 B2 | 12/2005 | Eng et al. |
| 6,980,852 B2 | 12/2005 | Jersey-Willuhn et al. |
| 6,980,921 B2 | 12/2005 | Anderson et al. |
| 6,986,739 B2 | 1/2006 | Warren et al. |
| 6,986,744 B1 | 1/2006 | Krivitski |
| 6,999,821 B2 | 2/2006 | Jenney et al. |
| 7,001,355 B2 | 2/2006 | Nunomura et al. |
| 7,008,418 B2 | 3/2006 | Hall et al. |
| 7,010,338 B2 | 3/2006 | Ritter et al. |
| 7,015,393 B2 | 3/2006 | Weiner et al. |
| 7,017,584 B2 | 3/2006 | Garibaldi et al. |
| 7,019,610 B2 | 3/2006 | Creighton, IV et al. |
| 7,020,512 B2 | 3/2006 | Ritter et al. |
| D518,574 S | 4/2006 | Chaggares |
| 7,022,075 B2 | 4/2006 | Grunwald et al. |
| 7,022,082 B2 | 4/2006 | Sonek |
| 7,026,927 B2 | 4/2006 | Wright et al. |
| 7,027,634 B2 | 4/2006 | Odell |
| 7,028,387 B1 | 4/2006 | Huynh et al. |
| 7,029,446 B2 | 4/2006 | Wendelken et al. |
| 7,033,603 B2 | 4/2006 | Nelson et al. |
| D520,139 S | 5/2006 | Chaggares |
| D520,140 S | 5/2006 | Chaggares |
| 7,038,398 B1 | 5/2006 | Lys et al. |
| 7,038,657 B2 | 5/2006 | Rosenberg et al. |
| 7,043,293 B1 | 5/2006 | Baura |
| 7,048,733 B2 | 5/2006 | Hartley et al. |
| 7,054,228 B1 | 5/2006 | Hickling |
| 7,065,403 B1 | 6/2006 | Mouchawar et al. |
| 7,066,914 B2 | 6/2006 | Andersen |
| 7,066,924 B1 | 6/2006 | Garibaldi et al. |
| 7,069,072 B2 | 6/2006 | Jansen et al. |
| D525,363 S | 7/2006 | Chaggares |
| 7,070,565 B2 | 7/2006 | Vaezy et al. |
| 7,072,704 B2 | 7/2006 | Bucholz |
| 7,082,325 B2 | 7/2006 | Hashimshony et al. |
| 7,090,639 B2 | 8/2006 | Govari |

(56) References Cited

U.S. PATENT DOCUMENTS

| | | |
|---|---|---|
| 7,096,059 B2 | 8/2006 | Geddes et al. |
| 7,096,148 B2 | 8/2006 | Anderson et al. |
| 7,096,870 B2 | 8/2006 | Lamprich et al. |
| 7,098,907 B2 | 8/2006 | Houston et al. |
| 7,103,205 B2 | 9/2006 | Wang et al. |
| 7,104,980 B1 | 9/2006 | Laherty et al. |
| 7,106,043 B1 | 9/2006 | Da Silva et al. |
| 7,106,431 B2 | 9/2006 | Odell |
| 7,106,479 B2 | 9/2006 | Roy et al. |
| 7,107,105 B2 | 9/2006 | Bjorklund et al. |
| 7,112,197 B2 | 9/2006 | Hartley et al. |
| 7,128,734 B1 | 10/2006 | Wilson et al. |
| 7,132,804 B2 | 11/2006 | Lys et al. |
| 7,137,976 B2 | 11/2006 | Ritter et al. |
| 7,141,019 B2 | 11/2006 | Pearlman |
| 7,141,812 B2 | 11/2006 | Appleby et al. |
| 7,142,905 B2 | 11/2006 | Slayton et al. |
| 7,148,970 B2 | 12/2006 | de Boer |
| 7,153,291 B2 | 12/2006 | Bierman |
| 7,161,453 B2 | 1/2007 | Creighton, IV |
| 7,162,291 B1 | 1/2007 | Nachaliel |
| 7,167,738 B2 | 1/2007 | Schweikard et al. |
| 7,169,107 B2 | 1/2007 | Jersey-Willuhn et al. |
| 7,169,109 B2 | 1/2007 | Jansen et al. |
| 7,174,201 B2 | 2/2007 | Govari et al. |
| 7,175,646 B2 | 2/2007 | Brenneman et al. |
| 7,180,252 B2 | 2/2007 | Lys et al. |
| 7,184,820 B2 | 2/2007 | Jersey-Willuhn et al. |
| 7,189,198 B2 | 3/2007 | Harburn et al. |
| 7,189,205 B2 | 3/2007 | McMorrow et al. |
| 7,189,208 B1 | 3/2007 | Beatty et al. |
| 7,190,819 B2 | 3/2007 | Viswanathan |
| 7,194,295 B2 | 3/2007 | Vilsmeier |
| 7,204,798 B2 | 4/2007 | Zdeblick et al. |
| 7,206,064 B2 | 4/2007 | Rogers et al. |
| 7,207,941 B2 | 4/2007 | Sharf |
| 7,211,082 B2 | 5/2007 | Hall et al. |
| 7,214,191 B2 | 5/2007 | Stringer et al. |
| 7,215,326 B2 | 5/2007 | Rosenberg |
| 7,221,104 B2 | 5/2007 | Lys et al. |
| 7,223,256 B2 | 5/2007 | Bierman |
| 7,229,400 B2 | 6/2007 | Elliott et al. |
| 7,231,243 B2 | 6/2007 | Tearney et al. |
| 7,236,157 B2 | 6/2007 | Schena et al. |
| 7,236,816 B2 | 6/2007 | Kumar et al. |
| 7,236,820 B2 | 6/2007 | Mabary et al. |
| 7,237,313 B2 | 7/2007 | Skujins et al. |
| 7,241,267 B2 | 7/2007 | Furia |
| 7,244,234 B2 | 7/2007 | Ridley et al. |
| 7,248,032 B1 | 7/2007 | Hular et al. |
| 7,248,914 B2 | 7/2007 | Hastings et al. |
| 7,252,633 B2 | 8/2007 | Obata et al. |
| 7,261,691 B1 | 8/2007 | Asomani |
| 7,264,584 B2 | 9/2007 | Ritter et al. |
| 7,270,662 B2 | 9/2007 | Visram et al. |
| 7,276,044 B2 | 10/2007 | Ferry et al. |
| 7,286,034 B2 | 10/2007 | Creighton |
| 7,291,146 B2 | 11/2007 | Steinke et al. |
| 7,297,140 B2 | 11/2007 | Orlu et al. |
| 7,299,085 B2 | 11/2007 | Bergelson et al. |
| 7,300,430 B2 | 11/2007 | Wilson et al. |
| 7,302,288 B1 | 11/2007 | Schellenberg |
| 7,308,296 B2 | 12/2007 | Lys et al. |
| 7,310,150 B2 | 12/2007 | Guillermo et al. |
| 7,311,702 B2 | 12/2007 | Tallarida et al. |
| 7,321,228 B2 | 1/2008 | Govari |
| 7,326,241 B2 | 2/2008 | Jang |
| 7,327,872 B2 | 2/2008 | Vaillant et al. |
| 7,331,462 B2 | 2/2008 | Steppe |
| 7,342,058 B2 | 3/2008 | Peppmoller et al. |
| 7,349,732 B1 | 3/2008 | Kil et al. |
| 7,355,716 B2 | 4/2008 | de Boer et al. |
| 7,360,427 B2 | 4/2008 | Drinkwater et al. |
| 7,366,376 B2 | 4/2008 | Shishkov et al. |
| 7,366,562 B2 | 4/2008 | Dukesherer et al. |
| 7,366,563 B2 | 4/2008 | Kleen et al. |
| 7,373,271 B1 | 5/2008 | Schneider |
| 7,381,204 B2 | 6/2008 | Wilson et al. |
| 7,382,949 B2 | 6/2008 | Bouma et al. |
| 7,384,407 B2 | 6/2008 | Rodriguez et al. |
| 7,418,169 B2 | 8/2008 | Tearney et al. |
| 7,447,408 B2 | 11/2008 | Bouma et al. |
| 7,452,331 B1 | 11/2008 | Pruter |
| 7,452,358 B2 | 11/2008 | Stern et al. |
| 7,454,244 B2 | 11/2008 | Kassab et al. |
| D585,556 S | 1/2009 | Kosaku |
| 7,479,141 B2 | 1/2009 | Kleen et al. |
| 7,519,424 B2 | 4/2009 | Dennis et al. |
| 7,529,584 B2 | 5/2009 | Laske et al. |
| 7,534,223 B2 | 5/2009 | Boutilette et al. |
| 7,538,859 B2 | 5/2009 | Tearney et al. |
| 7,543,239 B2 | 6/2009 | Viswanathan et al. |
| 7,546,158 B2 | 6/2009 | Allison et al. |
| 7,547,282 B2 | 6/2009 | Lo et al. |
| 7,551,293 B2 | 6/2009 | Yelin et al. |
| D603,050 S | 10/2009 | Chen |
| 7,599,730 B2 | 10/2009 | Hunter et al. |
| 7,606,615 B2 | 10/2009 | Makower et al. |
| 7,613,478 B2 | 11/2009 | Jabri et al. |
| 7,616,992 B2 | 11/2009 | Dennis et al. |
| 7,627,376 B2 | 12/2009 | Dennis et al. |
| 7,635,336 B1 | 12/2009 | Pruter |
| 7,637,163 B2 | 12/2009 | Fetzer et al. |
| 7,640,053 B2 | 12/2009 | Verin |
| 7,651,469 B2 | 1/2010 | Osborne et al. |
| 7,652,080 B2 | 1/2010 | Peppmoller et al. |
| 7,660,623 B2 | 2/2010 | Hunter et al. |
| 7,665,893 B2 | 2/2010 | Buchalter |
| 7,666,191 B2 | 2/2010 | Orban, III et al. |
| 7,668,583 B2 | 2/2010 | Fegert et al. |
| 7,697,972 B2 | 4/2010 | Verard et al. |
| 7,699,782 B2 | 4/2010 | Angelsen et al. |
| 7,699,829 B2 | 4/2010 | Harris et al. |
| 7,715,925 B2 | 5/2010 | Hafer et al. |
| 7,727,192 B2 | 6/2010 | Tokumoto et al. |
| 7,729,743 B2 | 6/2010 | Sabczynski et al. |
| 7,751,865 B2 | 7/2010 | Jascob et al. |
| 7,766,839 B2 | 8/2010 | Rogers et al. |
| 7,771,437 B2 | 8/2010 | Hogg et al. |
| 7,774,051 B2 | 8/2010 | Voth |
| 7,774,055 B1 | 8/2010 | Min |
| 7,794,407 B2 | 9/2010 | Rothenberg |
| 7,798,970 B2 | 9/2010 | Lo et al. |
| 7,819,810 B2 | 10/2010 | Stringer et al. |
| 7,822,464 B2 | 10/2010 | Maschke et al. |
| 7,828,528 B2 | 11/2010 | Estes et al. |
| 7,831,294 B2 | 11/2010 | Viswanathan |
| 7,833,168 B2 | 11/2010 | Taylor et al. |
| 7,833,214 B2 | 11/2010 | Wilson et al. |
| 7,840,252 B2 | 11/2010 | Strommer et al. |
| D629,526 S | 12/2010 | Ladwig et al. |
| D629,527 S | 12/2010 | Crunkilton |
| 7,846,157 B2 | 12/2010 | Kozel |
| 7,850,613 B2 | 12/2010 | Stribling |
| D630,756 S | 1/2011 | Kitayama |
| D630,757 S | 1/2011 | Kitayama |
| 7,869,854 B2 | 1/2011 | Shachar et al. |
| 7,869,865 B2 | 1/2011 | Govari et al. |
| 7,873,402 B2 | 1/2011 | Shachar |
| 7,909,815 B2 | 3/2011 | Whitmore, III et al. |
| 7,931,596 B2 | 4/2011 | Rachlin et al. |
| 7,947,040 B2 | 5/2011 | Davies et al. |
| 7,969,142 B2 | 6/2011 | Krueger et al. |
| 7,976,469 B2 | 7/2011 | Bonde et al. |
| 7,976,518 B2 | 7/2011 | Shaughnessy et al. |
| 7,981,038 B2 | 7/2011 | Kanade et al. |
| 7,988,633 B2 | 8/2011 | Hossack et al. |
| 8,016,814 B2 | 9/2011 | Blakstvedt et al. |
| 8,046,052 B2 | 10/2011 | Verard et al. |
| 8,055,327 B2 | 11/2011 | Strommer et al. |
| 8,057,394 B2 | 11/2011 | Dala-Krishna |
| 8,060,185 B2 | 11/2011 | Hunter et al. |
| 8,078,274 B2 | 12/2011 | Kassab |
| 8,078,279 B2 | 12/2011 | Dennis et al. |

(56) References Cited

U.S. PATENT DOCUMENTS

| | | |
|---|---|---|
| 8,082,025 B2 | 12/2011 | Amitai et al. |
| 8,082,032 B2 | 12/2011 | Kassab et al. |
| 8,088,072 B2 | 1/2012 | Munrow et al. |
| 8,090,430 B2 | 1/2012 | Makower et al. |
| 8,099,161 B2 | 1/2012 | Kassab |
| 8,105,338 B2 | 1/2012 | Anderson et al. |
| 8,114,143 B2 | 2/2012 | Kassab et al. |
| 8,118,743 B2 | 2/2012 | Park et al. |
| 8,123,691 B2 | 2/2012 | Mine et al. |
| 8,133,698 B2 | 3/2012 | Silver |
| 8,142,417 B2 | 3/2012 | Pajunk et al. |
| 8,150,522 B2 | 4/2012 | Echauz et al. |
| 8,152,724 B2 | 4/2012 | Ridley et al. |
| 8,155,732 B2 | 4/2012 | Scholz et al. |
| 8,204,582 B2 | 6/2012 | Zantos et al. |
| 8,214,018 B2 | 7/2012 | Markowitz et al. |
| 8,221,402 B2 | 7/2012 | Francischelli et al. |
| 8,240,211 B2 | 8/2012 | Zeitner et al. |
| 8,241,274 B2 | 8/2012 | Keogh et al. |
| 8,244,339 B2 | 8/2012 | Shen et al. |
| 8,255,035 B2 | 8/2012 | Cao et al. |
| 8,260,395 B2 | 9/2012 | Markowitz et al. |
| 8,262,577 B2 | 9/2012 | Munrow et al. |
| 8,298,149 B2 | 10/2012 | Hastings et al. |
| 8,303,502 B2 | 11/2012 | Washburn et al. |
| 8,303,505 B2 | 11/2012 | Webler et al. |
| 8,326,419 B2 | 12/2012 | Rosenberg et al. |
| 8,326,651 B2 | 12/2012 | McLaren et al. |
| 8,340,751 B2 | 12/2012 | Markowitz et al. |
| 8,346,343 B2 | 1/2013 | Kimura et al. |
| 8,369,922 B2 | 2/2013 | Paul et al. |
| 8,388,541 B2 | 3/2013 | Messerly et al. |
| 8,388,546 B2 | 3/2013 | Rothenberg |
| 8,391,956 B2 | 3/2013 | Zellers et al. |
| 8,400,164 B2 | 3/2013 | Osadchy et al. |
| 8,401,616 B2 | 3/2013 | Verard et al. |
| 8,409,103 B2 | 4/2013 | Grunwald et al. |
| 8,412,313 B2 | 4/2013 | Amitai et al. |
| 8,425,425 B2 | 4/2013 | Hagy et al. |
| 8,437,833 B2 | 5/2013 | Silverstein |
| 8,439,873 B1 | 5/2013 | Donovan |
| 8,442,621 B2 | 5/2013 | Gorek et al. |
| 8,447,384 B2 | 5/2013 | Xu et al. |
| D684,265 S | 6/2013 | Cadera |
| 8,456,182 B2 | 6/2013 | Bar-Tal et al. |
| 8,478,382 B2 | 7/2013 | Burnside et al. |
| 8,478,388 B2 | 7/2013 | Nguyen et al. |
| 8,485,980 B2 | 7/2013 | Sinderby et al. |
| 8,494,608 B2 | 7/2013 | Markowitz et al. |
| 8,496,592 B2 | 7/2013 | Ridley et al. |
| 8,504,139 B2 | 8/2013 | Jacobsen et al. |
| 8,512,256 B2 | 8/2013 | Rothenberg |
| 8,521,122 B2 | 8/2013 | Scott et al. |
| 8,527,036 B2 | 9/2013 | Jalde et al. |
| 8,538,509 B2 | 9/2013 | Harlev et al. |
| 8,597,193 B2 | 12/2013 | Grunwald et al. |
| 8,620,412 B2 | 12/2013 | Griffiths et al. |
| 8,644,907 B2 | 2/2014 | Hartmann et al. |
| 8,663,116 B2 | 3/2014 | Hamilton, Jr. |
| 8,690,776 B2 | 4/2014 | Razzaque et al. |
| 8,700,137 B2 | 4/2014 | Albert |
| 8,715,195 B2 | 5/2014 | Ziv |
| 8,721,655 B2 | 5/2014 | Viswanathan et al. |
| 8,734,440 B2 | 5/2014 | Wu |
| 8,761,862 B2 | 6/2014 | Ridley et al. |
| 8,774,907 B2 | 7/2014 | Rothenberg |
| 8,781,555 B2 | 7/2014 | Burnside et al. |
| 8,784,336 B2 | 7/2014 | Bown et al. |
| 8,801,693 B2 | 8/2014 | He et al. |
| 8,849,382 B2 | 9/2014 | Cox et al. |
| 8,858,455 B2 | 10/2014 | Rothenberg |
| 8,934,961 B2 | 1/2015 | Lakin et al. |
| 8,942,784 B2 | 1/2015 | Neidert et al. |
| 8,965,490 B2 | 2/2015 | Lee et al. |
| 8,971,994 B2 | 3/2015 | Burnside et al. |
| 9,014,794 B2 | 4/2015 | Brodnick et al. |
| 9,033,889 B2 | 5/2015 | Hamilton, Jr. |
| 9,125,578 B2 | 9/2015 | Grunwald |
| 9,179,860 B2 | 11/2015 | Markowitz et al. |
| 9,198,600 B2 | 12/2015 | Grunwald et al. |
| 9,339,206 B2 | 5/2016 | Grunwald |
| 9,415,188 B2 | 8/2016 | He et al. |
| 9,456,766 B2 | 10/2016 | Cox et al. |
| 9,492,097 B2 | 11/2016 | Wilkes et al. |
| 9,521,961 B2 | 12/2016 | Silverstein et al. |
| 9,526,440 B2 | 12/2016 | Burnside et al. |
| 9,532,724 B2 | 1/2017 | Grunwald |
| 9,554,716 B2 | 1/2017 | Burnside et al. |
| 9,636,031 B2 | 5/2017 | Cox |
| 9,642,986 B2 | 5/2017 | Beasley |
| 9,649,048 B2 | 5/2017 | Cox et al. |
| 9,681,823 B2 | 6/2017 | Messerly et al. |
| 9,833,169 B2 | 12/2017 | Rothenberg |
| 9,839,372 B2 | 12/2017 | Bukhman et al. |
| 9,901,714 B2 | 2/2018 | Lemon et al. |
| 9,907,513 B2 | 3/2018 | Silverstein |
| 9,999,371 B2 | 6/2018 | Messerly et al. |
| 10,004,875 B2 | 6/2018 | Bown et al. |
| 10,046,139 B2 | 8/2018 | Powers et al. |
| 10,105,121 B2 | 10/2018 | Burnside et al. |
| 10,165,962 B2 | 1/2019 | Messerly et al. |
| 10,231,643 B2 | 3/2019 | Grunwald |
| 10,231,753 B2 | 3/2019 | Burnside et al. |
| 10,238,418 B2 | 3/2019 | Cox et al. |
| 10,271,762 B2 | 4/2019 | Grunwald |
| 10,349,857 B2 | 7/2019 | Grunwald |
| 10,349,890 B2 | 7/2019 | Misener et al. |
| 10,449,330 B2 | 10/2019 | Newman et al. |
| 10,524,691 B2 | 1/2020 | Newman et al. |
| 10,602,958 B2 | 3/2020 | Silverstein et al. |
| 2001/0014774 A1 | 8/2001 | Grunwald |
| 2001/0027332 A1 | 10/2001 | Grunwald et al. |
| 2002/0010392 A1 | 1/2002 | Desai |
| 2002/0016549 A1 | 2/2002 | Mejia |
| 2002/0019447 A1 | 2/2002 | Renn et al. |
| 2002/0022777 A1 | 2/2002 | Crieghton et al. |
| 2002/0032391 A1 | 3/2002 | McFann et al. |
| 2002/0045810 A1 | 4/2002 | Ben-Haim |
| 2002/0049488 A1 | 4/2002 | Boneau |
| 2002/0055680 A1 | 5/2002 | Miele et al. |
| 2002/0082559 A1 | 6/2002 | Chang et al. |
| 2002/0113555 A1 | 8/2002 | Lys et al. |
| 2002/0123679 A1 | 9/2002 | Dominguez |
| 2002/0128554 A1 | 9/2002 | Seward |
| 2002/0129952 A1 | 9/2002 | Matsudate et al. |
| 2002/0133079 A1 | 9/2002 | Sandhu |
| 2002/0156363 A1 | 10/2002 | Hunter et al. |
| 2002/0156376 A1 | 10/2002 | Wang et al. |
| 2002/0165448 A1 | 11/2002 | Ben-Haim et al. |
| 2002/0165534 A1 | 11/2002 | Hayzelden et al. |
| 2002/0165537 A1 | 11/2002 | Kelley et al. |
| 2002/0173721 A1 | 11/2002 | Grunwald et al. |
| 2002/0193756 A1 | 12/2002 | Prindle |
| 2002/0198568 A1 | 12/2002 | Hafer et al. |
| 2003/0009132 A1 | 1/2003 | Schwartz et al. |
| 2003/0011359 A1 | 1/2003 | Ashe |
| 2003/0013959 A1 | 1/2003 | Grunwald et al. |
| 2003/0013966 A1 | 1/2003 | Barnes et al. |
| 2003/0013986 A1 | 1/2003 | Saadat |
| 2003/0018251 A1 | 1/2003 | Solomon |
| 2003/0036696 A1 | 2/2003 | Willis et al. |
| 2003/0040671 A1 | 2/2003 | Somogyi et al. |
| 2003/0040743 A1 | 2/2003 | Cosman et al. |
| 2003/0072805 A1 | 4/2003 | Miyazawa et al. |
| 2003/0073901 A1 | 4/2003 | Simon et al. |
| 2003/0076281 A1 | 4/2003 | Morgan et al. |
| 2003/0083698 A1 | 5/2003 | Whitehurst et al. |
| 2003/0088195 A1 | 5/2003 | Vardi et al. |
| 2003/0092993 A1 | 5/2003 | Grunwald |
| 2003/0100849 A1 | 5/2003 | Jang |
| 2003/0114742 A1 | 6/2003 | Lewkowicz et al. |
| 2003/0114777 A1 | 6/2003 | Griffin et al. |
| 2003/0120150 A1 | 6/2003 | Govari |
| 2003/0120154 A1 | 6/2003 | Sauer et al. |

(56) References Cited

U.S. PATENT DOCUMENTS

| | | |
|---|---|---|
| 2003/0139661 A1 | 7/2003 | Kimchy et al. |
| 2003/0149328 A1 | 8/2003 | Elliott et al. |
| 2003/0149368 A1 | 8/2003 | Hennemann et al. |
| 2003/0152290 A1 | 8/2003 | Odell |
| 2003/0160721 A1 | 8/2003 | Gilboa et al. |
| 2003/0162414 A1 | 8/2003 | Schulz et al. |
| 2003/0163037 A1 | 8/2003 | Bladen et al. |
| 2003/0163142 A1 | 8/2003 | Paltieli et al. |
| 2003/0171691 A1 | 9/2003 | Casscells et al. |
| 2003/0173953 A1 | 9/2003 | Ashe |
| 2003/0181892 A1 | 9/2003 | Pajunk et al. |
| 2003/0184544 A1 | 10/2003 | Prudent |
| 2003/0191392 A1 | 10/2003 | Haldeman |
| 2003/0191460 A1 | 10/2003 | Hobbs et al. |
| 2003/0195420 A1 | 10/2003 | Mendlein et al. |
| 2003/0199746 A1 | 10/2003 | Fuimaono et al. |
| 2003/0208142 A1 | 11/2003 | Boudewijn et al. |
| 2003/0216639 A1 | 11/2003 | Gilboa et al. |
| 2003/0216723 A1 | 11/2003 | Shinmura et al. |
| 2003/0220557 A1 | 11/2003 | Cleary et al. |
| 2003/0220578 A1 | 11/2003 | Ho et al. |
| 2003/0229298 A1 | 12/2003 | Iwami et al. |
| 2003/0233042 A1 | 12/2003 | Ashe |
| 2003/0236445 A1 | 12/2003 | Couvillon |
| 2004/0010189 A1 | 1/2004 | van Sloun et al. |
| 2004/0015070 A1 | 1/2004 | Liang et al. |
| 2004/0024301 A1 | 2/2004 | Rockett et al. |
| 2004/0030319 A1 | 2/2004 | Korkor et al. |
| 2004/0054278 A1 | 3/2004 | Kimchy et al. |
| 2004/0059217 A1 | 3/2004 | Kessman et al. |
| 2004/0059237 A1 | 3/2004 | Narayan et al. |
| 2004/0082916 A1 | 4/2004 | Jenkins |
| 2004/0087877 A1 | 5/2004 | Besz et al. |
| 2004/0088136 A1 | 5/2004 | Ashe |
| 2004/0092962 A1 | 5/2004 | Thornton et al. |
| 2004/0097803 A1 | 5/2004 | Panescu |
| 2004/0097804 A1 | 5/2004 | Sobe |
| 2004/0097805 A1 | 5/2004 | Verard et al. |
| 2004/0097806 A1 | 5/2004 | Hunter et al. |
| 2004/0116809 A1 | 6/2004 | Chow et al. |
| 2004/0127805 A1 | 7/2004 | MacAdam et al. |
| 2004/0131998 A1 | 7/2004 | Marom et al. |
| 2004/0133111 A1 | 7/2004 | Szczech et al. |
| 2004/0133130 A1 | 7/2004 | Ferry et al. |
| 2004/0135069 A1 | 7/2004 | Odell |
| 2004/0138557 A1 | 7/2004 | Le et al. |
| 2004/0138564 A1 | 7/2004 | Hwang et al. |
| 2004/0138569 A1 | 7/2004 | Grunwald et al. |
| 2004/0138570 A1 | 7/2004 | Nita et al. |
| 2004/0143183 A1 | 7/2004 | Toyoda et al. |
| 2004/0147837 A1 | 7/2004 | Macaulay et al. |
| 2004/0150963 A1 | 8/2004 | Holmberg et al. |
| 2004/0152972 A1 | 8/2004 | Hunter |
| 2004/0155609 A1 | 8/2004 | Lys et al. |
| 2004/0158140 A1 | 8/2004 | Fuimaono et al. |
| 2004/0162487 A1 | 8/2004 | Klingenbeck-Regn et al. |
| 2004/0171924 A1 | 9/2004 | Mire et al. |
| 2004/0176688 A1 | 9/2004 | Haldeman |
| 2004/0186461 A1 | 9/2004 | DiMatteo |
| 2004/0199069 A1 | 10/2004 | Connelly et al. |
| 2004/0210289 A1 | 10/2004 | Wang et al. |
| 2004/0225233 A1 | 11/2004 | Frankowski et al. |
| 2004/0230131 A1 | 11/2004 | Kassab et al. |
| 2004/0230271 A1 | 11/2004 | Wang et al. |
| 2004/0234453 A1 | 11/2004 | Smith |
| 2004/0243018 A1 | 12/2004 | Organ et al. |
| 2004/0243116 A1 | 12/2004 | Joye et al. |
| 2004/0243118 A1 | 12/2004 | Ayers et al. |
| 2004/0253365 A1 | 12/2004 | Warren et al. |
| 2004/0254470 A1 | 12/2004 | Drinkwater et al. |
| 2004/0254495 A1 | 12/2004 | Mabary et al. |
| 2004/0260174 A1 | 12/2004 | Keene |
| 2004/0267086 A1 | 12/2004 | Anstadt et al. |
| 2005/0004450 A1 | 1/2005 | Ben-Haim et al. |
| 2005/0021019 A1 | 1/2005 | Hashimshony et al. |
| 2005/0033150 A1 | 2/2005 | Takahashi et al. |
| 2005/0038355 A1 | 2/2005 | Gellman et al. |
| 2005/0043640 A1 | 2/2005 | Chang |
| 2005/0049486 A1 | 3/2005 | Urquhart et al. |
| 2005/0049510 A1 | 3/2005 | Haldeman et al. |
| 2005/0063194 A1 | 3/2005 | Lys et al. |
| 2005/0070788 A1 | 3/2005 | Wilson et al. |
| 2005/0075561 A1 | 4/2005 | Golden |
| 2005/0085715 A1 | 4/2005 | Dukesherer et al. |
| 2005/0085716 A1 | 4/2005 | Hamm et al. |
| 2005/0085718 A1 | 4/2005 | Shahidi |
| 2005/0085720 A1 | 4/2005 | Jascob et al. |
| 2005/0090746 A1 | 4/2005 | Ohtake |
| 2005/0101868 A1 | 5/2005 | Ridley et al. |
| 2005/0101869 A1 | 5/2005 | Burba et al. |
| 2005/0105081 A1 | 5/2005 | Odell |
| 2005/0105101 A1 | 5/2005 | Duling et al. |
| 2005/0112135 A1 | 5/2005 | Cormier et al. |
| 2005/0113669 A1 | 5/2005 | Helfer et al. |
| 2005/0113676 A1 | 5/2005 | Weiner et al. |
| 2005/0113700 A1 | 5/2005 | Yanagihara et al. |
| 2005/0113873 A1 | 5/2005 | Weiner et al. |
| 2005/0113874 A1 | 5/2005 | Connelly et al. |
| 2005/0113876 A1 | 5/2005 | Weiner et al. |
| 2005/0143689 A1 | 6/2005 | Ramsey |
| 2005/0148836 A1 | 7/2005 | Kleen et al. |
| 2005/0148902 A1 | 7/2005 | Minar et al. |
| 2005/0149002 A1 | 7/2005 | Wang et al. |
| 2005/0151489 A1 | 7/2005 | Lys et al. |
| 2005/0154308 A1 | 7/2005 | Quistgaard et al. |
| 2005/0159644 A1 | 7/2005 | Takano |
| 2005/0159790 A1 | 7/2005 | Shalev |
| 2005/0165301 A1 | 7/2005 | Smith et al. |
| 2005/0165313 A1 | 7/2005 | Byron et al. |
| 2005/0175665 A1 | 8/2005 | Hunter et al. |
| 2005/0175703 A1 | 8/2005 | Hunter et al. |
| 2005/0178395 A1 | 8/2005 | Hunter et al. |
| 2005/0178396 A1 | 8/2005 | Hunter et al. |
| 2005/0182295 A1 | 8/2005 | Soper et al. |
| 2005/0182454 A1 | 8/2005 | Gharib et al. |
| 2005/0197674 A1 | 9/2005 | McCabe et al. |
| 2005/0203368 A1 | 9/2005 | Verin |
| 2005/0203396 A1 | 9/2005 | Angelsen et al. |
| 2005/0205081 A1 | 9/2005 | Barker et al. |
| 2005/0215901 A1 | 9/2005 | Anderson et al. |
| 2005/0215945 A1 | 9/2005 | Harris et al. |
| 2005/0222532 A1 | 10/2005 | Bertolero et al. |
| 2005/0240102 A1 | 10/2005 | Rachlin et al. |
| 2005/0245811 A1 | 11/2005 | Scheffler |
| 2005/0256398 A1 | 11/2005 | Hastings et al. |
| 2005/0256451 A1 | 11/2005 | Adams et al. |
| 2005/0256521 A1 | 11/2005 | Kozel |
| 2005/0256541 A1 | 11/2005 | Stypulkowski |
| 2005/0283210 A1 | 12/2005 | Blischak et al. |
| 2005/0283216 A1 | 12/2005 | Pyles |
| 2005/0288586 A1 | 12/2005 | Ferek-Petric |
| 2005/0288695 A1 | 12/2005 | Jenson et al. |
| 2006/0009759 A1 | 1/2006 | Chrisitian et al. |
| 2006/0015003 A1 | 1/2006 | Moaddes et al. |
| 2006/0025677 A1 | 2/2006 | Verard et al. |
| 2006/0025697 A1 | 2/2006 | Kurzweil et al. |
| 2006/0058633 A1 | 3/2006 | Hoshino et al. |
| 2006/0065275 A1 | 3/2006 | Lamprich et al. |
| 2006/0068074 A1 | 3/2006 | Stefandl |
| 2006/0084867 A1 | 4/2006 | Tremblay et al. |
| 2006/0106306 A1 | 5/2006 | Essner et al. |
| 2006/0116571 A1 | 6/2006 | Maschke et al. |
| 2006/0116576 A1 | 6/2006 | McGee et al. |
| 2006/0116578 A1 | 6/2006 | Grunwald et al. |
| 2006/0122514 A1 | 6/2006 | Byrd et al. |
| 2006/0142656 A1 | 6/2006 | Malackowski et al. |
| 2006/0149134 A1 | 7/2006 | Soper et al. |
| 2006/0173251 A1 | 8/2006 | Govari et al. |
| 2006/0173329 A1 | 8/2006 | Irioka et al. |
| 2006/0173407 A1 | 8/2006 | Shaughnessy et al. |
| 2006/0176242 A1 | 8/2006 | Jaramaz et al. |
| 2006/0184074 A1 | 8/2006 | Vaezy et al. |
| 2006/0206037 A1 | 9/2006 | Braxton |
| 2006/0211944 A1 | 9/2006 | Mauge et al. |

(56) References Cited

U.S. PATENT DOCUMENTS

| | | |
|---|---|---|
| 2006/0217655 A1 | 9/2006 | Vitullo et al. |
| 2006/0217755 A1 | 9/2006 | Eversull et al. |
| 2006/0224188 A1 | 10/2006 | Libbus et al. |
| 2006/0241432 A1 | 10/2006 | Herline et al. |
| 2006/0247746 A1 | 11/2006 | Danek et al. |
| 2006/0253029 A1 | 11/2006 | Altmann et al. |
| 2006/0253115 A1 | 11/2006 | Avitall et al. |
| 2006/0258895 A1 | 11/2006 | Maschke |
| 2006/0276867 A1 | 12/2006 | Viswanathan |
| 2006/0287595 A1 | 12/2006 | Maschke |
| 2007/0010753 A1 | 1/2007 | MacAdam |
| 2007/0016007 A1 | 1/2007 | Govari et al. |
| 2007/0016013 A1 | 1/2007 | Camus |
| 2007/0016068 A1 | 1/2007 | Grunwald et al. |
| 2007/0016069 A1 | 1/2007 | Grunwald et al. |
| 2007/0016070 A1 | 1/2007 | Grunwald et al. |
| 2007/0016072 A1 | 1/2007 | Grunwald et al. |
| 2007/0032746 A1 | 2/2007 | Sell |
| 2007/0038113 A1 | 2/2007 | Oonuki et al. |
| 2007/0049817 A1 | 3/2007 | Preiss et al. |
| 2007/0049822 A1 | 3/2007 | Bunce et al. |
| 2007/0049846 A1 | 3/2007 | Bown et al. |
| 2007/0055141 A1 | 3/2007 | Kruger et al. |
| 2007/0055142 A1 | 3/2007 | Webler |
| 2007/0055294 A1 | 3/2007 | Giap |
| 2007/0060992 A1 | 3/2007 | Pappone |
| 2007/0062544 A1 | 3/2007 | Rauk Bergstrom et al. |
| 2007/0066888 A1 | 3/2007 | Maschke |
| 2007/0073155 A1 | 3/2007 | Park et al. |
| 2007/0078343 A1 | 4/2007 | Kawashima et al. |
| 2007/0087038 A1 | 4/2007 | Richardson et al. |
| 2007/0093710 A1 | 4/2007 | Maschke |
| 2007/0100236 A1 | 5/2007 | McMorrow et al. |
| 2007/0100285 A1 | 5/2007 | Griffin et al. |
| 2007/0112282 A1 | 5/2007 | Skujins et al. |
| 2007/0123805 A1 | 5/2007 | Shireman et al. |
| 2007/0129770 A1 | 6/2007 | Younis |
| 2007/0135803 A1 | 6/2007 | Belson |
| 2007/0135886 A1 | 6/2007 | Maschke |
| 2007/0156205 A1 | 7/2007 | Larson et al. |
| 2007/0161853 A1 | 7/2007 | Yagi et al. |
| 2007/0161914 A1 | 7/2007 | Zdeblick et al. |
| 2007/0161915 A1 | 7/2007 | Desai |
| 2007/0167738 A1 | 7/2007 | Timinger et al. |
| 2007/0167762 A1 | 7/2007 | Kim et al. |
| 2007/0167769 A1 | 7/2007 | Ikuma et al. |
| 2007/0167801 A1 | 7/2007 | Webler et al. |
| 2007/0167997 A1 | 7/2007 | Forsberg et al. |
| 2007/0197891 A1 | 8/2007 | Shachar et al. |
| 2007/0197905 A1 | 8/2007 | Timinger et al. |
| 2007/0197926 A1 | 8/2007 | Danehorn et al. |
| 2007/0208255 A1 | 9/2007 | Ridley et al. |
| 2007/0219453 A1 | 9/2007 | Kremliovsky et al. |
| 2007/0225589 A1 | 9/2007 | Viswanathan |
| 2007/0225610 A1 | 9/2007 | Mickley et al. |
| 2007/0232882 A1 | 10/2007 | Glossop et al. |
| 2007/0232896 A1 | 10/2007 | Gilboa et al. |
| 2007/0238984 A1 | 10/2007 | Maschke et al. |
| 2007/0239004 A1 | 10/2007 | Kakee et al. |
| 2007/0239018 A1 | 10/2007 | Fetzer et al. |
| 2007/0244413 A1 | 10/2007 | Biggins |
| 2007/0247454 A1 | 10/2007 | Rahn et al. |
| 2007/0249911 A1 | 10/2007 | Simon |
| 2007/0250150 A1 | 10/2007 | Pal et al. |
| 2007/0255270 A1 | 11/2007 | Carney |
| 2007/0265526 A1 | 11/2007 | Govari et al. |
| 2007/0280974 A1 | 12/2007 | Son et al. |
| 2007/0282196 A1 | 12/2007 | Birk et al. |
| 2007/0282197 A1 | 12/2007 | Bill et al. |
| 2007/0299352 A1 | 12/2007 | Harlev et al. |
| 2007/0299353 A1 | 12/2007 | Harlev et al. |
| 2008/0004652 A1 | 1/2008 | Abboud et al. |
| 2008/0008745 A1 | 1/2008 | Stinchcomb et al. |
| 2008/0009720 A1 | 1/2008 | Schefelker et al. |
| 2008/0015442 A1 | 1/2008 | Watson et al. |
| 2008/0021283 A1 | 1/2008 | Kuranda |
| 2008/0027320 A1 | 1/2008 | Bolorforosh et al. |
| 2008/0033282 A1 | 2/2008 | Bar-Tal et al. |
| 2008/0033283 A1 | 2/2008 | Dellaca et al. |
| 2008/0033316 A1 | 2/2008 | Kassab et al. |
| 2008/0033350 A1 | 2/2008 | Wilson et al. |
| 2008/0045908 A1 | 2/2008 | Gould et al. |
| 2008/0051626 A1 | 2/2008 | Sato et al. |
| 2008/0077158 A1 | 3/2008 | Haider et al. |
| 2008/0081958 A1 | 4/2008 | Denison et al. |
| 2008/0082136 A1 | 4/2008 | Gaudiani |
| 2008/0097232 A1 | 4/2008 | Rothenberg |
| 2008/0108949 A1 | 5/2008 | Beasley et al. |
| 2008/0114095 A1 | 5/2008 | Peppmoller et al. |
| 2008/0119697 A1 | 5/2008 | Vadodaria et al. |
| 2008/0125772 A1 | 5/2008 | Stone et al. |
| 2008/0137927 A1 | 6/2008 | Altmann et al. |
| 2008/0139944 A1 | 6/2008 | Weymer et al. |
| 2008/0146939 A1 | 6/2008 | McMorrow et al. |
| 2008/0146940 A1 | 6/2008 | Jenkins et al. |
| 2008/0146941 A1 | 6/2008 | Dala-Krishna |
| 2008/0146942 A1 | 6/2008 | Dala-Krishna |
| 2008/0154100 A1 | 6/2008 | Thalmeier et al. |
| 2008/0166453 A1 | 7/2008 | Steele et al. |
| 2008/0171934 A1 | 7/2008 | Greenan et al. |
| 2008/0183075 A1 | 7/2008 | Govari et al. |
| 2008/0188830 A1 | 8/2008 | Rosenblatt et al. |
| 2008/0190438 A1 | 8/2008 | Harlev et al. |
| 2008/0195169 A1 | 8/2008 | Pinter et al. |
| 2008/0200754 A1 | 8/2008 | Buchalter |
| 2008/0200801 A1 | 8/2008 | Wildes et al. |
| 2008/0200913 A1 | 8/2008 | Viswanathan |
| 2008/0228082 A1 | 9/2008 | Scheirer et al. |
| 2008/0236598 A1 | 10/2008 | Gobel |
| 2008/0255404 A1 | 10/2008 | Nogawa et al. |
| 2008/0255475 A1 | 10/2008 | Kondrosky et al. |
| 2008/0269581 A1 | 10/2008 | Wood et al. |
| 2008/0269611 A1 | 10/2008 | Pedrizzetti et al. |
| 2008/0275465 A1 | 11/2008 | Paul et al. |
| 2008/0275765 A1 | 11/2008 | Kuchar |
| 2008/0288038 A1 | 11/2008 | Paul et al. |
| 2008/0294041 A1 | 11/2008 | Kassab |
| 2008/0319350 A1 | 12/2008 | Wallace et al. |
| 2009/0005674 A1 | 1/2009 | Saadat et al. |
| 2009/0005675 A1 | 1/2009 | Grunwald et al. |
| 2009/0005679 A1 | 1/2009 | Dala-Krishna |
| 2009/0018497 A1 | 1/2009 | Birchard et al. |
| 2009/0024018 A1 | 1/2009 | Boyden et al. |
| 2009/0030380 A1 | 1/2009 | Binmoeller |
| 2009/0043205 A1 | 2/2009 | Pelissier et al. |
| 2009/0062646 A1 | 3/2009 | Creighton, IV et al. |
| 2009/0062684 A1 | 3/2009 | Gregersen et al. |
| 2009/0062772 A1 | 3/2009 | Wakeford et al. |
| 2009/0080738 A1 | 3/2009 | Zur et al. |
| 2009/0082661 A1 | 3/2009 | Saladin et al. |
| 2009/0084382 A1 | 4/2009 | Jalde et al. |
| 2009/0099468 A1 | 4/2009 | Thiagalingam et al. |
| 2009/0101577 A1 | 4/2009 | Fulkerson et al. |
| 2009/0115406 A1 | 5/2009 | Anderson et al. |
| 2009/0118612 A1 | 5/2009 | Grunwald et al. |
| 2009/0118637 A1 | 5/2009 | Kassab et al. |
| 2009/0118706 A1 | 5/2009 | Schweikert et al. |
| 2009/0124901 A1 | 5/2009 | Fink et al. |
| 2009/0143736 A1 | 6/2009 | Mittermeyer et al. |
| 2009/0156926 A1 | 6/2009 | Messerly et al. |
| 2009/0163810 A1 | 6/2009 | Kanade et al. |
| 2009/0171217 A1 | 7/2009 | Kim et al. |
| 2009/0177083 A1 | 7/2009 | Matsumura |
| 2009/0177090 A1 | 7/2009 | Grunwald et al. |
| 2009/0182224 A1 | 7/2009 | Shmarak et al. |
| 2009/0203989 A1 | 8/2009 | Burnside et al. |
| 2009/0204113 A1 | 8/2009 | MacAdam et al. |
| 2009/0209872 A1 | 8/2009 | Pop |
| 2009/0209950 A1 | 8/2009 | Starksen |
| 2009/0221908 A1 | 9/2009 | Glossop |
| 2009/0227952 A1 | 9/2009 | Blakstvedt et al. |
| 2009/0234328 A1 | 9/2009 | Cox et al. |
| 2009/0247835 A1 | 10/2009 | Voipio |
| 2009/0253976 A1 | 10/2009 | Harlev et al. |

(56) References Cited

U.S. PATENT DOCUMENTS

| | | |
|---|---|---|
| 2009/0258171 A1 | 10/2009 | Uang |
| 2009/0259124 A1 | 10/2009 | Rothenberg |
| 2009/0262982 A1 | 10/2009 | Markowitz et al. |
| 2009/0270729 A1 | 10/2009 | Corbucci et al. |
| 2009/0270746 A1 | 10/2009 | Min |
| 2009/0275828 A1 | 11/2009 | Shachar et al. |
| 2009/0281419 A1 | 11/2009 | Troesken et al. |
| 2009/0297441 A1 | 12/2009 | Canham et al. |
| 2009/0312629 A1 | 12/2009 | Razzaque et al. |
| 2010/0004543 A1 | 1/2010 | Ahlund et al. |
| 2010/0004547 A1 | 1/2010 | Scholz et al. |
| 2010/0010355 A1 | 1/2010 | Kassab |
| 2010/0010444 A1 | 1/2010 | Bettuchi |
| 2010/0010612 A1 | 1/2010 | Gelbart et al. |
| 2010/0016726 A1 | 1/2010 | Meier |
| 2010/0036227 A1 | 2/2010 | Cox et al. |
| 2010/0036284 A1 | 2/2010 | Laynes et al. |
| 2010/0041973 A1 | 2/2010 | Vu et al. |
| 2010/0041984 A1 | 2/2010 | Shapland et al. |
| 2010/0049062 A1 | 2/2010 | Ziv |
| 2010/0055153 A1 | 3/2010 | Majmudar |
| 2010/0055184 A1 | 3/2010 | Zeitels et al. |
| 2010/0057157 A1 | 3/2010 | Govari et al. |
| 2010/0060472 A1 | 3/2010 | Kimura et al. |
| 2010/0063401 A1 | 3/2010 | Nishina et al. |
| 2010/0076305 A1 | 3/2010 | Maier-Hein et al. |
| 2010/0076328 A1 | 3/2010 | Matsumura et al. |
| 2010/0081934 A1 | 4/2010 | Soltani et al. |
| 2010/0083719 A1 | 4/2010 | Peppmoller et al. |
| 2010/0094116 A1 | 4/2010 | Silverstein |
| 2010/0106011 A1 | 4/2010 | Byrd et al. |
| 2010/0113917 A1 | 5/2010 | Anderson |
| 2010/0114573 A1 | 5/2010 | Huang et al. |
| 2010/0117659 A1 | 5/2010 | Osadchy et al. |
| 2010/0130858 A1 | 5/2010 | Arai et al. |
| 2010/0143119 A1 | 6/2010 | Kooijman et al. |
| 2010/0152596 A1 | 6/2010 | Griffiths et al. |
| 2010/0152604 A1 | 6/2010 | Kaula et al. |
| 2010/0160772 A1 | 6/2010 | Gardeski et al. |
| 2010/0168557 A1 | 7/2010 | Deno et al. |
| 2010/0185097 A1 | 7/2010 | Hall |
| 2010/0198048 A1 | 8/2010 | Togawa |
| 2010/0198346 A1 | 8/2010 | Keogh et al. |
| 2010/0204569 A1 | 8/2010 | Burnside et al. |
| 2010/0204614 A1 | 8/2010 | Lindquist et al. |
| 2010/0210938 A1 | 8/2010 | Verard et al. |
| 2010/0210950 A1 | 8/2010 | Dunbar et al. |
| 2010/0217116 A1 | 8/2010 | Eck et al. |
| 2010/0222664 A1 | 9/2010 | Lemon et al. |
| 2010/0222786 A1 | 9/2010 | Kassab |
| 2010/0234724 A1 | 9/2010 | Jacobsen et al. |
| 2010/0234733 A1 | 9/2010 | Wahlheim |
| 2010/0249598 A1 | 9/2010 | Smith et al. |
| 2010/0258033 A1 | 10/2010 | Yang et al. |
| 2010/0268059 A1 | 10/2010 | Ryu et al. |
| 2010/0273895 A1 | 10/2010 | Stinchcomb et al. |
| 2010/0274150 A1 | 10/2010 | Harlev et al. |
| 2010/0291521 A1 | 11/2010 | Simon |
| 2010/0298702 A1 | 11/2010 | Rogers et al. |
| 2010/0298704 A1 | 11/2010 | Pelissier et al. |
| 2010/0298705 A1 | 11/2010 | Pelissier et al. |
| 2010/0298712 A1 | 11/2010 | Pelissier et al. |
| 2010/0312086 A9 | 12/2010 | Beatty et al. |
| 2010/0317981 A1 | 12/2010 | Grunwald |
| 2010/0318026 A1 | 12/2010 | Grunwald |
| 2010/0331712 A1 | 12/2010 | Rothenberg |
| 2011/0015496 A1 | 1/2011 | Sherman et al. |
| 2011/0015527 A1 | 1/2011 | Heasty et al. |
| 2011/0015533 A1 | 1/2011 | Cox et al. |
| 2011/0034823 A1 | 2/2011 | Gelbart et al. |
| 2011/0034940 A1 | 2/2011 | Payner |
| 2011/0040212 A1 | 2/2011 | Dietz et al. |
| 2011/0052694 A1 | 3/2011 | Stinchcomb et al. |
| 2011/0087105 A1 | 4/2011 | Ridley et al. |
| 2011/0087106 A1 | 4/2011 | Ridley et al. |
| 2011/0087107 A1 | 4/2011 | Lindekugel et al. |
| 2011/0106101 A1 | 5/2011 | Tortonese et al. |
| 2011/0112396 A1 | 5/2011 | Shachar et al. |
| 2011/0136242 A1 | 6/2011 | Marx et al. |
| 2011/0137156 A1 | 6/2011 | Razzaque et al. |
| 2011/0196235 A1 | 8/2011 | Dunbar et al. |
| 2011/0196248 A1 | 8/2011 | Grunwald |
| 2011/0196255 A1 | 8/2011 | Kassab |
| 2011/0237935 A1 | 9/2011 | Kalpin et al. |
| 2011/0245659 A1 | 10/2011 | Ma et al. |
| 2011/0282187 A1 | 11/2011 | Harlev et al. |
| 2011/0282188 A1 | 11/2011 | Burnside et al. |
| 2011/0282285 A1 | 11/2011 | Blanchard et al. |
| 2011/0282686 A1 | 11/2011 | Venon et al. |
| 2011/0295108 A1 | 12/2011 | Cox et al. |
| 2011/0306859 A1 | 12/2011 | Saldivar et al. |
| 2011/0306867 A1 | 12/2011 | Gopinathan et al. |
| 2011/0313293 A1 | 12/2011 | Lindekugel et al. |
| 2012/0004564 A1 | 1/2012 | Dobak, III |
| 2012/0035460 A1 | 2/2012 | Stangenes et al. |
| 2012/0046562 A1 | 2/2012 | Powers et al. |
| 2012/0059249 A1 | 3/2012 | Verard et al. |
| 2012/0059270 A1 | 3/2012 | Grunwald |
| 2012/0059271 A1 | 3/2012 | Amitai et al. |
| 2012/0071751 A1 | 3/2012 | Sra et al. |
| 2012/0071759 A1 | 3/2012 | Hagy et al. |
| 2012/0071782 A1 | 3/2012 | Patil et al. |
| 2012/0078342 A1 | 3/2012 | Vollkron et al. |
| 2012/0095319 A1 | 4/2012 | Kondrosky et al. |
| 2012/0108950 A1 | 5/2012 | He et al. |
| 2012/0115007 A1 | 5/2012 | Felder et al. |
| 2012/0143029 A1 | 6/2012 | Silverstein et al. |
| 2012/0143078 A1 | 6/2012 | Kassab et al. |
| 2012/0172727 A1 | 7/2012 | Hastings et al. |
| 2012/0220854 A1 | 8/2012 | Messerly et al. |
| 2012/0265084 A1 | 10/2012 | Stewart et al. |
| 2012/0283582 A1 | 11/2012 | Mahapatra et al. |
| 2012/0296200 A1 | 11/2012 | Shachar et al. |
| 2012/0310052 A1 | 12/2012 | Mahapatra et al. |
| 2012/0310066 A1 | 12/2012 | Shachar et al. |
| 2012/0310660 A1 | 12/2012 | Liu et al. |
| 2012/0316440 A1 | 12/2012 | Munrow et al. |
| 2013/0006100 A1 | 1/2013 | Shachar et al. |
| 2013/0006102 A1 | 1/2013 | Wilkes et al. |
| 2013/0018248 A1 | 1/2013 | Hurezan |
| 2013/0035590 A1 | 2/2013 | Ma et al. |
| 2013/0041254 A1 | 2/2013 | Hagy et al. |
| 2013/0041269 A1 | 2/2013 | Stahmann et al. |
| 2013/0060116 A1 | 3/2013 | Messerly et al. |
| 2013/0079628 A1 | 3/2013 | Groszmann et al. |
| 2013/0085416 A1 | 4/2013 | Mest |
| 2013/0090938 A1 | 4/2013 | Fishman et al. |
| 2013/0102890 A1 | 4/2013 | Dib |
| 2013/0123597 A1 | 5/2013 | Rothenberg |
| 2013/0131503 A1 | 5/2013 | Schneider et al. |
| 2013/0169272 A1 | 7/2013 | Eichler et al. |
| 2013/0217999 A1 | 8/2013 | Burnside et al. |
| 2013/0223702 A1 | 8/2013 | Holsing et al. |
| 2013/0245434 A1 | 9/2013 | Messerly et al. |
| 2013/0281837 A1 | 10/2013 | Ridley et al. |
| 2013/0289417 A1 | 10/2013 | Grunwald et al. |
| 2013/0296691 A1 | 11/2013 | Ashe |
| 2013/0296693 A1 | 11/2013 | Wenzel et al. |
| 2013/0303878 A1 | 11/2013 | Nevo et al. |
| 2013/0303896 A1 | 11/2013 | Kalpin et al. |
| 2013/0303945 A1 | 11/2013 | Blumenkranz et al. |
| 2013/0317338 A1 | 11/2013 | Silverstein |
| 2013/0324841 A1 | 12/2013 | Kamen et al. |
| 2013/0338503 A1 | 12/2013 | Cohen et al. |
| 2013/0338517 A1 | 12/2013 | Rothenberg |
| 2013/0345555 A1 | 12/2013 | Kanade et al. |
| 2014/0031674 A1 | 1/2014 | Newman et al. |
| 2014/0046261 A1 | 2/2014 | Newman et al. |
| 2014/0066798 A1 | 3/2014 | Albert |
| 2014/0089836 A1 | 3/2014 | Damani et al. |
| 2014/0094694 A1 | 4/2014 | Moctezuma de la Barrera |
| 2014/0094768 A1 | 4/2014 | Stangenes et al. |
| 2014/0107475 A1 | 4/2014 | Cox et al. |
| 2014/0128712 A1 | 5/2014 | Banet et al. |

(56) References Cited

U.S. PATENT DOCUMENTS

| | | |
|---|---|---|
| 2014/0163356 A2 | 6/2014 | Burnside et al. |
| 2014/0180074 A1 | 6/2014 | Green et al. |
| 2014/0187917 A1 | 7/2014 | Clark et al. |
| 2014/0187990 A1 | 7/2014 | Banet et al. |
| 2014/0188133 A1 | 7/2014 | Misener |
| 2014/0221862 A1 | 8/2014 | Tambe |
| 2014/0228689 A1 | 8/2014 | Ishikawa et al. |
| 2014/0243659 A1 | 8/2014 | Rothenberg |
| 2014/0249428 A1 | 9/2014 | Ingold, Jr. et al. |
| 2014/0249505 A1 | 9/2014 | Bukhman |
| 2014/0253270 A1 | 9/2014 | Nicholls et al. |
| 2014/0257080 A1 | 9/2014 | Dunbar et al. |
| 2014/0275957 A1 | 9/2014 | Lupotti |
| 2014/0275990 A1 | 9/2014 | Hagy et al. |
| 2014/0276010 A1 | 9/2014 | Anderson |
| 2014/0303492 A1 | 10/2014 | Burnside et al. |
| 2014/0309624 A1 | 10/2014 | Bown et al. |
| 2014/0343398 A1 | 11/2014 | He et al. |
| 2015/0005621 A1 | 1/2015 | Liu |
| 2015/0018701 A1 | 1/2015 | Cox et al. |
| 2015/0025365 A1 | 1/2015 | Esguerra Wilczynski et al. |
| 2015/0025402 A1 | 1/2015 | Rothenberg |
| 2015/0051489 A1 | 2/2015 | Caluser et al. |
| 2015/0073285 A1 | 3/2015 | Albert et al. |
| 2015/0080716 A1 | 3/2015 | Powers et al. |
| 2015/0209008 A1 | 7/2015 | Ridley et al. |
| 2015/0216445 A1 | 8/2015 | Carmeli et al. |
| 2015/0216446 A1 | 8/2015 | Bukhman et al. |
| 2015/0223775 A1 | 8/2015 | Hamilton, Jr. |
| 2015/0245809 A1 | 9/2015 | Hagy et al. |
| 2015/0245872 A1 | 9/2015 | Hagy et al. |
| 2015/0246247 A1 | 9/2015 | Binnekamp et al. |
| 2015/0282734 A1 | 10/2015 | Schweikert et al. |
| 2015/0289781 A1 | 10/2015 | Grunwald et al. |
| 2015/0297114 A1 | 10/2015 | Cox et al. |
| 2015/0317810 A1 | 11/2015 | Grunwald et al. |
| 2015/0335310 A1 | 11/2015 | Bernstein et al. |
| 2015/0335383 A9 | 11/2015 | Cohen |
| 2016/0067449 A1 | 3/2016 | Misener et al. |
| 2016/0278869 A1 | 9/2016 | Grunwald |
| 2016/0374589 A1 | 12/2016 | Misener et al. |
| 2017/0000367 A1 | 1/2017 | Grunwald |
| 2017/0020561 A1 | 1/2017 | Cox et al. |
| 2017/0079548 A1 | 3/2017 | Silverstein et al. |
| 2017/0079552 A1 | 3/2017 | Grunwald |
| 2017/0079615 A1 | 3/2017 | Burnside et al. |
| 2017/0079681 A1 | 3/2017 | Burnside et al. |
| 2017/0086782 A1 | 3/2017 | Hagy et al. |
| 2017/0151022 A1 | 6/2017 | Jascob et al. |
| 2017/0215762 A1 | 8/2017 | Burnside et al. |
| 2017/0231700 A1 | 8/2017 | Cox et al. |
| 2017/0281029 A1 | 10/2017 | Messerly et al. |
| 2018/0103869 A1 | 4/2018 | Bukhman et al. |
| 2018/0116551 A1 | 5/2018 | Newman et al. |
| 2018/0145443 A1 | 5/2018 | Andreason et al. |
| 2018/0169389 A1 | 6/2018 | Lemon et al. |
| 2018/0296122 A1 | 10/2018 | Messerly et al. |
| 2019/0069877 A1 | 3/2019 | Burnside et al. |
| 2019/0099108 A1 | 4/2019 | Messerly et al. |
| 2019/0246945 A1 | 8/2019 | Grunwald |
| 2019/0290208 A1 | 9/2019 | Toth et al. |
| 2019/0320982 A1 | 10/2019 | Misener et al. |
| 2020/0054858 A1 | 2/2020 | Newman et al. |
| 2020/0119488 A1 | 4/2020 | Stats et al. |
| 2020/0138332 A1 | 5/2020 | Newman et al. |
| 2020/0237255 A1 | 7/2020 | Silverstein et al. |
| 2020/0237403 A1 | 7/2020 | Southard et al. |

FOREIGN PATENT DOCUMENTS

| | | |
|---|---|---|
| AU | 20009592 | 9/2000 |
| AU | 20015250 | 6/2001 |
| AU | 768362 B2 | 12/2003 |
| AU | 2001229024 B2 | 9/2005 |
| AU | 2001283703 B2 | 5/2006 |
| AU | 2006904933 | 9/2006 |
| AU | 2006202149 B2 | 3/2009 |
| AU | 2006283022 B2 | 2/2012 |
| CA | 1197745 A | 12/1985 |
| CA | 2420676 C | 7/2010 |
| CA | 2619909 C | 1/2014 |
| CN | 2031655 U | 2/1989 |
| CN | 1672649 A | 9/2005 |
| CN | 1913833 A | 2/2007 |
| CN | 101854853 A | 10/2010 |
| CN | 102209490 A | 10/2011 |
| CN | 102802514 A | 11/2012 |
| CN | 102821679 A | 12/2012 |
| CN | 103037761 A | 4/2013 |
| CN | 103037762 A | 4/2013 |
| CN | 103118591 A | 5/2013 |
| CN | 103189009 A | 7/2013 |
| DE | 4319033 C1 | 6/1994 |
| EP | 0362821 A1 | 4/1990 |
| EP | 0399536 A1 | 11/1990 |
| EP | 0359697 B1 | 11/1994 |
| EP | 0823261 A2 | 2/1998 |
| EP | 0928976 A2 | 7/1999 |
| EP | 1025805 A1 | 8/2000 |
| EP | 1015967 B1 | 4/2002 |
| EP | 1311226 A1 | 5/2003 |
| EP | 1504713 A1 | 2/2005 |
| EP | 1117331 B1 | 5/2005 |
| EP | 1117332 B1 | 8/2005 |
| EP | 1118019 B1 | 5/2006 |
| EP | 1717601 A2 | 11/2006 |
| EP | 1887940 A2 | 2/2008 |
| EP | 1932477 A1 | 6/2008 |
| EP | 2337491 A1 | 6/2011 |
| EP | 2440122 A1 | 4/2012 |
| EP | 2464407 A2 | 6/2012 |
| EP | 2482719 A1 | 8/2012 |
| EP | 2531098 A1 | 12/2012 |
| EP | 2575610 A1 | 4/2013 |
| EP | 2575611 A1 | 4/2013 |
| EP | 2603145 A2 | 6/2013 |
| EP | 2605699 A2 | 6/2013 |
| EP | 2474268 B1 | 7/2013 |
| EP | 2618727 A1 | 7/2013 |
| EP | 2632360 A1 | 9/2013 |
| EP | 2219526 B1 | 3/2014 |
| EP | 2712547 A1 | 4/2014 |
| EP | 2313143 B1 | 9/2014 |
| EP | 2992825 B1 | 5/2017 |
| EP | 2170162 B1 | 8/2017 |
| EP | 2265175 B1 | 8/2017 |
| FR | 2545349 B1 | 9/1986 |
| JP | 01097440 | 4/1989 |
| JP | 03173542 A | 7/1991 |
| JP | 9-503054 | 3/1997 |
| JP | 09-094298 A | 4/1997 |
| JP | 10043310 | 2/1998 |
| JP | 10290839 A | 11/1998 |
| JP | 11128237 A | 5/1999 |
| JP | 2001-145630 A | 5/2001 |
| JP | 2001161683 A | 6/2001 |
| JP | 2001-514533 A | 9/2001 |
| JP | 2001-524339 A | 12/2001 |
| JP | 2001340334 A | 12/2001 |
| JP | 2002520893 A | 7/2002 |
| JP | 2002-224069 A | 8/2002 |
| JP | 2002-529133 A | 9/2002 |
| JP | 2002-541947 A | 12/2002 |
| JP | 2003-010138 A | 1/2003 |
| JP | 2003501127 A | 1/2003 |
| JP | 2003061752 A | 3/2003 |
| JP | 2003299654 A | 10/2003 |
| JP | 2003334191 A | 11/2003 |
| JP | 2004505748 T | 2/2004 |
| JP | 2004515298 A | 5/2004 |
| JP | 2006508744 A | 3/2006 |
| JP | 2006-338526 A | 12/2006 |
| JP | 2007-000226 A | 1/2007 |
| JP | 2007-068989 A | 3/2007 |

(56) References Cited

FOREIGN PATENT DOCUMENTS

| | | |
|---|---|---|
| JP | 2007-105450 A | 4/2007 |
| JP | 2007-313122 A | 12/2007 |
| JP | 4090741 B2 | 5/2008 |
| JP | 2009/271123 A | 11/2009 |
| JP | 5010604 B2 | 8/2012 |
| JP | 2012-529929 A | 11/2012 |
| JP | 2013-518676 A | 5/2013 |
| JP | 2013-526959 A | 6/2013 |
| JP | 2013-526961 A | 6/2013 |
| RU | 2009101949 A | 7/2010 |
| WO | 1980002376 A1 | 11/1980 |
| WO | 1991012836 A1 | 9/1991 |
| WO | 1992003090 A1 | 3/1992 |
| WO | 1994003159 A1 | 2/1994 |
| WO | 1994004938 A1 | 3/1994 |
| WO | 1996005768 A1 | 2/1996 |
| WO | 1996007352 A1 | 3/1996 |
| WO | 1996041119 A1 | 12/1996 |
| WO | 1997/22395 A1 | 6/1997 |
| WO | 1997029683 A1 | 8/1997 |
| WO | 1997043989 A1 | 11/1997 |
| WO | 97/48438 A2 | 12/1997 |
| WO | 1998025159 A1 | 6/1998 |
| WO | 98/29032 A1 | 7/1998 |
| WO | 1998035611 A1 | 8/1998 |
| WO | 1999016495 A1 | 4/1999 |
| WO | 1999027837 A2 | 6/1999 |
| WO | 1999049407 A1 | 9/1999 |
| WO | 2000019906 A1 | 4/2000 |
| WO | 2000027281 A1 | 5/2000 |
| WO | 2000040155 A1 | 7/2000 |
| WO | 2000063658 A2 | 10/2000 |
| WO | 2000074775 A1 | 12/2000 |
| WO | 2001013792 A1 | 3/2001 |
| WO | 2001039683 A1 | 6/2001 |
| WO | 2001076479 A1 | 10/2001 |
| WO | 02/07794 A2 | 1/2002 |
| WO | 2002015973 A1 | 2/2002 |
| WO | 2002019905 A1 | 3/2002 |
| WO | 2002025277 A1 | 3/2002 |
| WO | 2002085442 A1 | 10/2002 |
| WO | 2003061752 A1 | 7/2003 |
| WO | 2003077759 A1 | 9/2003 |
| WO | 03/088833 A1 | 10/2003 |
| WO | 2003091495 A1 | 11/2003 |
| WO | 2004002303 A1 | 1/2004 |
| WO | 2004049970 A2 | 6/2004 |
| WO | 2005033524 A1 | 4/2005 |
| WO | 2005033574 A1 | 4/2005 |
| WO | 2005/089851 A1 | 9/2005 |
| WO | 2005117690 A1 | 12/2005 |
| WO | 2005117733 A2 | 12/2005 |
| WO | 2006074509 A1 | 7/2006 |
| WO | 2006074510 A1 | 7/2006 |
| WO | 2006078677 A2 | 7/2006 |
| WO | 2006103661 A2 | 10/2006 |
| WO | 2006111056 A1 | 10/2006 |
| WO | 2007002541 A2 | 1/2007 |
| WO | 2007005976 A1 | 1/2007 |
| WO | 2007014447 A1 | 2/2007 |
| WO | 2007034196 A2 | 3/2007 |
| WO | 2007067324 A1 | 6/2007 |
| WO | 2007069168 A2 | 6/2007 |
| WO | 2007109123 A2 | 9/2007 |
| WO | 2007126536 A2 | 11/2007 |
| WO | 2007144894 A1 | 12/2007 |
| WO | 2008005480 A1 | 1/2008 |
| WO | 2008024596 A2 | 2/2008 |
| WO | 2008028253 A1 | 3/2008 |
| WO | 2008083111 A1 | 7/2008 |
| WO | 2008097767 A2 | 8/2008 |
| WO | 2008118992 A1 | 10/2008 |
| WO | 2008126074 A2 | 10/2008 |
| WO | 2008129326 A1 | 10/2008 |
| WO | 2008131017 A2 | 10/2008 |
| WO | 2008136008 A2 | 11/2008 |
| WO | 2009000439 A1 | 12/2008 |
| WO | 2009002514 A2 | 12/2008 |
| WO | 2009003138 A1 | 12/2008 |
| WO | 2009009064 A1 | 1/2009 |
| WO | 2009057774 A1 | 5/2009 |
| WO | 2009063166 A1 | 5/2009 |
| WO | 2009067654 A1 | 5/2009 |
| WO | 2009070616 A2 | 6/2009 |
| WO | 2009100158 A1 | 8/2009 |
| WO | 2009123819 A2 | 10/2009 |
| WO | 2009126340 A1 | 10/2009 |
| WO | 2009129475 A1 | 10/2009 |
| WO | 2009129477 A1 | 10/2009 |
| WO | 2009134605 A2 | 11/2009 |
| WO | 2009137262 A2 | 11/2009 |
| WO | 2010002313 A1 | 1/2010 |
| WO | 2010018500 A1 | 2/2010 |
| WO | 2010022370 A1 | 2/2010 |
| WO | 2010027349 A1 | 3/2010 |
| WO | 2010027471 A2 | 3/2010 |
| WO | 2010029906 A1 | 3/2010 |
| WO | 2010030820 A1 | 3/2010 |
| WO | 2010132857 A1 | 11/2010 |
| WO | 2010132985 A1 | 11/2010 |
| WO | 2010/144922 A1 | 12/2010 |
| WO | 2010143196 A1 | 12/2010 |
| WO | 2011019760 A2 | 2/2011 |
| WO | 2011041450 A1 | 4/2011 |
| WO | 2011044421 A1 | 4/2011 |
| WO | 2011057289 A2 | 5/2011 |
| WO | 2011064209 A1 | 6/2011 |
| WO | 2011084593 A2 | 7/2011 |
| WO | 2011097312 A1 | 8/2011 |
| WO | 2011128052 A2 | 10/2011 |
| WO | 2011150358 A1 | 12/2011 |
| WO | 2011150376 A1 | 12/2011 |
| WO | 2012021542 A2 | 2/2012 |
| WO | 2012024577 A2 | 2/2012 |
| WO | 2012039866 A1 | 3/2012 |
| WO | 2012040487 A1 | 3/2012 |
| WO | 2012058461 A1 | 5/2012 |
| WO | 2012083245 A1 | 6/2012 |
| WO | 2012088535 A1 | 6/2012 |
| WO | 2012110955 A1 | 8/2012 |
| WO | 2012173697 A1 | 12/2012 |
| WO | 2013006713 A2 | 1/2013 |
| WO | 2013006817 A1 | 1/2013 |
| WO | 2013034175 A1 | 3/2013 |
| WO | 2014042329 A1 | 3/2014 |
| WO | 2014052894 A2 | 4/2014 |
| WO | 2014062728 A1 | 4/2014 |
| WO | 2014138652 A1 | 9/2014 |
| WO | 2014138918 A1 | 9/2014 |
| WO | 2015/055797 A1 | 4/2015 |
| WO | 2015048514 A1 | 4/2015 |
| WO | 2015073962 A1 | 5/2015 |
| WO | 2015/120256 A2 | 8/2015 |
| WO | 2016/210325 A1 | 12/2016 |
| WO | 2018/112252 A1 | 6/2018 |
| WO | 2020/160315 A1 | 8/2020 |

OTHER PUBLICATIONS

EP 12177438.4 filed Jul. 23, 2012 extended European Search Report dated Mar. 25, 2013.
EP 12807886.2 filed Jan. 15, 2014 Extended European Search Report dated Feb. 6, 2015.
EP 13194818.4 filed Nov. 28, 2013 extended European search report dated Feb. 28, 2014.
EP 13840356.3 filed Apr. 27, 2015 Extended European Search Report dated Mar. 22, 2017.
EP 13840356.3 filed Apr. 27, 2015 Partial European Search Report dated Oct. 19, 2016.
EP 13846380.7 filed May 15, 2015 Extended European Search Report dated Sep. 30, 2016.
EP 13846380.7 filed May 15, 2015 Partial European Search Report dated Sep. 30, 2016.

(56) References Cited

OTHER PUBLICATIONS

EP 14151268.1 filed Jan. 15, 2014 European Search Report dated Feb. 21, 2014.
EP 14197137.4 filed Dec. 10, 2014 Extended European Search Report dated Nov. 4, 2015.
EP 14197137.4 filed Dec. 10, 2014 Office Action dated Sep. 20, 2017.
EP 14197137.4 filed Dec. 10, 2014, Partial European Search Report dated May 29, 2015.
EP 14761249.3 Filed Sep. 3, 2015 Extended European Search Report dated Sep. 19, 2016.
EP 14761249.3 Filed Sep. 3, 2015 Office Action dated Sep. 28, 2017.
EP 15179061.5 filed Jul. 30, 2015 Extended European Search Report dated Jan. 14, 2016.
EP 15746326.6 filed Jul. 1, 2016 Extended European Search Report dated Jun. 9, 2017.
EP 17157118.5 filed Feb. 21, 2017 Extended European Search Report dated Jun. 8, 2017.
EP14197136.6 filed Dec. 10, 2014 Extended European Search Report dated May 26, 2015.
Fearon, William F et al, Evaluating Intermediate Coronary Lesions in the Cardiac Catheterization Laboratory, vol. 4, No. 1, 7 pages, Reviews in Cardiovascular Medicine, 2003.
Felleiter P et al, Use of Electrocardiographic Placement Control of Central Venous Catheters in Austria, Acta Med Austriaca, pp. 109-113, vol. 26 No. 3, 1999 (Abstract only).
Forauer, AR et al, Change in Peripherally Inserted Central Catheter Tip Location with Abduction and Adduction of the Upper Extremity, J Vasc Intery Radiol, pp. 1315-1318, vol. 11 No. 10, Nov.-Dec. 2000.
Frassinelli, P et al, Utility of Chest Radiographs after Guidewire Exchanges of Central Venous Catheters, Crit Care Med, pp. 611-615, vol. 26 No. 3, Mar. 1998.
Frazin L et al, A Doppler Guided Retrograde Catheterization System, Cathet. Cardiovasc Diagn, pp. 41-50, May 1992.
French, PJ et al, Sensors for Catheter Applications, Sensors Update, vol. 13 Issue 1 pp. 107-153, Dec. 2003.
GB Application 0800474.9 filed Aug. 24, 2006 Office Action dated Aug. 9, 2010.
GB Application 0800474.9 filed Aug. 24, 2006 Office Action dated Mar. 17, 2010.
Gebauer, B et al, Ultrasound and Fluoroscopy-guided Implantation of Peripherally Inserted Central Venous Catheters (PICCs), ROFO, pp. 386-391, vol. 176 No. 3, Mar. 2004 (Abstract only).
Gebhard, et al., "The accuracy of Electrocardiogram-Controlled Central Line Placement." The International Anesthesia Research Society, vol. 104, No. 1 Jan. 2007.
Gjendemsjo, Anders, et al., Energy and Power, The Connexions Project, Version 1.2, Feb. 20, 2004.
Gladwin, MT et al, Cannulation of the Internal Jugular Vein: is postpocedural chest radiography always necessary?, Crit Care Med, 33 pages, Oct. 2000.
Gonzales, et al. "Peripherally Inserted Central Catheter Placement in Swine Using Magnet Detection." Journal of Intravenous Nursing, vol. 22, No. 3, May/Jun. 1999.
Greenall, M.J. et al, Cardiac Tamponade and Central Venous Catheters, British Medical Journal, pp. 595-597, Jun. 14, 1975.
Guillory, "Basic Principles of Technologies for Catheter Localization." C.R. Bard internal paper, Oct. 20, 2004.
Guth, AA, Routine Chest X-rays after Insertion of Implantable Long-Term Venous Catheters: Necessary or Not?, Am Surg, pp. 26-29, vol. 67 No. 1, Jan. 2001 (Abstract only).
Hill, Bradley et al, Abstract of article discussing Vasallova VPS as guide for placement of PICCs. 2009.
Hill, Bradley, Identifying the Caval-Atrial Junction Using Smart-Catheter Technology presentation, 22nd Annual Scientific Meeting of the AVA in Savannah, Georgia, Sep. 13, 2008.
Hoffman, Thomas et al, Simultaneous Measurement of Pulmonary Venous Flow by Intravascular Catheter Doppler Velocimetry and Transesophageal Doppler Echocardiography: Relation to Left Atrial Pressure and Left Atrial and Left Ventricular Function, pp. 239-249, J Am Coll Cardiol, Jul. 1995.
Hoffmann, et al. "New Procedure in Transesophageal Echocardiography: Multiplane Transesophageal Echocardiography and Transesophageal Stress Echocardiography." Herz, vol. 18, No. 5, pp. 269-277, Oct. 1993.
Iacopino, Domenico Gerardo et al, Intraoperative Microvascular Doppler Monitoring of Blood Flow within a Spinal Dural Arteriovenous Fistula: A Precious Surgical Tool, vol. 10, 5 pages, Neurosurg. Focus, Feb. 2001.
Jeon, Yunseok et al., "Transesophageal Echocardiographic Evaluation of ECG-guided Central Venous Catheter Placement," Canadian Journal of Anesthesia, vol. 53, No. 10, Oct. 1, 2006, pp. 978-983.
Joosting, Jean-Pierre, "Dual-interface RFID-compatible EEPROM enables remote access to electronic device parameters," EE Times, Mar. 8, 2010.
JP 2008-528151 filed Aug 24, 2006 Notice of Grant dated May 6, 2012.
JP 2010-504220 filed Sep. 3, 2009 Final Office Action dated Apr. 18, 2013.
JP 2010-504220 filed Sep. 3, 2009 Office Action dated Apr. 1, 2014.
JP 2010-504220 filed Sep. 3, 2009 Office Action dated Apr. 18, 2013.
JP 2010-504220 filed Sep. 3, 2009 Office Action dated May 21, 2012.
JP 2010-535117 filed May 26, 2011 First Office Action dated Aug. 5, 2013.
JP 2012-515222 filed Dec. 9, 2011 Office Action dated Feb. 23, 2015.
JP 2012-515222 filed Dec. 9, 2011 Office Action dated Mar. 24, 2014.
JP 2012-552060 filed Aug. 1, 2012 Office Action dated Nov. 12, 2014.
UAB Health Systems, Arrhythmias, retrieved from http://www.health,uab.edu/14564/ on Nov. 15, 2007, 12 pages.
U.S. Appl. No. 11/466,602, filed Aug. 23, 2006 Advisory Action dated Jun. 22, 2009.
U.S. Appl. No. 11/466,602, filed Aug. 23, 2006 Appeal Board Decision dated Sep. 17, 2012.
U.S. Appl. No. 11/466,602, filed Aug. 23, 2006 Final Office Action dated Apr. 8, 2010.
U.S. Appl. No. 11/466,602, filed Aug. 23, 2006 Final Office Action dated Jan. 30, 2009.
U.S. Appl. No. 11/466,602, filed Aug. 23, 2006 Final Office Action dated Oct. 28, 2013.
U.S. Appl. No. 11/466,602, filed Aug. 23, 2006 Non-Final Office Action dated Mar. 28, 2013.
U.S. Appl. No. 11/466,602, filed Aug. 23, 2006 Non-Final Office Action dated Sep. 25, 2009.
U.S. Appl. No. 11/466,602, filed Aug. 23, 2006 Notice of Allowance dated Dec. 3, 2012.
U.S. Appl. No. 11/466,602, filed Aug. 23, 2006 Notice of Allowance dated Mar. 14, 2014.
U.S. Appl. No. 11/552,094, filed Oct. 23, 2006 Notice of Allowability dated Apr. 2, 2010.
U.S. Appl. No. 11/552,094, filed Oct. 23, 2006 Non-Final Office Action dated Apr. 27, 2009.
U.S. Appl. No. 11/552,094, filed Oct. 23, 2006 Notice of Allowance dated May 20, 2010.
U.S. Appl. No. 12/104,253, filed Apr. 16, 2008 Final Office Action dated Jul. 27, 2011.
U.S. Appl. No. 12/104,253, filed Apr. 16, 2008 Non-Final Office Action dated Nov. 29, 2010.
U.S. Appl. No. 12/323,273, filed Nov. 25, 2008 Non-Final Office Action dated Jun. 8, 2012.
U.S. Appl. No. 12/369,625, filed Feb. 11, 2009 Final Office Action dated Feb. 23, 2012.
U.S. Appl. No. 12/369,625, filed Feb. 11, 2009 Notice of Allowance dated Oct. 5, 2012.
U.S. Appl. No. 12/369,625, filed Feb. 11, 2009 Notice of Panel Decision dated Aug. 1, 2012.

(56) References Cited

OTHER PUBLICATIONS

U.S. Appl. No. 12/369,625, filed Feb. 11, 2009 Non-Final Office Action dated Jul. 20, 2011.
U.S. Appl. No. 12/426,175, filed Apr. 17, 2009 Advisory Action dated Nov. 26, 2013.
U.S. Appl. No. 12/426,175, filed Apr. 17, 2009 Decision on Appeal dated Nov. 7, 2016.
U.S. Appl. No. 12/426,175, filed Apr. 17, 2009 Examiner's Answer dated Oct. 7, 2014.
U.S. Appl. No. 12/426,175, filed Apr. 17, 2009 Final Office Action dated Aug. 2, 2013.
U.S. Appl. No. 12/426,175, filed Apr. 17, 2009 Final Office Action dated Jan. 31, 2014.
U.S. Appl. No. 12/426,175, filed Apr. 17, 2009 Non-Final Office Action dated Dec. 3, 2012.
U.S. Appl. No. 12/426,175, filed Apr. 17, 2009 Notice of Allowance dated Dec. 13, 2016.
U.S. Appl. No. 12/427,244, filed Apr. 21, 2009 Non-Final Office Action dated Jan. 19, 2012.
U.S. Appl. No. 12/545,762, filed Aug. 21, 2009 Final Office Action dated Apr. 10, 2017.
U.S. Appl. No. 12/545,762, filed Aug. 21, 2009 Final Office Action dated Mar. 7, 2013.
U.S. Appl. No. 12/545,762, filed Aug. 21, 2009 Non-Final Office Action dated Aug. 1, 2012.
U.S. Appl. No. 12/545,762, filed Aug. 21, 2009 Non-Final Office Action dated Dec. 13, 2013.
U.S. Appl. No. 12/545,762, filed Aug. 21, 2009 Non-Final Office Action dated Feb. 16, 2016.
U.S. Appl. No. 12/545,762, filed Aug. 21, 2009 Non-Final Office Action dated Nov. 7, 2014.
U.S. Appl. No. 12/545,762, filed Aug. 21, 2009 Non-Final Office Action dated Sep. 11, 2015.
U.S. Appl. No. 12/545,762, filed Aug. 21, 2009 Non-Final Office Action dated Sep. 26, 2016.
U.S. Appl. No. 12/545,762, filed Aug. 21, 2009 Notice of Panel Decision dated Jul. 14, 2017.
U.S. Appl. No. 12/557,401, filed Sep. 10, 2009 Non-Final Office Action dated Apr. 24, 2012.
U.S. Appl. No. 12/557,401, filed Sep. 10, 2009 Non-Final Office Action dated Jan. 6, 2014.
U.S. Appl. No. 12/575,456, filed Oct. 7, 2009 Non-Final Office Action dated Oct. 5, 2012.
U.S. Appl. No. 12/715,556, filed Mar. 2, 2010 Final Office Action dated Oct. 2, 2013.
U.S. Appl. No. 12/715,556, filed Mar. 2, 2010 Non-Final Office Action dated Sep. 13, 2012.
U.S. Appl. No. 12/815,331, filed Jun. 14, 2010 Advisory Action dated Mar. 5, 2015.
U.S. Appl. No. 12/815,331, filed Jun. 14, 2010 Advisory Action dated Oct. 4, 2013.
U.S. Appl. No. 12/815,331, filed Jun. 14, 2010 Final Office Action dated Dec. 23, 2014.
U.S. Appl. No. 12/815,331, filed Jun. 14, 2010 Final Office Action dated Jul. 26, 2013.
U.S. Appl. No. 12/815,331, filed Jun. 14, 2010 Final Office Action dated Nov. 4, 2015.
U.S. Appl. No. 12/815,331, filed Jun. 14, 2010 Non-Final Office Action dated Jan. 22, 2013.
U.S. Appl. No. 12/815,331, filed Jun. 14, 2010 Non-Final Office Action dated Jul. 2, 2014.
U.S. Appl. No. 12/815,331, filed Jun. 14, 2010 Non-Final Office Action dated Jun. 1, 2015.
U.S. Appl. No. 14/054,700, filed Oct. 15, 2013 Notice of Allowance dated Jun. 6, 2019.
U.S. Appl. No. 14/201,300, filed Mar. 7, 2014 Board Decision dated Jul. 23, 2019.
U.S. Appl. No. 14/996,247, filed Jan. 15, 2016 Non-Final Office Action dated Jul. 18, 2019.
U.S. Appl. No. 15/900,623, filed Feb. 20, 2018 Non-Final Office Action dated Jul. 16, 2019.
Odd, De et al, Does Radio-opaque Contrast Improve Radiographic localisation of Percutaneous Central Venous Lines?, Arch Dis Child Fetal Neonatal Ed, pp. 41-43, vol. 89 No. 1, Jan. 2004.
Palesty, JA et al, Routine Chest Radiographs Following Central Venous Recatherization over a Wire are not Justified, Am J Surg, pp. 618-621, vol. 176 No. 6, Dec. 1998.
Paliotti, Roberta P. et al, Intravascular Doppler Technique for Monitoring Renal Venous Blood Flow in Man, J Nephrol, pp. 57-62, 2003.
Parker, K.H. et al, Cardiovascular Fluid Dynamics, Department of Bioengineering, National Heart and Lung Institute, Imperial College of Science, Technology and Medicine, Cardiovascular Haemodynamics, pp. 1-28, Sep. 26, 2005.
Pawlik, et al., "Central Venous Catheter Placement: Comparison of the Intravascular Guidewire and the Fluid Column Electrocardiograms." European Journal of Anaesthesiology, vol. 41, pp. 594-599, 2004.
PCT/US13/62409 filed Sep. 27, 2013 International Search Report and Written Opinion dated Feb. 24, 2014.
PCT/US2006/033079 filed Aug. 24, 2006 International Preliminary Report on Patentability dated Feb. 26, 2008.
PCT/US2006/033079 filed Aug. 24, 2006 Search Report dated Dec. 19, 2006.
PCT/US2006/033079 filed Aug. 24, 2006 Written Opinion dated Dec. 19, 2006.
PCT/US2008/060502 filed Apr. 16, 2008 International Search Report and Written Opinion dated Oct. 16, 2008.
PCT/US2008/084751 filed Nov. 25, 2008 International Preliminary Report on Patentability dated Jun. 1, 2010.
PCT/US2008/084751 filed Nov. 25, 2008 Search Report dated May 20, 2009.
PCT/US2008/084751 filed Nov. 25, 2008 Written Opinion dated May 20, 2009.
PCT/US2009/033116 filed Feb. 4, 2009 International Preliminary Report on Patentability dated Aug. 10, 2010.
PCT/US2009/033116 filed Feb. 4, 2009 Search Report dated Mar. 13, 2009.
PCT/US2009/033116 filed Feb. 4, 2009 Written Opinion dated Mar. 13, 2009.
PCT/US2009/041051 filed Apr. 17, 2009 International Preliminary Report on Patentability dated Apr. 8, 2014.
PCT/US2009/041051 filed Apr. 17, 2009 Search Report dated Jul. 28, 2009.
PCT/US2009/041051 fled Apr. 17, 2009 Written Opinion dated Jul. 28, 2009.
PCT/US2009/054687 filed Aug. 21, 2009 International Preliminary Report on Patentability dated Feb. 22, 2011.
PCT/US2009/054687 filed Aug. 21, 2009 Search Report dated Oct. 6, 2009.
PCT/US2009/054687 filed Aug. 21, 2009 Written Opinion dated Oct. 6, 2009.
PCT/US2009/056567 filed Sep. 10, 2009 International Preliminary Report on Patentability dated Mar. 15, 2011.
PCT/US2009/056567 filed Sep. 10, 2009 Search Report dated Nov. 6, 2009.
PCT/US2009/056567 filed Sep. 10, 2009 Written Opinion dated Nov. 6, 2009.
PCT/US2010/038555 filed Jun. 14, 2010 Search Report dated Oct. 5, 2010.
PCT/US2010/038555 filed Jun. 14, 2010 Written Opinion dated Oct. 5, 2010.
PCT/US2010/045084 filed Aug. 10, 2010 International Preliminary Report on Patentability dated Feb. 23, 2012.
PCT/US2010/045084 filed Aug. 10, 2010 Search Report dated Apr. 14, 2011.
PCT/US2010/045084 filed Aug. 10, 2010 Written Opinion dated Apr. 14, 2011.
PCT/US2010/050773 filed Sep. 29, 2010 Search Report dated Jan. 24, 2011.
PCT/US2010/050773 filed Sep. 29, 2010 Written Opinion dated Jan. 24, 2011.

(56) References Cited

OTHER PUBLICATIONS

PCT/US2010/051917 filed Oct. 8, 2010 Search Report dated Nov. 29, 2010.
PCT/US2010/051917 filed Oct. 8, 2010 Written Opinion dated Nov. 29, 2010.
PCT/US2011/023497 filed Feb. 2, 2011 Search Report dated Jun. 6, 2011.
PCT/US2011/023497 filed Feb. 2, 2011 Written Opinion dated Jun. 6, 2011.
PCT/US2011/038391 filed May 27, 2011 International Preliminary Report on Patentability and Written Opinion dated Dec. 4, 2012.
PCT/US2011/038391 filed May 27, 2011 International Search Report dated Sep. 21, 2011.
PCT/US2011/038415 filed May 27, 2011 International Preliminary Report on Patentability dated Dec. 13, 2012.
PCT/US2011/038415 filed May 27, 2011 International Search Report dated Sep. 28, 2011.
PCT/US2011/038415 filed May 27, 2011 Written Opinion dated Sep. 28, 2011.
PCT/US2011/047127 filed Aug. 9, 2011 International Preliminary Report on Patentability dated Apr. 18, 2013.
PCT/US2011/047127 filed Aug. 9, 2011 International Search Report dated Feb. 29, 2012.
PCT/US2011/047127 filed Aug. 9, 2011 Written Opinion dated Feb. 29, 2012.
PCT/US2011/048403 filed Aug. 19, 2011 International Preliminary Report on Patentability dated Jul. 30, 2013.
PCT/US2011/048403 filed Aug. 19, 2011 International Search Report dated Dec. 15, 2011.
PCT/US2011/048403 filed Aug. 19, 2011 Written Opinion dated Dec. 15, 2011.
PCT/US2011/052793 filed Sep. 22, 2011 International Preliminary Report on Patentability dated Apr. 4, 2013.
PCT/US2011/052793 filed Sep. 22, 2011 International Search Report dated Jan. 6, 2012.
PCT/US2011/052793 filed Sep. 22, 2011 Written Opinion dated Jan. 6, 2012.
U.S. Appl. No. 13/336,919, filed Dec. 23, 2011 Non-Final Office Action dated Dec. 27, 2013.
U.S. Appl. No. 13/336,919, filed Dec. 23, 2011 Non-Final Office Action dated Jul. 9, 2015.
U.S. Appl. No. 13/336,919, filed Dec. 23, 2011 Non-Final Office Action dated Oct. 16, 2012.
U.S. Appl. No. 13/336,919, filed Dec. 23, 2011 Notice of Allowance dated Jul. 26, 2016.
U.S. Appl. No. 13/337,987, filed Dec. 27, 2011 Examiner's Answer dated Jul. 2, 2014.
U.S. Appl. No. 13/337,987, filed Dec. 27, 2011 Final Office Action dated Sep. 19, 2013.
U.S. Appl. No. 13/337,987, filed Dec. 27, 2011 Non-Final Office Action dated Mar. 15, 2013.
U.S. Appl. No. 13/469,932, filed May 11, 2012 Advisory Action dated Jun. 27, 2016.
U.S. Appl. No. 13/469,932, filed May 11, 2012 Non-Final Office Action dated Jan. 3, 2014.
U.S. Appl. No. 13/469,932, filed May 11, 2012 Non-Final Office Action dated Jul. 31, 2014.
U.S. Appl. No. 13/469,932, filed May 11, 2012 Non-Final Office Action dated Sep. 4, 2015.
U.S. Appl. No. 13/469,932, filed May 11, 2012 Notice of Allowance dated Jan. 31, 2017.
U.S. Appl. No. 13/469,932, filed May 11, 2012 Final Office Action dated Apr. 7, 2016.
U.S. Appl. No. 13/665,420, filed Oct. 31, 2012 Final Office Action dated Apr. 8, 2016.
U.S. Appl. No. 13/665,420, filed Oct. 31, 2012 Non-Final Office Action dated Jan. 6, 2014.
U.S. Appl. No. 13/665,420, filed Oct. 31, 2012 Non-Final Office Action dated Jul. 9, 2015.
U.S. Appl. No. 13/665,420, filed Oct. 31, 2012 Non-Final Office Action dated Mar. 15, 2017.
U.S. Appl. No. 13/665,420, filed Oct. 31, 2012 Non-Final Office Action dated Oct. 9, 2014.
U.S. Appl. No. 13/737,806, filed Jan. 9, 2013 Notice of Allowance dated Oct. 31, 2013.
U.S. Appl. No. 13/858,782, filed Apr. 8, 2013 Notice of Allowance dated Oct. 9, 2014.
U.S. Appl. No. 13/887,166, filed May 3, 2013 Advisory Action dated Aug. 27, 2014.
U.S. Appl. No. 13/887,166, filed May 3, 2013 Appeal Decision dated Aug. 17, 2017.
U.S. Appl. No. 13/887,166, filed May 3, 2013 Examiner's Answer dated Jul. 16, 2015.
U.S. Appl. No. 13/887,166, filed May 3, 2013 Final Office Action dated Jun. 23, 2014.
U.S. Appl. No. 13/887,166, filed May 3, 2013 Non-Final Office Action dated Jan. 7, 2014.
U.S. Appl. No. 13/887,166, filed May 3, 2013 Notice of Allowance dated Nov. 6, 2017.
U.S. Appl. No. 13/890,158, filed May 8, 2013 Advisory Action dated Jul. 26, 2016.
U.S. Appl. No. 13/890,158, filed May 8, 2013 Non-Final Office Action dated Apr. 7, 2017.
U.S. Appl. No. 13/890,158, filed May 8, 2013 Non-Final Office Action dated Aug. 15, 2014.
U.S. Appl. No. 13/890,158, filed May 8, 2013 Non-Final Office Action dated Jul. 9, 2015.
U.S. Appl. No. 13/969,265, filed Aug. 16, 2013 Non-Final Office Action dated Dec. 19, 2013.
U.S. Appl. No. 13/969,265, filed Aug. 16, 2013 Notice of Allowance dated Jun. 23, 2014.
U.S. Appl. No. 14/040,205, filed Sep. 27, 2013 Advisory Action dated Dec. 15, 2016.
U.S. Appl. No. 14/040,205, filed Sep. 27, 2013 Examiner's Answer dated Jul. 20, 2017.
U.S. Appl. No. 14/040,205, filed Sep. 27, 2013 Final Office Action dated Oct. 19, 2016.
U.S. Appl. No. 14/040,205, filed Sep. 27, 2013 Non-Final Office Action dated Mar. 10, 2016.
U.S. Appl. No. 14/054,700, filed Oct. 15, 2013 Advisory Action dated Dec. 15, 2016.
U.S. Appl. No. 14/054,700, filed Oct. 15, 2013 Examiner's Answer dated Jul. 3, 2017.
U.S. Appl. No. 14/054,700, filed Oct. 15, 2013 Final Office Action dated Oct. 19, 2016.
U.S. Appl. No. 14/141,046, filed Dec. 26, 2013 Advisory Action dated Aug. 4, 2016.
U.S. Appl. No. 14/141,046, filed Dec. 26, 2013 Final Office Action dated May 11, 2016.
U.S. Appl. No. 14/141,046, filed Dec. 26, 2013 Non-Final Office Action dated Apr. 7, 2017.
U.S. Appl. No. 14/141,046, filed Dec. 26, 2013 Non-Final Office Action dated Feb. 11, 2015.
U.S. Appl. No. 14/141,046, filed Dec. 26, 2013 Non-Final Office Action dated Jun. 20, 2014.
U.S. Appl. No. 14/141,046, filed Dec. 26, 2013 Non-Final Office Action dated Nov. 5, 2015.
U.S. Appl. No. 14/201,300, filed Mar. 7, 2014 Advisory Action dated Jul. 18, 2016.
U.S. Appl. No. 14/201,300, filed Mar. 7, 2014 Advisory Action dated Mar. 2, 2017.
U.S. Appl. No. 14/201,300, filed Mar. 7, 2014 Final Office Action dated Dec. 19, 2016.
U.S. Appl. No. 14/201,300, filed Mar. 7, 2014 Final Office Action dated Jul. 10, 2017.
U.S. Appl. No. 14/201,300, filed Mar. 7, 2014 Final Office Action dated May 5, 2016.
U.S. Appl. No. 12/854,083, filed Aug. 10, 2010 Advisory Action dated Sep. 8, 2014.
U.S. Appl. No. 12/854,083, filed Aug. 10, 2010 Final Office Action dated Aug. 15, 2013.

(56) References Cited

OTHER PUBLICATIONS

U.S. Appl. No. 12/854,083, filed Aug. 10, 2010 Final Office Action dated Aug. 21, 2015.
U.S. Appl. No. 12/854,083, filed Aug. 10, 2010 Final Office Action dated Jul. 1, 2014.
U.S. Appl. No. 12/854,083, filed Aug. 10, 2010 Non-Final Office Action dated Feb. 1, 2016.
U.S. Appl. No. 12/854,083, filed Aug. 10, 2010 Non-Final Office Action dated Jan. 29, 2013.
U.S. Appl. No. 12/854,083, filed Aug. 10, 2010 Non-Final Office Action dated Jan. 29, 2014.
U.S. Appl. No. 12/854,083, filed Aug. 10, 2010 Non-Final Office Action dated Mar. 16, 2015.
U.S. Appl. No. 12/878,915, filed Sep. 9, 2010 Final Office Action dated Sep. 26, 2012.
U.S. Appl. No. 12/878,915, filed Sep. 9, 2010 Non-Final Office Action dated Mar. 15, 2012.
U.S. Appl. No. 12/878,915, filed Sep. 9, 2010 Notice of Allowance dated Jan. 8, 2013.
U.S. Appl. No. 12/893,916, filed Sep. 29, 2010 Advisory Action dated Aug. 15, 2014.
U.S. Appl. No. 12/893,916, filed Sep. 29, 2010 Advisory Action dated Jun. 2, 2016.
U.S. Appl. No. 12/893,916, filed Sep. 29, 2010 Final Office Action dated Jan. 15, 2015.
U.S. Appl. No. 12/893,916, filed Sep. 29, 2010 Final Office Action dated Jun. 18, 2014.
U.S. Appl. No. 12/893,916, filed Sep. 29, 2010 Final Office Action dated Mar. 25, 2016.
U.S. Appl. No. 12/893,916, filed Sep. 29, 2010 Non-Final Office Action dated Aug. 31, 2016.
U.S. Appl. No. 12/893,916, filed Sep. 29, 2010 Non-Final Office Action dated Dec. 24, 2013.
U.S. Appl. No. 12/893,916, filed Sep. 29, 2010 Non-Final Office Action dated Sep. 10, 2015.
U.S. Appl. No. 12/893,916, filed Sep. 29, 2010 Non-Final Office Action dated Sep. 25, 2014.
U.S. Appl. No. 12/900,750, filed Oct. 8, 2010 Non-Final Office Action dated Jun. 3, 2013.
U.S. Appl. No. 13/019,939, filed Feb. 2, 2011 Final Office Action dated Apr. 2, 2014.
U.S. Appl. No. 13/019,939, filed Feb. 2, 2011 Non-Final Office Action dated Feb. 9, 2015.
U.S. Appl. No. 13/019,939, filed Feb. 2, 2011 Non-Final Office Action dated Oct. 11, 2013.
U.S. Appl. No. 13/118,033, filed May 27, 2011 Final Office Action dated Apr. 1, 2016.
U.S. Appl. No. 13/118,033, filed May 27, 2011 Non-Final Office Action dated Aug. 1, 2013.
U.S. Appl. No. 13/118,033, filed May 27, 2011 Non-Final Office Action dated Feb. 3, 2015.
U.S. Appl. No. 13/118,033, filed May 27, 2011 Non-Final Office Action dated Jul. 8, 2015.
U.S. Appl. No. 13/118,033, filed May 27, 2011 Non-Final Office Action dated May 22, 2014.
U.S. Appl. No. 13/118,033, filed May 27, 2011 Notice of Allowance dated Sep. 2, 2016.
U.S. Appl. No. 13/118,138, filed May 27, 2011 Final Office Action dated Apr. 1, 2016.
U.S. Appl. No. 13/118,138, filed May 27, 2011 Final Office Action dated Apr. 3, 2013.
U.S. Appl. No. 13/118,138, filed May 27, 2011 Non-Final Office Action dated Jul. 15, 2015.
U.S. Appl. No. 13/118,138, filed May 27, 2011 Non-Final Office Action dated Oct. 3, 2012.
U.S. Appl. No. 13/118,138, filed May 27, 2011 Non-Final Office Action dated Oct. 9, 2014.
U.S. Appl. No. 13/213,622, filed Aug. 19, 2011 Final Office Action dated Feb. 19, 2013.
U.S. Appl. No. 13/213,622, filed Aug. 19, 2011 Non-Final Office Action dated Jul. 31, 2012.
U.S. Appl. No. 13/213,622, filed Aug. 19, 2011 Non-Final Office Action dated May 22, 2014.
U.S. Appl. No. 13/240,171, filed Sep. 22, 2011 Advisory Action dated Aug. 18, 2015.
U.S. Appl. No. 13/240,171, filed Sep. 22, 2011 Advisory Action dated Jul. 22, 2016.
U.S. Appl. No. 13/240,171, filed Sep. 22, 2011 Final Office Action dated Jun. 10, 2015.
U.S. Appl. No. 13/240,171, filed Sep. 22, 2011 Final Office Action dated May 6, 2016.
U.S. Appl. No. 13/240,171, filed Sep. 22, 2011 Non-Final Office Action dated Dec. 1, 2015.
U.S. Appl. No. 13/240,171, filed Sep. 22, 2011 Non-Final Office Action dated Dec. 26, 2014.
U.S. Appl. No. 13/283,395, filed Oct. 27, 2011 Advisory Action dated Jan. 28, 2014.
U.S. Appl. No. 13/283,395, filed Oct. 27, 2011 Final Office Action dated Nov. 14, 2013.
U.S. Appl. No. 13/283,395, filed Oct. 27, 2011 Non-Final Office Action dated Apr. 23, 2013.
U.S. Appl. No. 13/336,919, filed Dec. 23, 2011 Advisory Action dated May 23, 2013.
U.S. Appl. No. 13/336,919, filed Dec. 23, 2011 Final Office Action dated Dec. 19, 2014.
U.S. Appl. No. 13/336,919, filed Dec. 23, 2011 Final Office Action dated Mar. 1, 2013.
CN 201580007645.0 filed Aug. 8, 2016 Office Action dated Sep. 12, 2018.
CN 201610127217.8 filed Mar. 7, 2016 Office Action dated Nov. 19, 2018.
EP 10786978.6 filed Dec. 19, 2011 Office Action dated Jan. 16, 2019.
EP 11850625.2 filed Jul. 22, 2013 Office Action dated Feb. 25, 2019.
EP 14197137.4 filed Dec. 10, 2014, Office Action dated Nov. 21, 2018.
EP 15746326.6 filed Jul. 1, 2016 Office Action dated Jan. 29, 2019.
EP14197136.6 filed Dec. 10, 2014 Office Action dated Nov. 21, 2018.
KR 10-2014-7002789 filed Feb. 3, 2014 Office Action dated Feb. 22, 2019.
RU 2015110633 filed Mar. 26, 2015 Office Action dated Oct. 25, 2018.
U.S. Appl. No. 14/040,205, filed Sep. 27, 2013 Board Decision dated May 1, 2019.
U.S. Appl. No. 14/054,700, filed Oct. 15, 2013 Board Decision dated May 1, 2019.
U.S. Appl. No. 14/201,300, filed Mar. 7, 2014 Board Decision dated Apr. 12, 2019.
U.S. Appl. No. 141/88,305, filed Jun. 30, 2015 Notice of Allowance dated Nov. 15, 2018.
U.S. Appl. No. 14/996,247, filed Jan. 15, 2016 Restriction Requirement dated Mar. 22, 2019.
U.S. Appl. No. 15/284,355, filed Oct. 3, 2016 Notice of Allowance dated Feb. 21, 2019.
U.S. Appl. No. 15/365,698, filed Nov. 30, 2016 Non-Final Office Action dated Apr. 18, 2019.
U.S. Appl. No. 15/365,872, filed Nov. 30, 2016 Notice of Allowance dated Dec. 21, 2018.
U.S. Appl. No. 15/585,051, filed May 2, 2017 Examiner's Answer dated May 2, 2019.
Chen, Zhongping et al, Optical Doppler Tomography: Imaging in vivo Blood Flow Dynamics Following Pharmacological Intervention and Photodynamic Therapy, 7 pages, vol. 67, Photochemistry and Photobiology, 1998.
Cheng, Ki et al, A Novel Approach of Intravenous Electrocardiograph Technique in Correct Position the Long-Term Central Venous Catheter, Kaohsiung J Med Sci, pp. 241-247, vol. 16 No. 5, May 2000 (Abstract only).
Cheung, P., et al., The Effect of a Disposable Probe Cover on Pulse Oximetry, Anaesth Intensive Care 2002; 30: 211-214.

(56) References Cited

OTHER PUBLICATIONS

Chu, et al., "Accurate Central Venous Port—A Catheter Placement: Intravenous Electrocardiography and Surface Landmark Techniques Compared by Using Transesophageal Echocardiography." The International Anesthesia Research Society, vol. 98, pp. 910-914, 2004.
Claasz, Antonia et al, A Study of the Relationship of the Superior Vena Cava to the Bony Landmarks of the Sternum in the Supine Adult: Implications for Magnetic Guidance Systems, Journal, vol. 12 No. 3, JAVA, Jul. 24, 2007.
Clifford, et al. "Assessment of Hepatic Motion Secondary to Respiration for Computer Assisted Interventions." Computer Aided Surgery, vol. 7, pp. 291-299, 2002.
CN 200880012117.4 filed Apr. 16, 2008 First Office Action dated Dec. 23, 2011.
CN 200880012117.4 filed Apr. 16, 2008 Fourth Office Action dated Sep. 4, 2013.
CN 200880012117.4 filed Apr. 16, 2008 Second Office Action dated Oct. 8, 2012.
CN 200880012117.4 filed Apr. 16, 2008 Third Office Action dated Apr. 27, 2013.
CN 200880125528.4 filed Nov. 25, 2008 First Office Action dated Jun. 5, 2012.
CN 200880125528.4 filed Nov. 25, 2008 Second Office Action dated Mar. 6, 2013.
CN 200880125528.4 filed Nov. 25, 2008 Third Office Action dated Jul. 1, 2013.
CN 200980123021.X filed Dec. 17, 2010 First Office Action dated Nov. 19, 2012.
CN 200980123021.X filed Dec. 17, 2010 Second Office Action dated Aug. 13, 2011.
CN 200980123021.X filed Dec. 17, 2010 Third Office Action dated Apr. 22, 2014.
CN 200980144663.8 filed May 9, 2011 Decision of Re-Examination dated Feb. 21, 2017.
CN 200980144663.8 filed May 9, 2011 Fifth Office Action dated May 26, 2015.
CN 200980144663.8 filed May 9, 2011 First Office Action dated Dec. 5, 2012.
CN 200980144663.8 filed May 9, 2011 Fourth Office Action dated Nov. 15, 2014.
CN 200980144663.8 filed May 9, 2011 Notice of Reexamination dated Aug. 5, 2016.
CN 200980144663.8 filed May 9, 2011 Second Office Action dated Aug. 22, 2013.
CN 200980144663.8 filed May 9, 2011 Third Office Action dated May 4, 2014.
CN 201080035659.0 filed Feb. 10, 2012 First Office Action dated Jan. 26, 2014.
CN 201080035659.0 filed Feb. 10, 2012 Second Office Action dated Oct. 9, 2014.
CN 201080035659.0 filed Feb. 10, 2012 Third Office Action dated Mar. 19, 2015.
CN 201080053838.7 filed May 28, 2012 First Office Action dated Jan. 6, 2014.
CN 201080053838.7 filed May 28, 2012 Fourth Office Action dated Jun. 2, 2015.
CN 201080053838.7 filed May 28, 2012 Second Office Action dated Jun. 17, 2014.
CN 201080053838.7 filed May 28, 2012 Third Office Action dated Dec. 4, 2014.
CN 201180016462.7 filed Sep. 27, 2012 First Office Action dated Mar. 21, 2014.
CN 201180016462.7 filed Sep. 27, 2012 Second Office Action dated Dec. 9, 2014.
CN 201180016462.7 filed Sep. 27, 2012 Third Office Action dated Jun. 10, 2015.
CN 201180037065.8 filed Jan. 28, 2013 First Office Action dated Sep. 28, 2014.
CN 201180037065.8 filed Jan. 28, 2013 Fourth Office Action dated May 5, 2016.
CN 201180037065.8 filed Jan. 28, 2013 Notice of Grant dated Aug. 30, 2016.
CN 201180037065.8 filed Jan. 28, 2013 Second Office Action dated Jun. 2, 2015.
CN 201180037065.8 filed Jan. 28, 2013 Third Office Action dated Nov. 24, 2015.
CN 201180037068.1 filed Jan. 28, 2013 First Office Action dated Apr. 20, 2015.
CN 201180037068.1 filed Jan. 28, 2013 First Office Action dated Sep. 9, 2014.
CN 201180037068.1 filed Jan. 28, 2013 Third Office Action dated Oct. 19, 2015.
CN 201180040151.4 filed Feb. 19, 2013 First Office Action dated Oct. 28, 2014.
CN 201180040151.4 filed Feb. 19, 2013 Office Action dated Dec. 10, 2015.
CN 201180040151.4 filed Feb. 19, 2013 Second Office Action dated Jun. 19, 2015.
CN 201180043512.0 filed Mar. 8, 2013 First Office Action dated Jul. 31, 2014.
CN 201180043512.0 filed Mar. 8, 2013 Second Office Action dated Apr. 14, 2015.
CN 201180052587.5 filed Apr. 28, 2013 First Office Action dated Jan. 26, 2015.
CN 201180052587.5 filed Apr. 28, 2013 Office Action dated Feb. 24, 2016.
CN 201180052587.5 filed Apr. 28, 2013 Second Office Action dated Aug. 19, 2015.
CN 201180068309.9 filed Aug. 22, 2013 First Office Action dated Oct. 16, 2014.
U.S. Appl. No. 14/201,300, filed Mar. 7, 2014 Non-Final Office Action dated Aug. 24, 2016.
U.S. Appl. No. 14/201,300, filed Mar. 7, 2014 Non-Final Office Action dated Jan. 6, 2016.
U.S. Appl. No. 14/201,300, filed Mar. 7, 2014 Non-Final Office Action dated Mar. 30, 2017.
U.S. Appl. No. 14/270,241, filed May 5, 2014 Non-Final Office Action dated Apr. 23, 2015.
U.S. Appl. No. 14/270,241, filed May 5, 2014 Notice of Allowance dated Oct. 7, 2015.
U.S. Appl. No. 14/309,511, filed Jun. 19, 2014 Non-Final Office Action, dated Sep. 24, 2015.
U.S. Appl. No. 14/309,511, filed Jun. 19, 2014 Notice of Allowance, dated Jul. 26, 2016.
U.S. Appl. No. 14/317,501, filed Jun. 27, 2014 Advisory Action dated Sep. 16, 2015.
U.S. Appl. No. 14/317,501, filed Jun. 27, 2014 Examiner's Answer dated Jun. 30, 2016.
U.S. Appl. No. 14/317,501, filed Jun. 27, 2014 Final Office Action dated Jul. 1, 2015.
U.S. Appl. No. 14/317,501, filed Jun. 27, 2014 Non-Final Office Action dated Mar. 3, 2015.
U.S. Appl. No. 14/317,501, filed Jun. 27, 2014 Non-Final Office Action dated Sep. 12, 2014.
U.S. Appl. No. 14/449,061, filed Jul. 31, 2014 Final Office Action dated Nov. 6, 2015.
U.S. Appl. No. 14/449,061, filed Jul. 31, 2014 Non-Final Office Action dated Apr. 27, 2015.
U.S. Appl. No. 14/449,061, filed Jul. 31, 2014 Notice of Allowance dated Apr. 13, 2016.
U.S. Appl. No. 14/498,887, filed Sep. 26, 2014 Advisory Action dated Aug. 22, 2016.
U.S. Appl. No. 14/498,887, filed Sep. 26, 2014 Final Office Action dated Jun. 15, 2016.
U.S. Appl. No. 14/498,887, filed Sep. 26, 2014 Non-Final Office Action dated Feb. 19, 2016.
U.S. Appl. No. 14/506,552, filed Oct. 3, 2014 Non-Final Office Action dated Oct. 1, 2015.
U.S. Appl. No. 14/548,151, filed Nov. 19, 2014 Advisory Action dated Aug. 1, 2017.

(56) References Cited

OTHER PUBLICATIONS

U.S. Appl. No. 14/548,151, filed Nov. 19, 2014 Advisory Action dated Jul. 22, 2016.
U.S. Appl. No. 14/548,151, filed Nov. 19, 2014 Final Office Action dated Apr. 19, 2017.
U.S. Appl. No. 14/548,151, filed Nov. 19, 2014 Non-Final Office Action dated Jun. 5, 2015.
U.S. Appl. No. 14/548,151, filed Nov. 19, 2014 Non-Final Office Action dated Sep. 21, 2017.
U.S. Appl. No. 14/548,151, filed Nov. 19, 2014 Non-Final Office Action dated Sep. 28, 2016.
U.S. Appl. No. 14/615,932, filed Feb. 6, 2015 Non-Final Office dated Dec. 29, 2016.
U.S. Appl. No. 14/788,305, filed Jun. 30, 2015 Restriction Requirement dated Aug. 25, 2017.
U.S. Appl. No. 14/846,496, filed Sep. 4, 2015 Non-Final Office Action dated Nov. 25, 2016.
U.S. Appl. No. 15/160,958, filed May 20, 2016 Advisory Action dated Jul. 10, 2017.
U.S. Appl. No. 15/160,958, filed May 20, 2016 Final Office Action dated Apr. 21, 2017.
U.S. Appl. No. 15/160,958, filed May 20, 2016 Non-Final Office Action dated Dec. 15, 2016.
U.S. Appl. No. 15/160,958, filed May 20, 2016 Notice of Allowance dated Jul. 26, 2017.
U.S. Appl. No. 15/284,355, filed Oct. 3, 2016 Non-Final Office Action dated Apr. 24, 2017.
U.S. Appl. No. 15/585,051, filed May 2, 2017 Non-Final Office Action dated Jul. 14, 2017.
U.S. Appl. No. 29/428,649, filed Aug. 1, 2012 Notice of Allowance dated Jul. 5, 2013.
Valdivieso, J.R. Perez, et al., Evaluation of a formula for optimal positioning of a central venous catheter inserted trough the right internal jugular vein, Rev. Esp. Anestesiol. Reanim. 2003; 50: 77-79.
VasoNova Inc, Vascular navigation system for accurate placement of PICCs, Start-Up Emerging Medical Ventures, pp. 44-45, vol. 14 No. 7, Jul.-Aug. 2009.
Vesely, Thomas M. et al., Central Venous Catheter Tip Position: A Continuing Controversy, J Vasc Intery Radiol 2003; 14:527-534.
VIASYS Health Care Inc. Cortrak® Fact Sheet, 2005.
VIASYS Healthcare MedSystems, Navigator® Benefits, 2008.
VIASYS Healthcare MedSystems, Navigator® Research in Cost Justification, 2008.
VIASYS MedSystems, Cortrak™ Systems Brochure, 2005.
Volcano ComboMap Features and Benefits/Technical Specifications, 2 pages, 2011.
Watters, et al. "Use of Electrocardiogram to Position Right Atrial Catheters During Surgery." Annals of Surgery, vol. V5, No. 2, pp. 165-171, 1997.
Welch Allyn Cardioperfect® PC-Based Resting ECG, 2003.
Wilson, R. G. et al, Right Atrial Electrocardiography in Placement of Central Venous Catheters, The Lancet, pp. 162-463, Feb. 27, 1988.
Wong, Jeffrey J. et al., Azygos Tip Placement for Hemodialysis Catheters in Patients with Superior Vena Cava Occlusion, Cardiovasc Intervent Radiol (2006) 29:143-146.
Worley, Seth J. "Use of a Real-Time Three-Dimensional Magenetic Navigation System for Radiofrequency Ablation of Accessory Pathways." PACE, vol. 21 pp. 1636-1643, Aug. 1998.
Yilmazlar A et al, Complications of 1303 Central Venous Cannulations, J R Soc Med, pp. 319-321, vol. 90 No. 6, Jun. 1997 (Abstract only).
Yoon, SZ et al, Usefulness of the Carina as a Radiographic Landmark for Central Venous Catheter Placement in Paediatric Patients, Br J Anaesth, Jul. 2005.
JP 2012-552060 filed Aug. 1, 2012 Second Office Action dated Nov. 6, 2015.
JP 2013-512046 filed Nov. 26, 2012 First Office Action dated Mar. 23, 2015.
JP 2013-512046 filed Nov. 26, 2012 Office Action dated Dec. 8, 2015.
JP 2013-512046 filed Nov. 26, 2012 Office Action dated May 16, 2016.
JP 2013-512051 filed Nov. 26, 2012 First Office Action dated Mar. 23, 2015.
JP 2013-524999 filed Jan. 22, 2013 First Office Action dated Jun. 1, 2015.
JP 2013-530322 filed Mar. 18, 2013, Office Action dated Mar. 2, 2017.
JP 2014-519081 filed Dec. 27, 2013 First Office Action dated Apr. 26, 2016.
JP 2015-534770 filed Mar. 26, 2015 Office Action dated Jun. 12, 2017.
JP2013-530322 filed Mar. 18, 2013, Office Action dated May 2, 2016.
JP2013-530322 filed Mar. 18, 2013, First Office Action dated Jul. 31, 2015.
Kim, Ko et al, Positioning Internal Jugular Venous Catheters using the Right Third Intercostal Space in Children, Acta Anaesthesiol Scand, pp. 1284-1286, vol. 47 No. 10, Nov. 2003.
Kjelstrup T et al, Positioning of Central Venous Catheters using ECG, Tidssk nor Laegeforen, pp. 599-601, vol. 111 No. 5, Feb. 1999 (Abstract only).
Kofler, Julia, et al., Epinephrine application via an endotracheal airway and via the Combitube in esophageal position, Critical Care Medicine: May 2000, vol. 28: Issue 5, pp. 1445-1449.
Konings, MK, et al., Development of an intravascular impedance catheter for detection of fatty lesions in arteries, IEEE Trans Med Imaging Aug. 1997; 16(4):439-46.
Kowalski, CM et al, Migration of Central Venous Catheters: Implications for Initial Catheter Tip Positioning, J Vasc Intery Radiol, pp. 443-447, vol. 8 No. 3, May-Jun. 1997.
KR 10-2012-7000866 filed Jan. 11, 2012 First Office Action dated Jun. 16, 2016.
KR 10-2012-7000866 filed Jan. 11, 2012 Second Office Action dated Nov. 3, 2016.
KR 10-2013-7006933 filed Mar. 19, 2013 Office Action dated Aug. 7, 2017.
Leowenthal, MR et al, The Peripherally Inserted Central Catheter (PICC): A Prospective Study of its Natural History after Fossa Insertion, Anaesth Intensive Care, pp. 21-24; vol. 30 No. 1, Feb. 2002.
Lepage Ronan et al. ECG Segmentation and P-wave Feature Extraction: Application to Patients Prone to Atrial Fibrillation, IEEE/EMBS Proceedings, 23rd Annual Conference, Istanbul, Turkey, Oct. 25-28, 2001.
Liu , Ji-Bin et al, Catheter-Based Intralumincal Sonography, J Ultrasound Med, pp. 145-160, vol. 23, 2004.
Lucey, B et al, Routine Chest Radiographs after Central Line Insertion: Mandatory Postprocedural Evaluation or Unnecessary Waste of Resources?, Cardiovasc Intervent Radiol, pp. 381-384, vol. 22 No. 5, Sep.-Oct. 1999.
Lum, Phillip, A New Formula-Based Measurement Guide for Optimal Positioning of Central Venous Catheters, JAVA, vol. 9, No. 2, pp. 80-85, 2004.
Lynch, RE et al, A Procedure for Placing Pediatric Femoral Venous Catheter Tips near the Right Atrium, Pediatr Emerg Care, pp. 130-132, vol. 18 No. 2, Apr. 2002.
Madan, et al. "Right Atrial Electrocardiography: A Technique for the Placement of Central Venous Catheters for Chemotherapy or Intravenous Nutrition." British Journal of Surgery, vol. B1, pp. 1604-1605, 1994.
Madias, John E, Intracardiac (Superior Vena Cava/Right Atrial) ECGs using Saline Solution as the Conductive Medium for the Proper Positioning of the Shiley Hemodialysis Catheter: Is it Not Time to Forego the Postinsertion Chest Radiograph?, pp. 2363-2367, CHEST, 2003.
Markovich, Mary B., Central Venous Catheter Tip Placement: Determination of Posterior Malposition—A Case Study, JAVA, vol. 11, No. 2, pp. 85-89, 2006.

(56) References Cited

OTHER PUBLICATIONS

Martin, Roy W, An Ultrasoundic Catheter for Intravascular Measurement of Blood Flow: Technical Details, IEEE Transactions on Sonics and Ultrasonics, vol. SU-27, No. 6, pp. 277-286, Nov. 1980.
McDonnall, "Intra-Atrial Electrocardiography (ECG) for Catheter Placement." Literature review prepared for Bard Access Systems, Oct. 2007.
McGee et al., "Accurate Placement of Central Venous Catheters: A Prospective, Randomize, Multicenter Trail." critical Care Medicine, vol. 21 No. 8, Aug. 1993.
MedGraphics, CardioPerfect® Resting/Stress ECG System, 3 pages, 2001.
Michenfelder, John et al, Air Embolism During Neurosurgery—An Evaluation of Right-Atrial Catheters for Diagnosis and Treatment, JAMA, pp. 1353-1358, vol. 208, No. 8, May 26, 1969.
Michenfelder, John et al, Air Embolism During Neurosurgery. A New Method of Treatment, Anesthesia and Analgesia. Current Researches, pp. 390-395, vol. 45, No. 4, Jul.-Aug. 1966.
Microbird™ Miniaturized DC Magnetic Sensors for Intra-body Navigation and Localization, Specifications, 2005.
Micronix CathRite™ Cardiac Access Device Brochure. Jun. 2004.
Micronix Pty Ltd "CathRite" Guiding Styled Core Manufacturing, Jun. 15, 2006.
Moureau, Nancy L. et al., "Electrocardiogram (EKG) Guided Peripherally Inserted Central Catheter Placement and Tip Position: Results of a Trial to Replace Radiological Confirmation," Journal of the Association for Vascular Access, pp. 8-14, vol. 15, No. 1, 2010.
Murthy, Vrudhula et al, Analysis of Power Spectral Densities of Electrocardiograms, Mathematical Biosciences, pp. 41-51, vol. 12 No. 1-2, Oct. 1971.
MX/a/2012/013672 filed Nov. 23, 2012 First Office Action dated Aug. 10, 2015.
MX/a/2012/013858 filed Nov. 28, 2012 First Office Action dated Sep. 26, 2014.
MX/a/2012/013858 filed Nov. 28, 2012 Second Office Action dated Jun. 10, 2015.
MX/a/2013/001317 filed Jan. 31, 2013 First Office Action dated Nov. 26, 2015.
Nadroo, AM et al, Changes in Upper Extremity Position Cause Migration of Peripherally Inserted Central Catheters in Neonates, Pediatrics, pp. 131-136, vol. 110, Jul. 2002.
Nakatani, K et al, Accurate Placement of Central Venous Catheters—ECG-guided method vs Patient Height Method, MASUI, pp. 34-38, vol. 51 No. 1, Jan. 2002.
Nazarian, GK et al, Changes in Tunneled Catheter Tip Position when a patient is Upright, J Vasc Intery Radiol, pp. 437-441, vol. 8 No. 3, May-Jun. 1997.
Neurometer® CPT, Clinical Applications. Neurotron , Inc. website: www.neurotron.com/CLINAPS.html, last accessed Oct. 23, 2006.
Neurometer® CPT, Frequently Asked Questions. Neurotron , Inc. website: www.neurotron.com/CPTFAQ/html, last accessed Oct. 23, 2006.
Neurometer® CPT, Products Page. Neurotron , Inc. website: www.neurotron.com/products.html, last accessed Oct. 23, 2006.
Neurometer® Electrodiagnostic Neuroselective Sensory Nerve Evaluation: Charts, Tables, Documents & Downloads. Neurotron , Inc. website: www.neurotron.com/downloads.html, last accessed Oct. 23, 2006.
PCT/US2011/058138 filed Oct. 27, 2011 International Preliminary Report on Patentability dated May 10, 2013.
PCT/US2011/058138 filed Oct. 27, 2011 International Search Report dated Feb. 7, 2012.
PCT/US2011/058138 filed Oct. 27, 2011 Written Opinion dated Feb. 7, 2012.
PCT/US2011/067268 filed Dec. 23, 2011 International Preliminary Report on Patentability dated Jul. 4, 2013.
PCT/US2011/067268 filed Dec. 23, 2011 International Search Report and Written Opinion dated Apr. 27, 2012.
PCT/US2012/045814 filed Jul. 6, 2012 International Search Report and Written Opinion dated Oct. 1, 2012.
PCT/US2013/065121 filed Oct. 15, 2013 International Search Report and Written Opinion dated Jan. 16, 2014.
PCT/US2014/022019 filed Mar. 7, 2014 International Search Report and Written Opinion dated Jun. 11, 2014.
PCT/US2015/014795 filed Feb. 6, 2015 International Search Report and Written Opinion dated May 14, 2015.
PCT/US2016/039356 filed Jun. 24, 2016 International Search Report and Written Opinion dated Sep. 16, 2016.
Pennington, C.R., Right Atrial Thrombus: a Complication of Total Parenteral Nutrition, British Medical Journal, pp. 446-447, vol. 295, Aug. 15, 1987.
Petersen, J et al, Silicone Venous Access Devices Positioned with their Tip High in the Superior Vena Cava are More Likely to Malfunction, Am J Surg, pp. 38-41, vol. 178 No. 1, Jul. 1999.
Pittiruti, et al, "The intracavitary ECG method for positioning the tip of central venous catheters: results of an Italian multicenter study," J Vasc Access, pp. 1-9, Nov. 21, 2011.
Pittiruti, et al, Intracavitary EKG Monitoring: A reliable method for controlling tip position during and after PICC Insertion presentation in Catholic University, Rome, Italy in 2008.
Pittiruti, et al. "The EKG Method for Positioning the Tip of PICCs: Results from Two Preliminary Studies." JAVA, vol. 13, No. 4, pp. 179-185, 2008.
Pittiruti, et al. "The electrocardiographic method for positioning the tip of central venous catheters" JAVA, pp. 1-12, Feb. 12, 2011.
Polos, PG et al, Tips for Monitoring the Position of a Central Venous Catheter—How Placement can go awry—even when the anatomy is normal, J Crit Illn, pp. 660-674, vol. 8 No. 6, Jun. 1993 (Abstract only).
Pop, Gheorghe A. et al., Catheter-based impedance measurements in the right atrium for continuously monitoring hematocrit and estimating blood viscosity changes; an in vivo feasibility study in swine, Biosensors and Bioelectronics 19 (2004) 1685-1693.
Popp, M. B. et al., Accuracy of implanted port placement with the use of the electromagnetic CathTrack® catheter locator system, The Journal of Vascular Access 2005; 6: 9-12.
Randolph AG et al, Ultrasound guidance for placement of central venous catheters: a meta-analysis of the literature, Critcal Care Medicine, pp. 2053-2058, vol. 24, Dec. 1996.
Reece, A et al, Posititioning Long Lines: Contrast Versus Plain Radiography, Arch Dis Child Fetal Neonatal Ed, pp. 129-130, vol. 84 No. 2, Mar. 2001.
Reynolds, N et al, Assessment of Distal Tip Position of Long Term Central Venous Feeding Catheters using Transesophageal Echocardiology, JPEN J Parenter Enteral Nutr, pp. 39-41, vol. 25 No. 1, Jan.-Feb. 2001.
RU 2011150917 filed Dec. 15, 2011 First Office Action dated Apr. 24, 2014.
RU 2011150917 filed Dec. 15, 2011 Second Office Action dated Aug. 28, 2014.
RU 2013158008 filed Dec. 26, 2013 First Office Action dated May 27, 2016.
RU 2015111669 filed Apr. 1, 2015 Office Action dated Sep. 5, 2017.
Ruschulte, Heiner et al, Prevention of Central Venous Catheter related infections with chlorhex idine gluconate impregnated wound dressings: A randomized controlled trial, presented as an abstract at the Annual meeting of the European Society of Anaesthesiologists (ESA) in Madrid, Spain in Jun. 2006, 12 pages, Annals of Hematology, Jul. 14, 2008.
Rutherford, J. S. et al., Depth of Central Venous Catheterization: An Audit of Practice in a Cardiac Surgical Unit, Anaesth Intens Care 1994; 22: 267-271.
Sacolick, et al. "Electromagnetically Tracked Placement of a Peripherally Inserted Central Catheter." SPIE Medical Imaging, 2004 Proceedings.
Salem, et al. "A New Peripherally Implanted Subcutaneous Permanent Central Venous Access Device for Patients Requiring Chemotherapy." Journal of Clinical Oncology, vol. 11, No. 11, pp. 2181-2185, Nov. 1993.
Savary, D et al, Intra-atrial Monitoring to Add Insertion of a Central Venous Line in Pre-Hospital Emergency Care Journal Europeen des Urgences, pp. 75-78, vol. 17 No. 2, 2004.

(56) References Cited

OTHER PUBLICATIONS

Schafer et al. "Incorrect placement of a vena cava catheter and its prevention by intra-atrial ECG." Anaesthesist. Jan. 1988;37(1):49-51.
Schummer, et al. "Central Venous Catheters—The inability of 'intra-atrial ECG' to prove adequate positioning." British Journal of Anaesthesia, vol. 93, No. 2, pp. 193-198, 2004.
Schummer, W et al, ECG-guided Central Venous Catheter Positioning: Does it detect the Pericardial Reflection rather than the Right Atrium?, Eur J Anaesthesiol, pp. 600-605, vol. 21 No. 8, Aug. 2004 (Abstract only).
Schummer, W et al, Intra-Atrial ECG is not a Reliable Method for Positioning Left Internal Jugular Vein Catheters, Br J Anaesth, pp. 481-486, vol. 91 No. 4, Oct. 2003.
Schummer, W, Central Venous Catheter—the Inability of "Intra-Atrial ECG" to prove Adequate Positioning, Br J Anaesth, pp. 193-198, vol. 93 No. 2, Aug. 2004.
Schuster, M. et al., The carina as a landmark in central venous catheter placement, British Journal of Anaesthesia 85 (2): 192-4 (2000).
Siela, Debra, Using Chest Radiography in the Intensive Care Unit, Crit Care Nurse Aug. 1, 2002 vol. 22 No. 4, pp. 18-27.
Simon, et al., "Central Venous Catheter Placement in Children: Evaluation of Electrocardiography Using J-Wire." Paediatric Anaesthesia vol. 9, pp. 501-504, 1999.
Smith, Brigham, et al., Intravenous electrocardiographic guidance for placement of peripherally inserted central catheters, Journal of Electrocardiology 43 (2010) 274-278.
Stark, DD et al, Radiographic Assessment of Venous Catheter Position in Children: Value of the Lateral View, Pediatric Radiology, pp. 76-80, vol. 14 No. 2, 1984.
Starkhammar et al. "Cath-Finder Catheter Tracking System: A New Device for Positioning of Central Venous catheters. Early Experience from Implantation of Brachial portal Systems." Acta Anaesthesiol Scandinavia, vol. 34, No. 4 pp. 296-300, May 1990.
Starkhammer, H et al, Central Venous Catheter Placement using Electromagnetic Position Sensing: A Clinical Evaluation, Biomed. Instrum Technol, vol. 30 No. 2, pp. 164-170; Mar.-Apr. 1996.
Starr, David S et al, EKG Guided Placement of Subclavian CVP Catheters Using J-Wire, pp. 673-676, Ann. Surg, Dec. 1986.
Stas, M et al, Peroperative Intravasal Electrographic Control of Catheter Tip Position in Access Ports Placed by Venous Cut-Down Technique, EJSO, pp. 316-320, vol. 27, 2001.
Stereotaxis Magetic Navigation System with Navigan™ User Interface, 2005 Brochure.
Stereotaxis, Expanding the Possibilites of Interventional Medicine: Remote Navigation and Automation, pp. 1-8, Apr. 2011.
Tepa® Health Innovation PC based ECG System Introduction and Technical Specifications, EKG Master USB, 2 pages, Nov. 2003.
The FloWire Doppler Guide Wire located <http://www.volcanocorp.com/products/flowire-doppler-guide-wire.php>, 2011.
Traxal Technologies, Tracking Technology website overview: www.traxal.com/rd/rd_classroom_trackingtechnology.htm, last accessed Dec. 1, 2006.
Yoshida, Teruhisa et al, Detection of Concealed Left Sided Accessory Atrioventricular Pathway by P Wave Signal Averaged Electrocardiogram, J Am Coll Cardiol, pp. 55-62, 1999.
Zaaroor, et al. "Novel Magnetic Technology for Intraoperative Intracranial Frameless Navigation: In Vivo and in Vitro Results." Neurosurgery, vol. 48, No. 5. pp. 1100-1107, May 2001.
Zachariou, Zacharias et al., Intra-atrial ECG recording: a new and safe method for implantation of Broviac catheters in children, Pediatr Surg Int (1994) 9: 457-458.
Zaidi, Naveed A., et al. "Room temperature magnetic order in an organic magnet derived from polyaniline." 2004, Polymer, vol. 45, pp. 5683-5689.
AZoMaterials. Nickel-Based Super Alloy Inconel 625—Properties and Applications by United Performance Alloys. Oct. 27, 2015. Last accessed Mar. 23, 2018. <URL:https:I/web.archive.org/web/20151027202821/https://www.azom.com/article.aspx?ArticleID=4461>.
CA 2800810 filed Nov. 26, 2012 Office Action dated Mar. 13, 2018.
CA 2800813 filed Nov. 26, 2012 Office Action dated Mar. 5, 2018.
CN 201380051172.5 filed Mar. 30, 2015 Office Action dated Jan. 16, 2018.
CN 201380051172.5 filed Mar. 30, 2015 Office Action dated Jul. 30, 2018.
CN 201480010988.8 filed Aug. 27, 2015 Office Action dated Aug. 17, 2018.
CN 201480010988.8 filed Aug. 27, 2015 Office Action dated Dec. 13, 2017.
CN 201610127217.8 filed Mar. 7, 2016 Office Action dated Dec. 28, 2017.
CN 201610127217.8 filed Mar. 7, 2016 Office Action dated Jun. 11, 2018.
CN 201610166569.4 filed Dec. 23, 2010, Office Action dated Nov. 1, 2017.
Enrique Company-Bosch, "ECG Front-End Design is Simplified with MicroConverter." Analog Dialogue 37-11, (dated Nov. 2003).
EP 11850625.2 filed Jul. 22, 2013 Office Action dated Sep. 24, 2018.
EP 14197137.4 filed Dec. 10, 2014 Office Action dated Apr. 5, 2018.
EP 15179061.5 filed Jul. 30, 2015 Partial European Search Report dated Jan. 17, 2018.
EP 17186624.7 filed Aug. 17, 2017 Extended European Search Report dated Jan. 17, 2018.
EP 17186624.7 filed Aug. 17, 2017 Partial European Search Report dated Jan. 17, 2018.
Hamza, N. et al. "Interference reduction in ECG signal acquisition: Ground electrode removal." 2013 International Conference on Computer Medical Applications (ICCMA), Jan. 2013.
Honeywell, "1, 2 and 3 Axis Magnetic Sensors HMC1051/HMC1052L/HMC1053" dated Jan. 2010.
JP 2013-530322 filed Mar. 18, 2013, Office Action dated Jul. 6, 2018.
JP 2013-530322 filed Mar. 18, 2013, Office Action dated Nov. 6, 2017.
JP 2015-534770 filed Mar. 26, 2015 Office Action dated Feb. 21, 2018.
KR 10-2014-7002789 filed Feb. 3, 2014 Office Action dated Jun. 21, 2018.
MX/a/2015/004864 filed Apr. 16, 2015 Office Action dated Apr. 24, 2018.
MX/a/2015/004864 filed Apr. 16, 2015 Office Action dated Dec. 18, 2017.
NOT Resource Center. Magnetic Permeability. Oct. 18, 2014. Last accessed Mar. 23, 2018. <URL:https://web.archive.org/web/20141018213902/https://www.nde-ed.org/EducationResources/CommunityCollege/Materials/Physical_Chemical/Permeability.htm>.
PCT/US2017/066503 filed Dec. 14, 2017 International Search Report and Written Opinion dated Feb. 20, 2018.
RU 2015111669 filed Apr. 1, 2015 Office Action dated Jan. 25, 2018.
RU 2015111669 filed Apr. 1, 2015 Office Action dated May 18, 2018.
Thakor, N. V., et al. "Ground-Free ECG Recording with Two Electrodes." IEEE Transactions on Biomedical Engineering, vol. BME-27, No. 12, Dec. 1980.
U.S. Appl. No. 13/665,420, filed Oct. 31, 2012 Notice of Allowance dated Feb. 7, 2018.
U.S. Appl. No. 13/890,158, filed May 8, 2013 Advisory Action dated Feb. 13, 2018.
U.S. Appl. No. 13/890,158, filed May 8, 2013 Final Office Action dated Nov. 21, 2017.
U.S. Appl. No. 13/890,158, filed May 8, 2013 Notice of Allowance dated May 30, 2018.
U.S. Appl. No. 14/141,046, filed Dec. 26, 2013 Examiner's Answer dated Oct. 15, 2018.
U.S. Appl. No. 14/141,046, filed Dec. 26, 2013 Final Office Action dated Dec. 11, 2017.

(56) References Cited

OTHER PUBLICATIONS

U.S. Appl. No. 14/201,300, filed Mar. 7, 2014 Examiner's Answer dated Apr. 19, 2018.
U.S. Appl. No. 14/317,501, filed Jun. 27, 2014 Decision on Appeal dated Nov. 17, 2017.
U.S. Appl. No. 14/317,501, filed Jun. 27, 2014 Notice of Allowance dated Feb. 9, 2018.
U.S. Appl. No. 14/788,305, filed Jun. 30, 2015 Advisory Action dated Oct. 19, 2018.
U.S. Appl. No. 14/788,305, filed Jun. 30, 2015 Final Office Action dated Jul. 27, 2018.
U.S. Appl. No. 14/788,305, filed Jun. 30, 2015 Non-Final Office Action dated Jan. 10, 2018.
U.S. Appl. No. 15/192,561, filed Jun. 24, 2016 Final Office Action dated Nov. 1, 2018.
U.S. Appl. No. 15/192,561, filed Jun. 24, 2016 Non-Final Office Action dated Apr. 6, 2018.
U.S. Appl. No. 15/266,977, filed Sep. 15, 2016 Non-Final Office Action dated Oct. 30, 2018.
U.S. Appl. No. 15/284,355, filed Oct. 3, 2016 Advisory Action dated Aug. 13, 2018.
U.S. Appl. No. 15/284,355, filed Oct. 3, 2016 Final Office Action dated May 24, 2018.
U.S. Appl. No. 15/284,355, filed Oct. 3, 2016 Non-Final Office Action dated Nov. 17, 2017.
U.S. Appl. No. 15/365,698, filed Nov. 30, 2016 Final Office Action dated Jul. 12, 2018.
U.S. Appl. No. 15/365,698, filed Nov. 30, 2016 Non-Final Office Action dated Dec. 14, 2017.
U.S. Appl. No. 15/365,734, filed Nov. 30, 2016 Non-Final Office Action dated Feb. 23, 2018.
U.S. Appl. No. 15/365,734, filed Nov. 30, 2016 Notice of Allowance dated Jun. 4, 2018.
U.S. Appl. No. 15/365,752, filed Nov. 30, 2016 Final Office Action dated Jul. 12, 2018.
U.S. Appl. No. 15/365,752, filed Nov. 30, 2016 Non-Final Office Action dated Dec. 13, 2017.
U.S. Appl. No. 15/365,752, filed Nov. 30, 2016 Notice of Allowance dated Nov. 6, 2018.
U.S. Appl. No. 15/365,872, filed Nov. 30, 2016 Non-Final Office Action dated Aug. 27, 2018.
U.S. Appl. No. 15/365,872, filed Nov. 30, 2016 Restriction Requirement dated Apr. 5, 2018.
U.S. Appl. No. 15/585,051, filed May 2, 2017 Final Office Action dated Feb. 28, 2018.
U.S. Appl. No. 15/585,051, filed May 2, 2017 Final Office Action dated Mar. 15, 2018.
U.S. Appl. No. 15/900,623, filed Feb. 20, 2018 Final Office Action dated Sep. 20, 2018.
U.S. Appl. No. 15/900,623, filed Feb. 20, 2018 Non-Final Office Action dated May 3, 2018.
CN 201180068309.9 filed Aug. 22, 2013 Second Office Action dated May 6, 2015.
CN 201180068309.9 filed Aug. 22, 2013 Third Office Action dated Sep. 2, 2015.
CN 201280033189.3 filed Jan. 3, 2014 First Office Action dated Apr. 3, 2014.
CN 201280033189.3 filed Jan. 3, 2014 Second Office Action dated Sep. 14, 2015.
CN 201380051172.5 filed Mar. 30, 2015 Office Action dated May 2, 2017.
CN 201380065663.5 filed Jun. 15, 2015 Office Action dated Mar. 15, 2017.
CN 201380065663.5 filed Jun. 15, 2015 Office Action dated Oct. 10, 2017.
CN 201410009216.4 filed Jan. 8, 2014 Office Action dated Jun. 15, 2016.
CN 201410009216.4 filed Jan. 8, 2014 Second Office Action dated Sep. 25, 2015.
CN 201510144728.6 filed Apr. 17, 2015 Office Action dated Aug. 29, 2017.
CN 201510144728.6 filed Apr. 17, 2015 Office Action dated Jan. 23, 2017.
CO 15110530 filed May 14, 2015 Office Action dated May 8, 2017.
CO 15110530 filed May 14, 2015 Office Action dated Nov. 25, 2016.
Colley, Peter S et al, ECG-Guided Placement of Sorenson CVP Catheters via Arm Veins, Anesthesia and Analgesia, pp. 953-956, vol. 63, 1984.
Collier, PE et al, Cardiac Tamponade from Central Venous Catheters, Am J Surg, pp. 212-214, vol. 176 No. 2, Aug. 1998.
ComboWire® Pressure/Flow Guide Wire Ref 9500 Series, Instructions for Use, Apr. 2011.
Corsten, et al., "Central Placement Catheter Placement Using the ECG-Guided Cavafix-Certodyn SD Catheter." Journal of Clinical Anesthesiology, vol. 6, Nov./Dec. 1994.
Cucchiara, Roy et al, Time Required and Success Rate of Percantaneous Right Atrial Catherization: Description of a Technique, Canad. Anaesth. Soc. J., pp. 572-573, vol. 27, No. 6, Nov. 1980.
Cullinane, DC et al, The Futility of Chest Roentgenograms Following Routine Central Venous Line Changes, Am J Surg, pp. 283-285, vol. 176 No. 3, Sep. 1998.
Curet, Myriam J. et al., University and Practice-based Physicians' Input on the Content of a Surgical Curriculum, The American Journal of Surgery® vol. 178 Jul. 1999, 78-84.
David, et al., "Is ECG-Guidance a Helpful Method to Correctly Position a Central Venous Catheter During Prehospital Emergency Care?" Acta Anaesthesiologica Scandinavica, vol. 49, pp. 1010-1014, 2005.
Deltec Cath-Finder® Tracking System Operation Manual, 1994.
Egelhof, Petra, Effects of Somatostatin on Portal Blood Flow and Portal Vein Pressure in Patients with Portal Hypertension due to Liver Cirrhosis Invasive Monitoring during TIPSS Procedures, Dissertation submitted to: Technical University of Munich, Faculty of Medicine, May 13, 2002; Date of examination: Feb. 26, 2003.
Engelhardt, W et al, ECG-Controlled Placement of Central Venous Catheters in Patients with Atrial Fibrallation, Anaesthesist, pp. 476-479, vol. 38 No. 9, Sep. 1989 (Abstract only).
EP 08855396.1 filed Jun. 15, 2010 European Search Report dated Jul. 31, 2012.
EP 08855396.1 filed Jun. 15, 2010 Intent to Grant dated Jul. 5, 2013.
EP 09707467.8 supplemental European search report dated Jun. 18, 2013.
EP 09743249.6 filed Oct. 18, 2010 Extended European Search Report dated Jan. 13, 2016.
EP 09743249.6 filed Oct. 18, 2010 Intention to Grant dated Mar. 2, 2017.
EP 09808901.4 filed Aug. 21, 2009 European Search Report dated May 23, 2012.
EP 09808901.4 filed Aug. 21, 2009 Examination Report dated May 10, 2013.
EP 09813632.8 filed Apr. 5, 2011 European Search Report dated Jul. 4, 2012.
EP 09813632.8 filed Apr. 5, 2011 Office Action dated Apr. 30, 2013.
EP 09813632.8 filed Apr. 5, 2011 Summons to Attend Oral Proceedings dated Apr. 16, 2014.
EP 10 808 660.4 filed Feb. 15, 2012 Extended European Search Report dated Mar. 4, 2014.
EP 10786978.6 filed Dec. 19, 2011 Extended European Search Report dated Mar. 7, 2014.
EP 10786978.6 filed Dec. 19, 2011 Office Action dated Aug. 11, 2017.
EP 10821193.9 filed Mar. 27 2012 Partial European Search Report dated Oct. 9, 2015.
EP 11 818 828.3 filed Mar. 18, 2013 Extended European Search Report dated Dec. 10, 2014.
EP 11740309.7 filed Aug. 23, 2012 Extended European Search Report dated Aug. 3, 2015.
EP 11787515.3 filed Dec. 12, 2012 partial European search report dated Jun. 23, 2015.
EP 11787515.3 filed Dec. 12, 2012 partial European search report dated Oct. 27, 2015.

(56) References Cited

OTHER PUBLICATIONS

EP 11787527.8 filed Dec. 19 2012 Extended European Search Report dated Oct. 9, 2015.
EP 11787527.8 filed Dec. 19, 2012 partial European search report dated May 26, 2015.
EP 11827551.0 filed Feb. 7, 2013 Extended European Search Report dated Sep. 19, 2017.
EP 11837113.7 filed May 28, 2013 Extended European Search Report dated Apr. 24, 2014.
EP 11850625.2 filed Jul. 22, 2013 Extended European Search Report dated Jun. 21, 2017.
EP 12177438.4 filed Jul. 23, 2012 Communication dated Jan. 13, 2014.
EP 12177438.4 filed Jul. 23, 2012 European Search Report dated Dec. 4, 2012.
EP 12177438.4 filed Jul. 23, 2012 European Search Report dated Jun. 7, 2015.
"Ascension to Launch New 3D Guidance™ Tracker at TCT 2006." Press Releases from Ascension website: www.ascension-tech.com/news/press_101106.php, last accessed Dec. 1, 2006.
Acuson—The Value of Vision, AcuNav Diagnostic Ultrasound Catheter, 2000.
Advertising flyer for GAVECELT—The Italian Group for Long Term Venous Access Devices, for program on International Meeting on PICC's, Midline Catheters and Long Term Venous Access Devices in Catholic University, Rome, Italy on Dec. 3, 4, 5, 2008.
Alexander, GD et al, The Role of Nitrous Oxide in Postoperative Nausea and Vomiting, Collection of Abstracts Presented at the International Anesthesia Research Society by various speakers, 58th Congress, Mar. 12-14, 1984, Anesthesia and Analgesia, pp. 175-284, vol. 63, 1984.
Allan, P.L. et al, Role of Ultrsound in the Assessment of Chronic Venous Insufficiency, Ultrasound Quarterly, vol. 17, No. 1, pp. 3-10, 2001.
Andropoulos, et al. "A Controlled Study of the Transesophageal Echocardiography to Guide Central Venous Catheter Placement in Congetital Heart Surgery Patients." The International Anesthesia Research Society, vol. 89, pp. 65-70, 1999.
Anonymous author, Correct Catheter Placement with a low-impact, reliable and economical method, <http://www.cvc-partner.com/index.cfm?103A955CC6844BF58ACFE3C9C1471959>, last accessed Dec. 22, 2011.
Arai, J et al, Detection of Peripherally Inserted Central Catheter Occlusion by in-line Pressure Monitoring, Paediatr Anaesth, pp. 621-624, vol. 12 No. 7, Sep. 2002.
Arrow International, Inc., The Arrow-Johans RAECG Adapter-Making Proper Central Venous Catheter Placement More Reliable (Modle No. EG-04900), Technical Report 1987, USA.
Aslamy, et al. "MRI of Central Venous Anatomy: Implications for Central Venous Catheter Insertion." American College of Chest Physicians, Jun. 8, 2009.
AU 2006283022 filed Aug. 24, 2006 Office Action dated Dec. 22, 2010.
AU 2008329807 exam requested Aug. 13, 2012 Examination Report No. 1 dated Feb. 15, 2013.
AU 2008329807 exam requested Aug. 13, 2012 Notice of Acceptance dated Feb. 14, 2014.
AU 2010300677 filed Mar. 12, 2012 First Examination Report dated Mar. 9, 2014.
AU 2011289513 filed Jan. 21, 2013 Examiner's Report dated Jul. 5, 2013.
AU 2012202293 filed Apr. 19, 2012 Examination Report No. 1 dated Apr. 24, 2013.
AU 2012278809 filed Nov. 12, 2013 Notice of Acceptance dated Sep. 13, 2016.
AU 2013201648 filed Mar. 19, 2013 Examiner's Report dated Mar. 5, 2014.
AU 2013201648 filed Mar. 19, 2013 Examiner's Report dated Oct. 14, 2013.
AU 2013202824 filed Apr. 6, 2013 First Examiner's Report dated Mar. 10, 2014.
AU 2013204243 filed Apr. 12, 2013 Examiner's Report dated Jun. 5, 2013.
Aurora® System Technical Specifications, Oct. 2003.
B. Braun Website, "The Optimal Position of the Central Venous Catheter." http://www.cvcpartner.com/index.cfm18F1BDEA1310466194960A39F4E90968 (2009).
B. Braun, Certofix Central Venous Catheter for Placement Using the Seldinger Technique with Simultaneous ECG Lead Option, Feb. 2010.
Bailey, SH et al, Is Immediate Chest Radiograph Necessary after Central Venous Catheter Placement in a Surgical Intensive Care Unit?, Am J Surg, pp. 517-522, vol. 180 No. 6, Dec. 2000.
Bankier, Alexander A., Azygos Arch Cannulation by Central Venous Catheters: Radiographic Detection of Malposition and Subsequent Complications, Journal of Thoracic Imaging 12:64-69 (1997).
Barber, JM et al, A Nurse led Peripherally Inserted Central Catheter Line Insertion Service is Effective with Radiological Support, Clin Radiol, pp. 352-354, vol. 57 No. 5, May 2002.
Bard Access Systems, Sherlock Tip Location System, 5 pages, 2006.
Bard Access Systems, Site Rite Vascular Acess Ultrasound System, 4 pages, 2005.
Benchimol, Alberto at al, Right Atrium and Superior Vena Cava Flow Velocity in Man Measured with the Doppler-Catheter Flowmeter-Telemetry System, The Amer Journal of Medicine, pp. 303-309, vol. 48, Mar. 1970.
Benzadon, M. N. et al: "Comparison of the Amplitude of the P-Wave from Intracardiac Electrocardiogram Obtained by Means of a Central Venous Catheter Filled With Saline Solution to That Obtained Via Esophageal Electrocardiogram", American Journal of Cardiology, Cahners Publishing Co., Newton, MA, US, vol. 98, No. 7, Oct. 1, 2006 (Oct. 1, 2006), pp. 978-981.
BioAdvance Lumen Vu, Greenhouse Fund Feb. 2004 Recipient, www.bioadvance.com <http://www.bioadvance.com>, 2005.
Borgobello, Bridget, App allows users to view electrocardiograms on smartphones dated Oct. 15, 2010; printed from http://www.gizmag.com/app-to-view-electrocardiograms-on-smartphones/16664/ on Feb. 4, 2011.
Buehrle, Douglas, PICC Placement in Humans using Electromagnetic Detection, <http://www.corpakmedsystems.com/supplement_material/supplementpages/navigator/navarticle.html>, 2008.
C.R. Bard, CathTrack™ Catheter Location System at www.bardaccess.com <http://www.bardaccess.com>, last accessed Apr. 28, 2011.
C.R. Bard, Inc., Bard Electrophysiology Product Catalogue, Bard Catheters, pp. 74-75 (2002), USA.
CA 2,619,909 filed Aug. 24, 2006 Examiner's Report dated Oct. 26, 2012.
CA 2,721,715 filed Apr. 17, 2009 Examiner's Report dated Aug. 18, 2015.
CA 2,721,715 filed Apr. 17, 2009 Examiner's Report dated Oct. 25, 2016.
CA 2800810 filed Nov. 26, 2012 Office Action dated Mar. 30, 2017.
Cadman, A et al, To Clot or Not to Clot? That is the question in Central Venous Catheters, Clinical Radiology, pp. 349-355, vol. 59 No. 4, Apr. 2004.
Calvert, N et al, The Effectiveness and Cost-effectiveness of Ultrasound Locating Devices for Central Venous Access: A Systematic Review and Economic Evaluation, Health Technology Assessment, vol. 7, No. 12, 2003.
Cardella, John F. et al., Interventinal Radiologic Placement of Peripherally Inserted Central Catheters, Journal of Vascular and Interventional Radiology 1993; 4:653-660.
Carlon, R et al, Secondary Migration of a Central Venous Catheter—A Case Report, Minerva Anestesiol, pp. 927-931, vol. 69 No. 12, Dec. 2003.
Caruso, LJ et al, A Better Landmark for Positioning a Central Venous Catheter, J Clinical Monitoring and Computing, pp. 331-334, vol. 17 No. 6, Aug. 2002.
Cavatorta, et al., "Central Venous Catheter Placement in Hemodialysis: Evaluation of Electrocardiography Using a Guidewire." The Journal of Vascular Access, vol. 2, pp. 45-50, 2001.

(56) References Cited

OTHER PUBLICATIONS

Chalkiadis, GA et al, Depth of Central Venous Catheter Insertion in Adults: An Audit and Assessment of a Technique to Improve Tip Position, Anaesth Intensive Care, pp. 61-66, vol. 26 No. 1, Feb. 1998.
Chamsi-Pasha, Hassan et al, Cardiac Complications of Total Parenteral Nutrition: The Role of Two-Dimensional Echocardiography in Diagnosis, Annals of the Royal College of Surgeons of England, pp. 120-123, vol. 71, 1989.
Chang, Thomas C. et al., Are Routine Ch Ladiographs Necessary After Image-Guided Placement of Internal Jugular Central Venous Access Devices?, AJR Feb. 1998;170:335-337.
Chaturvedi et al., "Catheter Malplacement During Central Venous Cannulation Through Arm Veins in Pediatric Patients." Journal of Neurosurgical Anesthesiology, vol. 15, No. 3 pp. 170-175, Jan. 2003.
U.S. Appl. No. 14/040,205, filed Sep. 27, 2013 Notice of Allowance dated Aug. 21, 2019.
U.S. Appl. No. 15/365,698, filed Nov. 30, 2016 Notice of Allowance dated Nov. 4, 2019.
U.S. Appl. No. 15/418,475, filed Jan. 27, 2017 Non-Final Office Action dated Oct. 18, 2019.
U.S. Appl. No. 15/418,475, filed Jan. 27, 2017 Restriction Requirement dated Jul. 23, 2019.
PCT/US2019/055716 filed Oct. 10, 2019 International Search Report and Written Opinion dated Feb. 4, 2020.
U.S. Appl. No. 14/996,247, filed Jan. 15, 2016 Advisory Action dated Feb. 20, 2020.
U.S. Appl. No. 14/996,247, filed Jan. 15, 2016 Final Office Action dated Dec. 11, 2019.
U.S. Appl. No. 15/900,623, filed Feb. 20, 2018 Non-Final Office Action dated Dec. 30, 2019.
EP 11827551.0 filed Feb. 7, 2013 Office Action dated Mar. 13, 2020.
EP 17157118.5 filed Feb. 8, 2018 Communication under Rule 71(3) dated May 7, 2020.
U.S. Appl. No. 14/201,300, filed Mar. 7, 2014 Final Office Action dated Mar. 9, 2020.
U.S. Appl. No. 14/201,300, filed Mar. 7, 2014 Notice of Allowance dated May 8, 2020.
U.S. Appl. No. 15/418,475, filed Jan. 27, 2017 Advisory Action dated May 28, 2020.
U.S. Appl. No. 15/418,475, filed Jan. 27, 2017 Final Office Action dated Apr. 2, 2020.
U.S. Appl. No. 15/585,051, filed May 2, 2017 Board Decision dated Apr. 21, 2020.
U.S. Appl. No. 15/625,842, filed Jun. 16, 2017 Non-Final Office Action dated Mar. 18, 2020.
EP 20154593.6 filed Jan. 30, 2020 Extended European Search Report dated Jun. 2, 2020.
U.S. Appl. No. 14/141,046, filed Dec. 26, 2013 Board Decision dated Nov. 26, 2019.
U.S. Appl. No. 14/201,300, filed Mar. 7, 2014 Non-Final Office Action dated Nov. 27, 2019.
U.S. Appl. No. 14/996,247, filed Jan. 15, 2016 Non-Final Office Action dated Sep. 1, 2020.
U.S. Appl. No. 15/418,475, filed Jan. 27, 2017 Non-Final Office Action dated Sep. 1, 2020.
U.S. Appl. No. 15/585,051, filed May 2, 2017 Notice of Allowance dated Jul. 31, 2020.
U.S. Appl. No. 15/836,741, filed Jan. 8, 2017 Non-Final Office Action dated Jun. 12, 2020.
U.S. Appl. No. 15/836,741, filed Jan. 8, 2017 Restriction Requirement dated Mar. 3, 2020.
U.S. Appl. No. 15/900,623, filed Feb. 20, 2018 Advisory Action dated Aug. 7, 2020.
U.S. Appl. No. 15/900,623, filed Feb. 20, 2018 Final Office Action dated Jun. 12, 2020.
U.S. Appl. No. 16/017,695, filed Jun. 25, 2018 Non-Final Office Action dated Jul. 20, 2020.
U.S. Appl. No. 15/836,741 filed Jan. 8, 2017 Notice of Allowance dated Sep. 10, 2020.
U.S. Appl. No. 16/457,606 filed Jun. 28, 2017 Non-Final Office Action dated Sep. 15, 2020.

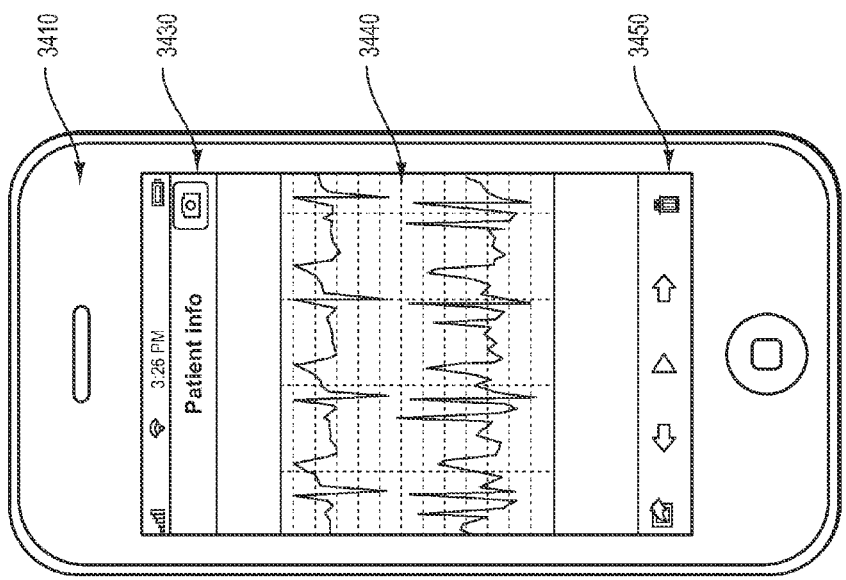
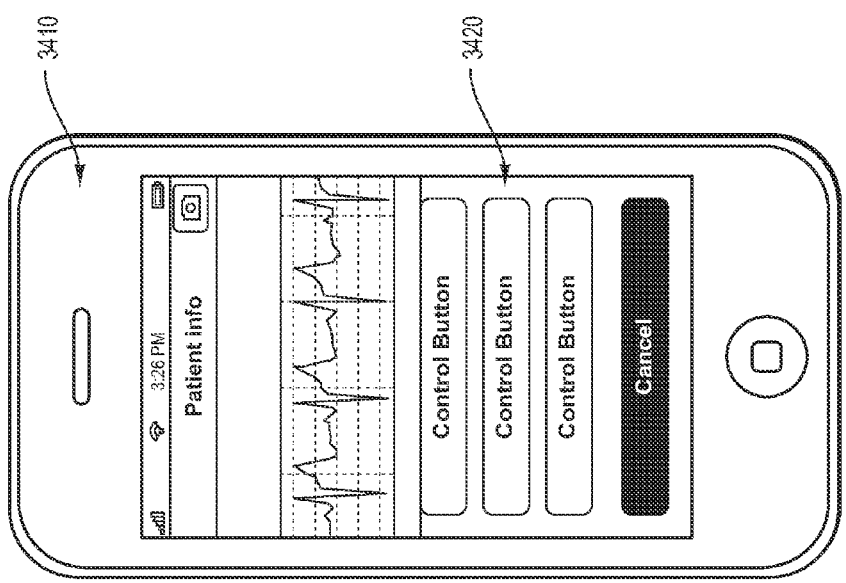
FIG. 27B
FIG. 27A

APPARATUS AND METHOD FOR CATHETER NAVIGATION AND TIP LOCATION

CROSS-REFERENCE TO RELATED APPLICATIONS

This application is a division of U.S. patent application Ser. No. 14/846,496, filed Sep. 4, 2014, now U.S. Pat. No. 10,231,643, which is a division of U.S. patent application Ser. No. 13/019,939, filed Feb. 2, 2011, now U.S. Pat. No. 9,125,578, which claims the benefit of U.S. Provisional Patent Application No. 61/282,397, filed on Feb. 2, 2010 and which is a continuation-in-part of U.S. patent application Ser. No. 12/854,083, filed Aug. 10, 2010, now U.S. Pat. No. 9,445,734, which claims the benefit of U.S. Provisional Patent Application No. 61/272,025, filed on Aug. 10, 2009 and which is a continuation-in-part of U.S. patent application Ser. No. 12/815,331, filed Jun. 14, 2010, now U.S. Pat. No. 9,339,206, which claims the benefit of U.S. Provisional Patent Application No. 61/213,474, filed on Jun. 12, 2009, the disclosures of which are incorporated herein by reference in their entireties.

BACKGROUND

The electrical conduction system of the heart creates specific electrical signals, electrical energy distributions and behaviors thereof which are indicative of specific locations in the thoracic cavity and/or of specific heart functions or conditions. When measured endovascularly, i.e., from within blood vessels or from within the heart, certain parameters of the electrical activity of the heart can be used to identify specific locations in the cardiovascular system and/or functional conditions, normal or abnormal. Moreover, by locally and accurately identifying the location and the type of condition, therapy of such conditions can be optimized and the effect of the therapy monitored in real-time.

Two types of clinical applications are typically addressed. The first is related to guiding endovascular devices through the cardiovascular system, while the second is related to the non-invasive or the minimally invasive remote monitoring of the electrical activity of the heart.

The guidance, positioning, and placement confirmation of endovascular catheters are necessary in a number of clinical applications, such as, for example:
1. Central venous access, e.g., CVC, PICC, implantable ports;
2. Hemodialysis catheters;
3. Placement of pacemaker leads;
4. Hemodynamics monitoring catheters, e.g., Swan-Ganz and central pressure monitoring catheters; and
5. Guiding guidewires and catheters into the left heart.

The location of the catheter tip is very important to the patient safety, the duration and the success of the procedure. Today's golden standard for confirming the target location of the catheter tip is the chest X-ray. In addition, there are currently two types of real-time guiding products available on the market, which try to overcome the limitations of chest X-ray confirmation: electromagnetic and ECG-based. In hospitals where real-time guidance is used results have improved in terms of reducing the number of X-rays, the procedure time, and the cost of the procedure. Under real-time guidance first-time success rate has typically increased from 75%-80% to 90%-95%. In addition, in hospitals where ECG guidance is used, e.g., in Italy, Belgium, Germany, chest X-ray confirmation has been eliminated for more than 90% of the patients. Electromagnetic systems are used mostly in the United States while ECG-based systems are used mostly in Europe. Amongst other factors which determine the difference between the markets in the United States and Europe in terms of technology adoption: a) type of health care personnel allowed to perform procedures: nurses have more flexibility in the United States, b) type of devices placed: PICCs are placed more and more often in the United States, c) price sensitivity: the European market seems to be more price sensitive, and d) the current guiding devices are commercialized by specific manufacturers to work exclusively with their catheters: market penetration of the guiding systems reflects the market penetration of the catheter manufacturer.

It was also found that different opinions exist regarding where the target tip location should be: for example, lower third of the SVC or RA. Therefore guiding technologies should allow for discrimination of these locations. The chest X-ray, which is the current golden standard does not always allow for such discrimination requiring an accuracy of typically better than 2 cm. Also, because ECG-based systems make use of physiological information related to the heart activity, their ability to guide placement is accurate with respect to the anatomy. This is not the case with electromagnetic guiding systems which measure the distance between the catheter tip in the vasculature and an external reference placed typically on the patient's chest. Because of this aspect, ECG-based systems can be used to document the final result of the catheter placement potentially replacing the chest X-ray as the golden standard.

One of the most valuable diagnostic tools available, the ECG records the heart's electrical activity as waveforms. By interpreting these waveforms, one can identify rhythm disturbances, conduction abnormalities, and electrolyte imbalance. An ECG aids in diagnosing and monitoring such conditions as acute coronary syndromes and pericarditis. The heart's electrical activity produces currents that radiate through the surrounding tissue to the skin. When electrodes are attached to the skin, they sense these electrical currents and transmit them the electrocardiograph. Because the electrical currents from the heart radiate to the skin in many directions, electrodes are placed at different locations on the skin to obtain a total picture of the heart's electrical activity. The electrodes are then connected to an electrocardiograph device, or computer, and record information from different perspectives, which are called leads and planes. A lead provides a view of the heart's electrical activity between two points or poles. A plane is a cross section of the heart which provides a different view of the heart's electrical activity. Currently, the interpretation of an ECG waveform is based on identifying waveform component amplitudes, analyzing and then comparing the amplitudes with certain standards. Modifications of these amplitude components are indicative of certain conditions, e.g., the elevation of the ST segment or of certain locations in the heart, e.g., the amplitude of the P-wave. In today's practice ECG monitors are widely used to record ECG waveforms. More and more often applications are made available for automatic identification of the ECG amplitude components. In certain cases tools are available for decision making support and for automatic interpretation of ECG amplitude components with respect to underlying heart conditions.

Remote patient monitoring is a well-established medical field. Still remote monitoring of heart conditions is not as widely accepted as it would be need and possible. One of the reasons is related to the relatively complicated way of acquiring signals related to the heart activity, in particular ECG signals. Another important limiting factor of the current remote monitoring technologies is the use of communications channels, like the telephone line, which are difficult to interface with at both the patient and the physician ends.

BRIEF SUMMARY

Briefly summarized, embodiments of the present invention are directed to systems, devices, and methods for obtaining and using endovascular electrograms (or electrocardiograms/ECGs) in a number of clinical applications and settings. For example, the devices can be used to guide endovascular devices in and around the heart, e.g., guiding central venous access devices in the superior vena cava, right atrium, and right ventricle. Such central venous access devices may include central venous catheters (CVC), peripherally inserted central catheters (PICC), implantable ports, hemodialysis catheters, tunneled catheters and others.

In one aspect, one or several skin electrodes are used to obtain skin surface ECG signals simultaneous with the acquisition of endovascular (intracavitary) electrogram (ECG) signals via the use of endovascular (intracavitary) electrodes. The simultaneous and synchronized skin surface and endovascular ECG signals are used in one of several ways to analyze and quantify the ECG signals as a function of the location of the endovascular electrode, e.g. as a function of the tip of a catheter.

In light of the above, in one embodiment the ease-of-use of the ECG-based catheter navigation and tip location is enhanced. In one aspect, for instance, skin ECG reference waveforms are simultaneously presented on a display with endovascular ECG waveforms measured at the tip of a catheter or other indwelling medical device. Such simultaneous acquisition and display of concurrent ECG signals allows for ready interpretation of the endovascular ECG waveform at the tip of the catheter. In another aspect, a skin ECG reference signal is used to synchronize information processing algorithms applied to the endovascular ECG signal, yielding results of enhanced reliability concerning changes of P-wave of the endovascular ECG signal in terms of shape and energy.

In greater detail, in one embodiment a skin ECG signal can be used as a reference and compared to an endovascular ECG signal in order to detect changes in the endovascular ECG relative to the skin ECG.

In another embodiment, analysis of the synchronized skin and/or endovascular ECG signals can be linked to one another and/or to the periodic electrical activity of the heart. For example, a skin ECG lead can be used to detect the R-peak of the QRS complex of a detected skin ECG waveform. Detection of the R-peak in the skin ECG waveform can be used to trigger analysis of the endovascular ECG signal in a simultaneously corresponding segments of the endovascular ECG waveform, e.g., in the segment corresponding to the P-wave. Such triggering is particularly useful in case of arrhythmia, wherein the skin ECG waveform does not typically demonstrate a consistent P-wave, while the endovascular ECG waveform indeed includes a detectable P-wave segment that changes as a function of the location in the vasculature.

In another embodiment, a skin ECG lead can be used to monitor the patient's heart activity at the same time an endovascular ECG lead is employed to guide a catheter or other suitable indwelling or endovascular devices through the vasculature. In another embodiment, R-peaks detected in the skin ECG waveform are used to trigger correlation computation and other types of signal processing on the endovascular ECG signal in order to allow for efficient noise reduction in the resultant endovascular ECG waveform.

In another aspect, a connector for establishing an operable connection between a catheter in the sterile field of the patient and an ECG cable outside of the sterile field is described, allowing for single operator utilization of the apparatus for catheter navigation and tip location introduced herein.

In another aspect, algorithms are introduced that allow for mapping certain ECG waveforms to corresponding locations in the vasculature. In one embodiment, the algorithm analyzes directional electrical energy present at the tip of a catheter or other endovascular device capable of detecting endovascular ECG signals. In another embodiment the algorithm can map the catheter tip to a certain location in the vasculature based on endovascular ECG signals so as to allow for catheter navigation.

In another aspect, a simplified graphical user interface is disclosed, depicting a moving graphical indicator over a heart icon so as to indicate a location of a catheter tip in the vasculature as determined by the endovascular ECG signal. The graphical indicator can include different colors and shapes, such as dots or arrows, for instance. The colors and shapes of the graphic indicator may change as a function of the tip location in the vasculature.

In another aspect, an ECG signal acquisition module is disclosed that is operably connectable, via a suitable interface, to a mobile phone or other portable electronic device. This enables control of the ECG signal acquisition module, including ECG signal analysis, by a user of the mobile phone. In another embodiment, the ECG signal acquisition module can be operably connected interfaced to other handheld or remote devices.

In another aspect, a user interface is included for use in connection with the mobile phone or other portable device to enable ECG signal-based guiding of endovascular devices by the mobile phone. In another embodiment, the user interface enables use of the mobile phone to support analysis and archival of ECG signals, catheter information, and results of a catheter placement procedure. In another embodiment, the user interface optimizes ECG signal acquisition for remote patient monitoring via the mobile phone or other handheld device.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the embodiments are not limited in their application to the details of construction and to the arrangements of the components set forth in the following description or illustrated in the drawings. Indeed, other embodiments in addition to those described herein can be conceived of, practiced, and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of embodiments of the present invention. It is important, therefore, that the claims be regarded as including such equivalent constructions insofar as they do not depart from the spirit and scope of this disclosure.

These and other features of embodiments of the present invention will become more fully apparent from the following description and appended claims, or may be learned by the practice of embodiments of the invention as set forth hereinafter.

BRIEF DESCRIPTION OF DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 4A depicts a single lead configuration, FIG. 4B depicts a modified 3-lead configuration with monitoring and guiding capabilities, FIG. 4C depicts a telemetry configuration with a single grounded lead, and FIG. 4D depicts one use of ECG monitors for guiding endovascular devices.

FIGS. 27A and 27B show additional ECG waveform-related depictions as displayed on a mobile phone according to one embodiment.

DETAILED DESCRIPTION OF SELECTED EMBODIMENTS

Figure 1A:
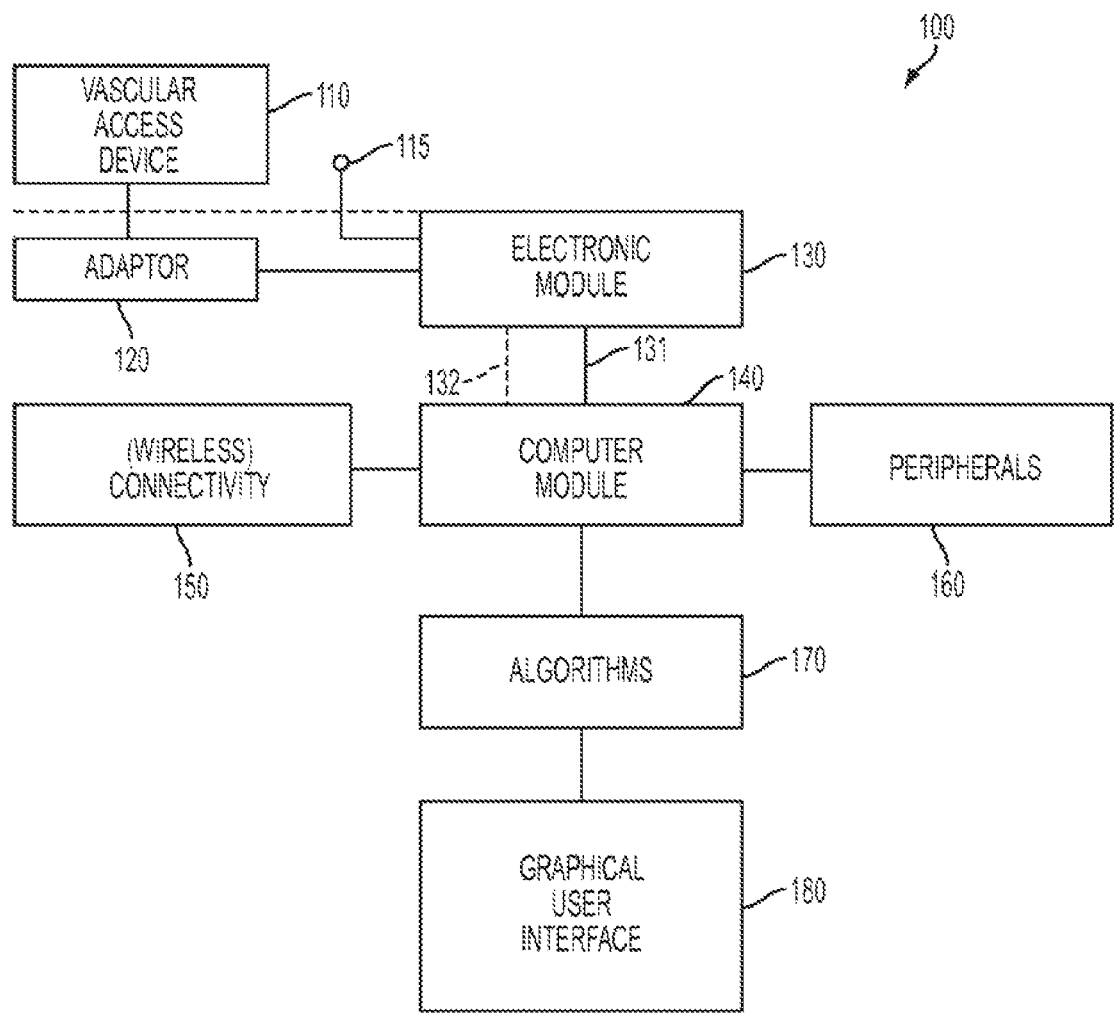
FIG. 1A is a block diagram that depicts an apparatus according to an embodiment of the present invention.

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention advantageously provide an inventive apparatus(es), computer-based data processing algorithms and methods for obtaining and using endovascular ECGs in a number of clinical applications and settings. For example, once device can be used to guide endovascular devices in and around the heart, e.g., guiding central venous access devices in the superior vena cava, right atrium, and right ventricle. Such central venous access devices may include central venous catheters (CVC), peripherally inserted central catheters (PICC), implantable ports, hemodialysis catheters, tunneled catheters and others. Other devices which may benefit from guidance with the inventive apparatus are temporary pacemaker leads placed through the central venous system. Catheters and guidewires used in left heart procedures may also benefit from the embodiments described herein by decreasing the amount of contrast and radiation required to guide these devices in position. In another example, the apparatus can be used for minimally invasive monitoring and assessing heart conditions based on its electrical activity, e.g., assessing preload in a heart cycle or monitoring ST segments and T-waves in congestive heart failure.

In one aspect, an apparatus is described consisting of sterile adaptors, an electronic module for signal acquisition, a computer module, software, and peripheral devices and connections. In one embodiment, the electronic module for signal acquisition can be dedicated to acquiring and processing endovascular electrical signals generated by the body (endovascular ECG), in another embodiment the electronic module can be dedicated to acquiring and processing endovascular ECGs as well as skin ECGs.

In one embodiment, the electronic module and the computer module can be separate modules, in another embodiment they can be integrated in the same module and enclosure, and yet in another embodiment they can communicate with each other via a wireless connection, such as Bluetooth. In one embodiment, the apparatus can contain an integrated printer, while in another embodiment the printer can be external and attached to the apparatus and the apparatus connected via network, e.g., wireless to other devices. In yet another embodiment the apparatus can be used for telemetry and for transmitting the endovascular electrograms to a remote location, e.g., via a telephone line, Internet, and/or wireless phone. Any combination of embodiments mentioned above is also possible.

In another aspect, various configurations allow the connection of endovascular devices, such as central venous access devices, to the electronic module for signal acquisition and processing. In one embodiment, the device consists of a connecting wire with two ends and special connectors at each end. At one end, the wire can be connected to a metal or nitinol guidewire or stylet as commonly available on the market. At the other end, the wire can be safely connected to the electronic module. In another embodiment, the device includes a coated guidewire, e.g., made of nitinol or stainless steel with uncoated distal and proximal ends and cm markings. In such an embodiment, the coated guidewire is inserted endovascularly, while the connecting wire is connected to the proximal end of the coated guidewire. In another embodiment, the device includes a catheter-syringe adaptor provided with an electrical connecting wire. At one end, the electrical connecting wire is in contact with the fluid, e.g., saline flowing within the catheter-syringe adapter. At the other end the connecting wire can be connected to the electronic module.

In another aspect, various electrode configurations allow for the optimal acquisition of endovascular ECGs. In one embodiment, a single lead is used to provide information about the tip location of an endovascular device within the vasculature. In another embodiment a modified three lead configuration is used to provide simultaneous 3-lead monitoring of the heart activity at the same time with providing tip location information. In another embodiment a modified single lead configuration plus ground is used for telemetry and transferring information from the tip of the catheter remotely.

In another aspect, algorithms are introduced for the analysis of the ECG waveforms and for supporting decision making based on these waveforms. These algorithms discriminate between different locations in the vasculature and assess body functions (systemic and at specific locations in the body), in particular heart functionality. In various embodiments, these algorithms use time domain analysis of waveforms: morphologic, for example shape; statistic, for example behavior.

In other embodiments, the algorithms use frequency domain analysis of waveforms: morphologic, for example shape; statistic, for example behavior. In further embodiments, signal energy analysis in time and frequency domains is also performed, morphologic and statistic. Fuzzy, statistical, and knowledge-based decision making are also contemplated by the present embodiments as decision support tools.

In another aspect, a user interface is provided that advantageously simplifies interpretation of data and workflow. In one embodiment the user interface includes simplified graphics showing the location in the vasculature and in the heart of the tip of the endovascular device in use without showing any of the ECG waveforms. In another embodiment, the user interface shows, in real-time, the change in location of the tip of the endovascular device in use.

In another aspect, several inventive methods are presented which use the apparatus described herein in clinical applications. In one embodiment, a computer-based method is provided that guides central venous catheters (CVC, PICCs, hemodialysis, implantable ports, and others) using stylets, guidewires and saline solution to the superior vena cava, inferior vena cava, the right atrium, and the right ventricle. This method is advantageously less sensitive to patients with arrhythmias than the prior art, and represents an alternative to chest X-ray confirmation of tip location of central venous catheters in most clinical cases. In another embodiment, a computer-based method is provided that guides coated guidewires in the right and left heart. In another embodiment, a computer-based method is provided that guides the placement of temporary pacemaker leads through the central venous system. In another embodiment, a method is provided that is minimally invasive and monitors preload using depolarization and heart rhythms. In another embodiment, a method is provided that is minimally invasive and monitors arrhythmias using P-wave analysis. In another embodiment, a method is provided that is minimally invasive and monitors heart failure using ST segment and T-wave analysis.

In another aspect, one or several skin electrodes are used to obtain skin surface ECG signals simultaneous with the acquisition of endovascular (intracavitary) electrogram (ECG) signals via the use of endovascular (intracavitary) electrodes. The simultaneous and synchronized skin surface and endovascular ECG signals are used in one of several ways to analyze and quantify the ECG signals as a function of the location of the endovascular electrode, e.g. as a function of the tip of a catheter.

In light of the above, in one embodiment the ease-of-use of the ECG-based catheter navigation and tip location is enhanced. In one aspect, for instance, skin ECG reference waveforms are simultaneously presented on a display with endovascular ECG waveforms measured at the tip of a catheter or other indwelling medical device. Such simultaneous acquisition and display of concurrent ECG signals allows for ready interpretation of the endovascular ECG waveform at the tip of the catheter. In another aspect, a skin ECG reference signal is used to synchronize information processing algorithms applied to the endovascular ECG signal, yielding results of enhanced reliability concerning changes of P-wave of the endovascular ECG signal in terms of shape and energy.

In another embodiment, analysis of the synchronized skin and/or endovascular ECG signals can be linked to one another and/or to the periodic electrical activity of the heart. For example, a skin ECG lead can be used to detect the R-peak of the QRS complex of a detected skin ECG waveform. Detection of the R-peak in the skin ECG waveform can be used to trigger analysis of the endovascular ECG signal in a simultaneously corresponding segments of the endovascular ECG waveform, e.g., in the segment corresponding to the P-wave. Such triggering is particularly useful in case of arrhythmia, wherein the skin ECG waveform does not typically demonstrate a consistent P-wave, while the endovascular ECG waveform indeed includes a detectable P-wave segment that changes as a function of the location in the vasculature.

In other embodiments, magnetic and steerable sterile connectors are disclosed, as well as aspects of display and control solutions to enable a mobile phone or other handheld device to control an ECG-based system including one or more of the above aspects.

FIG. 1A is a block diagram that depicts an apparatus according to an embodiment of the present invention.

The apparatus 100 can be attached through an adaptor (120) to a large variety of commercially available and custom designed vascular access devices (110). Examples of such devices are: central venous catheters (CVC), peripherally inserted central catheters (PICC), implantable ports, tunneled catheters, hemodialysis catheters, guiding catheters for pacemaker leads, guidewires used for coronary and other vascular interventions, guiding catheters for coronary and other vascular interventions, stylets, syringe needles, and others. If the vascular access devices is a stylet, a guidewire, or a syringe needle, its material must be sufficiently electrically conductive, e.g., stainless steel or nitinol. In such a case the hook or the alligator clip adaptor according to one embodiment should be used. If the vascular access device is a catheter, than saline should be used to establish a conductive path through one of the catheter's lumens. In such a case, the syringe-catheter adaptor according to one embodiment should be used.

The electronic module (130) receives electrical signals from the adaptor and from one or more other electrodes placed on the patient's skin (115). Alternatively, more than one adaptor can be used at the same time to connect to more than one endovascular device in order to provide different electrical signals to the electronic module. The use of skin electrodes is optional in certain device configurations. The electronic module processes the electrical signals and transmits them to a computer module (140) for further processing and other functions. In one embodiment the electronic module and the computer module can be packaged separately, in another embodiment they can be integrated in the same package. In one embodiment the connection between the electronic module and the computer module can be hardwired, in another embodiment it can be wireless, e.g., using Bluetooth.

The computer module processes the signals from the electronic module applying algorithms (170) as described by current embodiments. The computer module can also be connected to peripherals (160), e.g., a printer or a label printer and storage devices and provides connectivity including wireless connectivity (150) to other computers or to the internet. The storage device can be used to store a database of knowledge and information regarding the application at hand. The connectivity interface can be used to update this database remotely with newest relevant knowledge and information, e.g., new clinical cases, new findings regarding the relationship between electrograms and heart conditions. The computer module supports a graphical user interface (180) optimized for the purpose of the clinical application at hand.

Figure 1B:
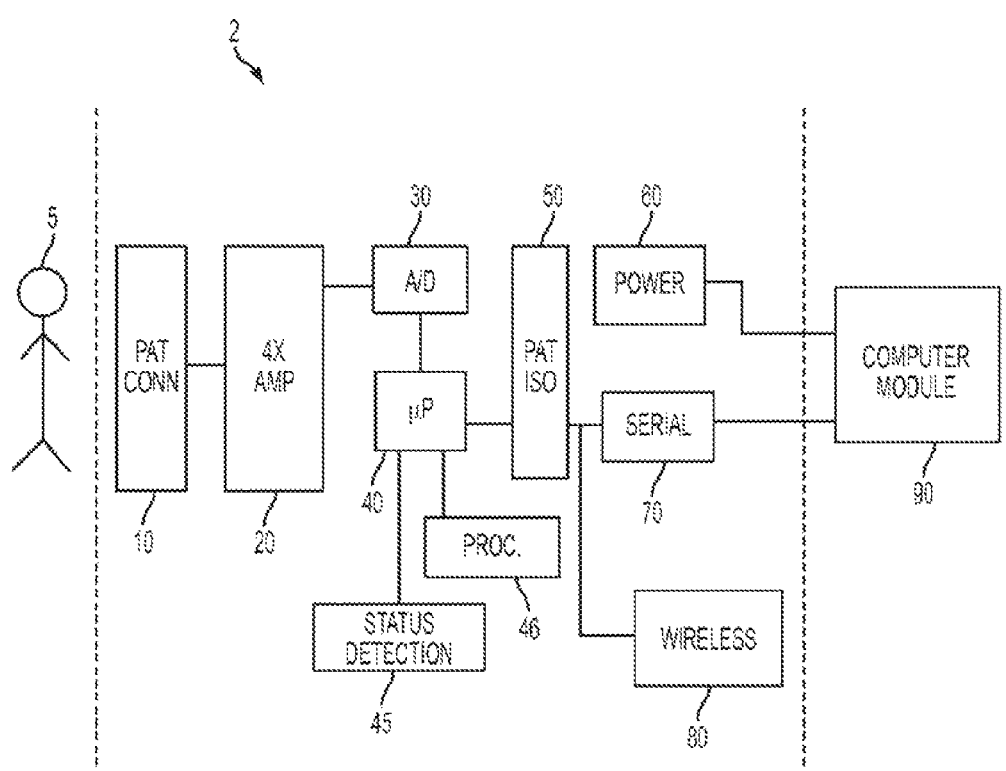
FIG. 1B is a block diagram of an electronic module for acquisition and processing of endovascular electrocardiogram according to an embodiment of the present invention.

FIG. 1B is a block diagram of an electronic module (2) for acquisition and processing of endovascular electrocardiogram according to an embodiment of the present invention.

The patient connector interface (10) allows for connecting electrical leads to the patient (5). Any combination of skin electrodes and/or electrical connections to endovascular devices using the adaptors discussed above can be used. In one embodiment, the amplifier (20) is a four stage amplifier with variable gain, which can amplify electrical signals coming through the patient cable, for example, typical of electrocardiographic values. The analog-to-digital converter (30) converts the signals in digital format readable by the micro-processor (40). Any number and configurations of microprocessors, microcontrollers, and digital signal processors can be used to implement the micro-processing function (45).

In one embodiment, a microcontroller is responsible for controlling the serial communication with a computer module (90) via the serial interface (70) or via the wireless interface (80) and a digital signal processor (DSP) is responsible for implementing one or several of the inventive algorithms described herein. Alternatively, a single processor (46) can be used for both communication and processing.

The micro-processor (40) also receives commands from the computer module (90) and controls different elements of the electronic module, e.g., the amplifier (20) accordingly. The patient isolation block (50) decouples electrically the power (60) and the serial communication channel (70) from the patient interface (10) in order to ensure patient protection to electrical shock. In one embodiment the isolation block (50) can consists of a transformer and/or couplers, e.g. optical couplers.

Figure 2:
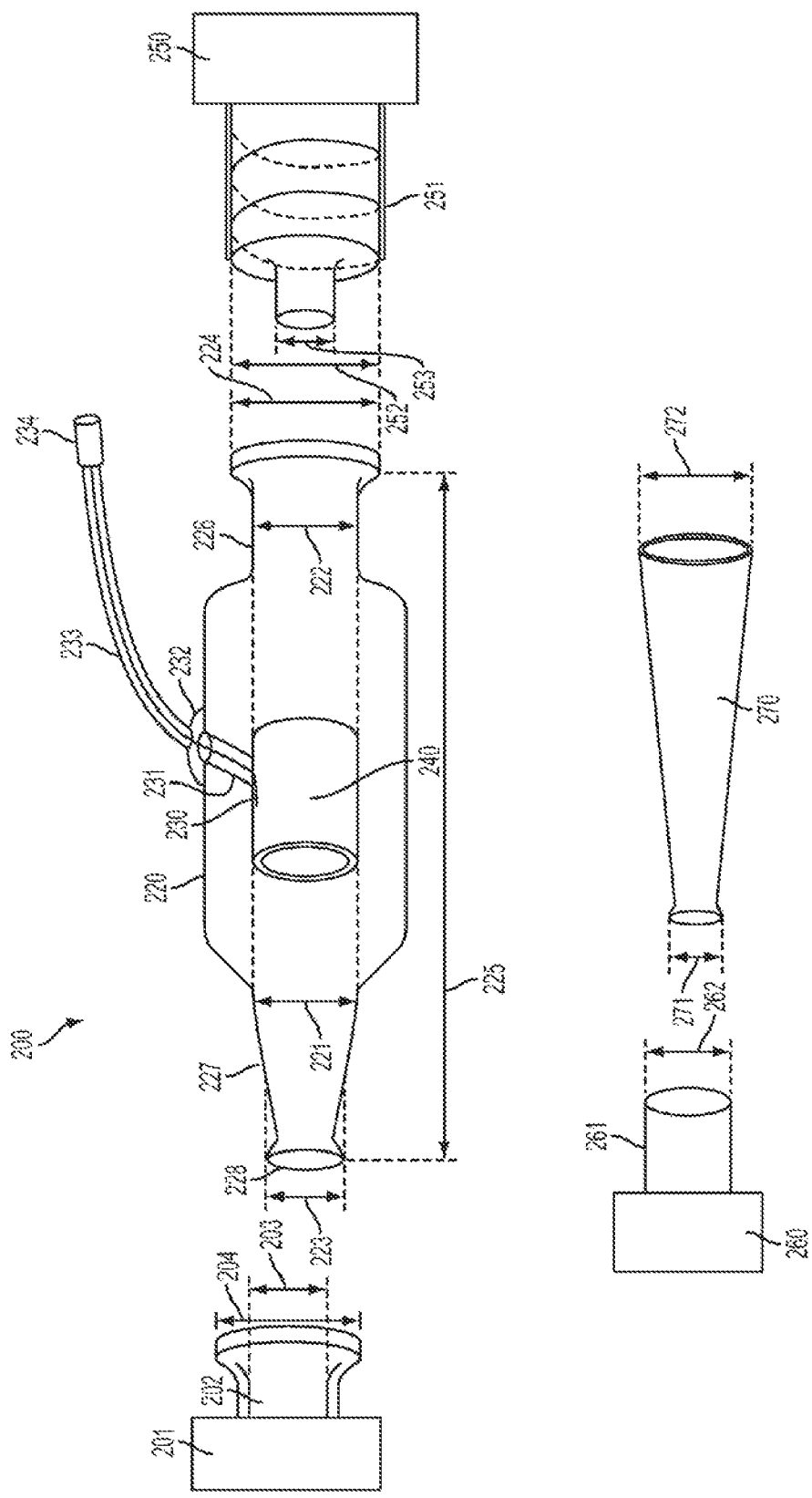
FIG. 2 depicts an adaptor for an endovascular device according to an embodiment of the present invention.

FIG. 2 depicts an adaptor (200) for an endovascular device according to an embodiment of the present invention. Vascular access devices like catheters, syringes, syringe needles, stopcocks, infusion pumps and others connect to each other through standard connections. For example, in FIG. 2 such a standard connection between two devices is illustrated on device (201) by the luer (202) with inner diameter (203) and outer diameter (204), and on device (250) by threaded port (251) with inner diameter (252) and fluid opening diameter (253). The threaded port (251) and the luer (202) allow for connecting the two devices (201, 250) by threading, attaching, coupling, etc., the port (251) into the luer (202).

The adaptor (200) has a body (220) with two ends (226, 227) with a length (225), and is made, for example, of strong biocompatible plastic material with some degree of elasticity. End (227) has a shape of a cone. In one embodiment, end (227) has an elastic sealing portion (228) such that end (227) can easily fit in the luer (202) of device (201) to seal the connection for fluid flow. The other end (226) is in the shape of a standard luer, such as, for example, luer (202) of device (201). The threaded port (251) of the device (250) can be connected to end (226) of the adaptor (200). The cone piece (227) also allows a connection to a device that does not have a luer. The standalone cone piece (270) allows a connection between two devices with different accessible diameters. The end (227) of adaptor (200) has a diameter (223) and fits inside the diameter (272) of the cone piece (270). The end (271) of the cone piece (270) fits in a simple catheter end portion (261) with a diameter (262) of a typical device (260). For example, device (260) can be a catheter for an implantable port.

In one embodiment, device (201) is a syringe needle, and device (250) is a syringe. Fluid, e.g., a conductive electrolyte, flows through adaptor (200) through a central inner bore or lumen (222) having a certain diameter, and provides a fluid path between the devices (250, 201). A conductive metal ring (240) is attached to a portion of the substantially cylindrical surface of lumen (222) and, preferably, induces very little perturbations to the fluid flow. For example, the metal ring (240) may be disposed within a recessed portion of the substantially cylindrical surface of the lumen (222). One end (230) of a conductive wire (233) is electrically coupled to the metal ring (240); in one embodiment, the end (230) is soldered to metal ring (240). In another embodiment, the end (230) is captured between the surface of the lumen (222) and the metal ring (240), and the end (230) and the metal ring (240) maintain good electrical contact through mechanical pressure. The wire (233) may be bare or insulated. In a preferred embodiment, the metal ring (240) is fixedly attached to the surface of lumen (222) using, for example, adhesive, an interference fit, a press fit, etc., while in other embodiments, the metal ring (240) may be removably attached to the surface of lumen (222), free-floating, etc.

The wire (233) passes through a channel (231), which extends from the lumen (222) to an opening in the outer surface of the body (220). Epoxy (232), or other suitable material, may be used to seal the opening of the channel (231), as well as to provide a strain relief for the wire (233). The metal ring (240) may be advantageously disposed adjacent to the channel (231) to provide additional sealing. Thus, the metal ring (240), the wire (233), the channel (231) and the epoxy (232) provide a sealed, electrical connection to the fluid flowing through the adaptor (200). A connector (234) may provide a standard electrical connection to the electrography system; a non-terminated wire may also be used. In one embodiment, the wire (233) terminates at the opening of the channel (231) and the connector (234) is attached directly to the body (222), while in another embodiment, the wire (233) extends through the opening of the channel (231) and the connector (234) is attached to the free end of the wire (233).

In one embodiment, the substantially cylindrical surface of lumen (222) is tapered along the longitudinal direction. This taper may extend along the entire length of lumen (222), or restricted to a certain portion thereof. For example, the surface of lumen (222) may be cone-shaped and have a larger diameter at the proximal end, or, alternatively, the larger diameter may be located at the distal end.

In one example, device (201) is a syringe needle that is inserted into a lumen of a catheter for an implantable port, and device (250) is a syringe. The syringe is filled with saline, which is then injected into the catheter through the adaptor (200). Thus, the adaptor (200) becomes filled with saline solution, and, because the conductive metal ring (240) is in contact with saline and the conductive wire (233), an electrical connection is established between the catheter lumen and the wire (233). In this way, the electrical signal at the tip of the catheter may be measured through the saline solution. Other electrically conductive solutions may also be used to obtain the endovascular electrogram using the adaptor (200). In another embodiment, the adaptor (200) may be used with infusion pumps, as well as other types of power injections. In an alternative embodiment, the adaptor (200) does not include the metal ring (240), and the electrically conductive ending (230) is in direct contact with the electrolyte.

Figure 3:
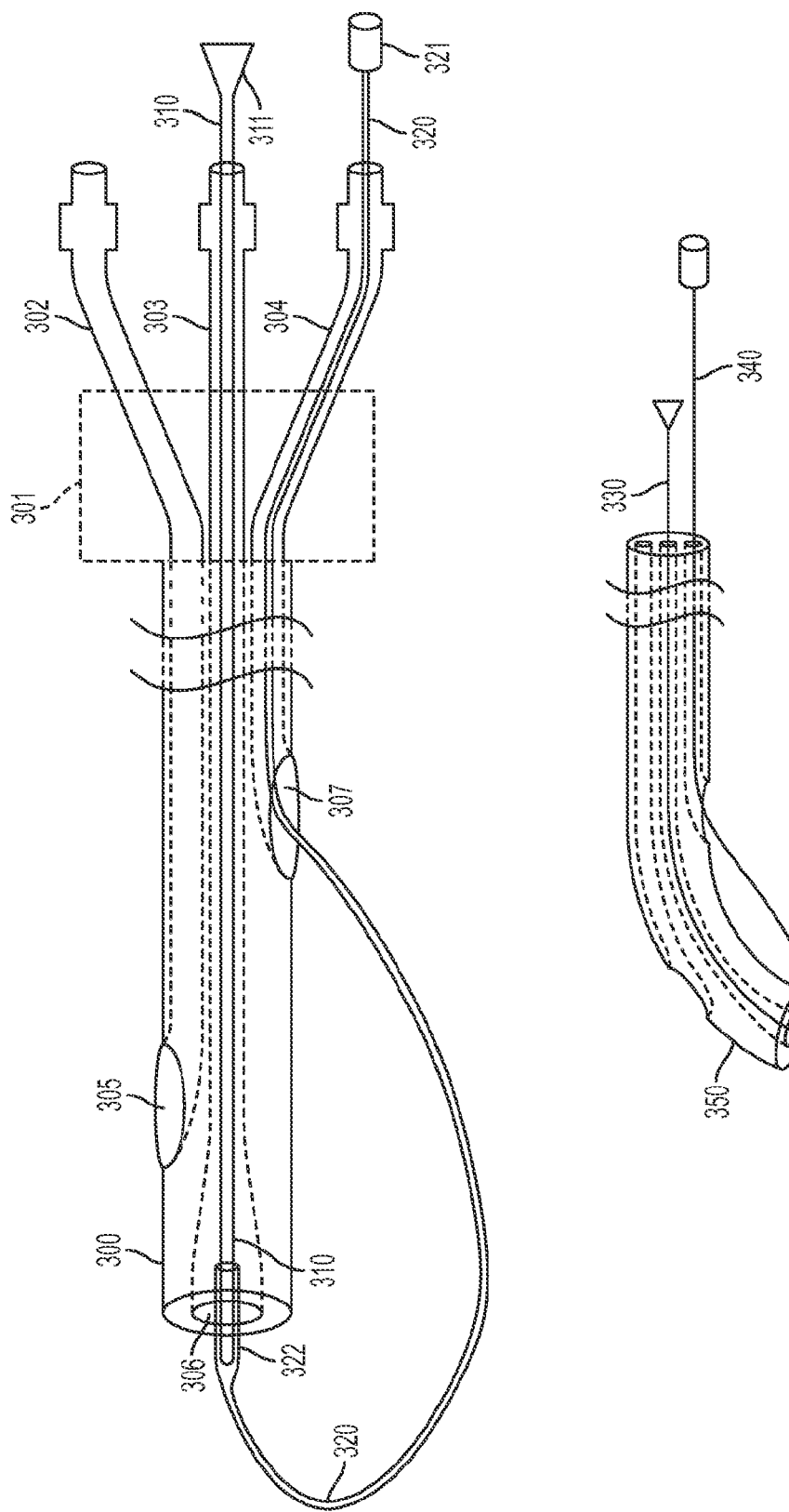
FIG. 3 depicts a catheter steering device according to an embodiment of the present invention.

FIG. 3 illustrates a catheter steering device according to an embodiment of the present invention. In this embodiment, the catheter (300) is a triple lumen catheter and the distal end of each of the lumens is spaced with respect to each other. The catheter steering device can be used with any catheter having two or more lumens with spaced distal lumen openings. The open end of one lumen (306) of catheter (300) is at the very distal end of the catheter, another end or opening of a lumen (305) is spaced back from the distal end and the end or opening of the third lumen (307) is spaced back compared to the second end (305). The distance between the open end (306) and the end (307) is typically from one to several centimeters.

Several types of catheters have multiple lumens with spaced ends, and the inventive steering device can accommodate such catheters. For example, in the case of a peripherally inserted central catheter, the typical length of a catheter is 50 to 60 centimeters and the spacing between the distal lumen ends (305, 306, and 307) is from one to several centimeters. A hemodialysis catheter with two lumens can typically be 20 to 40 centimeters in length, with one to several centimeters spacing between the distal ends of the two lumens. A multi-lumen central venous catheter (CVC) can typically be 15 to 25 cm in length with spacing between distal ends or openings of the lumens being from several millimeters to several centimeters.

At the proximal end, the catheter has a catheter hub (301) which splits the three lumens and connects each of them with a luer (302, 303, 304). The inventive catheter steering device includes a stylet (310) with a handle (311) at the proximal end to allow for pushing, pulling, and removal after use, and a steering member (320) which connects to the distal end of the stylet (322) and which can be fed back into a distal lumen opening of one of the other lumens, such as, for example, lumen (307). The steering member (320) returns to the proximal end of the catheter through the catheter lumen and exits at the proximal end through the luer corresponding to the respective lumen (304). So disposed, the steering device is in the installed position. In one embodiment, the member (320) has a handle (321) which can be used to pull the member through the lumen. In another embodiment, the handle (321) is detachable from the member (320).

The member (320) may be polyurethane, silicone, PTFE, or other similar materials. In different embodiments, the member (320) may be any kind of biocompatible thread, e.g., surgical thread. In another embodiment, the member (320) is stainless steel wire. In one embodiment, the stylet is provided pre-inserted into one of the catheter lumens, typically the central lumen with the most distal opening (306) with the member 320 attached at the distal end of the stylet (322) and pre-inserted into the lumen (304) through the lumen opening (307). In order to steer the catheter, the user pulls the member 320 out of the catheter while preventing the stylet 310 to be pulled into the catheter. Thus, the catheter tip can be bent in a desired direction. This situation is illustrated by the bent catheter tip (350), the member (340) which was pulled back and the member (330) which is its initial position with respect to the catheter. If the stylet (310) or the steering member (320), or both are made of any electrically conductive material, then each or both of them can be used to measure electrical signals or endovascular electrograms at the distal tip of the catheter by connecting their proximal ends to the endovascular electrography system. In one embodiment, the steering member (320) can be tied to the stylet (310) through the opening (307) of the catheter lumen.

In another embodiment, the stylet (310) and the steering member (320) are manufactured as a single component to form an extended steering member that is looped back through the opening (305) of a different catheter lumen. By pulling one of the two ends of the extended steering member coming out through luers (304) and (302), the same effect is achieved and the catheter tip can be bent in a desired direction. In another embodiment, in the case of a double lumen catheter, the stylet (310) can be inserted in one lumen and the steering member (320) can be inserted in the other lumen, such that the effect of bending the catheter tip can be achieved by pulling the proximal ends. In a further embodiment, the steering member (320) can be inserted in the lumen (302) and through the opening (305).

FIGS. 4A, 4B, 4C, and 4D depict electrode configurations that provide optimal acquisition of endovascular electrocardiogram according to various embodiments of the present invention.

Figure 4A:
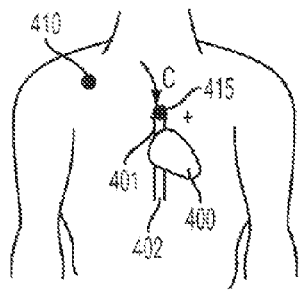
FIGS. 4A, 4B, 4C, and 4D depict electrode configurations that provide optimal acquisition of endovascular electrocardiogram according to various embodiments of the present invention.

FIG. 4A depicts a single lead configuration with a reference electrode (410), for example attached to the patient's skin over the right arm and with the other electrode attached through an adaptor to an endovascular device (415). The reference electrode attached to the skin over the right arm is presented in this configuration for illustration purposes only. Other locations of the reference electrode are possible depending on the type of ECG required. The reference electrode over the right arm together with the tip of the endovascular device used with the adaptor can be similar to lead II of a standard ECG. In this case the ECGs obtained from the superior vena cava (401) and inferior vena cava (402) can be optimized. The reference electrode can be attached to the skin in any other location in order to simulate other leads of the standard ECG. The reference electrode can be also connected to adaptors attached to other endovascular devices in order to obtain more local information from within the patient's heart (400).

Figure 4B:
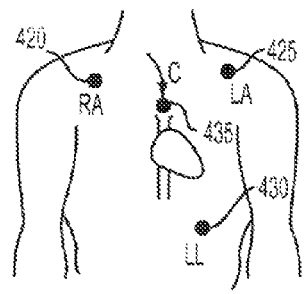

FIG. 4B depicts a modified 3-lead configuration, with monitoring and guiding capabilities, with 4 electrodes. Three (3) electrodes correspond to the standard ECG electrodes: right arm (RA, 420), left arm (LA, 425), and left leg (LL, 430) used as reference. The fourth electrode is attached through an adapter to the endovascular device (C, 435). In this configuration, the electronic module and the algorithm perform two functions simultaneously: the three standard electrodes (RA, LL, and LL) perform a monitoring function of the heart, while the C electrode (435) allow for recording the ECG at the tip of device.

Figure 4C:
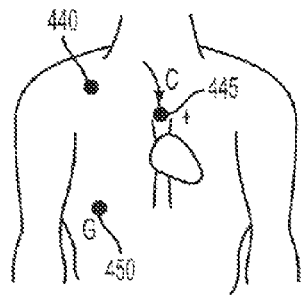

FIG. 4C depicts a telemetry configuration with a single grounded lead, including the configuration illustrated in FIG. 4A and a ground reference (450). This configuration can be used to transmit ECGs remotely through a telemetry system configuration.

Figure 4D:
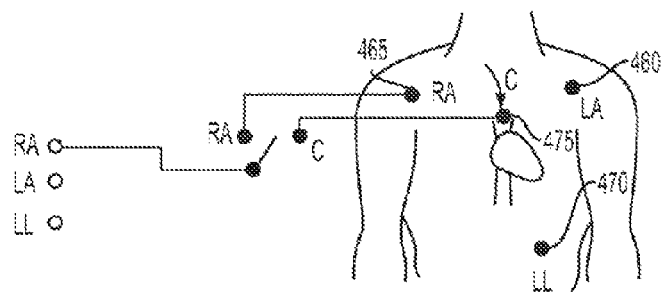

FIG. 4D depicts one use of ECG monitors for guiding endovascular devices. A standard ECG monitor is used having standard inputs RA (465), LA (460), and LL (470). LA (460) is connected to the left arm and LL (470) to the left leg of the patient. The RA input (465) is connected to a switch which can be used be the clinician to switch the RA input (465) between the RA electrode and the catheter (C) electrode 475. Thus either monitoring or guiding of catheter placement can be achieved alternatively.

Figure 5:
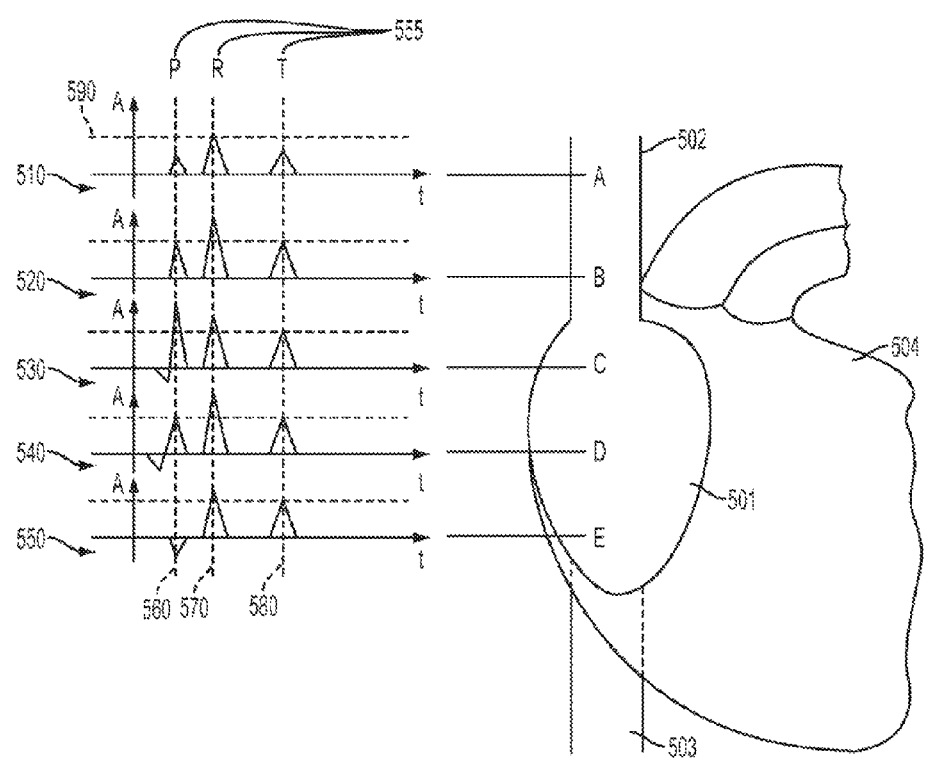
FIG. 5 illustrates exemplary electrocardiogram signal amplitudes at different locations in the central venous system.

FIG. 5 illustrates exemplary electrocardiogram signal amplitudes at different locations in the central venous system.

The heart (504), right atrium (501), superior vena cava (SVC) (502), and the inferior vena cava (IVC) (503) are illustrated. Location A is in the upper SVC, location B is in the lower third of the SVC, location C is at the caval-atrial junction, location D is in the right atrium, and location E is in the upper inferior vena cava.

Graph 510 illustrates an ECG waveform as a function of time at recorded at location A. The absolute amplitude of the waveforms is recorded on an amplitude scale (590). In the case of an endovascular ECG, the standard elements of the electrocardiogram are illustrated: the P-wave (560), the R-wave (570), and the T-wave (580). The amplitudes and shape at location A recorded with a lead configuration as in FIG. 4D are similar to an electrocardiogram recoded at the skin level with the same electrode configuration.

Graph 520 illustrates an endovascular ECG depicted at location B. The amplitude at this location is higher than the one at location A but the overall shapes of the waveform are similar at location A and B.

Graph 530 illustrates an endovascular ECG depicted at location C. At location C at the caval-atrial junction, the amplitude of the waveform is yet higher than the one at location B and the P-wave has dramatically changed becoming higher than the R-wave. This waveform is an indication of the proximity of the sino-atrial node.

Graph 540 illustrates an endovascular ECG depicted at location D. At location D in the right atrium, the amplitudes are similar to location C but the P-wave changes polarity becoming bi-polar. This is an indication that the measurement of the ECG occurs beyond the sino-atrial node.

Graph 550 illustrates an endovascular ECG depicted at location E. At location E in the inferior vena cava, the waveform is similar to the one at location A in terms of amplitude except the P-wave has reverse polarity. The differences in the ECG waveforms at different locations are used by the algorithms introduced herein to discriminate between the corresponding locations and to assess heart and blood vessel functionality.

Figure 6:
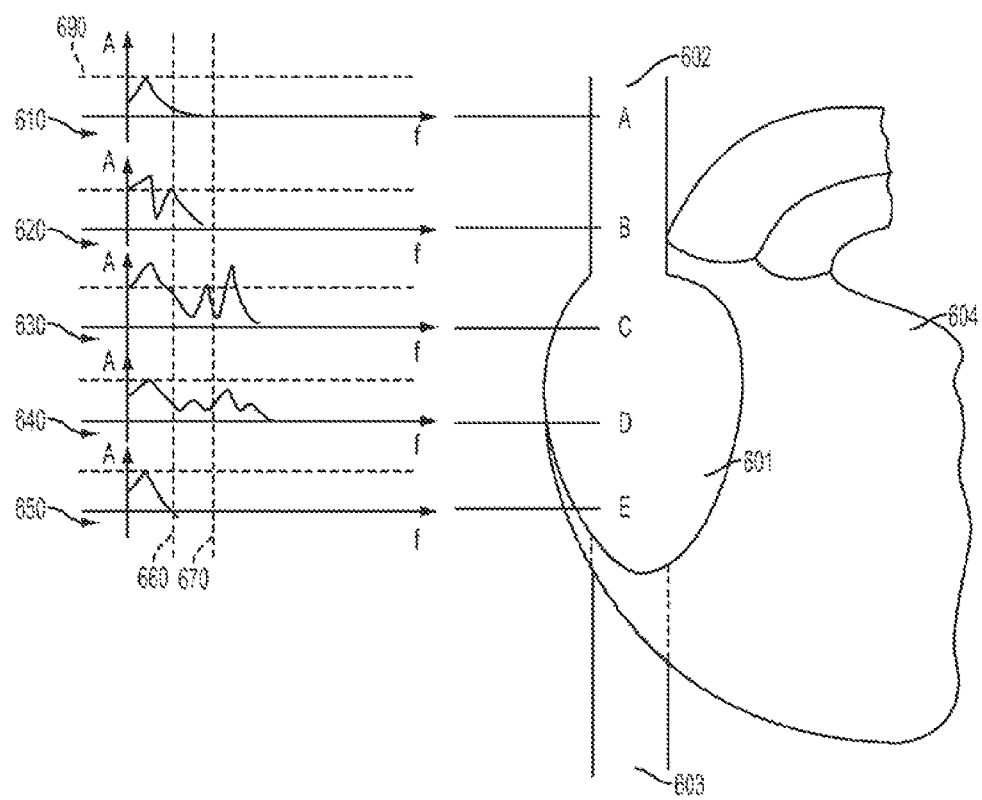
FIG. 6 illustrates exemplary electrocardiogram signal power spectra at different locations in the central venous system.

FIG. 6 illustrates exemplary electrocardiogram signal power spectra at different locations in the central venous system, using a spectral scale (690).

The heart (604), right atrium (601), superior vena cava (SVC) (602), and the inferior vena cava (IVC) (603) are illustrated. Graph 610 illustrates an endovascular ECG spectrum depicted at location A. At location A, the spectrum (610) has the appearance of a single central frequency or single band (660) and with a frequency distribution spectral power and energy similar to those at skin level.

Graph 620 illustrates an endovascular ECG spectrum depicted at location B. At location B the frequency distribution has two major bands and a higher energy and spectral power than the one at location A.

Graph 630 illustrates an endovascular ECG spectrum at location C. At location C, there are multiple (3-4) major frequencies or principal spectral components distributed over a wider range of frequencies (670). This spectral distribution is indicative of the energy distribution around the sino-atrial node. The spectral power and signal energy have increased compared to location B.

Graph 640 illustrates an endovascular ECG spectrum depicted at location D. At location D the spectrum is wider and more broadband indicative of the electrical activity of the right atrium.

Graph 650 illustrates an endovascular ECG spectrum depicted at location E. The frequency spectrum at location E is similar to the one at location A. The differences in the spectral waveforms at different locations are used by the algorithms introduced herein to discriminate between the corresponding locations and to assess heart and blood vessel functionality.

Figure 7:
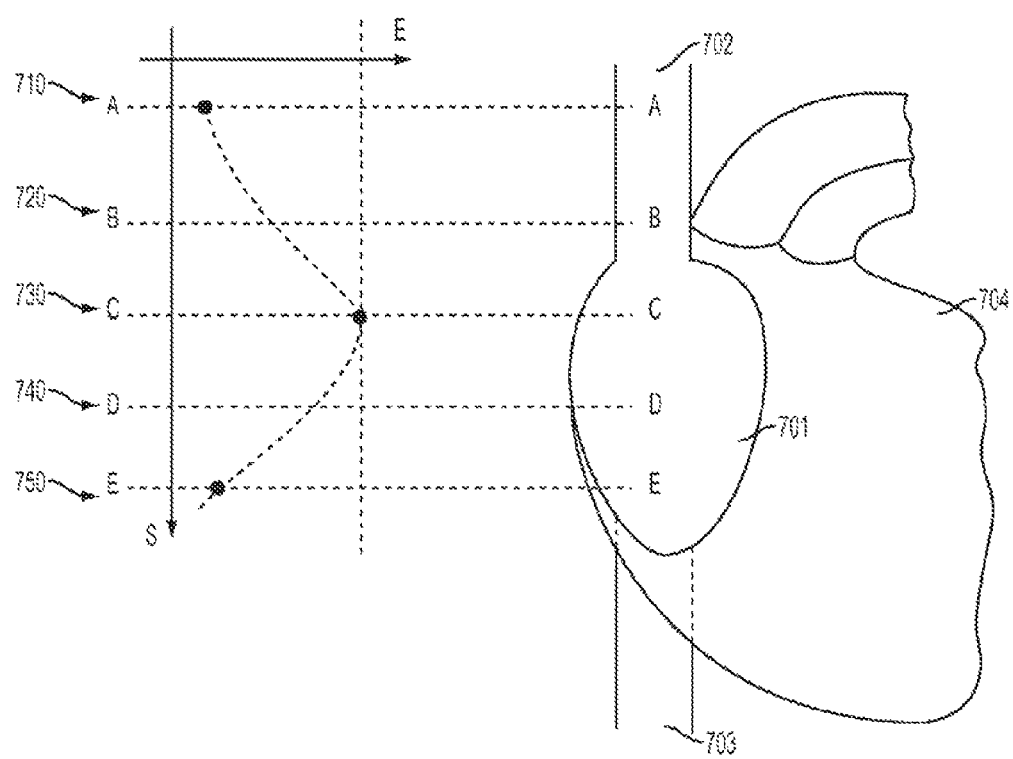
FIG. 7 illustrates exemplary electrocardiogram signal electrical energy distribution at different locations in the central venous system.

FIG. 7 illustrates exemplary electrocardiogram signal electrical energy distribution at different locations in the central venous system. The heart (704), right atrium (701), superior vena cava (SVC) (702), and the inferior vena cava (IVC) (703) are illustrated. Graphs (710, 720, 730, 740, 750) depict the energy distribution at different locations (A, B, C, D and E, respectively) and the changes in time are used by the algorithms introduced herein to discriminate between the corresponding locations and to assess heart and blood vessel functionality.

Figure 16:
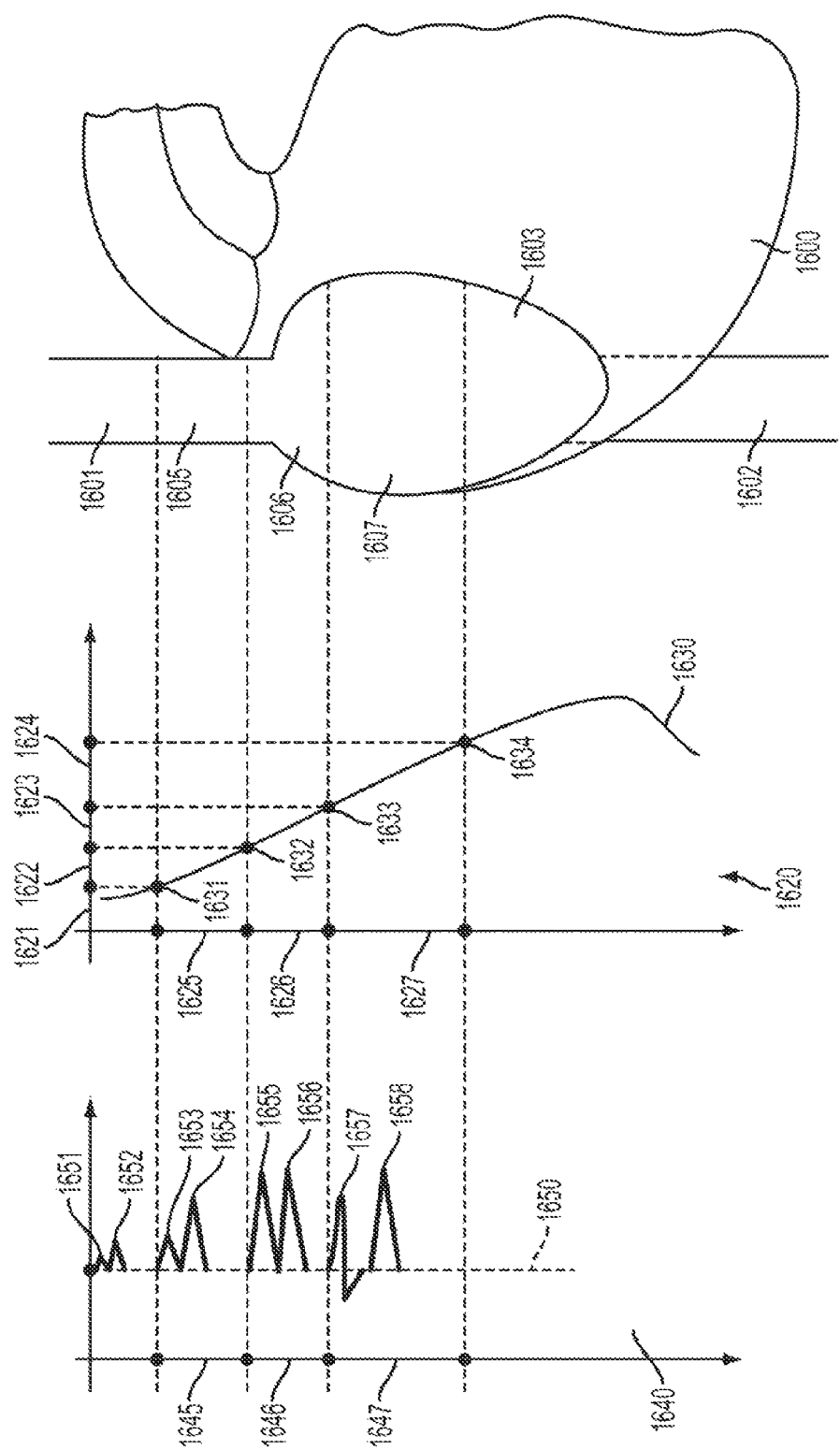
FIG. 16 illustrates a framework for analyzing the endovascular electrography signals, according to an embodiment of the present invention.

Considering FIG. 16 for a moment, a framework for analyzing the endovascular electrography signals according to an embodiment of the present invention is illustrated. The heart is represented by (1600), the superior vena cava by (1601), the inferior vena cava by (1602) and the right atrium by (1603). In this embodiment, there are three regions of interest for placing central venous access devices: the lower third of the superior vena cava or SVC (1605), the caval-atrial junction or CAJ (1606), and the upper right atrium or RA (1607).

The graph (1620) illustrates the electrical energy profile as a function of location in the heart and the graph (1640) illustrates the different electrography waveforms which can be obtained at different locations in the heart. The curve (1630) illustrates the increase of electrical energy detected in each of the regions at the tip of an endovascular catheter advancing from the superior vena cava into the heart. In one embodiment, the energy curve is calculated in time domain, while in another embodiment, the energy curve is calculated in the frequency domain using the frequency spectrum. In one embodiment, the energy is calculated for the actual signal levels, while in another embodiment, the baseline value or other mean values are first subtracted from the signal values before energy calculations. The signal energy or power is calculated in time domain by summing up the squared amplitude values before and/or after baseline subtraction over a determined period of time, e.g., a heartbeat. In the frequency domain, the signal energy or power is calculated by summing up the squared values of the frequency components. In one embodiment, the curve is calculated using the entire electrogram, while in other embodiments, only certain segments of the electrogram are used for the energy calculations, e.g., only the segment corresponding to a "P-wave" of an electrocardiogram. Such a "P-wave" segment is representative of the electrical activity of the sino-atrial node.

Different levels of energy characterize the different locations along the catheter path from the SVC to the heart. These regions can be differentiated in terms of their electrical energy level by using thresholds. Threshold (1631) of energy level defines the beginning of the lower third of the superior vena cava. The energy levels (1621) define the regions in the vasculature of low energy which are distant or further away from the sino-atrial node. The energy levels (1622) between thresholds (1631) and (1632) define the region labeled as the lower third of the superior vena cava (1625 and 1605). The energy levels (1623) between thresholds (1632) and (1633) define the region labeled as the caval-atrial junction (1626 and 1606). The energy levels (1624) between thresholds (1633) and (1634) define the region labeled right atrium (1627 and 1607).

Similarly, the shape and size of the electrogram in graph (1640) relative to a baseline (1650) can be correlated to a location in the heart. Thresholds (1631), (1632), (1633), and (1634) are determined specifically for the type of energy considered for calculations, e.g. the entire electrogram, the P-wave, and/or the S-T segment. Before the lower third of the SVC and corresponding to a relatively low level of energy (1621), the P-wave (1651) and the R-wave (1652) are similar in size and shape with a standard electrocardiogram lead II recorded at the skin level if the right arm standard ECG lead is connected to the catheter and measuring the electrogram signal at the tip of the catheter. In the lower third of the SVC (1605 and 1645), the energy level of the electrogram increases, the electrogram amplitudes increase and the P-wave (1653) increases amplitude and energy relative to the R-wave (1654) to where the P-wave amplitude and energy between half and three quarters of the amplitude and energy of the R-wave. At the caval-atrial junction (1606 and 1646), the energy level of the electrogram increases further, the electrogram amplitudes continue to increase and the P-wave (1655) increases amplitude and energy relative to the R-wave (1656) to where the P-wave amplitude and energy are larger or equal to the amplitude and energy of the R-wave. In the right atrium (1607 and 1647), the energy level of the electrogram increases further, the electrogram amplitudes increase, the P-wave (1657) becomes bipolar and its amplitude and energy relative to the R-wave (1658) start decreasing. These behaviors are quantified, analyzed, and used in order to provide location information regarding the tip of the catheter.

Figure 17:
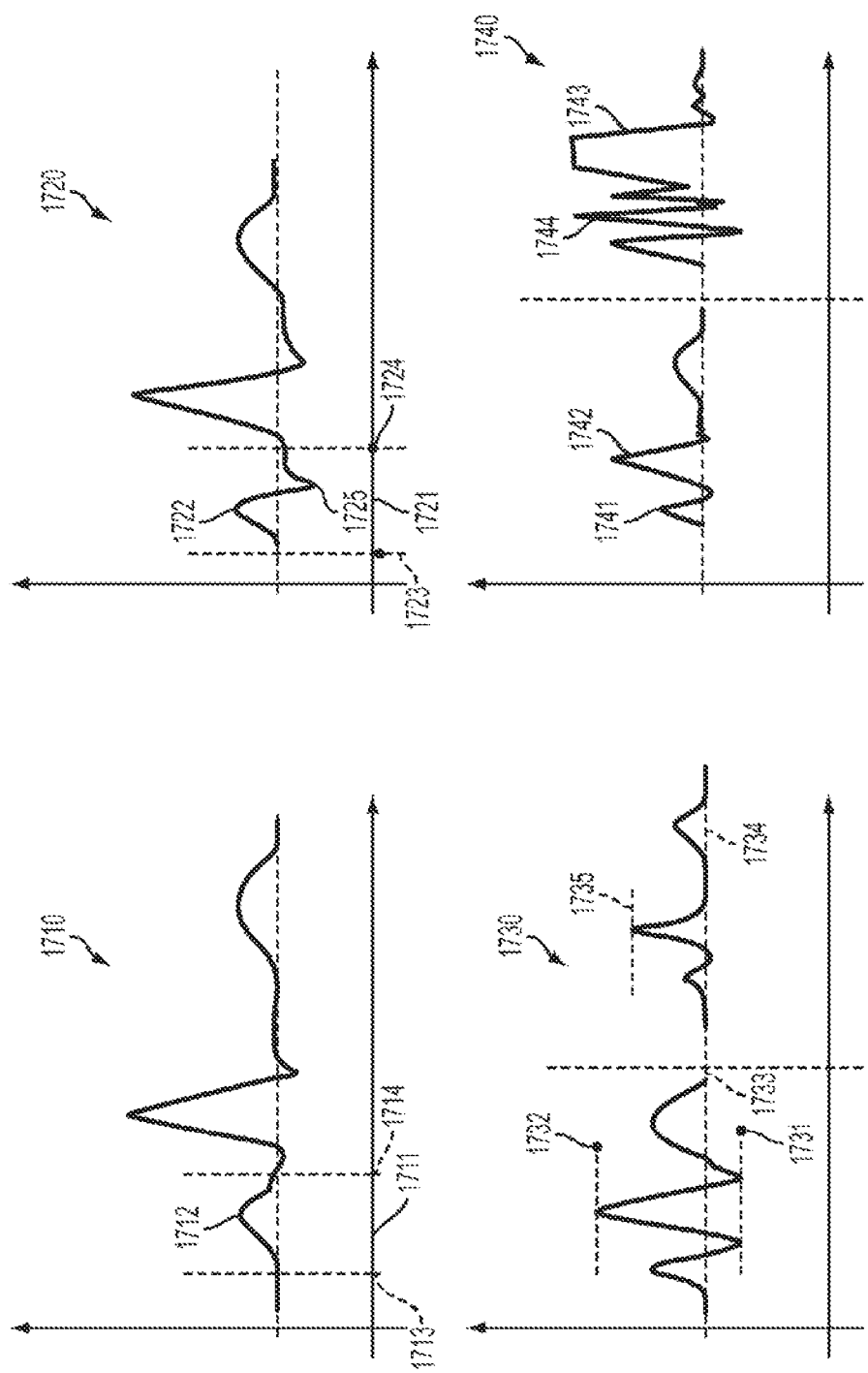
FIG. 17 illustrates several embodiments for electrogram waveform processing.

Considering FIG. 17 for a moment, several electrogram waveform processing embodiments are illustrated. Graphs (1710) and (1720) illustrate a P-wave analysis embodiment. Since the P-wave corresponds to electrical activity of the heart generated by the sino-atrial node, the changes of the P-wave are most relevant with respect to determining the proximity of the sino-atrial node in an endovascular approach. Therefore, in order to assess proximity of the sino-atrial node and location in the vasculature, signal analysis methods in time and frequency domains, as well as signal energy criteria can be applied only to the P-wave segment of an electrogram. In graph (1710), the segment designated for the P-wave analysis (1711) starts at moment (1713) and ends at moment (1714). During the period of time between the starting moment and the ending moment of the P-wave segment, the highest amplitude detected corresponds to the P-wave peak (1712). The starting moment (1713) of the P-wave segment analysis can be determined in a number of ways. In one embodiment, the heart beat is calculated and the R-peak is detected as the maximum amplitude of the heartbeat. Going back from each R-peak a certain percentage of the heartbeat, for example between 20% and 30%, determines the moment when the analysis of the P-wave starts (1713). Going back 2% to 5% of the heart beat from each R-peak determines the end of the segment designated for the P-wave analysis (1714). Similarly, in graph (1720), the designated segment for the P-wave analysis (1721) starts at moment (1723) in the heart cycle and ends at moment (1724). The P-wave in this case is bipolar with a positive maximum amplitude (1722) and a negative maximum amplitude (1725) when compared to the baseline (amplitude equals zero). For the P-waveform defined between the starting point (1713 on graph 1710 and 1723 on graph 1720) and the end point (1714 on graph 1710 and 1724 on graph 1720) time-domain and frequency-domain algorithms are applied according to embodiments of the present invention.

Graph (1730) illustrates the advantages of baseline subtraction prior to signal energy computation. If the signal energy is calculated in time domain as the sum of the squared signal amplitudes over a heartbeat, then the amplitude variations between levels (1731 and 1732) around baseline (1733) may lead to a lower energy level than the signal with amplitude variations between levels (1734 and 1735) whereby the level (1734) is the baseline. The baseline value (1733) is subtracted from the amplitude values (1731 to 1732) and the baseline value (1734) is subtracted from the amplitude values (1734 to 1735). After subtracting the baseline, the sum of squared amplitude values is calculated. Thus, this sum is proportional to the energy of signal variation around the baseline and therefore it is more appropriate to characterize changes in the signal values/behavior.

Graph (1740) shows a typical electrogram waveform with a P-wave (1741) and an R-wave (1742) and a distorted signal with the P-wave covered by high frequency noise (1744) and the R-wave saturated to a maximum value (1743). In the presence of these kinds of artifacts (1744 and 1743) it is very difficult and sometimes impossible to recover the original signal (1741 and 1742). Therefore, according to embodiments of the present invention, an algorithm is used to detect the presence of artifacts and reduce the amount of artifacts as much as possible. If, after reducing the artifacts, the signal cannot be recovered, then the signal is discarded for the computation of signal energy. The presence of artifacts can be detected in time domain by a high value of the derivative and of its integral, a jump in signal energy, a jump in the value of the baseline or in different averages calculated from the signal. In frequency domain, the artifacts can be detected as a jump in the value of the DC component (frequency zero of the spectrum), as the sudden appearance of high frequency components, and in a jump of the spectral power/energy. In the frequency domain, selective filtering can be applied and all components removed, which are not "typical" for the average behavior of the signal. After selective filtering, the signal is reconstructed in the time domain using an inverse Fourier transform in order to allow for verification of the success of the selective filtering.

Figure 8:
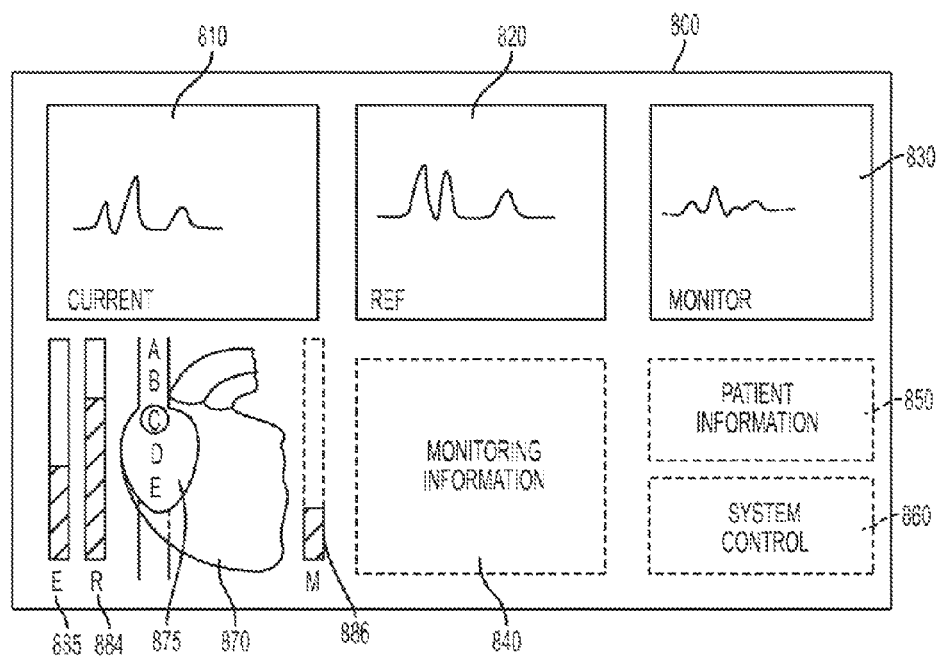
FIG. 8 depicts a graphical user interface according to an embodiment of the present invention.

FIG. 8 depicts a graphical user interface according to an embodiment of the present invention.

Window (810) presents the ECG waveform in real-time as it is acquired by the electronic module using the attached electrode configuration. Window (820) is a reference window and shows a frozen waveform used to compare with the current window. In one embodiment, the reference waveform in window (820) can be obtained through the electrodes connected to the electronic module at a reference location of the catheter and/or using a reference configuration of the skin electrodes. For example, such a reference waveform can be the ECG recorded using an adaptor according to an embodiment of the present invention connected to an endovascular device placed at the caval-atrial junction. In a different embodiment, the reference waveform in window 820 can be a typical waveform at a certain location in the vasculature or of a certain heart condition as it is recorded in a database of waveforms and as it is stored in the storage medium of the computer system. If the electrode configuration allows for simultaneous heart monitoring and recording of electrograms using an endovascular device, window (830) shows one of the standard ECG leads for heart monitoring, while window (810) shows the ECG at the tip of the endovascular devices when connected to an adaptor, such as the ones discussed above.

The icon (870) is a representation of the heart, and the locations A through E (875) illustrate different locations in the heart and vascular system which can be discriminated by analyzing endovascular ECGs in accordance with the methods disclosed herein. As a location in the vasculature is identified by the algorithms, the corresponding place and letter on the icon (875) becomes highlighted or in some other way is made visible to the user. The bars (884), (885), and (886) show signal energy levels. The "E" bar (885) presents the amount of electrical energy computed from the ECG frequency spectrum at the current location of the tip of the endovascular device. The "R" bar (884) presents the amount of electrical energy computed from the ECG frequency spectrum at a reference location. The "M" bar (886) presents amount of electrical energy computed from the ECG frequency spectrum using the monitoring ECG signal from the skin electrodes. The window (840) depicts monitoring information, e.g., heart rate. Patient information (name, date of procedure and others) are shown in window (850). Window (860) contains system control elements like buttons and status information, e.g., scale, scroll speed, system parameters and system diagnostics.

Figure 9:
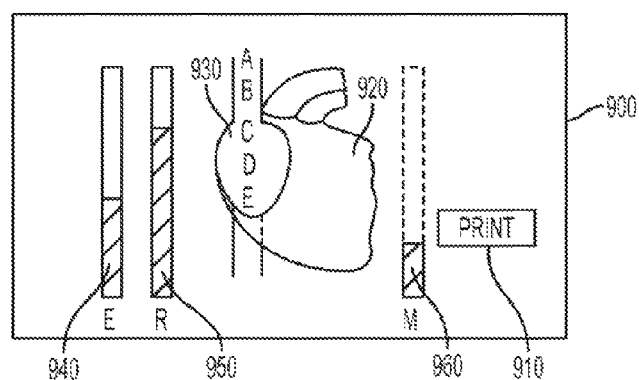
FIG. 9 depicts a graphical user interface according to another embodiment of the present invention.

FIG. 9 depicts a graphical user interface according to another embodiment of the present invention.

The icon (920) is a representation of the heart and the locations A through E (930) illustrate different locations in the heart and vascular system which can be discriminated by analyzing endovascular ECGs. As a location in the vasculature is identified by the algorithms, the corresponding place and letter on the icon (930) becomes highlighted or in some other way is made visible to the user. The bars (940), (950), and (960) show signal energy levels. The "E" bar (940) depicts the amount of electrical energy computed from the ECG frequency spectrum at the current location of the tip of the endovascular device. The "R" bar (950) shows the amount of electrical energy computed from the ECG frequency spectrum at a reference location. The "M" bar (960) shows amount of electrical energy computed from the ECG frequency spectrum using the monitoring ECG signal coming from the skin electrodes. The button "Print" (960) allows the user to print the information documenting the case on a printer, for example on a label printer for quick attachment to the patient's chart.

Figure 10A:
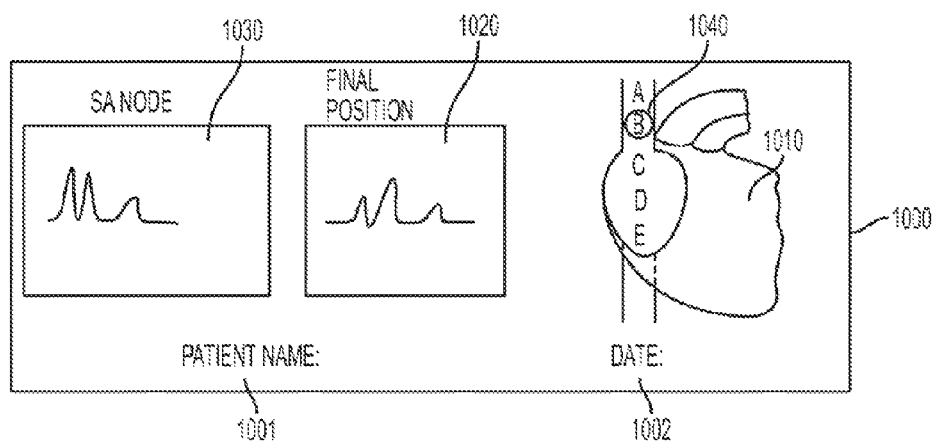
FIGS. 10A and 10B depict exemplary printouts for the information displayed by the graphical user interface, according to an embodiment of the present invention.
Figure 10B:
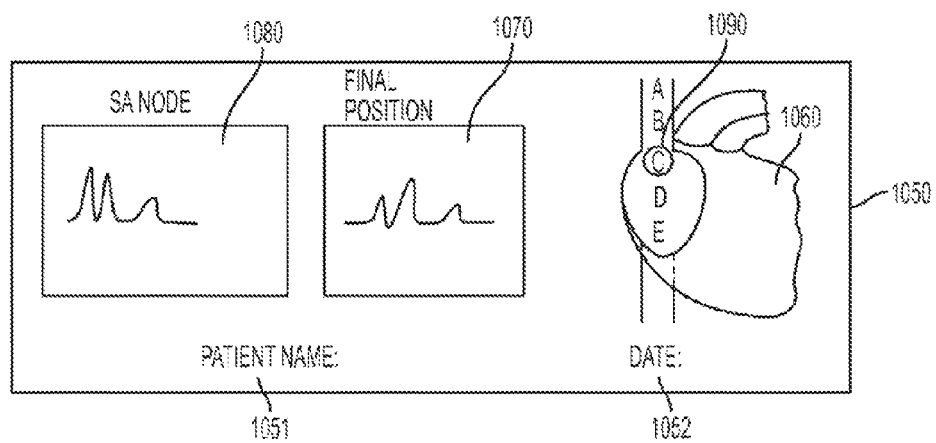

FIGS. 10A and 10B depict exemplary printouts for the information displayed by the graphical user interface, according to an embodiment of the present invention.

FIG. 10A illustrates a printout (1000) for the case of a catheter tip placement procedure in the lower third of the SVC. The field 1010 depicts the heart icon whereby the letter "B" corresponding to the lower third of the superior vena cava (SVC) is highlighted (1040). Field 1030 depicts the reference ECG waveform recorded at the tip of the catheter at the caval-atrial junction in the proximity of the sino-atrial node. Field 1020 depicts the ECG waveform at the tip of the catheter in the position in which it was placed at the end of the procedure. For FIG. 10A, this location is in the lower third of the SVC and the ECG waveform corresponds to this location. The patient name (1001) and the date of procedure (1002) are also printed.

FIG. 10B depicts a similar printout (1050) except that the final position at the end of the procedure is at the caval-atrial junction at location C (1090) on the heart icon (1060). The "SA Node" field depicts the reference ECG waveform (1080), and the "Final Position" field (1070) shows that the catheter was placed with the tip at the sino-atrial node: the ECG waveform in final location is similar or even identical with the one in the reference location at the sino-atrial node (SA Node). It is known that the proximity of the SA Node indicates a location at the caval-atrial junction. These locations are sometimes considered identical by some clinicians.

Figure 11:
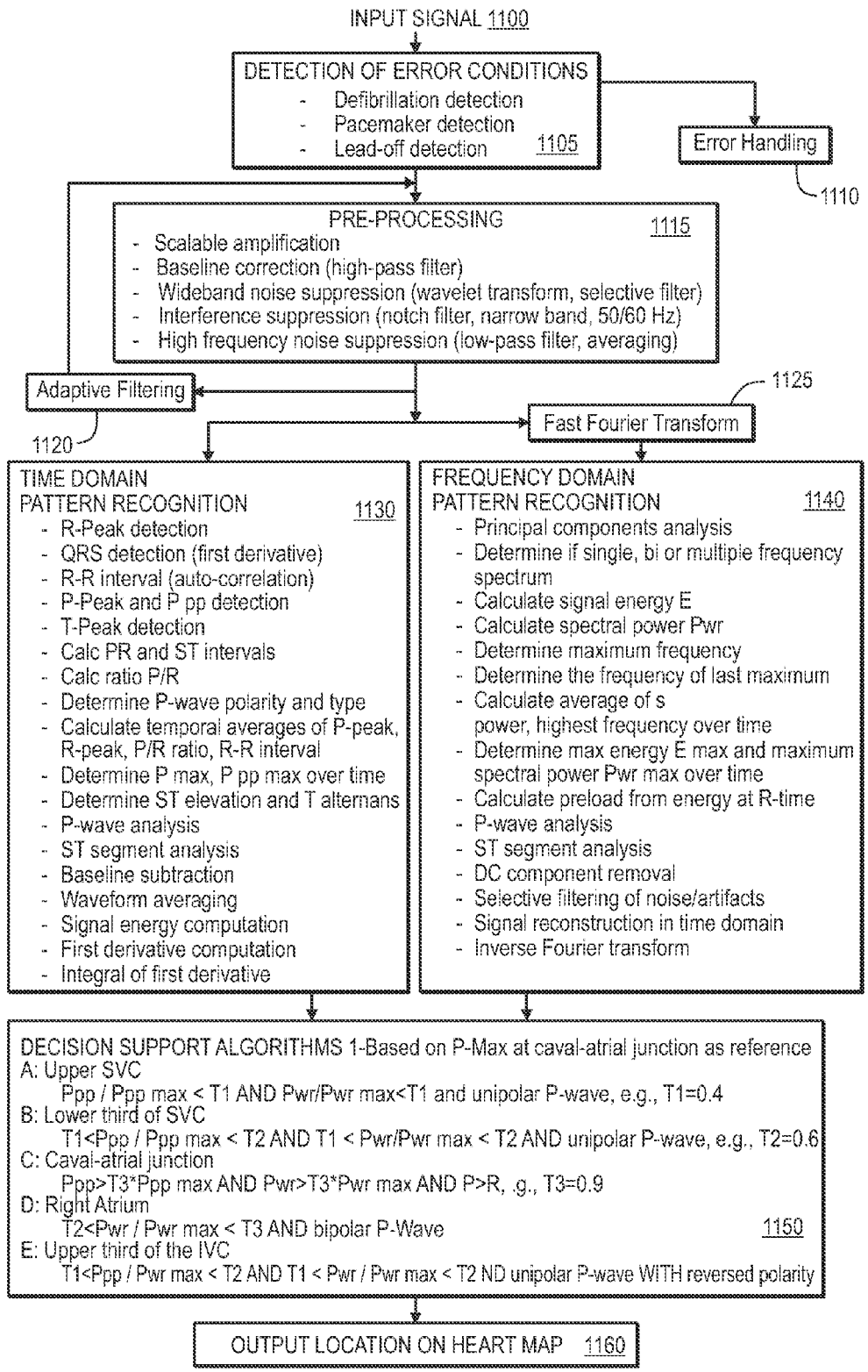
FIG. 11 is a block diagram for a computer-based method for positioning an endovascular device in or near the heart using electrocardiogram signals.

FIG. 11 is a block diagram for a computer-based method (1100) for positioning an endovascular device in or near the heart using electrocardiogram signals.

The algorithms are applied to the input signal (1102) (ECG) acquired by the adaptor to the endovascular devices and, optionally, through skin electrodes as well. The Error Detection Block (1105) detects at least three types of error conditions/exceptions, such as, for example, when a defibrillator has been applied to the patient, when a pacemaker is firing excitation pulses and/or when a lead/electrode is off. These errors/exceptions may be handled differently, and the user may be informed about the presence of an exception and the way of handling the exception (1110).

The Pre-Processing block (1115) may amplify the signal, reduce noise, eliminate artifacts, etc. In one embodiment, rescaling the signal to the display range occurs under user control and is not automatic, as with most currently available ECG monitors. Thus, changes in the amplitude of the ECGs are easily noticed. A high-pass filter corrects the baseline and reduces such artifacts as respiratory artifact. Wideband noise suppression may be achieved using a selective filter, e.g., a wavelet transform. Electromagnetic interference with other equipment and the power grid may be suppressed by a notch filter (narrow band filter) centered at 60 Hz or 50 Hz to accommodate domestic or international power supplies. High frequency noise may be suppressed with a low-pass filter, which, in one embodiment, is implemented with variable length averaging, such as, for example, a running window corresponding to a heart cycle, an averaging of the ECG over several consecutive heart cycles, etc. The Adaptive Filtering block (1120) optimizes the filter coefficients by minimizing an error signal.

The Time-Domain Pattern Recognition block (1130) identifies elements of the ECG waveform, their relationship(s) and their behavior(s) in time. An important aspect of the time-domain pattern recognition algorithm in block 1130, as well as of the Frequency Domain Patter Recognition block 1140, is data history. The ECGs are analyzed in real time for certain elements, and, for other elements, a data buffer with an appropriate buffer length is maintained in the memory of the electronic and/or computer modules in order to allow for historic data analysis and prediction based on this analysis. In one embodiment, the data history buffer is several seconds long allowing for the ECG signal corresponding to several heartbeats to be saved in the buffer. A double buffering technique allows the waveform in one buffer to be processed while the second buffer continues to store signals. Thus no signal data are lost while the waveform in one buffer is processed. After data processing on one buffer is completed, the results are sent to the Decision Support Algorithms (1150) and the two buffers switch roles. The length of the buffer accommodates the time duration of data processing in order to ensure that no data are lost. A similar double buffering technique is also applied to the data subject to Frequency Domain Pattern Recognition block (1140).

In the case of an endovascular ECG, elements of interest may include, but are not limited to, one or more of the following:
1. The P, Q, R, S, T, and U waves, their peaks, amplitudes and duration;
2. The duration of the P-R, S-T, and T-P segments/intervals;
3. The elevation of the S-T segment;
4. The variances of the P-P and R-R intervals;
5. The variance of the S-T and of the R-T intervals, etc.;
6. The peak-to-peak values of the P-wave and of the QRS complex;
7. The ratio of the P-wave and R-wave amplitudes and the ratio of the P-wave and QRS complex peak-to-peak amplitudes;
8. The polarity of the P-wave: single positive, single negative, or bipolarity;
9. The derivative of the P-wave, QRS-complex, and T-wave;
10. Temporal average of the R-R interval and the heart beat;
11. Maximum value of the P-wave amplitude/peak and of the P-wave peak-to-peak amplitude over a certain period of time;
12. Maximum value of the R-wave amplitude/peak and of the ORS complex peak-to-peak amplitude over a certain period of time.

In the time domain, additional computations include:
13. Baseline subtraction, for example for removing of respiratory artifacts and in order to allow for the analysis of changes with respect to the baseline;
14. Waveform averaging for noise reduction;
15. Signal energy computation in time domain as the sum of the squares of signal amplitudes (before and after baseline removal);
16. First derivative computations for estimation of signal changes and removal of high frequency artifacts;
17. Integral (sum) of the first derivative values;

In the frequency domain, additional computations include:
18. DC and quasi-DC component removal (equivalent to baseline subtraction and removal of respiratory artifact);
19. Selective filtering, i.e., the removal of certain frequencies associated with artifacts and noise, e.g., high frequency noise, muscle artifacts, changes in signal due to catheter and electrode handling, etc.;
20. Inverse Fourier transform for reconstructing the signal into the time domain.

Several techniques may be used to derive the information listed above from the ECG waveforms, including, but not limited to, one or more of the following:
1. "Peak detection;"
2. Computation of first derivatives;
3. Running averages along the signal in one heartbeat and along multiple heartbeats;
4. Adaptive thresholding;
5. Auto-correlation.

The Fast Fourier Transform in block (1125) performs a Fast Fourier Transform on a number of ECG samples stored in a buffer of a certain length, e.g., 256, 512, 1024, 2048 or more data samples. The Fourier Transform transforms the waveform from the time domain into the frequency domain.

The Frequency-Domain Pattern Recognition block (1140) illustrates various aspects of pattern recognition performed on the ECGs in the frequency domain, including, but not limited to, one or more of the following:
1. Principal components analysis, i.e., determination of the most significant elements of the frequency spectrum (similarly to determining the morphological elements of the electrograms, e.g., certain waves and segments in time domain);
2. Data compression in order to reduce the amount of computation based on the principal components;
3. Determination of the number and morphology of the principal components, in particular determination if the spectrum has only one, two or multiple main frequencies (frequency bands);

4. Calculation of the spectral power and of the signal energy from the frequency spectrum;
5. Running average along the frequency dimension over a single spectrum in order to reduce wideband noise;
6. Running average along several spectra in order to filter out artifacts;
7. Determination of additional morphological elements of the spectrum, e.g., the maximum frequency, the energy contained in the maximum frequency, the frequency histogram, i.e., what frequencies contain how much energy, the frequency of the highest significant maximum energy peak, etc.;
8. Calculation of behavior and averages over time of the principal components and other parameters determined from the spectral distribution, e.g., determining the maximum value of the signal energy and of the spectral power over a certain period of time;
9. Determine/estimate certain heart conditions based on the spectral analysis. This determination/estimation is also performed in more detailed in the decision support blocks 1150 and 1250.

Several decision support algorithms use the information provided by the time domain pattern recognition and frequency-domain pattern recognition algorithms. In one embodiment, block (1150) supports placing an endovascular device in either the lower third of the SVC or at the caval-atrial junction.

In particular, block 1150 is based on the concept of first reaching the caval-atrial junction during catheter placement. At the caval-atrial junction or near the sino-atrial node the P-wave and other electrical parameters reach a maximum value. At the caval-atrial junction the P-wave is unipolar. After reaching the sino-atrial node at the caval-atrial junction, i.e., the maximum value of the P-peak amplitude and spectral power, the catheter is pulled back several centimeters until the P-wave decreases to half the amplitude reached at the caval-atrial junction. At the location where the P-wave has decreased to half the amplitude as the caval-atrial junction, the catheter is considered to be in the lower third of the superior vena cava. The P-wave peak amplitude or peak-to-peak amplitude, as well as the spectral power, is used to map the location in the vasculature to the ECG waveform.

More particularly, after receiving an endovascular ECG signal associated with an endovascular device, the signal is processed, over a plurality of predetermined time periods, to calculate a P-wave amplitude and a spectral power for each predetermined time period. A maximum P-wave amplitude is then determined from the plurality of P-wave amplitudes, as well as an associated maximum spectral power from the plurality of spectral powers. The location at which these maximum values are determined is associated with a predetermined location in or near the heart, such as the cava-atrial junction. The location of the endovascular device is then calculated, for each predetermined time period, based on a ratio of the P-wave amplitude to the maximum P-wave amplitude and a ratio of the spectral power to the maximum spectral power, and the location of the endovascular device is then displayed to the user. Additionally, the polarity of the P-wave and the R-wave amplitude may also be used to determine the location of the endovascular device.

A single criterion or a combination of such criteria can be used to support decision making. In one embodiment, T1, T2, and T3 may be empirically established thresholds which are different for each patient, and the algorithm can use an adaptive loop to adjust the thresholds based on the current measurements. In another embodiment, these thresholds are predetermined.

In other embodiments, the ratio between the P-peak/P amplitude or the P-wave peak-to-peak amplitude to the R-peak/R amplitude or to the QRS complex peak-to-peak amplitude can also be used to establish location relative to the sino-atrial node. In one embodiment the P-peak/amplitude must be approximately half of the R-peak/amplitude and the P-wave must be unipolar for the location to correspond to the lower third of the SVC. In another embodiment, the P-wave peak-to-peak must be half of the QRS peak-to-peak amplitude and the P-wave must be unipolar for the location to correspond to the lower third of the SVC.

As discussed above, the results of the decision support algorithms block 1150 may be presented to the user, for example, by high lightening the appropriate location on the heart icon corresponding to the type of ECG identified by the system (1160).

Figure 12:
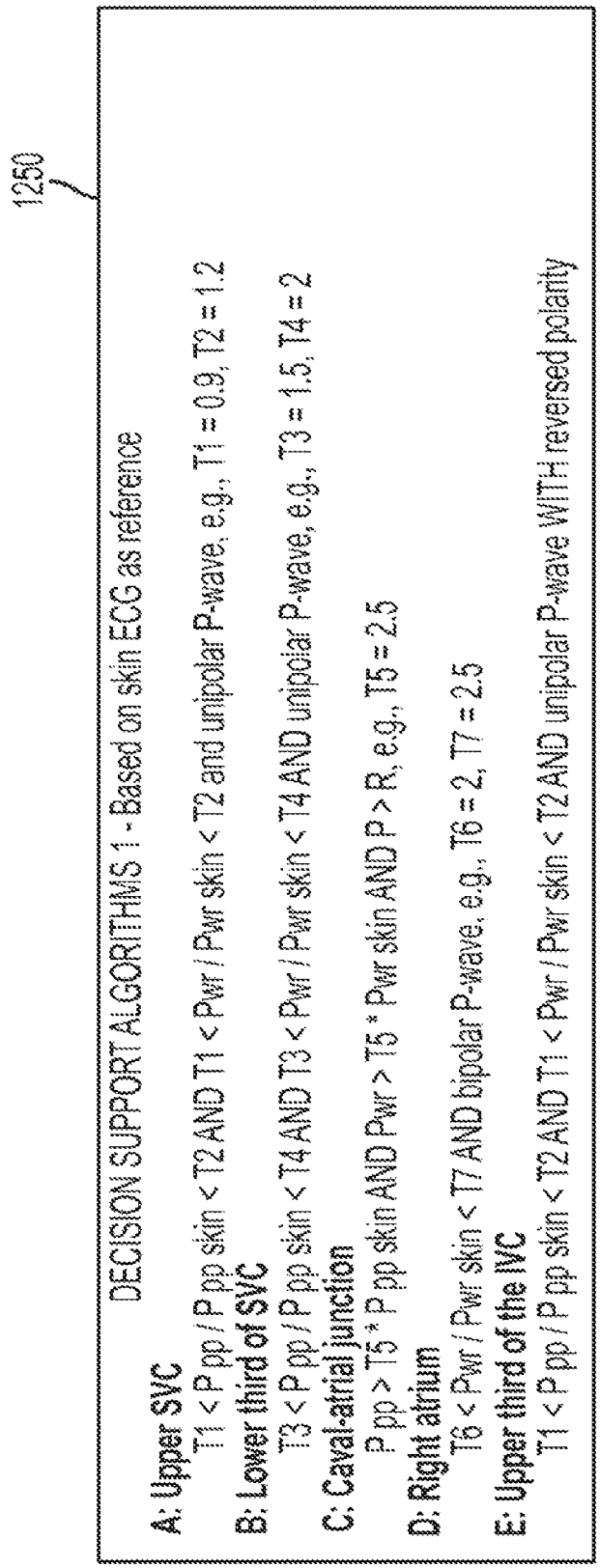
FIG. 12 illustrates another decision support algorithm for a computer-based method for positioning an endovascular device in or near the heart using electrocardiogram signals, according to one embodiment.

The decision support algorithm block 1250, depicted in FIG. 12, is based on comparing the P-wave, R-wave and P-wave spectral power at the current locations with the values of these parameters determined from the skin electrocardiograms in an equivalent lead, e.g., lead II. Thresholds T1 through T6 are empirical values subject to adaptive adjustments relative to each patient. Each of the criteria or a combination of criteria shown in FIG. 12 can be used.

Other decision algorithms can also be used, in particular related to the level of electrical energy as calculated from the ECG spectrum. In the case of placing endovascular devices, one criterion may be that, at the location corresponding to the lower third of the SVC, the average electrical energy calculated from the endovascular ECG is twice as high as the average electrical energy calculated from the endovascular ECG at skin level or from a skin ECG in a corresponding lead, e.g., lead II.

Method for Placement of Central Venous Catheters

A method of placing a central venous catheter (CVC) is presented below.

1. Estimate or measure the required length of the vascular access device (CVC) for the given patient.
2. If using saline and adaptor (200), go to step 11; if not, proceed as follows. Insert a guidewire into the CVC and flush align the guidewire tip and the catheter tip. Measure the length of the guidewire outside the CVC. This measurement is necessary in order to be able to realign the tip of the catheter and of the guidewire after inserting the guidewire in the vasculature. After taking the measurement, for example with sterile measuring tape or with surgical thread, remove the guidewire from the CVC.
3. Gain vascular access and insert the guidewire for the estimated required length.
4. Insert the CVC over the wire such as to leave outside the CVC the length of the guidewire measured at step 1. Thus the CVC inserted over the wire and the guidewire tips are flush-aligned.
5. Connect a sterile electrical adaptor to the guidewire per the instructions for use.
6. Connect the other end of the sterile electrical adapter to the ECG cable of the electrography system.
7. Check that the display of the electrography system indicates desired position of the catheter tip per the instructions for use of the electrography system: in the lower third of the SVC, at the caval atrial junction or in the right atrium. Typically, the location of the tip of the catheter will be identifiable through the specific shape of the P-wave and of the P-wave relative to the R-wave of the electrogram and/or by the energy levels and thresholds.
8. Adjust the position of the guidewire and CVC by pulling and/or pushing them together as not to change the flush alignment until the ECG waveform on the screen indicates that the desired position has been reached. Correlate the actual inserted length with the estimated length.
9. After the position has been reached, disconnect the electrical adaptor and remove the guidewire.
10. Secure the CVC in location.
11. Continue here if saline and adaptor (200) are used.
12. Gain vascular access and introduce the CVC over the guidewire as currently specified by the existing protocols.
13. Remove the guidewire
14. Attach the sterile adaptor (200) to the CVC.
15. Attach the electrical connection (234) of the adaptor (200) to the ECG cable of the electrography system.
16. Fill a syringe with saline and connect it to the other end of the adaptor (200). Flush the catheter lumen with saline as to create a conductive saline column all way through the catheter tip.
17. Check that the ECG waveform shown on the display of the electrography system indicates desired position of the catheter tip per the instructions for use of the electrography system: in the lower third of the SVC, at the caval atrial junction or in the right atrium. Typically, the location of the tip of the catheter will be identifiable through the specific shape of the P-wave and of the P-wave relative to the R-wave of the electrogram and/or by energy levels and thresholds.
18. Adjust the position of the CVC by pulling and/or pushing until the ECG waveform on the screen indicates that the desired position has been reached. Correlate the actual length with the estimated length.
19. After the desired position has been reached remove the syringe and the adaptor (200).
20. Secure the catheter.

Method for Placement of Implantable Ports

A method of placing the catheter piece of an implantable port is similar to the method for placing a CVC. The adaptor (200) should be connected to the catheter of the implantable port, and the syringe with saline must be connected to the other end of the universal adaptor. A different electrical adaptor should be connected to a syringe needle placed in the catheter of the implantable port. After reaching the desire position, the catheter should be connected to the implantable port.

Method for Placement of Peripherally Inserted Central Catheters Open and Closed Ended Both open-ended and closed-ended peripherally inserted central catheters (PICC) can be placed as described herein, and the method of PICC placement is similar to the one of placing CVCs. The inventive steering mechanism described herein can be used to bend the tip of the PICC in case the catheter fails to advance in the desired direction.

Method for Placement of Hemodialysis Catheters

A method for placing hemodialysis catheters is similar to the method introduced herein for placing CVCs. The inventive steering mechanism described herein can be used to bend the tip of the hemodialysis catheter in case the catheter fails to advance in the desired direction. Two different guidewires with adaptors (220) can be used for each of the lumens of the hemodialysis catheter as to guide placement of one lumen into the right atrium and of the other lumen at the caval atrial junction using the electrography system. Each of the lumens of the hemodialysis catheter can be placed independently in sequence or at the same time by connecting the adaptors (220) of each of the lumens with different electrodes of the ECG cable of the electrograph system.

Method for Placing Central Venous Access Devices in Patients with Arrhythmias

Traditionally, patients with arrhythmias have been excluded from procedures of guiding central venous lines placement using the endovascular ECG method because of the lack of visible changes in the shape of the P-wave. The energy criteria for the P-wave analysis described herein can be used to guide the placement of central venous access devices in patients with arrhythmias. In arrhythmia patients, the electrical signals generated by the sino-atrial node have a certain degree of randomness, such that they are not synchronized in order to produce a consistent P-wave. Nevertheless, as previous studies have shown, the electrical activity of the sino-atrial node exists and generates electrical energy of intensities typical to the proximity of the sino-atrial node. In one embodiment, the algorithm uses the energy as measured from the endovascular electrogram in order to map certain location in the vasculature. As such, this algorithm can be used to guide placement in patients with arrhythmias when only the electrical energy is indicative of location but not the shape of the P-wave.

Method for Monitoring Tip Location and Certain Aspects of the Electrical Activity of the Heart Certain aspects of the electrical activity of the heart can be monitored continuously or intermittently using the devices introduced herein. Either an electrical adaptor or adaptor (200) connected to the electrography system can be used for monitoring. The electrical adaptor can be connected to any stylet or other conductive member introduced in any venous access device or in any arterial device. Adapter (200) can also be connected to any venous or arterial line as long as the infusion of a conductive solution, e.g., saline is possible. Adapter (200) can also be used when electrically conductive fluids are inserted in the body using an infusion pump. Monitoring the tip location and/or certain aspects of the electrical activity of the heart can be performed in a number of clinical situations.

1. Adaptor (200) can be attached to a number of central venous devices post insertion, e.g., at bedside and/or in home care situations: PICCs, CVC, hemodialysis catheters. By connecting the adapter to such a catheter and to an electrography system according to an embodiment of the present invention and by injecting saline into the catheter, the location of the tip of the catheter can be confirmed and/or certain electrically activity of the heart can be monitored during the time the adapter is connected by using methods similar to those introduced above in embodiments of the present invention.
2. Adaptor (200) can be connected to an arterial line between the arterial line and the other devices connected to the arterial line. The blood present in the arterial line and in the universal adaptor ensures the electrical connection between the blood and the electrography system. Thus the electrical activity of the heart can be continuously monitored. This is particularly important in the case of monitoring the preload changes which translate in changes of the electrical energy of the heart during the S-T segment of the ECG waveform.
3. Monitoring of the tip location and of the electrical activity of the heart can also be achieved by using the electrography system and connecting the adaptor (200)

between a central venous line and a pressure measuring system while performing central venous pressure measurements.

4. In the case of an implanted port, a needle can be inserted into the port chamber and the catheter can be flushed with saline using a syringe filled with saline. An electrical adaptor can be attached to the needle and to the electrography system. The detected electrogram signal will contain information from the skin level where the needle is in contact with the skin and from the tip of the catheter through the injected saline column. Since the impedance of the path to the catheter tip is lower than the one to the skin, the detected signal contains both components, i.e., at the skin level and at the tip of the catheter. By subtracting the skin level signal, the signal at the tip of the catheter can be estimated and thus the tip position and certain electrical activity of the heart according to the algorithms described in embodiments of the present invention.

Figure 13:
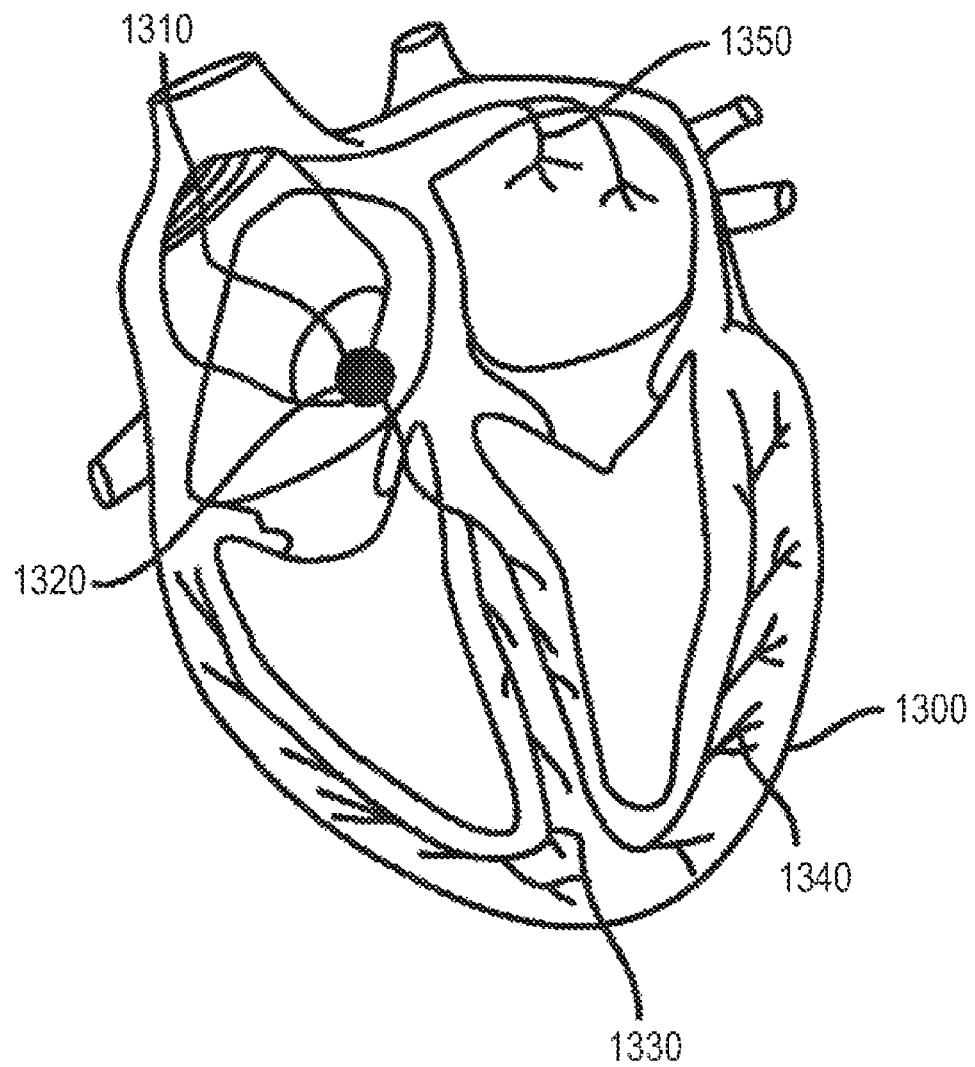
FIG. 13 illustrates the cardiac conduction system of the heart.
Figure 14:
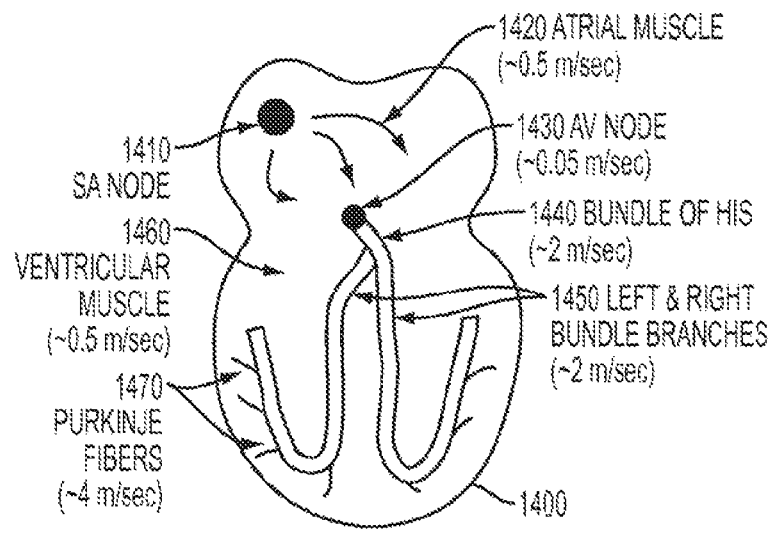
FIG. 14 illustrates electrical signal propagation in the conduction system of the heart.

FIG. 13 illustrates the cardiac conduction system of the heart, while FIG. 14 illustrates electrical signal propagation in the conduction system of the heart.

These figures illustrate the conductive mechanism of the heart, which explains why the electrical energy distribution within the heart as measured is indicative of specific locations within the heart. Accordingly, local electrical signals, behaviors and energy concentrations can be measured and locations within the heart and blood vessel can be determined more accurately; local heart conditions can also be described more accurately.

The conduction system of the heart begins with the heart's dominant pacemaker, the sino-atrial node (1310). The intrinsic rate of the SA node is 60 to 100 beats/minute. When an impulse leaves the SA node, it travels through the atria along the Bachmann's bundle (1350) and the inter-nodal pathways, on its way to the atro-ventricular (AV) node (1320) and ventricles. After the impulse passes through the AV node, it travels to the ventricles, first down to the bundle of His (1330) then along the bundle branches and finally down to the Purkinje fibers (1340). Pacemaker cells in the junctional tissue and Purkinje fibers on the ventricles normally remain dormant because they receive impulses from the SA node. They initiate an impulse only they do not receive one from the SA node. The intrinsic rate of the AV junction is 40 to 60 beats/minute, the intrinsic rate of the ventricles 20 to 40 beats/minute. The different propagation speeds of the electrical impulses are shown in FIG. 14. From the SA node (1410) the impulses propagate through the atrial muscle (1420) and through the ventricular muscle (1460) at app. 0.5 ms, through the bundle branches (1440) and (1450) at app. 2 m/sec, through the Purkinje fibers (1470) at app 4 m/s and through the AV node (1430) at app. 0.05 m/s.

The electrical signals and the electrical energy distribution are advantageously used to identify the proximity of the sino-atrial node and right atrial electrical activity even in the cases of arrhythmia, i.e., in the absence of a coherent P-wave measured by standard skin electrocardiogram. While in some cases of arrhythmia random electrical signal generated in the right atrium is not coherent enough to propagate through the body to the skin, the electrical energy is still present in the right atrium and can be detected by local endovascular measurements as a non-coherent P-wave, i.e., as significant electrical activity in the P-segment of the ECG waveform. Energy measurements are also less sensitive to some local abnormalities in impulse conduction: altered automaticity (arrhythmias), retrograde conduction of impulses, reentry abnormalities.

The electrical signals and the electrical energy distribution are also advantageously used to quantify heart functionality, e.g., preload which is related to the depolarization and extension of the heart muscle.

The electrical signals and the electrical energy distribution are also advantageously used to guide guidewires and guiding catheters through the aorta into the left heart. This method is useful in simplifying the access to the left atrium and to the coronary arteries and in reducing the amount of contrast and radiation needed to guide endovascular devices to those locations. In a different application, the inventive apparatus can also be used to guide catheters, e.g. Swan-Ganz through the right ventricle into the pulmonary artery. Other endovascular devices can be guided and be used to measure endovascular electrical activity in other locations of the cardiovascular system which are identifiable by the cardiograms measured with the new apparatus introduced in embodiments of the present invention.

Figure 15:
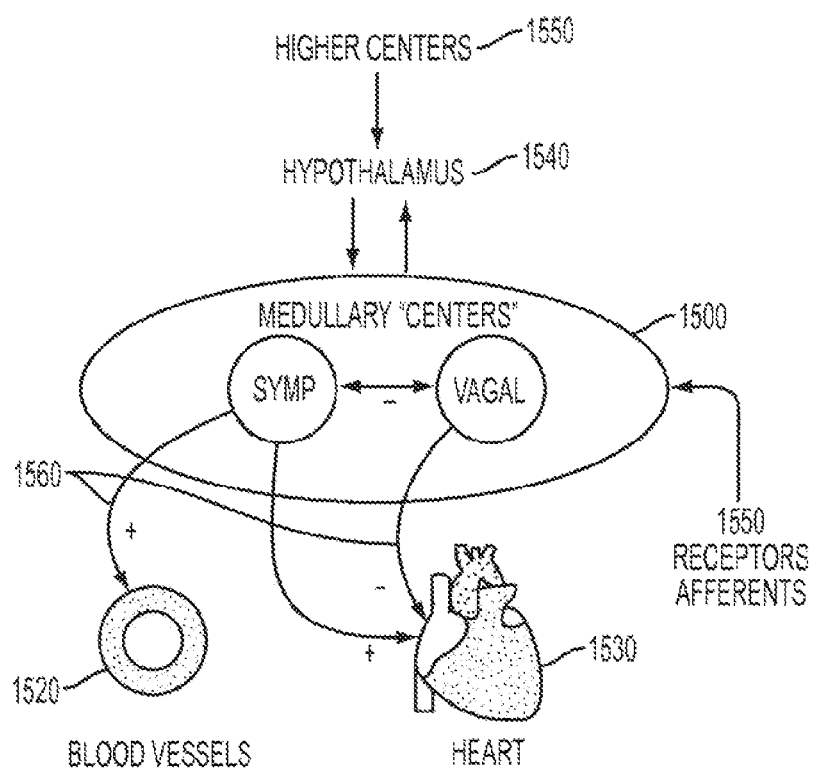
FIG. 15 illustrates electrical activity in the cardiovascular system due to neuronal control system.

FIG. 15 illustrates electrical activity in the cardiovascular system due to neuronal control system. Several paths of conduction are related to the mechanism of control of heart (1530) and blood vessel (1520) activity: receptors (1510), e.g., pressure receptors transmit information related to the state of the blood vessels and to the state of the heart to the nervous system through the Medullary centers (1500). The hypothalamus (1540) and the higher centers (1550) are involved in processing and reacting to the information received from the sensors/receptors. In turn they send impulses (1560) back to blood vessels and the heart. By measuring electrical activity related to the control system, information regarding heart conditions can be obtained which could not have been obtained previously.

Figure 18A:
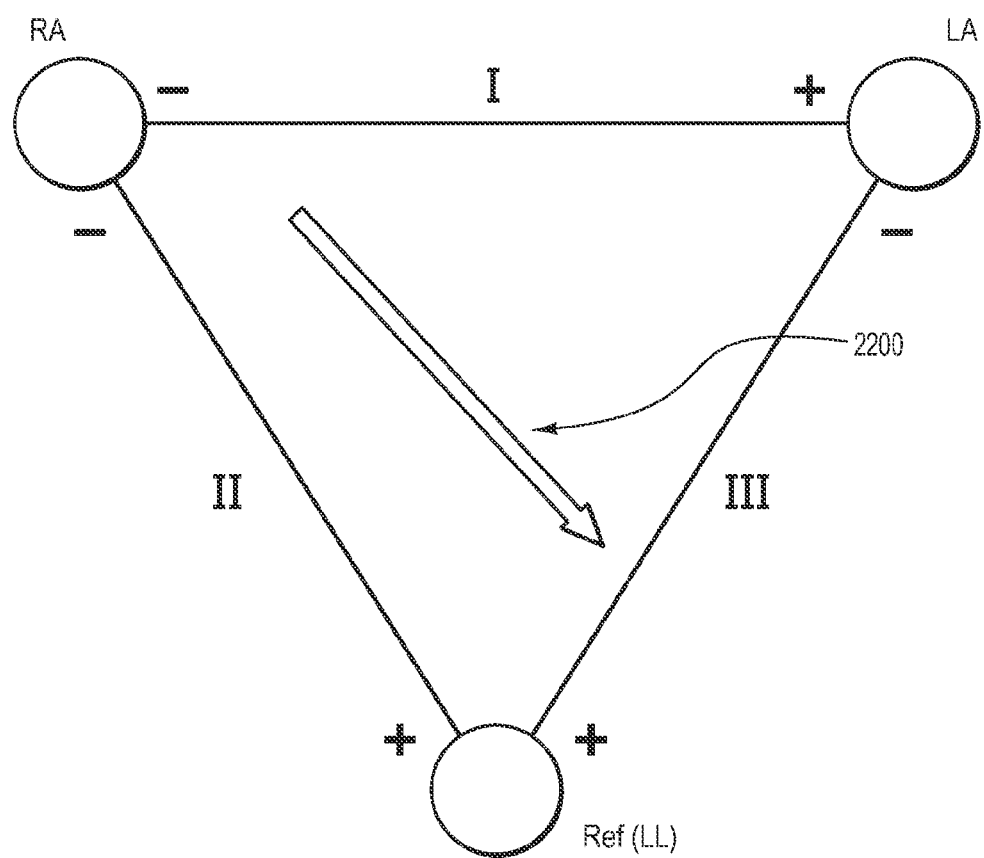
FIG. 18A shows ECG leads arranged to form an Einthoven triangle.

FIG. 18A illustrates the Einthoven ECG triangle and the naming convention for the ECG leads as they are used herein in connection with various embodiments. In order to obtain ECG signals from the patient, typically, one electrode is placed on the right arm (RA), one on the left arm (LA) and one is used as reference on the left leg (LL). The direction in which the P-wave changes most is shown by the arrow (2200). Therefore, when using endovascular ECG for catheter navigation and tip location, the electrode corresponding to the right arm (RA) is operably connected to the proximal end of the vascular access device (110) (FIG. 1A), such as a catheter, in one embodiment. In this way, an ECG waveform detected with respect to the distal end of the catheter, e.g., via an electrode disposed on the catheter, can be considered as detected by Lead II of the Einthoven triangle. Thus, when the catheter is advanced through the vasculature, Lead II will show most significant changes of the P-wave and therefore is best suited to detect the proximity of the sino-atrial node. The sino-atrial node is located at the caval-atrial junction and is responsible for generating the P-wave (indicative of the right-atrial electrical activity). The waveform corresponding to Lead III in the Einthoven triangle remains relatively unchanged as the catheter navigates through the vasculature in one embodiment if the RA electrode is operably connected to the catheter. Therefore, Lead III is used in an embodiment of the present invention as a reference lead which serves multiple purposes, as described herein. In one embodiment, the apparatus introduced herein displays simultaneously ECG signal-based waveforms for Lead II, also referred to herein as the endovascular ECG lead, (for catheter navigation and tip positioning) and for Lead III, also referred to herein as the skin ECG lead, (as a reference waveform).

Reference is again made to FIG. 5, which illustrates the mapping of different endovascular ECG waveforms to the corresponding locations in the vasculature and in the heart, according to one embodiment. In detail, Location A corresponds to the upper superior vena cava (SVC), Location B corresponds to the lower ⅓ of the SVC, Location C corresponds to the caval-atrial junction, Location D corresponds to the right atrium, and Location E corresponds to the lower atrium and/or to the inferior vena cava.

Figure 18B:
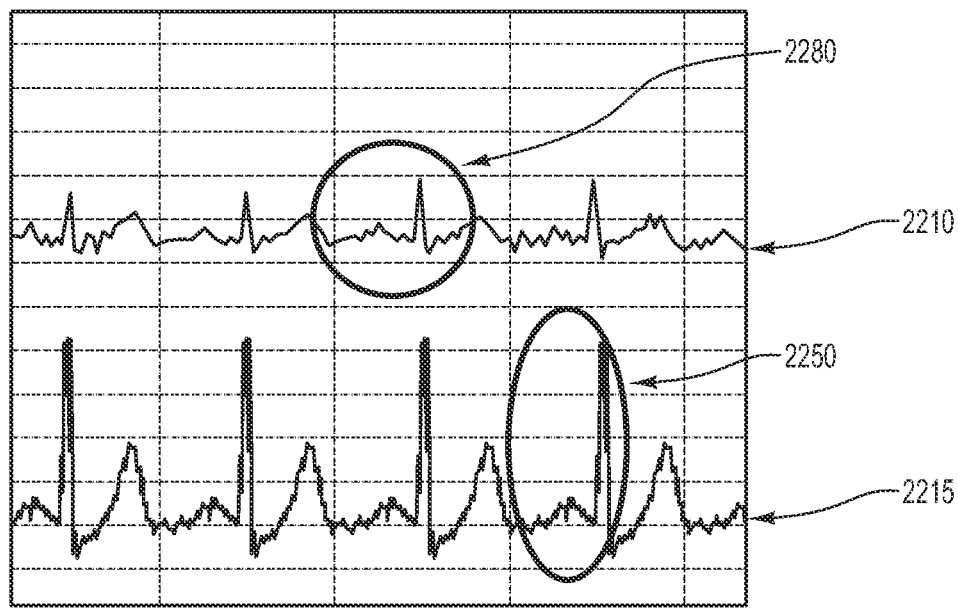
FIGS. 18B-18F show various views of a skin ECG waveform and an endovascular ECG waveform as depicted on a graphical user interface according to one embodiment.

FIG. 18B illustrates the endovascular (Lead II) ECG waveform (2215) obtained with a device disclosed herein, such as an ECG sensor-containing catheter, as measured at Location A in FIG. 5. The skin ECG waveform (2210) represents a skin reference ECG lead equivalent with Lead III. A reference P-R complex is illustrated by (2280). The typical P-R complex at Location A is illustrated by (2250). While the P-wave changes dramatically on Lead II according to movement of the catheter and its ECG sensor within the vasculature, as seen in the P-R complex (2250) for instance, the P-wave remains substantially constant on Lead III used as a reference (2280).

In one embodiment, waveforms from two ECG leads (e.g., Lead II and III in FIG. 18B) are simultaneously depicted on a display of an apparatus, such as a catheter placement system for example, as illustrated in FIGS. 18B-18F. In another embodiment, three leads (Lead I, II, and III of FIG. 18A) may be displayed at the same time as shown in FIG. 20F.

By using the method, apparatus, and ECG electrode configuration introduced herein, it is possible in one embodiment to monitor the patient condition, e.g., the patient's heart rate using the skin reference lead (Lead III) while at the same time guiding the catheter placement using endovascular Lead II.

Figure 18C:
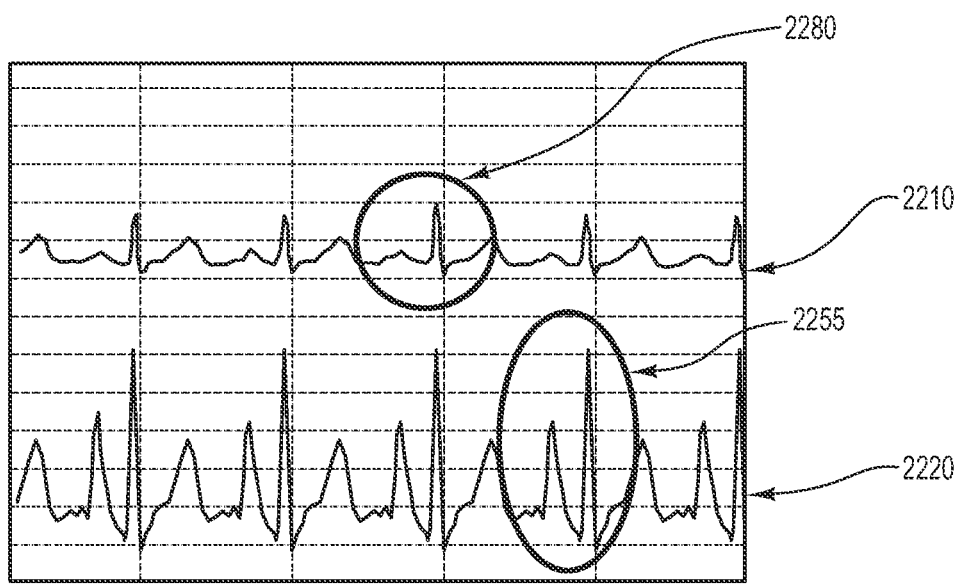

FIG. 18C illustrates the endovascular ECG waveform (2220) obtained with the device disclosed herein as measured at Location B in FIG. 5. The skin ECG waveform (2210) represents a skin reference lead equivalent with Lead III. A reference P-R complex is illustrated by (2280). The typical P-R complex at Location B is illustrated by (2255). As before, while the P-wave changes dramatically in the P-R complex (2250) on Lead II corresponding to the tip of the catheter, the P-wave remains quite constant on Lead III used as a reference (2280).

Figure 18D:
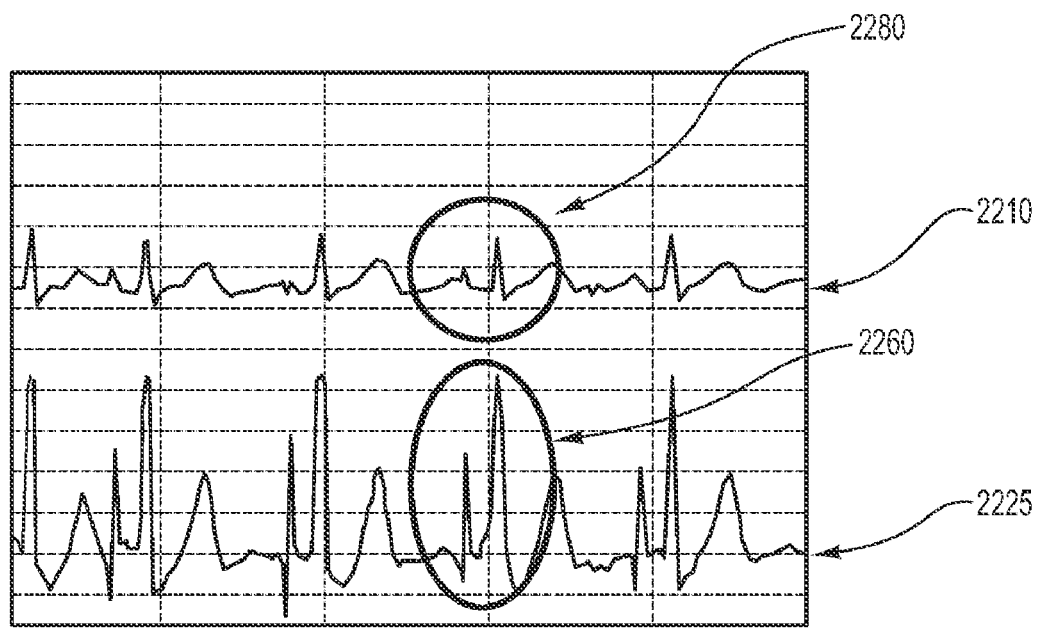

FIG. 18D illustrates the endovascular ECG waveform (2225) obtained with the device disclosed in an embodiment of the present invention at Location C in FIG. 5. The ECG waveform (2210) represents a skin reference lead equivalent with Lead III. A reference P-R complex is illustrated by (2280). The typical P-R complex at Location C is illustrated by (2260). While the P-wave changes dramatically in the P-R complex (2260) on Lead II corresponding to the tip of the catheter, the P-wave remains quite constant on Lead III used as a reference (2280).

Figure 18E:
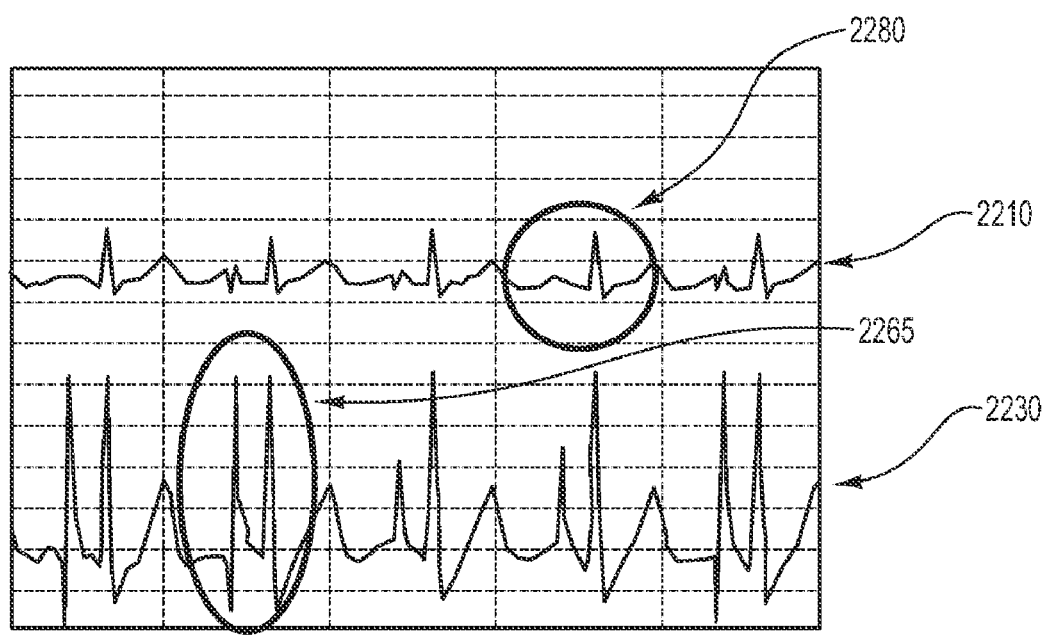

FIG. 18E illustrates the endovascular ECG waveform (2230) obtained with the device disclosed in an embodiment of the present invention at Location D in FIG. 5. The ECG waveform (2210) represents a skin reference lead equivalent with Lead III. A reference P-R complex is illustrated by (2280). The typical P-R complex at Location D is illustrated by (2265). While the P-wave changes dramatically in the P-R complex (2265) on Lead II corresponding to the tip of the catheter (265), the P-wave remains quite constant on Lead III used as a reference (2280).

Figure 18F:
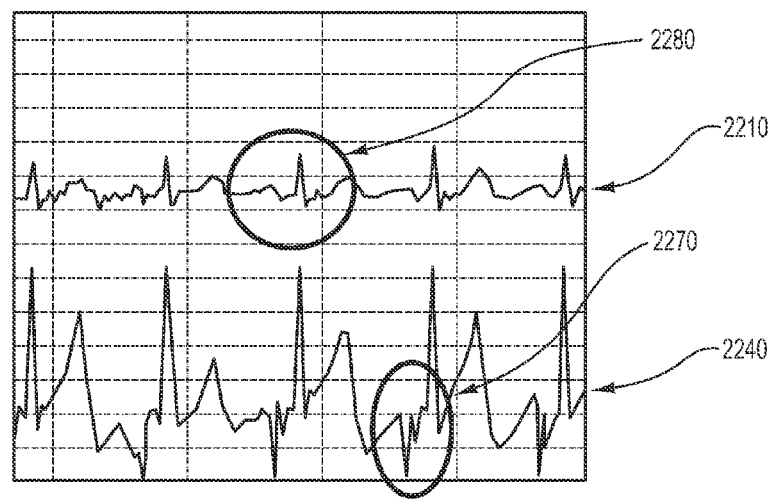

FIG. 18F illustrates the endovascular ECG waveform (2240) obtained with the device disclosed in an embodiment of the present invention at Location E in FIG. 5. The ECG waveform (2210) represents a skin reference lead equivalent with Lead III. A reference P-R complex is illustrated by (2280). The typical P-R complex at Location E is illustrated by (2270). While the P-wave changes dramatically in the P-R complex (2270) on Lead II corresponding to the tip of the catheter, the P-wave remains quite constant on Lead III used as a reference (2280).

Figures 19A, 19B:
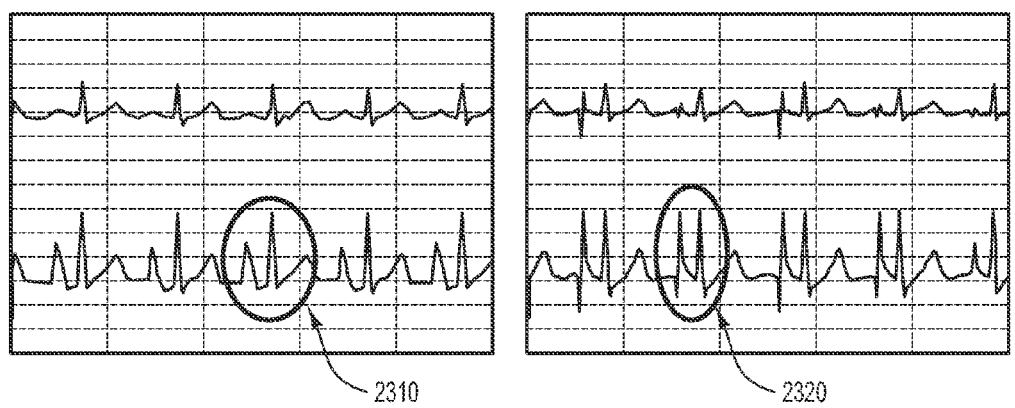
FIGS. 19A and 19B show various views of a skin ECG waveform and an endovascular ECG waveform as depicted on a graphical user interface according to one embodiment.

FIG. 19A illustrates the ability of the apparatus introduced herein, e.g., a catheter placement system, to show several display windows at the same time on the screen thereof. One, two, or more display windows can be included. Each of the display windows (3310 and 3320) can display one to three ECG waveforms (leads I, II, and III) in any combination, in real-time acquisition, in playback, or frozen modes. In one embodiment, one display window (3310) is used to show real-time ECG waveforms (catheter guiding, or endovascular, lead II and skin reference lead III) and another display window (320) is used to show frozen ECG waveforms (catheter guiding lead II and skin reference lead III). Thus, the user can compare the changes in the catheter guiding lead and in particular in the P-R complex at two different catheter tip locations: at the tip location frozen in display window (2320) and at the current (real-time) tip location displayed in window (2310).

The above multi-window comparison enables the use of the following catheter placement method, according to one embodiment: first advance the catheter in the atrium until the P-wave reaches its maximum amplitude as seen in window (2320) (FIG. 19B) and then pull back the catheter to a location where the P-wave is half the size of its maximum amplitude. Such a location where the amplitude of the P-wave is half the size of its maximum amplitude is indicative of the lower third of the superior vena cava (Location B in FIG. 5).

Figure 20A:
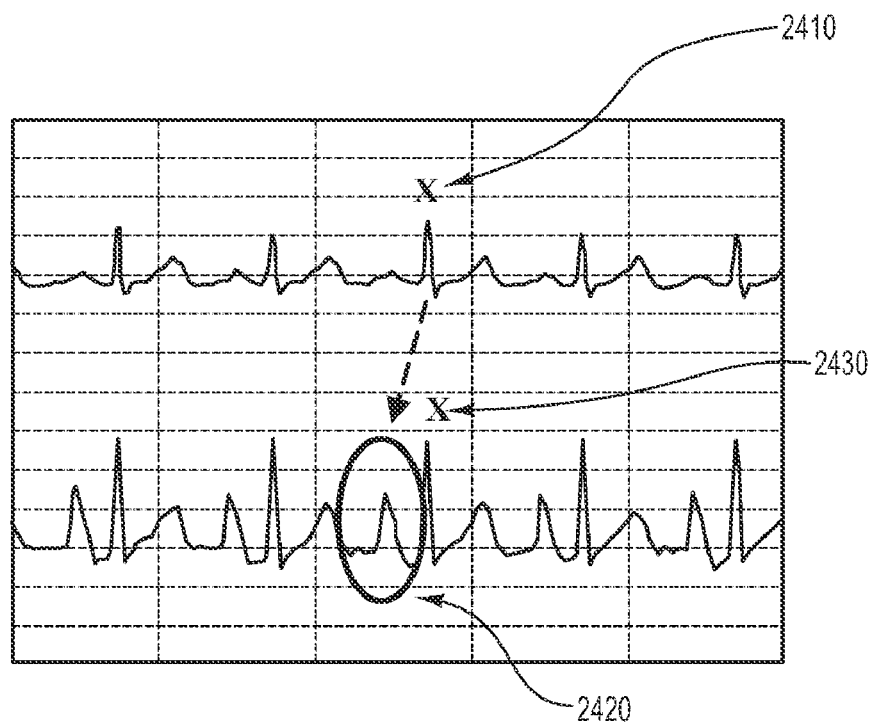
FIGS. 20A and 20F show various views of a skin ECG waveform and an endovascular ECG waveform as depicted on a graphical user interface according to one embodiment.

FIG. 20A illustrates how the skin reference lead can be used to analyze the P-wave segment of the catheter guiding lead (Lead II), according to one embodiment. The P-wave segment, in which is found the P-wave itself, is characterized by the fact that it immediately precedes the QRS complex of the same heartbeat. The P-wave segment of a heart beat also follows the T-wave of the previous beat. In order to detect the P-wave segment, an algorithm can be applied including detection of the R-peak of the QRS complex. The algorithm in one embodiment includes the following steps:

Detect R-peak.

Compute R-R interval.

Assume that a certain percentage of the R-R interval prior to the R-peak is the interval in which the P-wave occurs. This interval where the P-wave occurs is defined as the P-wave segment.

Detect the P-peak in the P-wave segment, its amplitude and polarity.

Apply processing, analysis and decision making algorithms as illustrated in FIGS. 11 and 12.

In one embodiment, in order to apply the algorithm described above, the R-peak and the R-R interval can be detected on endovascular Lead II, i.e., on the same ECG lead which is used for guidance. In another embodiment, the R-peak and the R-R interval can be detected using Lead III (the skin reference lead). In particular, the R-peak detection on Lead III (2410) in FIG. 20A can be used to trigger the analysis of any segment of the ECG waveform on Lead II including the analysis of the P-wave segment (2420) in FIG. 20A. It is also possible, if the signal quality of Lead II allows, to use the R-peak (2430) detected on lead II itself to trigger processing of the Lead II waveform. In other embodiments, other leads can be used to implement triggering on a different lead than the one used for catheter navigation and tip positioning. For example, Lead I can optionally be used for catheter navigation and tip positioning. The apparatus according to one embodiment allows also the use of Lead I for catheter navigation and tip positioning, though Lead II is suitable in many clinical settings. Note that in one embodiment the above triggering can occur for peaks on a waveform detected by the same lead. Also, a peak detected on Lead II can be used to trigger analysis of Lead I, in one embodiment. Thus, these and other variations are contemplated.

Triggering analysis on one ECG lead that is different than the ECG lead used for catheter navigation and positioning as introduced herein is useful in many practical situations regardless of which ECG lead is used for triggering the analysis and which ECG lead is used for catheter navigation and positioning. As will be seen in FIGS. 20B-20E and especially in FIG. 20E, triggering on a stable, noiseless lead, e.g., Lead III improves the ability to process different segments of other leads, e.g., endovascular Lead II used for catheter navigation and positioning in cases where the Lead II ECG signal includes a greater than desired amount of signal noise. Noisy Lead II ECG signals appear quite frequently in practical settings because of the manual handling of the Lead II connection by the user. Other situations can benefit from the trigger concept introduced herein, as will be seen below.

Figure 20B:
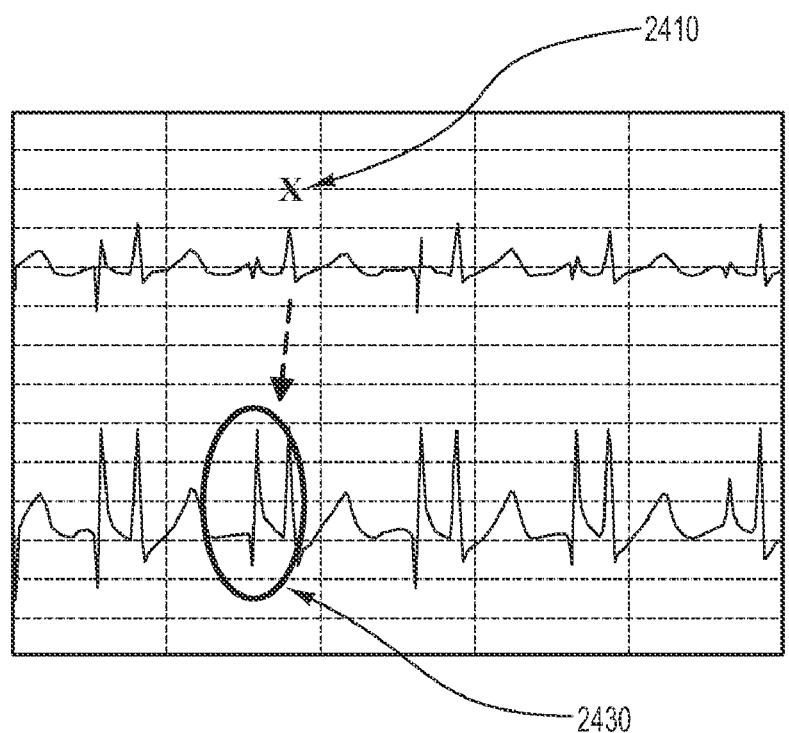

FIG. 20B illustrates how the R-peak detected on reference skin Lead III (2410) and the corresponding R-R interval trigger the analysis of the PQRS segment (2430) on the navigation Lead II. As described herein, the P-wave segment and the QRS complex of the ECG Lead II can be analyzed separately or in relationship to each other in order to predict the location of the catheter tip in the vasculature. In the case shown in FIG. 20B, the P-wave has a large positive amplitude which is equal to the R-amplitude and is also bipolar (has a negative first segment). In such a case, the detection of the R-peak on the Lead II itself is very difficult if not impossible through the use of algorithms. Triggering the ECG waveform analysis of Lead II (2430) based on detection of the R-peak detected on the reference Lead III (2410), as introduced herein, allows for detection and processing of the changes of the P-wave segment characteristics of the catheter tip location. Such algorithmic ECG waveform analysis of Lead II would otherwise be difficult in the case shown in FIG. 20B because of the difficulty of clearly detecting the R-peak on this lead.

Figure 20C:
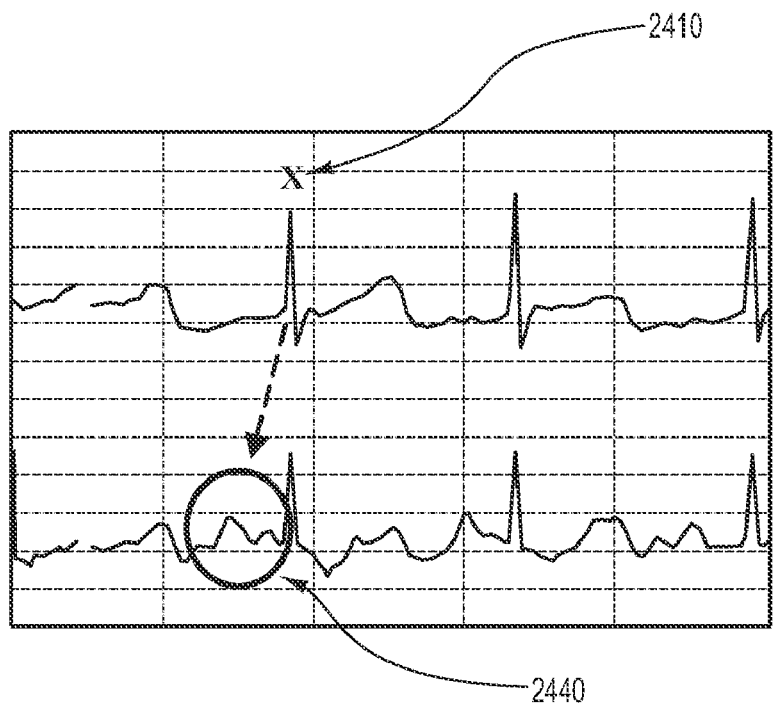
Figure 20D:
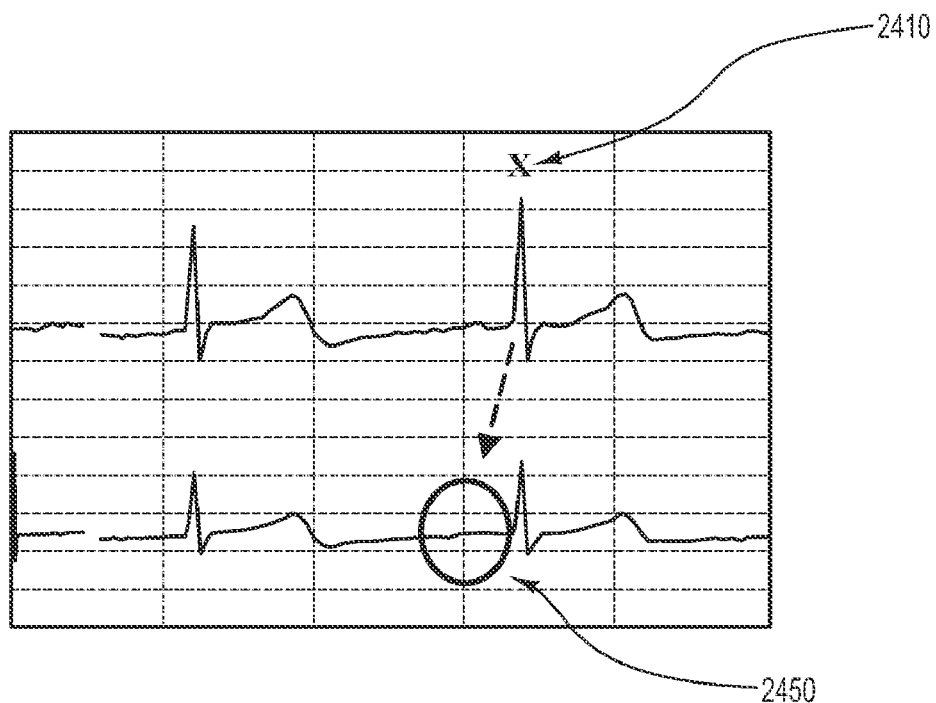

FIG. 20C illustrates how triggering on the R-peak of one lead, for example the R-peak of Lead III (2410) can be used to trigger the analysis of the P-wave segment on catheter navigation Lead II (2440) in the case of a patient with arrhythmias. Typically, the P-wave segment is not present in the skin ECG lead in patients with arrhythmias, as seen in FIGS. 20C and 20D. However, the catheter navigation and tip positioning lead, e.g., Lead II, can detect a relatively higher level of electrical activity in the P-wave segment as the catheter approaches the sino-atrial node and the caval-atrial junction. The level of electrical activity (energy) in the P-wave segment increases further as the catheter tip passes the sino-atrial node and enters the right atrium. Since the highest level of this increased electrical activity on the P-wave segment of navigation Lead II cannot be predicted, e.g., the P-wave amplitude could be higher than that of the R-wave on the Lead II, triggering the analysis of the said P-wave segment on the R-peak of a skin ECG lead provides a suitable solution to P-wave detection and subsequent catheter tip location and positioning.

FIG. 20D illustrates the lack of P-wave in the case of an arrhythmia patient on both ECG leads II and III. In FIG. 20D, lead II is connected to a skin electrode on the right arm of the patient and lead III to a skin electrode on the left arm of the patient. The R-peak on lead III (2410) is depicted in this figure and the corresponding segment showing the absence of a discernible P-wave on lead II is shown as (2450).

Figure 20E:
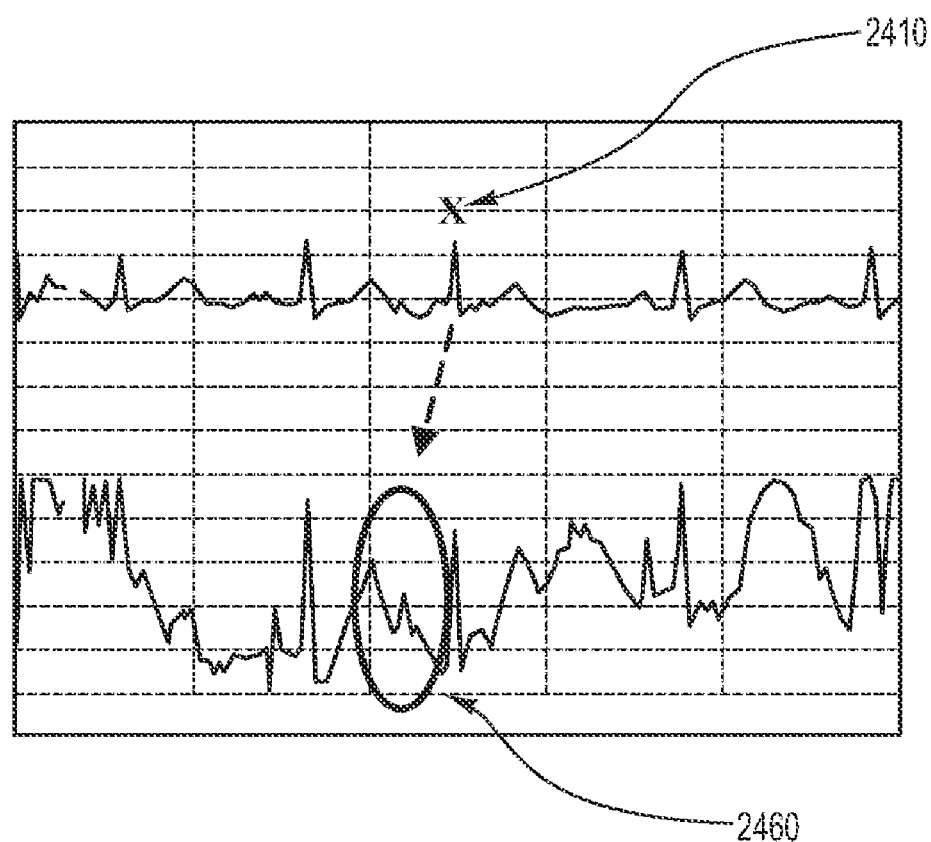
Figure 20F:
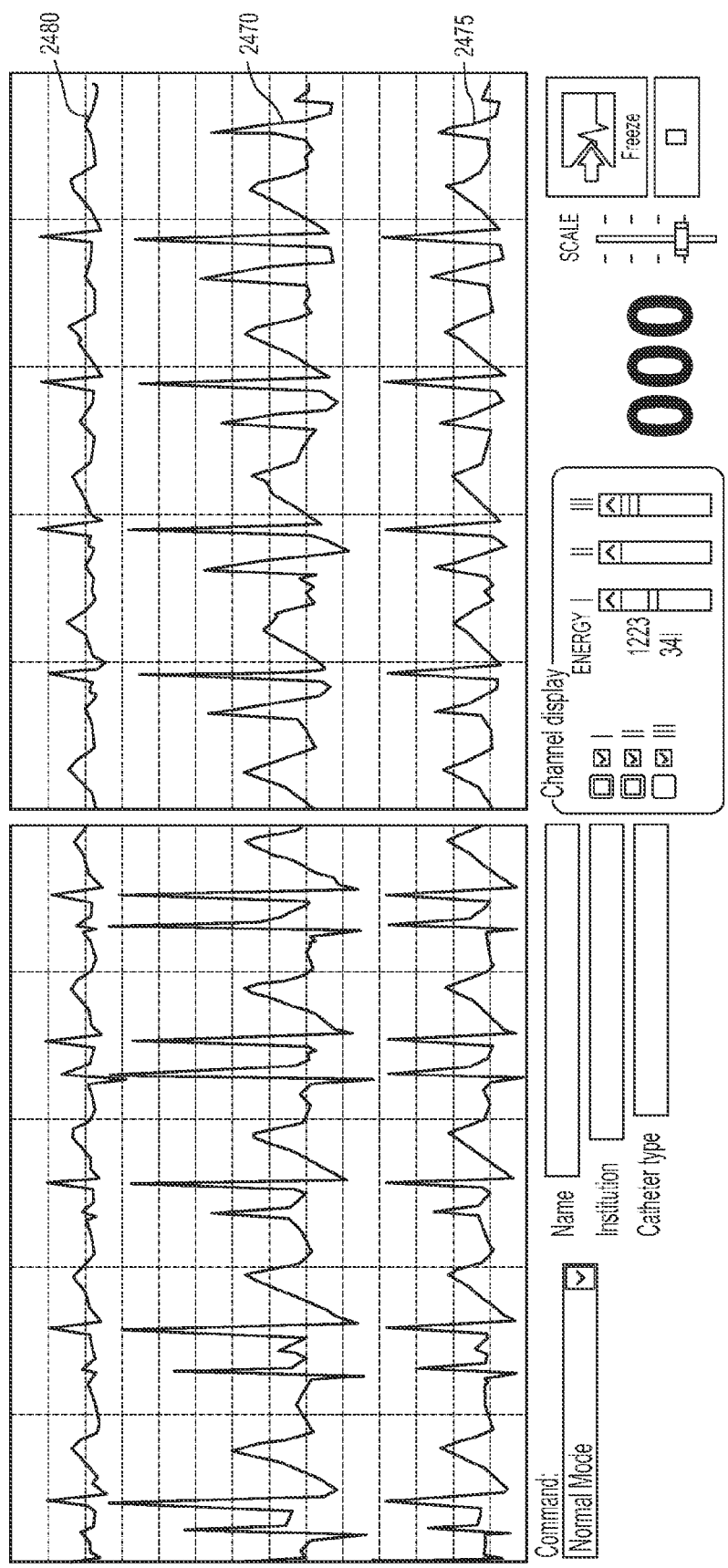

FIG. 20E illustrates the situation in which the catheter navigation lead, e.g., Lead II, is noisy or unstable and the detection of the R-peak and of the corresponding P-wave is thus difficult. In this case, as before, detecting the R-peak (2410) on a stable reference lead, e.g., the skin Lead III, preserves the ability via the above-described triggering, to find and analyze the P-wave segment (2460) on the noisier catheter navigation lead.

FIG. 20F illustrates another embodiment, wherein two leads (in this example Leads I and II—see FIG. 18A) are used to detect simultaneous, corresponding ECG waveforms (2470) and (2475) and triangulate, together with an additional, simultaneous ECG waveform (2480) of the reference lead (Lead III), the location of the catheter tip. In particular, a substantially accurate location of the catheter tip can be determined by looking at Leads I and II at the same time and use their correlation (or lack thereof) to reduce noise and more accurately determine the changes of the P-segment, of the QRS segment, and the relative changes between the P-wave and the QRS complex.

Figure 21A:
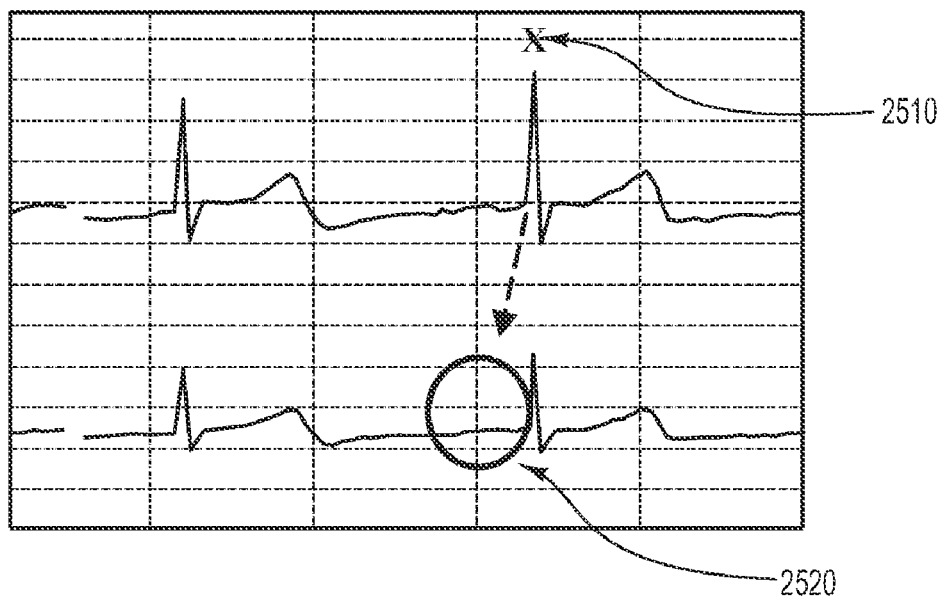
FIGS. 21A and 21B show various views of a skin ECG waveform and an endovascular ECG waveform as depicted on a graphical user interface according to one embodiment.
Figure 21B:
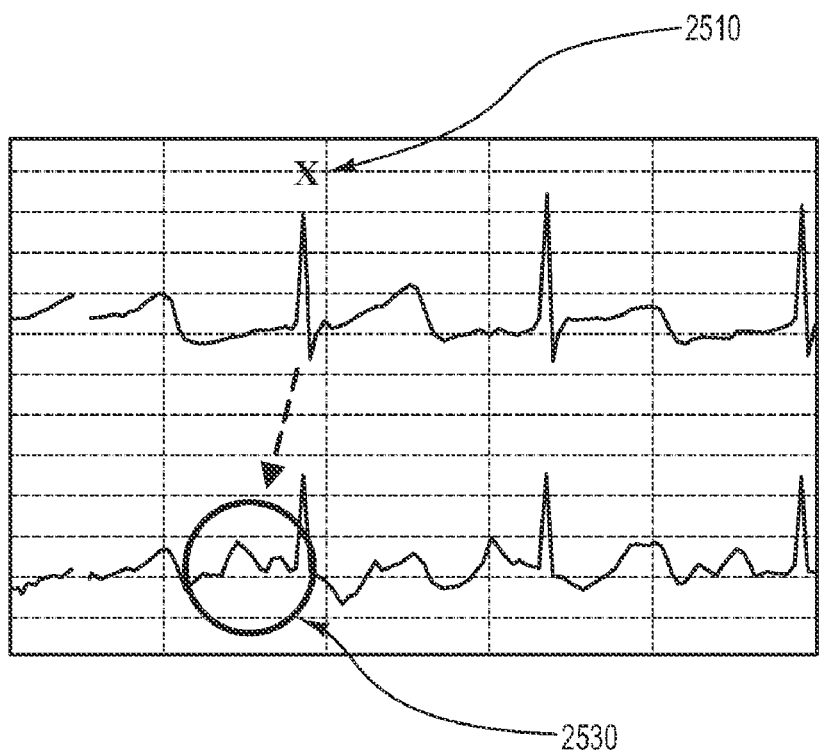

FIGS. 21A and 21B illustrate details regarding an algorithm to use the P-wave segment and/or its relationship with the QRS complex for catheter navigation and tip location in the case of arrhythmia, according to one embodiment.

Specifically, FIG. 21A illustrates the ECG waveforms for two skin ECG leads (using skin electrodes). In FIG. 21A, Lead III with its corresponding R-peak (2510) is detected using the skin left arm electrode and Lead II showing the lack of the P-wave (2520) is detected using the skin right arm electrode, both being compared with the skin left leg electrode, in one embodiment. Previously, patients showing these typical arrhythmia ECG waveforms were not considered as candidates for using the ECG-based method for catheter navigation and tip location. It was believed that, because the P-wave is not present at the skin level, the ECG method cannot be used to determine catheter tip location at the caval-atrial junction. FIG. 21A thus illustrates a situation where the R-peak of the skin reference lead (2510) can be used to compute the characteristics and the energy of the P-segment (P-wave) on the navigation lead at locations where the P-wave is not present.

In greater detail, FIG. 21B illustrates ECG waveforms as obtained with the apparatus described in connection with FIGS. 20A-20E and show that, with the apparatus and method described herein, even arrhythmia patients can be treated using ECG-based catheter navigation and tip location. Due to the processing algorithms described in FIGS. 11 and 12, the ECG signal obtained from the tip of the catheter on Lead II is more accurate and less noisy when compared to prior art. Thus, changes in the P-wave segment (2530) become visible when the catheter tip is in the proximity of the sino-atrial node. They correspond, as justified by physiology, to a random electrical activity of the right atrium. This random electrical activity and its changes can be detected with the apparatus introduced herein as illustrated by the P-wave segment (2530). This random electrical activity typically cancels out once reaching the skin and the Lead III and thus is difficult or impossible to detect by prior art ECG methods.

Sometimes the above random electrical activity of the right atrium is also very weak and an apparatus such as the one introduced herein is needed to detect it even at the tip of the catheter. By observing and/or analyzing the changes of the P-wave segment on the catheter navigation lead, the tip location of the catheter can be mapped, for example, to locations in the superior vena cava (weak, low energy or no P-wave), to locations at the caval atrial junction and to locations in the right atrium. FIG. 21B illustrates how the R-peak on the reference lead (e.g., skin Lead III) can trigger the analysis of the corresponding P-wave (P-segment) on the navigation lead (e.g., endovascular Lead II) at locations where a P-wave segment (2530) is present.

In addition to those described in FIGS. 11 and 12, it is appreciated that other decision algorithms can be used, such as those related to the level of electrical energy as calculated from the electrogram spectrum, in placing a catheter or other endovascular devices. For instance, one criterion specifies that at the location corresponding to the lower third of the SVC, the average electrical energy calculated from the endovascular electrogram is twice as high as the average electrical energy calculated from the endovascular electrogram at skin level, e.g., from a skin electrocardiogram in a corresponding lead, e.g., Lead III.

In addition to the algorithms disclosed above in connection with FIGS. 11 and 12, the concept of directional energy and of decision making based thereon are introduced herein. As seen, for example, in FIG. 18B at (2250) and 18C at (2255), the P-wave is uni-polar, i.e., has a single polarity, the polarity being positive. In comparison, FIG. 18D at (2260) and 18E at (2265) illustrate a bi-polar P-wave, i.e., a P-wave which has both a negative and a positive component. FIG. 18F illustrates a P-wave segment at (2270) with a uni-polar P-wave segment but of polarity reversed compared to that of the P-wave segment shown in FIGS. 18B and 18C.

The above change of polarity in the P-wave segment is due to the location of the catheter tip relative to the sinoatrial node and of the locations of the skin electrodes according to the Einthoven triangle (FIG. 18A). In the cases illustrated herein, as the catheter navigates from the superior vena cava through the caval-atrial junction, through the right atrium and into the inferior vena cava, the polarity of the P-wave segment changes correspondingly.

According to one embodiment and in light of the above, catheter tip location can be determined by the following: a positive energy value and a negative energy value are determined for a detected P-wave by the apparatus described herein, such as a catheter placement system. The positive P-wave energy value is determined according to the energy computation algorithms described herein, but only for positive values of the P-wave (i.e., values above the ECG baseline). Correspondingly, the negative P-wave energy value is determined according to the energy computation algorithms described herein, but only for negative values of the P-wave (i.e., values below the ECG baseline). These energy values (positive and negative) determined according to the present embodiment are also referred to herein as "directional energy" values because they are related to the direction and location of the catheter tip at which point the P-wave is being detected via an appropriate sensor in operable connection with a corresponding ECG lead, such as the endovascular Lead II discussed above.

The P-wave directional energy described above can be used to guide navigation of a catheter and for locating a tip thereof, according to one embodiment. Particularly, in one embodiment a standard Einthoven electrode configuration, with the right arm electrode detecting endovascular ECG signals at the catheter tip (as described above in connection with FIGS. 20A-20E) is considered. Note that other electrode configurations are also possible. If the P-wave energy is substantially entirely positive, the catheter tip is considered to be located above the sinoatrial node, for example in the superior vena cava. If the P-wave includes positive energy and a relatively small amount of negative energy, but the positive energy is smaller relative to the R-wave energy, such as is seen at (2260) in FIG. 18D, the catheter tip may be located at the caval atrial junction. If the P-wave segment includes a large amount of negative energy relative to its positive energy, and the positive energy is comparable to that of the R-wave energy, such as is seen in at (2265) in FIG. 18E, the catheter tip may be in the right atrium. If the P-wave includes substantially entirely negative energy, as seen at (2270) in FIG. 18F, the catheter tip is approaching the inferior vena cava or is in the inferior vena cava. In this way, the directional energy introduced herein is used by the present method described herein for catheter navigation and tip location.

FIGS. 22A-22D and 23A-23B illustrate various details regarding a connector according to example embodiments, which allow for the use of the apparatus and method described herein by a single operator in the sterile field.

Figure 22A:
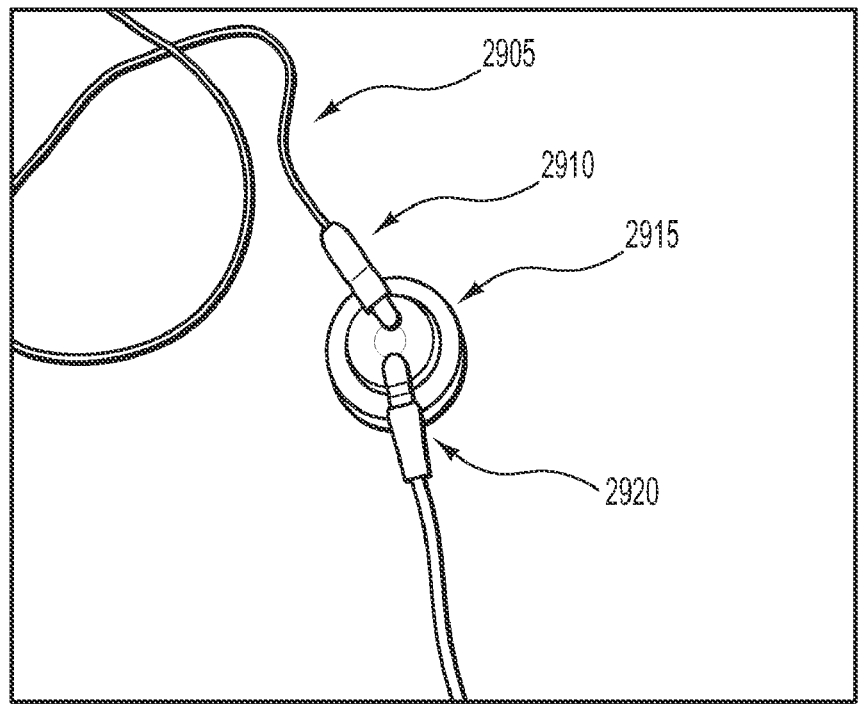
FIGS. 22A-22D show various magnetic sterile connectors according to certain embodiments.

In particular, FIG. 22A shows a connecting object (2915) including magnetic attraction properties and a surface including electrically conductive properties. The connecting object (2915) electrically connects to two connectors (2910) and (2920). The connector (2910) is connected to one end of a sterile device/adaptor (2905). The other end of the sterile device (2905) can be connected to a sterile guidewire or stylet or to a sterile saline adaptor as described further above. The connector (2920) can be attached to or be itself one end of an ECG cable connected to the apparatus illustrated herein in FIG. 1A.

The surface of the connecting object (2915) can be implemented in several ways. In one embodiment, a magnet is built into an enclosure with an electrical conductive surface. The magnet attracts the electrical connectors (2910) and (2920) to the metallic surface and locks them on the surface, thus establishing electrical contact between connector (2910) and the electrically conductive surface of the connecting object (2915) and another electrical contact between the electrically conductive surface of the connecting object (2915) and the other electrical contact (2920).

The connecting object 2915 illustrates one type of connector that can be used with the methods described herein by a single operator in the sterile field. Accordingly, in one embodiment, the object (2915) is placed prior to the commencement of a catheter placement procedure in the non-sterile field such that it can be reached by the single sterile operator during the procedure. Then, the as-yet non-sterile operator connects one end of the non-sterile connector (2920) to an ECG cable and "drops" the connector end shown in FIG. 22A onto the surface of the connecting object 2915. Because of the magnet incorporated in the object (2915), the connector (2920) is attracted to the electrically conductive surface of the connecting object and adheres to the surface thereof. The end of the ECG cable to which the connector (2920) is attached or included can be an ECG lead itself, thus simplifying the workflow.

During the procedure, the single operator is sterile. The operators opens the sterile package in which the connector (adaptor) (2910, 2905) is packaged, holds the sterile connector end (2915) with a sterile gloved hand and drops the sterile connector onto the electrically conductive surface of the connecting object (2915). Similarly to connector (2920), the connector (2910) is magnetically attracted to the connecting object (915) by the built-in magnet, which secures the connector (2910) on the electrically conductive surface of the connecting object. Using this method, an electrical connection can be established between a sterile electrical connector (2910) and a non-sterile connector (2920) without compromising the sterile field. Again, this method can be used by a single operator and enables the single sterile operator use of the apparatus described herein.

Figure 22B:
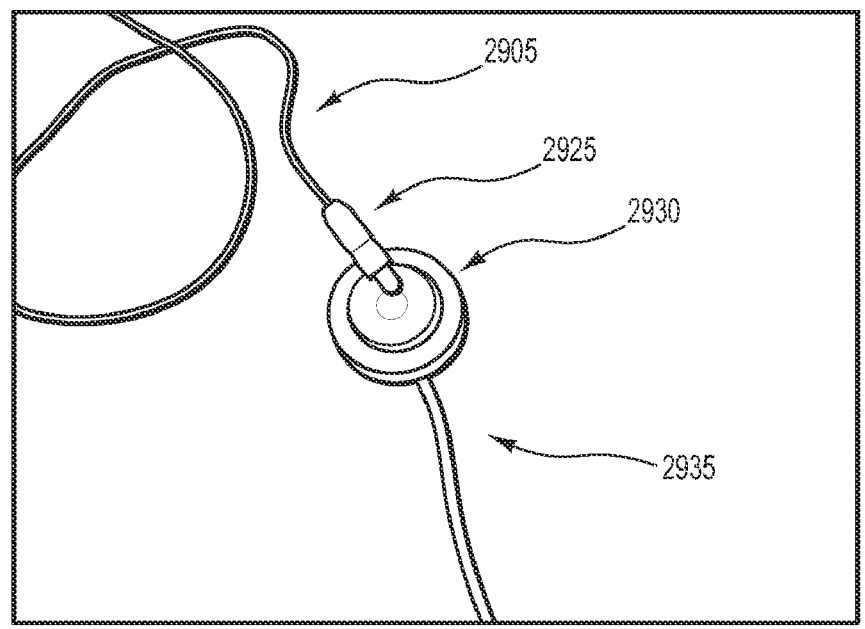

FIG. 22B illustrates another embodiment of the connector, wherein the connecting object (2930) is directly connected to a wire or is an integral part of an ECG cable (2935). This embodiment simplifies the method described above in connection with FIG. 22A, as only the sterile connector (2925) connected to the sterile adaptor (2905) must be dropped on to the electrically conductive surface (2930) of the connecting object (2930) during the sterile procedure.

Figure 22C:
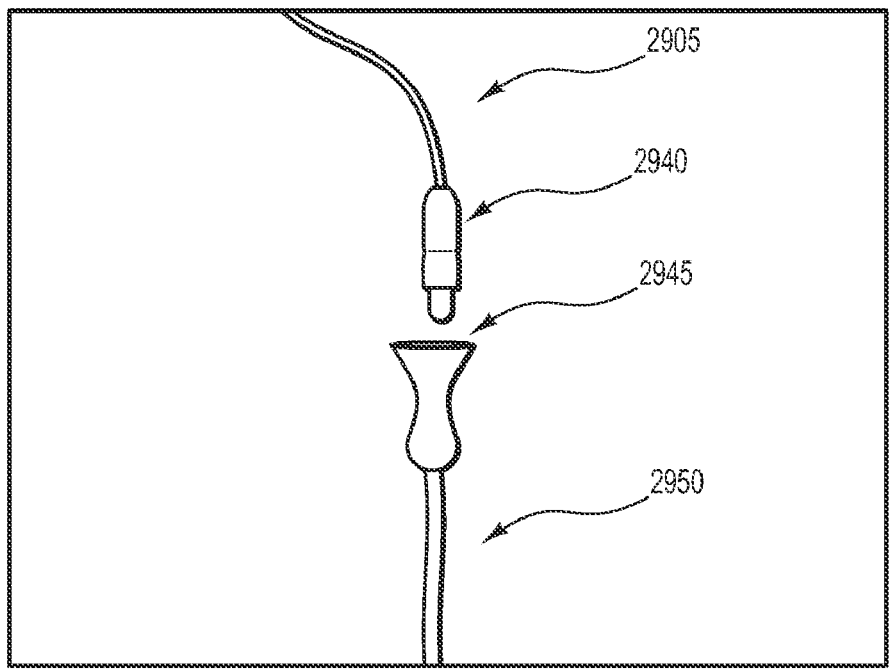

FIG. 22C illustrates another embodiment of the connecting object, wherein a connector (2940) of the sterile adaptor (2905) is similar to the adapter (2905) and connector (2910) described above in connection with FIG. 22A. During a catheter placement procedure, the sterile operator drops the sterile connector (2940) into a connecting object, or mating piece (2945). The mating piece (2945) includes a cup that receives therein the connector (2940). A magnet is built into the cup, which attracts the connector (2940) into the cup to secure it therein. At the same time, the cup ensures electrical connectivity. The mating piece (2945) can be an integral part of an ECG cable (2950) (e.g., one end of an ECG lead), one end of a wire for connection to an ECG cable, or some other suitable configuration. The method for using the mating piece 2945 is similar to that described in connection with FIG. 22B, with a difference being that the cup (2945) has the ability to suck in the connector (2940) for a relatively secure male/female-type connection. As is the case with the embodiments described in connection with FIGS. 22A, 22B, and 22D, the shapes and materials used for the connecting objects can vary while still ensuring proper electrical contact for the component interconnected therewith.

Figure 22D:
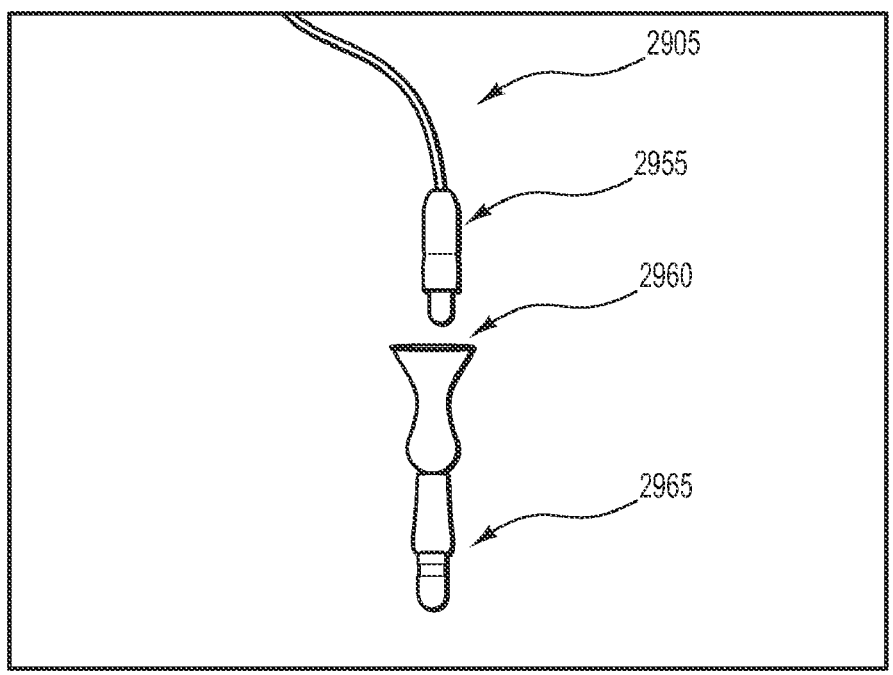

FIG. 22D illustrates a connecting object configuration similar to that described in connection with FIG. 22C, except that a cup (2960), which contains a magnet for operably connecting with a connector (2955), includes on an opposite end a connector (2965) to which an ECG cable clip can be attached. As such, during a placement procedure a non-sterile operator can connects the connector (2965) to a commercially available ECG cable by using the clip provided with the ECG cable. Later, during the sterile procedure, the sterile operator drops the sterile connector (2955) into the cup (2960), similar to the method described in connection with FIG. 22C.

Figure 23A:
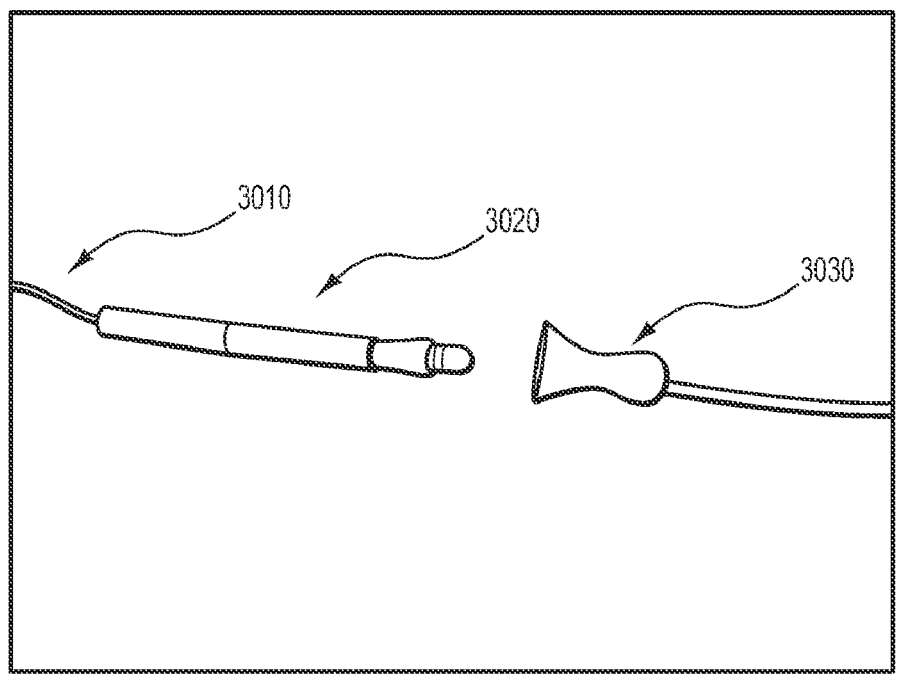
FIGS. 23A and 23B show various steerable sterile connectors according to certain embodiments.

FIG. 23A illustrates details of a steerable sterile adaptor (3010) according to one embodiment, including a reinforced sterile connector piece (3020) of rigid plastic, for instance. Instead of dropping the sterile connector piece (3020) into a mating piece (3030) as in FIGS. 22C and 22D, the sterile operator can use the rigid connector piece (3020) of the sterile adaptor (3010) to steer, e.g., push, rotate, etc., it into the mating piece. In one embodiment, the mating piece (3030) includes a built-in magnet to attract the connector piece 3020. In another embodiment, the mating piece (3030) includes no magnet, but is of an appropriate size and shape for the connector piece (3020) to fit therein so as to establish suitable electrical contact therebetween.

Figure 23B:
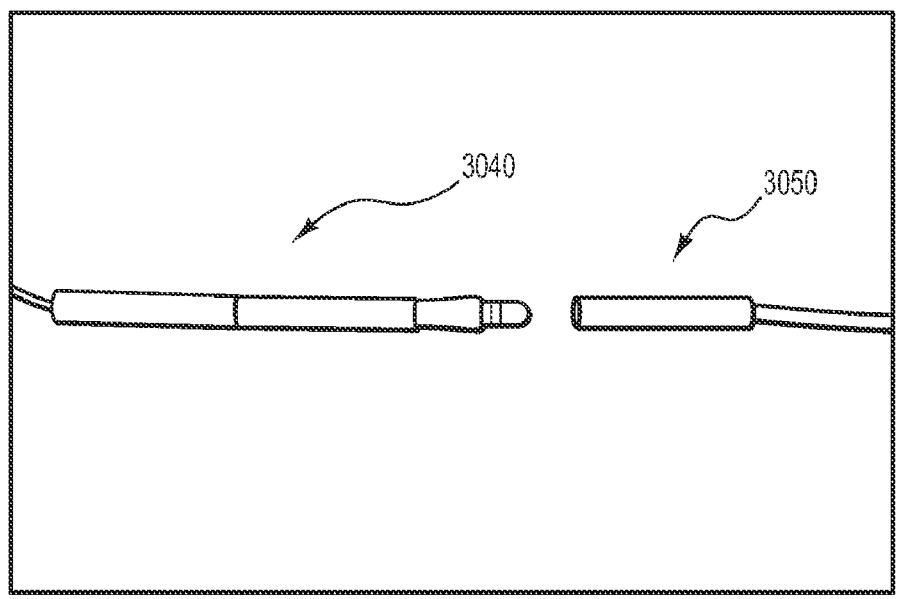

FIG. 23B illustrates a steerable connector piece (3040) according to one embodiment, which can be pushed into and operably connect with a simple mating piece (3050) without the need of a magnet. In addition to what has been shown and described, other shapes are possible for the connector (3040) and its mating piece (3050), e.g. rails or screws.

It is appreciated that any suitable combination of the connector embodiments discussed above can be used. For example, the steerable connector of FIG. 23B can include a mating piece like that shown in FIG. 22D.

FIGS. 24A-24F illustrate various details of catheter navigation according to one embodiment. As shown, each of these figures includes two display windows: a first window showing ECG waveforms, and a second window showing a representation, or icon, of a heart and an additional location icon indicating the point of measurement of the ECG signal to which the ECG waveforms in the first window correspond. The mapping between ECG waveforms and the location icon is performed in one embodiment using the algorithms and methods described above. The two display windows can be used independently or together. In one embodiment, the two display windows are shown simultaneously on the graphical user interface (FIG. 1A) in order to allow the operator to correlate the observed ECG waveform (s) with catheter tip location. In another embodiment, only the heart and location icon window is shown in order to simplify the user interface.

The location icon can include any one or more of several possible configurations, including an arrow to show advancement in a certain direction, a dot, a cross, a star, etc., to show an identifiable location. Each of these icons can include different colors to emphasize location relevance. In another embodiment, different sounds can be associated to each of the identifiable tip locations. Sounds and icons identifying tip locations can be used together or independently to help the user navigate the catheter and locate the tip within the patient vasculature.

In one embodiment a simplified user interface is employed, wherein only the heart icon and the corresponding location icon(s) are displayed. In this instance, the ECG waveforms and the computation behind the location mapping are not visible to the user. Thus, the apparatus described herein can be employed for navigation and tip location without requiring user interpretation of the ECG waveforms. The simplified user interface with only the heart and catheter tip location icons can be used as shown in the embodiment illustrated in FIG. 25B, for instance.

Figure 24A:
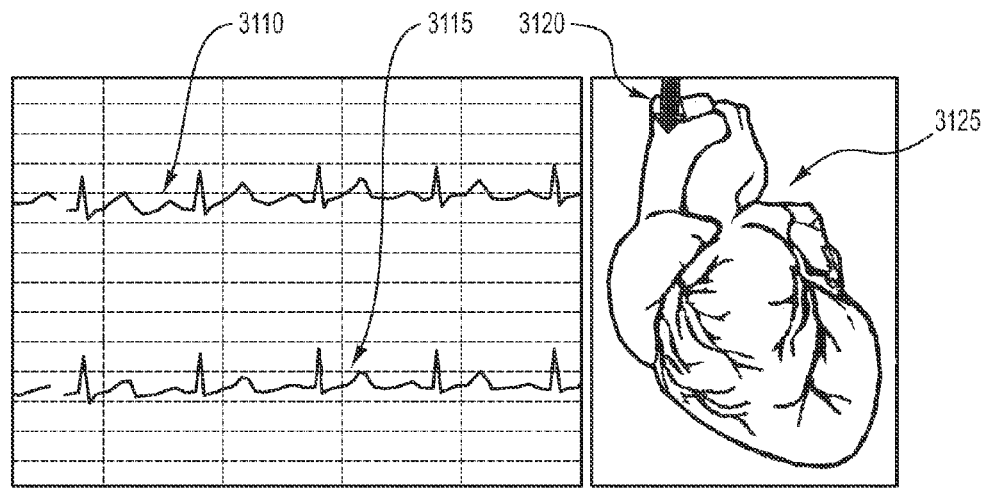
FIGS. 24A-24F show various views of a skin ECG waveform and an endovascular ECG waveform together with a heart icon to indicate a position of an endovascular device as depicted on a graphical user interface according to one embodiment.

In greater detail, FIG. 24A illustrates ECG waveforms corresponding to catheter tip locations outside the thoracic cavity in the upper body: a skin reference ECG Lead III (3110) and an endovascular catheter navigation ECG Lead II (3115). In the icon display window, a heart icon (3125) is displayed and a location icon (3120) shows that the catheter is moving towards the thoracic cavity. In another embodiment, the arrow-shaped location icon (3120) can be replaced with a cross, a dot, or any other suitable icon showing location above and outside the superior vena cava.

The arrow-shaped location icon (3120) is displayed by the apparatus according to one embodiment only if the algorithms detect changes in the navigation ECG Lead II that support the fact that the catheter tip is moving towards the heart, e.g., a steady increase in the electrical energy and a P-wave with positive directional energy, indicating that the tip is approaching the sino-atrial node. If the algorithms do not detect a steady increase in the electrical energy of the endovascular ECG signal as the catheter advances through the vasculature, only a dot, star, cross or other suitable location icon is displayed at a location above and outside the superior vena cava. Sounds associated with each of these locations and situations can be played in addition to or instead of the graphical icons.

Figure 24B:
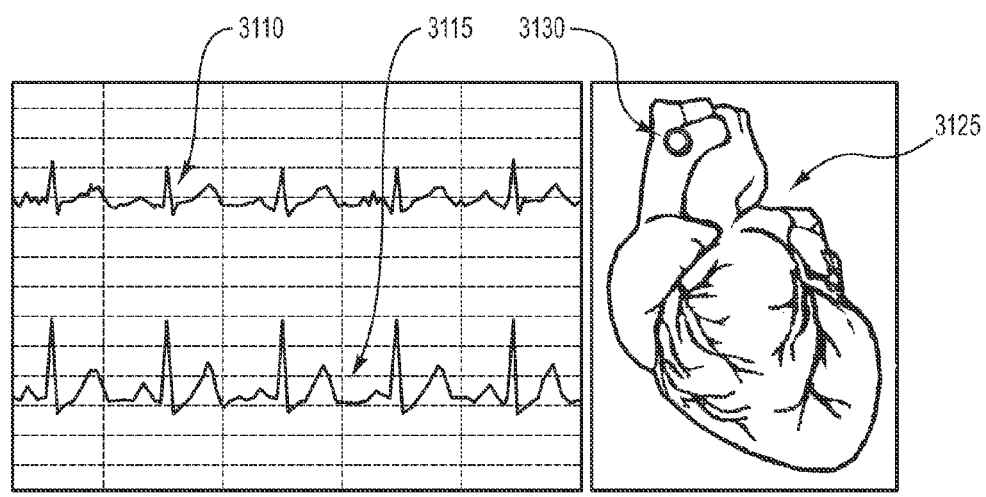

FIG. 24B illustrates the ECG waveforms corresponding to the reference lead (3110) and catheter navigation lead (3115) at a location corresponding to the upper superior vena cava. The icon display window shows the heart icon (3125) and a dot-shaped location icon (3130) indicating the upper superior vena cava on the heart icon. This location is determined by the apparatus, as described further above, based on the ECG waveforms (3110) and (3115). As in FIG. 24A, any suitable icon shape and color can be used, and/or a sound or tune can be played when the tip of the catheter reaches the location indicated by the detected ECG waveforms.

Figure 24C:
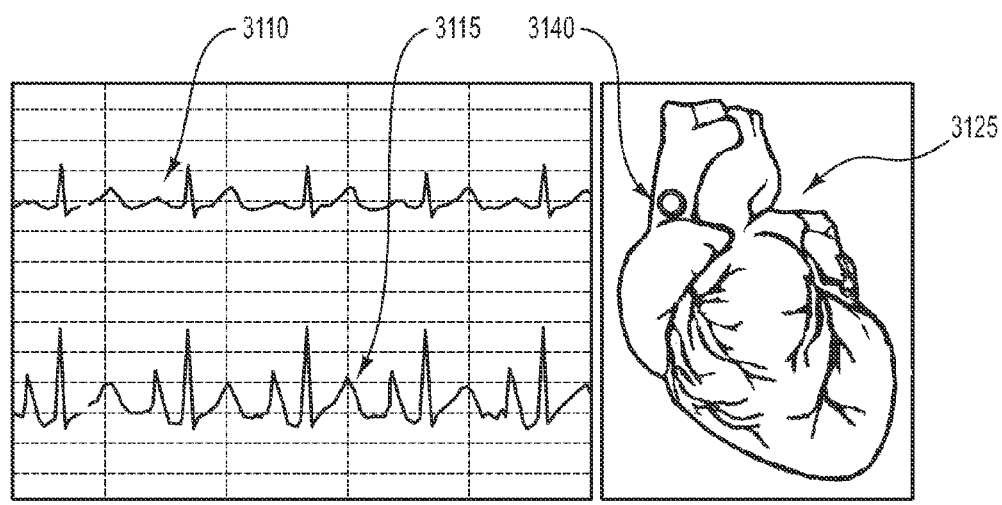

FIG. 24C illustrates the ECG waveforms corresponding to the reference lead (3110) and catheter navigation lead (3115) at a location corresponding to the lower third of the superior vena cava. The icon display window shows the heart icon (3125) and a dot-shaped location icon (3140) indicating the lower third of superior vena cava on the heart icon. This location is computed by the apparatus, as described further above, based on the ECG waveforms (3110) and (3115). As in FIG. 24A, any suitable icon shape and color can be used and/or a sound or tune can be played when the tip of the catheter reaches the location as indicated by the detected ECG waveforms.

Figure 24D:
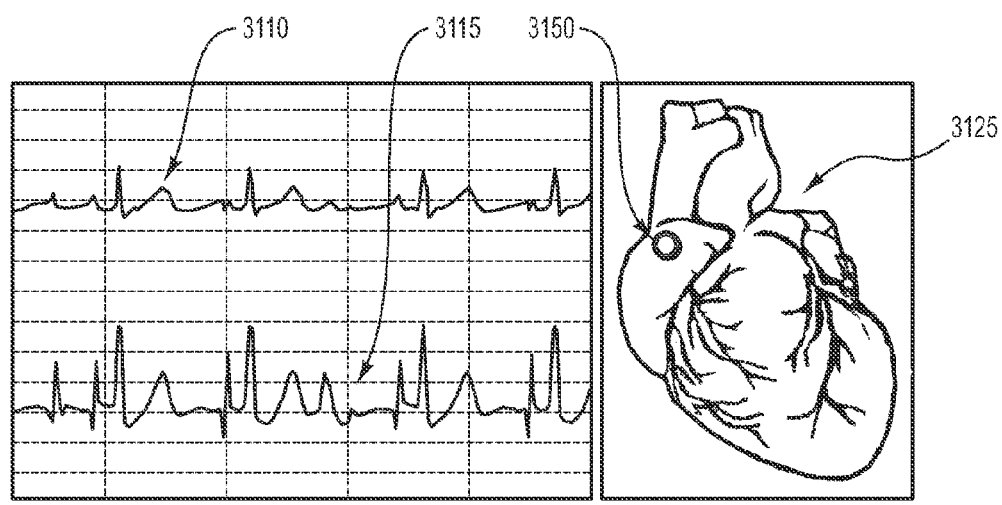

FIG. 24D illustrates the ECG waveforms corresponding to the reference lead (3110) and catheter navigation lead (3115) at a location corresponding to the caval-atrial junction. The icon display window shows the heart icon (3125) and a dot-shaped location icon (3150) indicating the caval-atrial junction on the heart icon. This location is computed by the apparatus, as described further above, based on the ECG waveforms (3110) and (3115). As in FIG. 24A, any suitable icon shape and color can be used and/or a sound or tune can be played when the tip of the catheter reaches this location as indicated by the detected ECG waveforms.

Figure 24E:
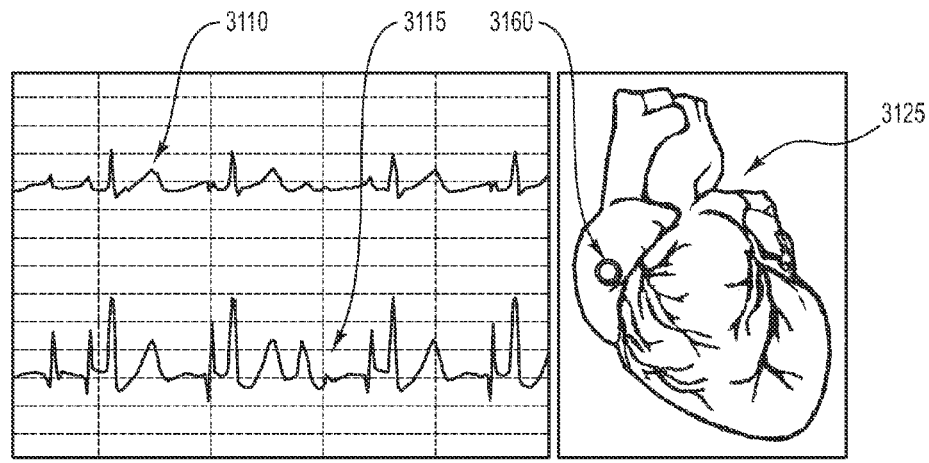

FIG. 24E illustrates the ECG waveforms corresponding to the reference lead (3110) and catheter navigation lead (3115) at a location corresponding to the right atrium. The icon display window shows the heart icon (3125) and a dot-shaped location icon (3160) indicating the right atrium on the heart icon. This location is computed by the apparatus, as described further above, based on the ECG waveforms (3110) and (3115). As in FIG. 24A, any suitable icon shape and color can be used and/or a sound or tune can be played when the tip of the catheter reaches this location as indicated by the detected ECG waveforms.

Figure 24F:
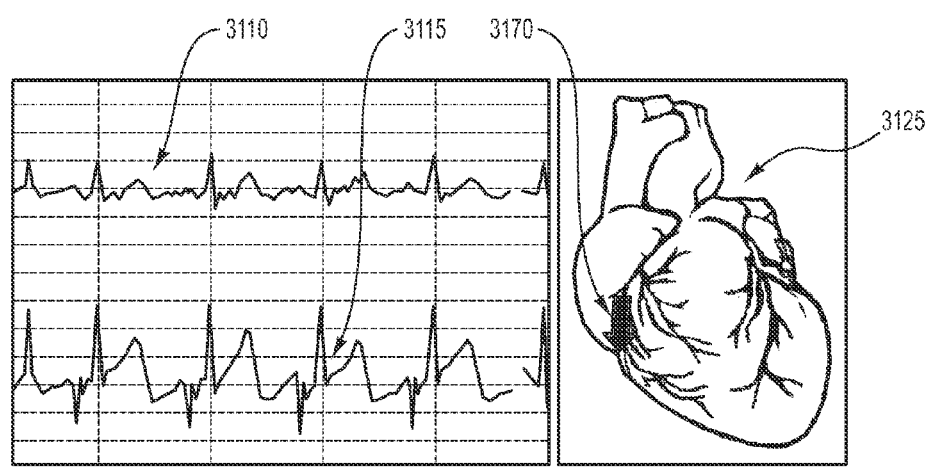

FIG. 24F illustrates ECG waveforms corresponding to catheter tip locations outside the thoracic cavity in the lower body: the skin reference ECG Lead III (3110) and the endovascular catheter navigation ECG Lead II (3115). In the icon display window, the heart icon is displayed (3125) and an arrow-shaped location icon (3170) showing that the catheter is moving away from the thoracic cavity, such as toward the inferior vena cava. In another embodiment, the arrow-shaped location icon (3170) can be replaced with a cross, a dot, or any other suitable icon showing location below the right atrium.

The arrow-shaped location icon (3170) is displayed by the apparatus in one embodiment only if the algorithms detect changes in the navigation ECG Lead II that support the fact that the catheter tip is moving away from the heart, e.g., a steady decrease in the electrical energy and a P-wave with negative directional energy, indicating that the tip is moving away from the sino-atrial node. If the algorithms do not detect a steady decrease in the electrical energy of the endovascular ECG signal as the catheter advances through the vasculature but detect a negative P-wave, only a dot, star, cross or any other location icon is displayed at a location below and outside the right atrium. The sounds associated with each of these locations and situations can be played in addition to or instead the graphical icons.

Figure 25A:
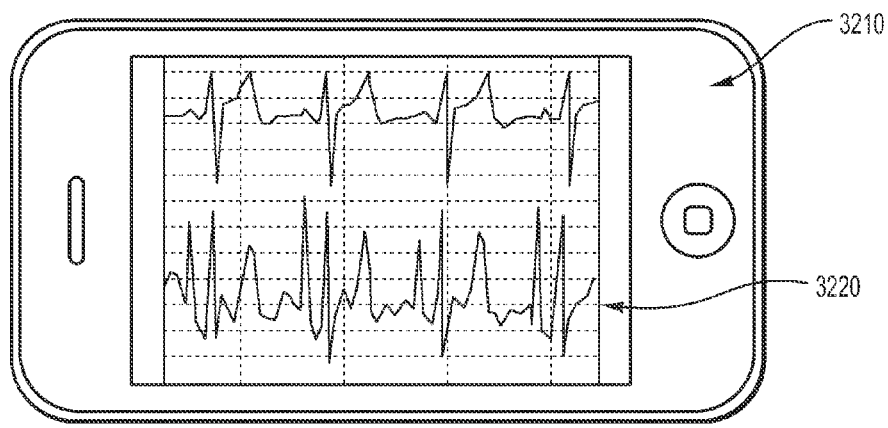
FIGS. 25A and 25B show various possible depictions for use in ECG signal-based guidance as displayed on a mobile phone according to one embodiment.

FIG. 25A illustrates a display window on a graphical user interface of a mobile phone (3210), tablet PC, or other suitable handheld or portable device. In particular, the user interface of the mobile phone is shown displaying waveforms (3220) of two ECG leads: the reference lead and the catheter navigation lead. The mobile phone or other suitable device is in held in one embodiment in a horizontal position as to allow for a longer time (more heart cycles) of the ECG waveform to be displayed. If the display device is in a real-time display mode, the display switches automatically to showing the ECG waveforms each time the device is turned horizontally. In another embodiment only one ECG lead is displayed at a time. In yet another embodiment, three or more leads can be displayed simultaneously. As described in an embodiment of the present invention, in another embodiment the screen of the display device can be split in real-time to depict a (current location) display window and a frozen (reference location) window to allow for easier assessment of ECG waveform changes. Two-way interaction between the apparatus shown in FIG. 1A and the mobile phone (3210) to enable the functionality shown and described in connection with FIGS. 25A-27B can be achieved in one embodiment via the wireless connectivity component 150, shown in FIG. 1A. It is appreciated that the mobile phone (3210) is equipped with corresponding wireless connectivity so as to enable communication therebetween, as appreciated by one skilled in the art.

Figure 25B:
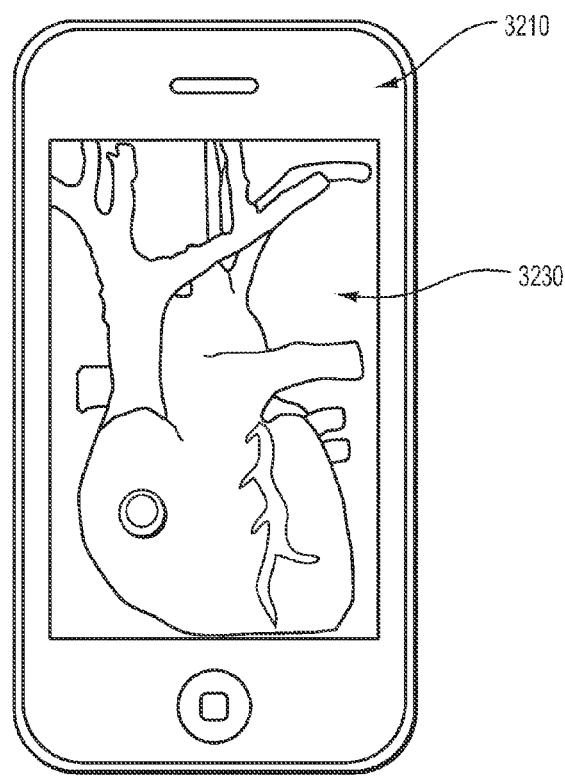

FIG. 25B illustrates a simplified user interface (3230) displayed on the screen of a mobile phone (3210) or other suitable handheld/portable device based on the navigation interface described in FIGS. 24A-24F. When in real-time display mode and if the display device is positioned vertically, the device automatically displays the simplified user interface shown in FIG. 25B. When in real-time display mode, the device automatically switches back and forth between displaying ECG waveforms when the device is held horizontally, illustrated in FIG. 25A, and displaying the navigation user interface, illustrated in FIG. 25B when the device is held vertically.

Figure 26:
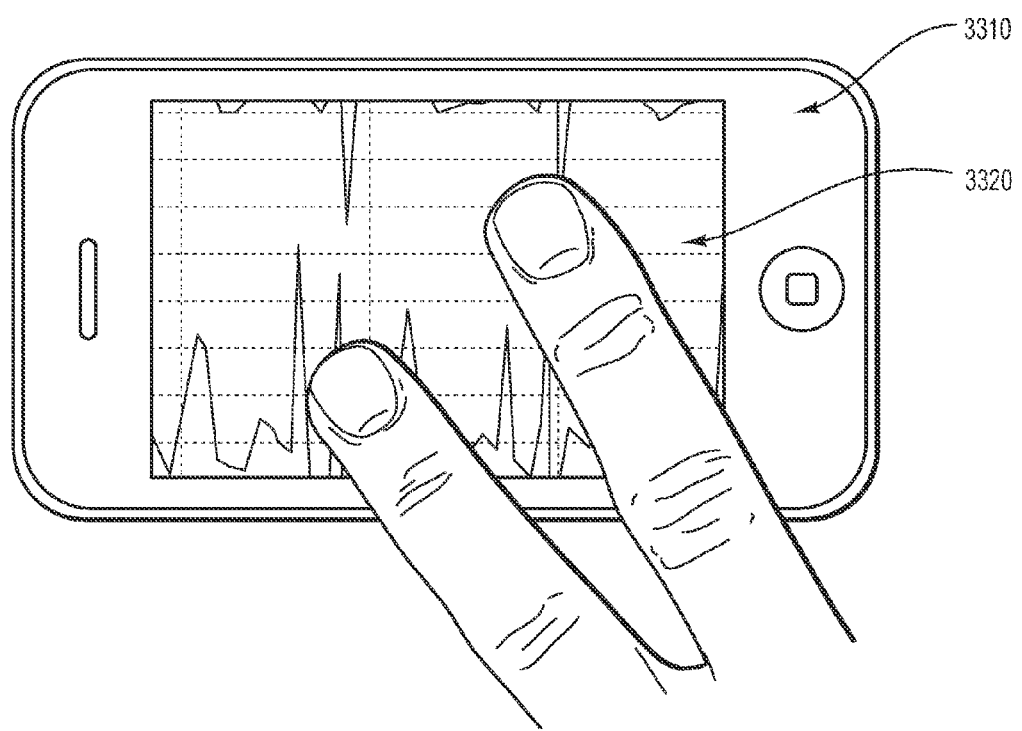
FIG. 26 shows a depiction of the zooming of multiple ECG waveforms as displayed on a mobile phone according to one embodiment.

FIG. 26 illustrates, in one embodiment, the zoom and scroll functions on the touch screen of a mobile phone (3310), tablet PC or similar device. The user can use two fingers (3320) to zoom in and out the ECG waveforms for better visualization. Scrolling through the ECG waveform recording can be also achieved using the fingers and the touch screen.

FIG. 27A illustrates the ability, in one embodiment to use a mobile phone (3410), tablet PC, or other suitable handheld/portable device to communicate the ECG waveforms and/or the simplified user interface and patient data to another computer or device. The communication interface is illustrated by (3420). Such transfer can be performed by the mobile phone (3410) via a Wi-Fi, cell phone, or other suitable network.

FIG. 27B illustrates the graphical user interface of a mobile phone (3410), tablet PC, or other suitable handheld/portable device, which allows for the display of patient data (3430), ECG waveforms (3440) or a simplified heart icon depending on the device orientation, and an interface (3450) browsing, control, and disposition of one or more patient records, including deleting, copying to memory, etc.

It is appreciated that the apparatus, algorithms, and methods described herein can be practiced in connection with a variety of environments and using a variety of components and systems. One example of an ECG monitoring system with which embodiments of the present invention can be practiced can be found in U.S. Patent Application Publication No. 2010/0036227, filed Sep. 10, 2009, and titled "Apparatus and Display Methods Relating to Intravascular Placement of a Catheter." Another example of an ECG monitoring system can be found in U.S. Pat. No. 8,388,546, filed Apr. 21, 2009, and titled "Method of Locating the Tip of a Central Venous Catheter." Each of the foregoing applications is incorporated herein by reference in its entirety.

Non-limiting examples of ECG sensor stylets that can be used in connection with embodiments of the present invention can be found in U.S. Pat. No. 9,901,714, filed Aug. 21, 2009, and titled "Catheter Assembly Including ECG Sensor and Magnetic Assemblies," and U.S. Pat. No. 9,636,031, filed Sep. 29, 2010, and titled "Stylets for use with Apparatus for Intravascular Placement of a Catheter," each of which is incorporated herein by reference in its entirety.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A method for locating an indwelling medical device within a body of a patient, the method comprising:
    placing a skin electrode on the body of the patient;
    inserting the medical device into the body of the patient, the medical device including a medical device electrode designed to sense an endovascular ECG signal;
    detecting a skin ECG waveform via the skin electrode;
    detecting an endovascular ECG waveform via the medical device electrode;
    locating a position of the medical device in the body of the patient;
    displaying the skin ECG waveform and the endovascular ECG waveform in a first window of a display in real-time; and
    displaying a frozen view of the skin ECG waveform and the endovascular ECG waveform in a second window of the display.

2. The method for locating according to claim 1, wherein the skin ECG waveform and the endovascular ECG waveform in real time are displayed in a time-synchronized manner, and wherein the display is included on a single user interface.

3. The method for locating according to claim 2, wherein the medical device electrode is positioned on a distal end of the medical device, wherein following the inserting step, the medical device electrode is within a vasculature of the patient.

4. The method for locating according to claim 1, further comprising:
    detecting a first peak in the skin ECG waveform;
    triggering analysis of the endovascular ECG waveform when the first peak is detected;
    detecting a second peak in the endovascular ECG waveform, the second peak including a P-wave peak; and
    determining a position of a portion of the medical device based on a characteristic of the second peak, including determining the portion of the medical device to be above and moving toward a sino-atrial node of a heart of the patient when an amplitude of the P-wave is positive and is increasing in positive amplitude.

5. The method for locating according to claim 4, further comprising iteratively detecting the second peak, wherein determining a position further comprises determining the position of the portion of the medical device based on a change of the characteristic as the second peak is iteratively detected.

6. The method for locating according to claim 4, wherein the first peak includes an R-wave peak and a P-wave peak is absent in the skin ECG waveform due to arrhythmia.

7. The method for locating according to claim 4, wherein the step of triggering the analysis of the endovascular ECG waveform is executed automatically by a processor coupled to the display.

8. The method for locating according to claim 1, further comprising:
    depicting on the display a location icon representing the position of the medical device in the body of the patient; and
    updating the location icon according to iteratively determining the position of the medical device in the body of the patient.

9. The method for locating according to claim 8, wherein depicting the location icon comprises depicting the location icon atop a representative image of a heart of the patient.

10. The method for locating according to claim 1, wherein the display is on a mobile phone or handheld device, and wherein the skin ECG waveform and the endovascular ECG waveform are transmitted to the mobile phone or handheld device via wireless transfer from the skin electrode and the medical device electrode.

11. A method for locating according to claim 1, further comprising:
    detecting a first peak in the skin ECG waveform;
    triggering analysis of the endovascular ECG waveform when the first peak is detected;
    detecting a second peak in the endovascular ECG waveform, the second peak including a P-wave peak; and
    determining a position of a portion of the medical device based on a characteristic of the second peak, including determining the portion of the medical device to be above and moving away from a sino-atrial node of a heart of the patient when an amplitude of the P-wave is negative and is increasing in negative amplitude.

12. The method for locating according to claim 11, further comprising iteratively detecting the second peak, wherein determining a position further comprises determining the position of the portion of the medical device based on a change of the characteristic as the second peak is iteratively detected.

13. The method for locating according to claim 11, wherein the first peak includes an R-wave peak and a P-wave peak is absent in the skin ECG waveform due to arrhythmia.

14. The method for locating according to claim 11, wherein the step of triggering the analysis of the endovascular ECG waveform is executed automatically by a processor coupled to the display.

* * * * *